US012662466B2

(12) United States Patent
Xie et al.

(10) Patent No.: US 12,662,466 B2
(45) Date of Patent: Jun. 23, 2026

(54) PYRIMIDINE COMPOUND AS WEE-1 INHIBITOR

(71) Applicant: WIGEN BIOMEDICINE TECHNOLOGY (SHANGHAI) CO., LTD., Shanghai (CN)

(72) Inventors: Yuli Xie, Shanghai (CN); Yingming Wu, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 455 days.

(21) Appl. No.: 18/273,536

(22) PCT Filed: Feb. 17, 2022

(86) PCT No.: PCT/CN2022/076671
§ 371 (c)(1),
(2) Date: Jul. 20, 2023

(87) PCT Pub. No.: WO2022/174796
PCT Pub. Date: Aug. 25, 2022

(65) Prior Publication Data

US 2024/0158369 A1 May 16, 2024

(30) Foreign Application Priority Data

Feb. 19, 2021 (CN) ......................... 202110192274.5
Jul. 19, 2021 (CN) ......................... 202110815600.3
Feb. 11, 2022 (CN) ......................... 202210129460.9

(51) Int. Cl.

| | |
|---|---|
| ***C07D 401/14*** | (2006.01) |
| ***A61P 35/00*** | (2006.01) |
| ***C07D 401/12*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |

(52) U.S. Cl.
CPC ............ *C07D 401/14* (2013.01); *A61P 35/00* (2018.01); *C07D 401/12* (2013.01); *C07D 405/14* (2013.01); *C07D 409/14* (2013.01); *C07D 413/14* (2013.01); *C07D 417/14* (2013.01)

(58) Field of Classification Search
None
See application file for complete search history.

(56) References Cited

FOREIGN PATENT DOCUMENTS

| | | | | |
|---|---|---|---|---|
| CN | 109627263 A | 4/2019 | | |
| CN | 110467615 A | 11/2019 | | |
| EP | 3722292 A1 | 10/2020 | | |
| JP | 2021505681 A | 2/2021 | | |
| KR | 2020-0016567 A | 2/2020 | | |
| WO | 2006099974 A1 | 9/2006 | | |
| WO | 2018011569 A1 | 1/2018 | | |
| WO | WO-2019112344 A1 * | 6/2019 | ........... | C07D 403/14 |
| WO | 2020192581 A1 | 10/2020 | | |

* cited by examiner

*Primary Examiner* — Jennifer A Berrios
*Assistant Examiner* — Sophia Reilly
(74) *Attorney, Agent, or Firm* — SZDC Law PC

(57) ABSTRACT

The present invention discloses a pyrimidine compound as a Wee-1 inhibitor. Specifically, the present invention relates to a compound of general formula (1), a method for preparing same, and use of the compound of general formula (1) or an isomer, a crystalline form, a pharmaceutically acceptable salt, a hydrate or a solvate thereof as a Wee-1 inhibitor in preparing an anti-tumor medicament.

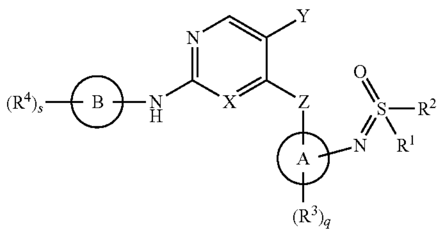

(1)

21 Claims, No Drawings

PYRIMIDINE COMPOUND AS WEE-1 INHIBITOR

The present application is the National Stage Application of PCT/CN2022/076671, filed on Feb. 17, 2022, which claims priority to Chinese Patent Application No. 2021101922745 filed on Feb. 19, 2021, Chinese Patent Application No. 2021108156003 filed on Jul. 19, 2021, and Chinese Patent Application No. 2022101294609 filed on Feb. 11, 2022. which are incorporated herein by reference in their entireties.

TECHNICAL FIELD

The present invention relates to the field of pharmaceutical chemistry, and particularly to a novel compound with an inhibitory effect on Wee-1 kinase, a method for preparing same and use of the compound in preparing an anti-tumor drug.

BACKGROUND

Wee-1 protein kinase is an important negative regulatory protein in cell cycle checkpoints. The cell cycle checkpoints include a G1 checkpoint for the transition from G1 phase (gap 1 phase) to S phase (DNA synthesis phase), a G2 checkpoint for the transition from G2 phase (gap 2 phase) to M phase (mitotic phase), and a spindle checkpoint for the transition from metaphase to anaphase of the M phase. The Wee-1 protein kinase plays an important role at the G2 phase checkpoint. The start of M phase depends on CDK1 kinase activity, and Wee-1 inhibits the activity of CDK1 by phosphorylating Tyr 15 of CDK1 protein, preventing cells from entering M phase. In contrast, polo kinase phosphorylates Wee-1 and activates the degradation of Wee-1 protein, promoting the start of M phase. Thus, Wee-1 kinase activity determines the activity of G2 checkpoint and regulates the G2-to-M transition of cells [Cell Cycle, 2013.12(19): p. 3159-3164].

The cell cycle checkpoints are activated primarily following DNA damage and play an important role in the repair of DNA in cells. The normal activation of the cell cycle checkpoints blocks the cell cycle and promotes DNA repair. If the functions of the checkpoints are inhibited, the DNA damage cannot be repaired, and the cells undergo apoptosis. Compared with normal cells, various tumor cells repair DNA damage and avoid apoptosis mainly depending on the activation of the G2 phase checkpoint due to the impaired function of the important protein p53 protein at the G1 phase checkpoint. Therefore, tumor cells can be selectively killed by inhibiting the G2 phase checkpoint. The important role of Wee-1 kinase activity in the G2 phase checkpoint suggests that Wee-1 kinase determines the repair or death of tumor cells after DNA damage, and the inhibition of Wee-1 activity can promote the start of M phase in unrepaired tumor cells after DNA damage and induce apoptosis [Curr Clin Pharmacol, 2010.5(3): p. 186-191].

Studies have shown that in addition to the role in the G2 checkpoint, Wee-1 is involved in DNA synthesis, DNA homologous repair, post-translational modification of chromosomal histones, and other functions closely related to the development and progression of tumors [J Cell Biol, 2011.194(4): p. 567-579]. Wee-1 expression is greatly increased in many tumors including liver cancer, breast cancer, cervical cancer, melanoma and lung cancer [PLoS One, 2009.4(4): p.e5120.; Hepatology, 2003.37(3): p. 534-543.; Mol Cancer, 2014.13: p. 72.]. The high expression of Wee-1 is in a positive correlation with the progression and poor prognosis of tumors, suggesting that Wee-1 kinase may be involved in the development and progression of tumors. Studies on in vitro cell models and in vivo animal models have shown that inhibiting Wee-1 activity while inducing DNA damage can significantly inhibit the growth of a variety of tumors [Cancer Biol Ther, 2010.9(7): p. 514-522.; Mol Cancer Ther, 2009.8(11): p. 2992-3000]. Therefore, the development of specific and highly active micromolecule inhibitors against Wee-1 kinase would be of important clinical value for tumor treatment, especially those targeting tumors with impaired G1 checkpoints such as P53 deletion.

SUMMARY

The present invention provides a compound of general formula (1), or an isomer, a crystalline form, a pharmaceutically acceptable salt, a hydrate or a solvate thereof:

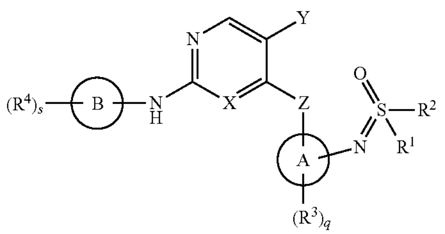

(1)

wherein, in general formula (1):

X is CH or N;

Y is —H, halogen, —CN, —$S(O)_2R^5$, —$P(O)(R^6)_2$, —$C(O)NR^8R^9$, (C1-C6) alkyl, (C1-C6) haloalkyl, (C2-C6) alkynyl, (C3-C14) cycloalkyl, (C6-C14) aryl, 3- to 11-membered heterocycloalkyl, or 5- to 11-membered heteroaryl, wherein the (C1-C6) alkyl, (C1-C6) haloalkyl, (C2-C6) alkynyl, (C3-C14) cycloalkyl, (C6-C14) aryl, 3- to 11-membered heterocycloalkyl, or 5- to 11-membered heteroaryl may be each independently and optionally substituted with 1, 2, 3, or 4 of the following groups: —H, halogen, $R^8$, —OH, —$(CH_2)_n$ $OR^8$—, —$(CH_2)_nNR^8R^9$, —$OR^8$, —$NR^8R^9$, —CN, —$C(O)NR^8R^9$, —$NR^9C(O)R^1$, —$NR^9S(O)_2R^8$, —$S(O)_pR^8$, and —$S(O)_2NR^8R^9$;

is a chemical bond, —$CH_2$—, —O—, or —NH—;

ring A is (C6-C14) aryl, 5- to 14-membered heteroaryl, or 3- to 14-membered heterocycloalkyl; $R^1$ and $R^2$ are each independently (C1-C6) alkyl, (C1-C6) haloalkyl, (C2-C6) alkenyl, or (C3-C6) cycloalkyl, wherein the (C1-C6) alkyl, (C1-C6) haloalkyl, (C2-C6) alkenyl, or (C3-C6) cycloalkyl may be each independently and optionally substituted with 1, 2, 3, or 4 of the following groups: —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^9C(O)R^1$, —$NR^9S(O)_2R^8$, —$S(O)_pR^8$, and —$S(O)_2NR^8R^9$; or $R^1$ and $R^2$, along with the S atom connected thereto, are capable of forming 4- to 7-membered heterocycloalkyl, wherein the 4- to 7-membered heterocycloalkyl may be optionally substituted with 1, 2, 3, or 4 of the following groups: —H, halogen, $R^8$, —$OR^8$, —$NR^8R^9$, and —CN;

each $R^3$ is independently —H, -D, halogen, $R^8$, —OH, —$(CH_2)$, $OR^8$, —$(CH_2)_nNR^8R^9$, —$OR^8$, —$NR^8R^9$, —CN, —$C(O)NR^8R^9$, —$NR^9C(O)R^1$, —$NR^9S(O)_2R^8$, —$S(O)_pR^8$, —$S(O)_2NR^8R^9$, (C1-C6) alkyl, (C1-C6)

haloalkyl, (C2-C6) alkenyl, (C2-C6) alkynyl, (C3-C9) cycloalkyl, (C6-C14) aryl, 3- to 11-membered heterocycloalkyl, or 5- to 11-membered heteroaryl, wherein the (C1-C6) alkyl, (C1-C6) haloalkyl, (C2-C6) alkenyl, (C2-C6) alkynyl, (C3-C9) cycloalkyl, (C6-C14) aryl, 3- to 11-membered heterocycloalkyl, or 5- to 11-membered heteroaryl may be each independently and optionally substituted with 1, 2, 3, or 4 of the following groups: —H, halogen, $R^8$, —OH, —$(CH_2)_n OR^8$, —$(CH_2)_n NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$, and —$S(O)_2NR^8R^9$; or two adjacent $R^3$, along with the atoms connected thereto, are capable of forming 5- to 9-membered heterocycloalkyl or (C5-C9) cycloalkyl, wherein the 5- to 9-membered heterocycloalkyl or the (C5-C9) cycloalkyl may be optionally substituted with 1, 2, 3, or 4 of the following groups: —H, halogen, $R^8$, —OH, —$(CH_2)_n OR^8$, —$(CH_2)_n NR^8R^9$, —$OR^8$, —$NR^8R^9$, —CN, —C(O)$NR^8R^9$, —$NR^9C(O)R^8$, —$NR^9S(O)_2R^8$, —$S(O)_pR^8$, and —$S(O)_2NR^8R^9$; ring B is (C6-C14) aryl or 5- to 11-membered heteroaryl;

each $R^4$ is independently —H, halogen, $R^8$, —OH, —$(CH_2)_n OR^8$, —$OR^8$, —$(CH_2)_n NR^8R^9$, —$NR^8R^9$, —CN, —$O(CH_2)_m NR^8R^9$, —$N(R^9)(CH_2)_m NR^8R^9$, —C(O)$NR^8R^9$, —$NR^9C(O)R^8$, —$NR^9S(O)_2R^8$, —$S(O)_pR^8$, —$S(O)_2NR^8R^9$, (C1-C6) alkyl, (C1-C6) haloalkyl, (C2-C6) alkenyl, (C2-C6) alkynyl, (C3-C9) cycloalkyl, (C1-C6) alkoxy, —$CH_2$-3- to 15-membered heterocycloalkyl, 3- to 15-membered heterocycloalkyl, 5- to 9-membered heteroaryl, or (C6-C10) aryl, wherein the (C1-C6) alkyl, (C1-C6) haloalkyl, (C2-C6) alkenyl, (C2-C6) alkynyl, (C3-C9) cycloalkyl, (C1-C6) alkoxy, —$CH_2$-3- to 15-membered heterocycloalkyl, 3- to 15-membered heterocycloalkyl, 5- to 9-membered heteroaryl, or (C6-C10) aryl may be optionally substituted with 1, 2, 3, or 4 of the following groups: —H, halogen, $R^8$, —OH, —$(CH_2)_n OR^8$, —$OR^8$, —$(CH_2)_n NR^8R^9$, —$NR^8R^9$, —CN, —$O(CH_2)_m NR^8R^9$, —$N(R^9)(CH_2)_m NR^8R^9$, (C1-C6) alkyl, (C1-C6) haloalkyl, (C2-C6) alkenyl, (C2-C6) alkynyl, (C3-C9) cycloalkyl, (C1-C6) alkoxy, —$CH_2$-3- to 15-membered heterocycloalkyl, 3- to 15-membered heterocycloalkyl, 5- to 9-membered heteroaryl, (C6-C10) aryl, and —$R^7$; or two adjacent $R^4$, along with the atoms connected thereto, are capable of forming 5- to 9-membered heterocycloalkyl or (C5-C9) cycloalkyl, wherein the 5- to 9-membered heterocycloalkyl or (C5-C9) cloalkyl may be optionally substituted with 1, 2, 3, or 4 of the following groups: —H, halogen, $R^8$, —OH, —$(CH_2)_n OR^8$, —$OR^8$, —$(CH_2)_n NR^8R^9$, —$NR^8R^9$, —CN, —$O(CH_2)_m NR^8R^9$, —$N(R^9)(CH_2)_m NR^8R^9$, —C(O)$R^8$, —C(O)$NR^8R^9$, —$NR^9C(O)R^8$, —$NR^9S(O)_2R^8$, —$S(O)_pR^8$, —$S(O)_2NR^8R^9$,

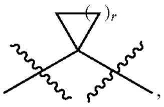, (C1-C6) alkyl, (C1-C6) haloalkyl, (C2-C6) alkenyl, (C2-C6) alkynyl, (C3-C9) cycloalkyl, (C1-C6) alkoxy, —$CH_2$-4- to 9-membered heterocycloalkyl, 4- to 9-membered heterocycloalkyl, 5- to 9-membered heteroaryl, and (C6-C10) aryl;

$R^5$ is (C1-C3) alkyl or (C3-C6) cycloalkyl;

$R^6$ is (C1-C3) alkyl or (C3-C6) cycloalkyl;

$R^7$ is 3- to 11-membered heterocycloalkyl, wherein the heterocycloalkyl may be optionally substituted with 1, 2, 3, or 4 of the following groups: —H, $R^8$, —$OR^8$, and —$NR^8R^9$;

$R^8$ and $R^9$ are each independently —H, (C1-C6) alkyl or (C3-C14) cycloalkyl, or $R^8$ and $R^9$ on the same N atom, along with the N atom connected thereto, are capable of forming 3- to 11-membered heterocycloalkyl, wherein the 3- to 11-membered heterocycloalkyl may be optionally substituted with 1, 2, 3, or 4 of the following groups: —H, halogen, $R^{10}$, and —$OR^{10}$;

$R^{10}$ is —H, (C1-C3) alkyl, or (C3-C6) cycloalkyl;

$R^{11}$ and $R^{12}$ are each independently —H, (C1-C3) alkyl or (C3-C6) cycloalkyl, or $R^1$ and $R^{12}$ on the same N atom, along with the N atom connected thereto, are capable of forming 4- to 6-membered heterocycloalkyl; and p is an integer of 0, 1, or 2, q is an integer of 1, 2, 3, or 4, r is an integer of 1, 2, or 3, s is an integer of 1, 2, 3, or 4, n is an integer of 0, 1, 2, or 3, and m is an integer of 1, 2, or 3.

In another preferred embodiment, in general formula (1), Y is —H, —F, —Cl, —Br, —I, —CN, —$S(O)_2CH_3$, —P(O)$(CH_3)_2$, —C(O)$NH_2$, —C(O)NH($CH_3$), —C(O)N$(CH_3)_2$, (C1-C3) alkyl, (C1-C3) haloalkyl, (C3-C5) cycloalkyl, (C2-C3) alkynyl, or 5- to 6-membered heteroaryl, wherein the (C1-C3) alkyl, (C1-C3) haloalkyl, (C3-C5) cycloalkyl, (C2-C3) alkynyl, or 5- to 6-membered heteroaryl may be each independently and optionally substituted with 1, 2, 3, or 4 of the following groups: —H, —F, —CN, —$CH_3$, and —$OCH_3$.

In another preferred embodiment, in general formula (1), Y is: —H, —F, —Cl, —Br, —I, —CN, —$S(O)_2CH_3$, —P(O)$(CH_3)_2$, —C(O)$NH_2$, —C(O)NH($CH_3$), —C(O)N$(CH_3)_2$, —$CH_3$, —$CF_3$,

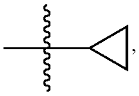, 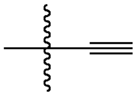, 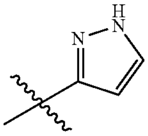,

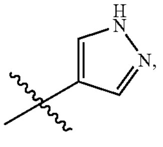 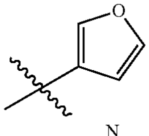, 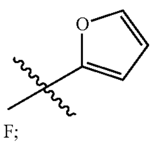, or

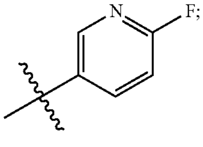;

preferably, Y is —H, —F, —Br, —I, —CN, —$S(O)_2CH_3$, —P(O)$(CH_3)_2$, —C(O)$NH_2$, —C(O)NH($CH_3$), —C(O)N$(CH_3)_2$, —$CF_3$,

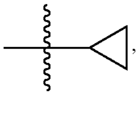, 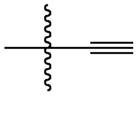, 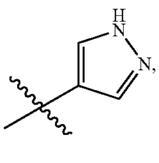 or

-continued
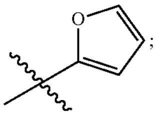
and more preferably, Y is —CN.
In another preferred embodiment, in general formula (1), ring A is (C6-C10) aryl, 5- to 10-membered heteroaryl, or 5- to 10-membered heterocycloalkyl.
In another preferred embodiment, in general formula (1) ring A is:
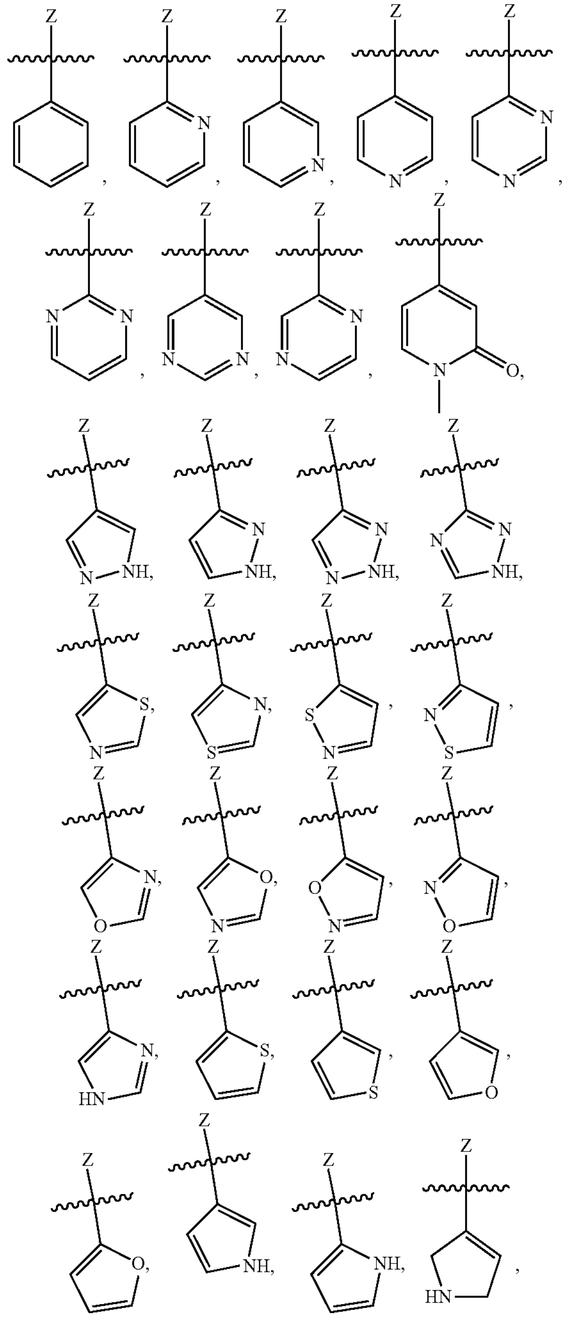
-continued
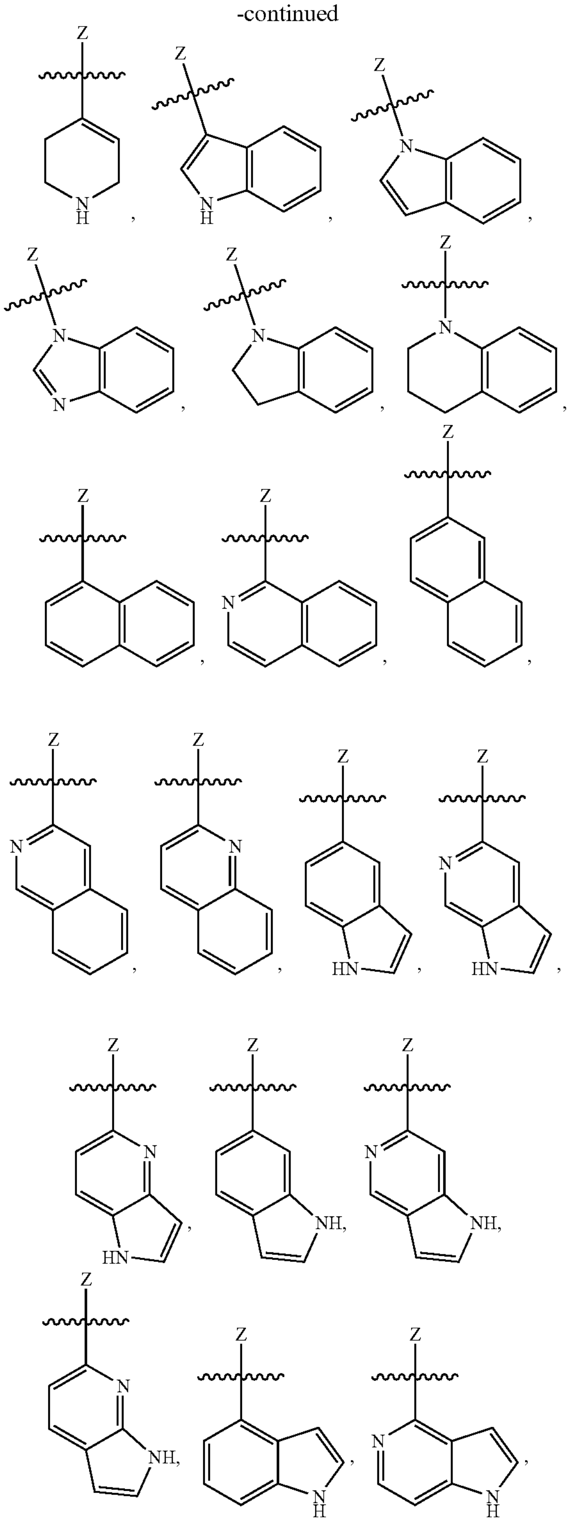
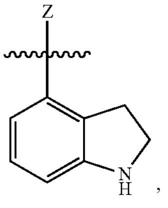
or
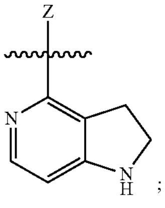

preferably, A is
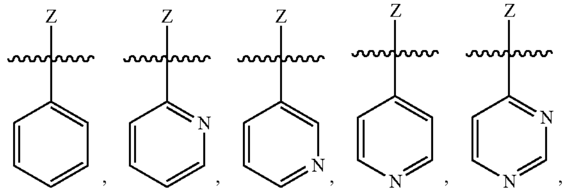
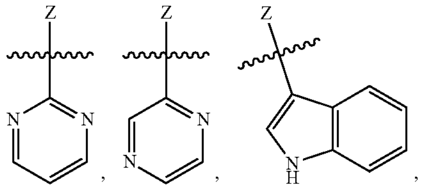
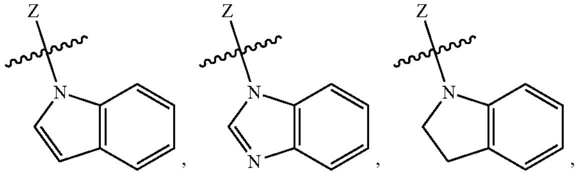
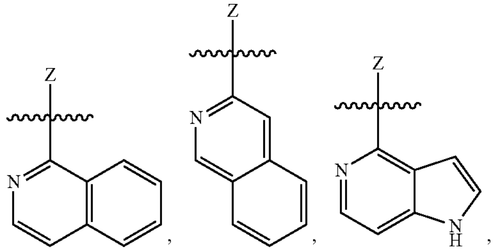
or
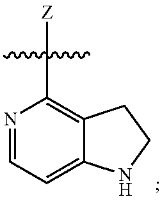
preferably, ring
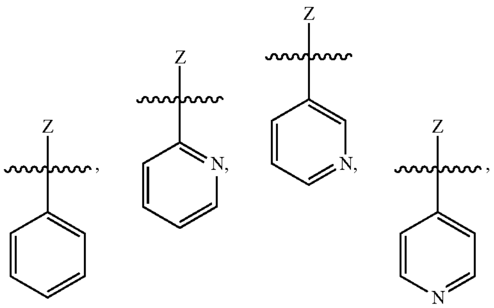
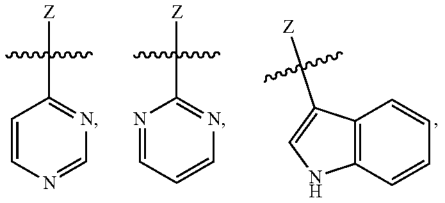
-continued
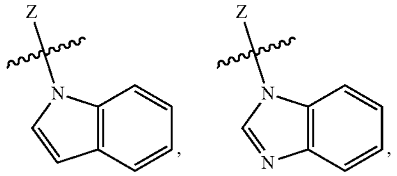
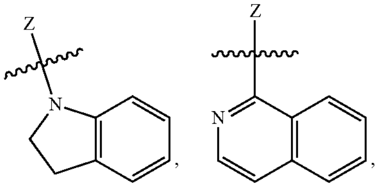
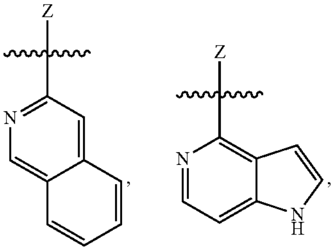
or
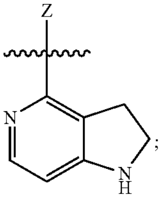
preferably, ring A is
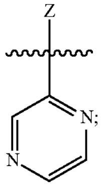
preferably, ring A is
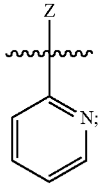

preferably, ring A is

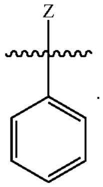

.

In another preferred embodiment, in general formula (1), $R^1$ and $R^2$ are each independently (C1-C3) alkyl, (C1-C3) haloalkyl, (C2-C4) alkenyl, or (C3-C5) cycloalkyl, wherein the (C1-C3) alkyl, (C1-C3) haloalkyl, (C2-C4) alkenyl, or (C3-C5) cycloalkyl may be each independently and optionally substituted with 1, 2, 3, or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$, and —CN; or $R^1$ and $R^2$, along with the S atom connected thereto, are capable of forming 4- to 6-membered heterocycloalkyl, wherein the 4- to 6-membered heterocycloalkyl may be optionally substituted with 1, 2, 3, or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$, and —CN.

In another preferred embodiment, in general formula (1), structural unit

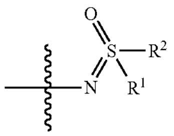

is:

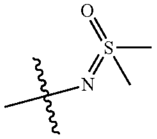, 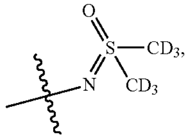, 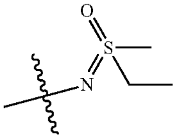, 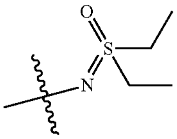, 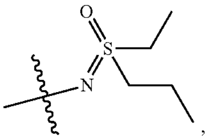, 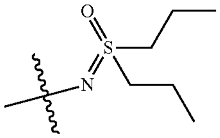, 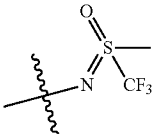, 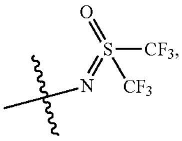, 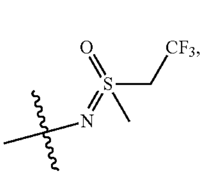, 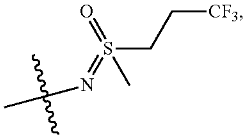, 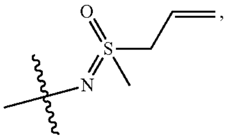, -continued

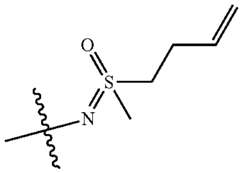, 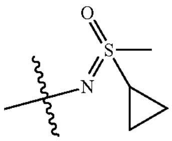, 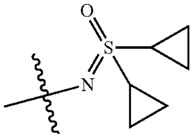, 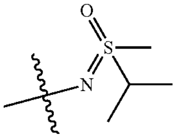, 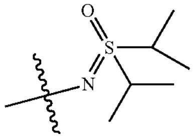, 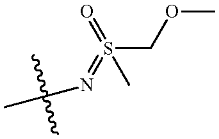, 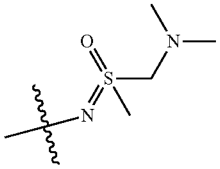, 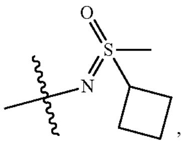, 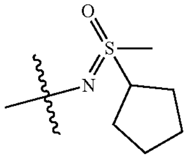, 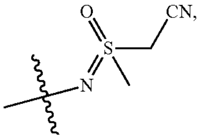, 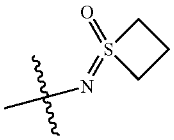, or 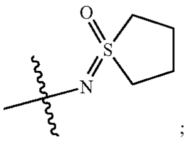;

preferably

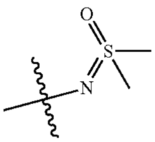, 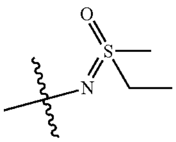, 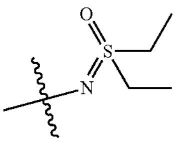, 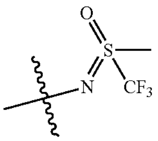, 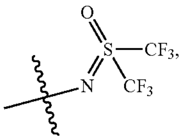, 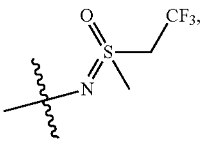, 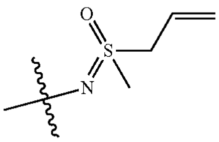, 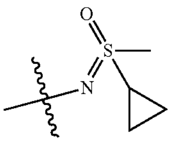, 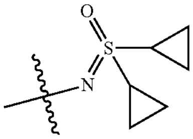, 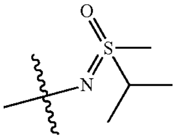, -continued

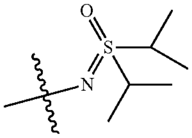,
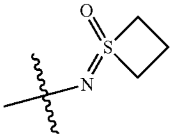 or
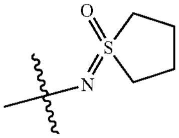;

more preferably

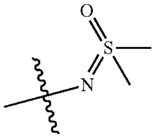, 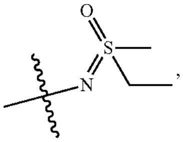, 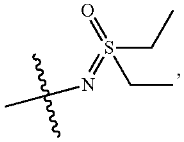,
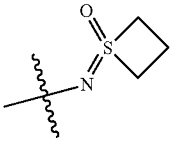 or 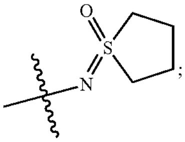;

more preferably

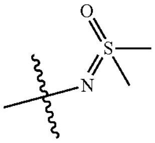.

In another preferred embodiment, in general formula (1), each $R^3$ is independently —H, -D, —F, —Cl, —Br, —I, —OH, —$CH_2OR^{11}$, —$CH_2NR^{11}R^{12}$, —$OR^{11}$, —$NR^{11}R^{12}$, —CN, —$C(O)NR^{11}R^{12}$, —$NR^{12}C(O)R^{11}$, —$NR^{12}S(O)_2R^{11}$, —$SR^{11}$, —$S(O)_2R^{11}$, —$S(O)_2NR^{11}R^{12}$, (C1-C3) alkyl, (C1-C3) haloalkyl, (C2-C4) alkenyl, (C2-C4) alkynyl, (C3-C6) cycloalkyl, phenyl, 4- to 8-membered heterocycloalkyl, or 5- to 6-membered heteroaryl, wherein the (C1-C3) alkyl, (C1-C3) haloalkyl, (C2-C4) alkenyl, (C2-C4) alkynyl, (C3-C6) cycloalkyl, phenyl, 4- to 8-membered heterocycloalkyl, or 5- to 6-membered heteroaryl may be each independently and optionally substituted with 1, 2, 3, or 4 of the following groups: —H, —F, —Cl, —Br, —I, —OH, —$OCH_3$, —$N(CH_3)_2$, and —CN; or two adjacent $R^3$, along with the atoms connected thereto, are capable of forming 5- to 7-membered heterocycloalkyl or (C5-C7) cycloalkyl, wherein the 5- to 7-membered heterocycloalkyl or (C5-C7) cycloalkyl may be optionally substituted with 1, 2, 3, or 4 of the following groups: —H, —F, —Cl, —Br, —I, —$CH_3$, —OH, —$CH_2OCH_3$, —$CH_2N(CH_3)_2$, —$OCH_3$, —$N(CH_3)_2$, and —CN.

In another preferred embodiment, in general formula (1), each $R^3$ is independently: —H, -D, —F, —Cl, —Br, —I, —OH, —$CH_2OCH_3$, —$CH_2N(CH_3)_2$, —$OCH_3$, —$N(CH_3)_2$, —CN, —$C(O)NH_2$, —$C(O)NH(CH_3)$, —$C(O)N(CH_3)_2$, —$NHC(O)CH_3$, —$N(CH_3)$—$C(O)CH_3$, —$NHS(O)_2CH_3$, -+$CH_3$, —$NCH_3S(O)_2CH_3$, —$SCH_3$, —$S(O)_2CH_3$, —$S(O)_2NH_2$, —$S(O)_2NH(CH_3)$, —$S(O)_2N(CH_3)_2$,

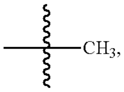, 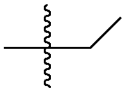, 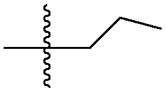,
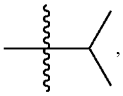, 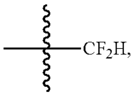, 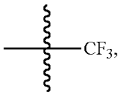, 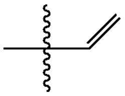,
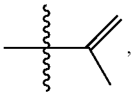, 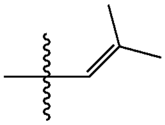, 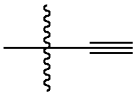,
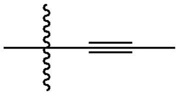, 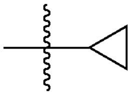, 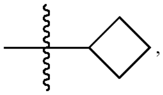,
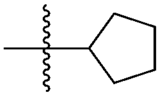, 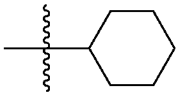, 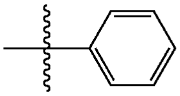,
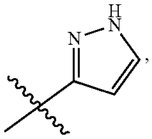, 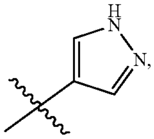, 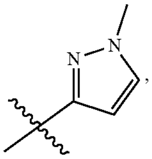,
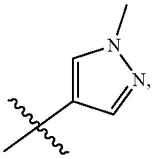, 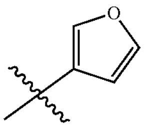, 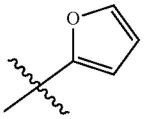,
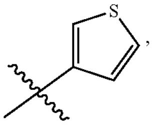, 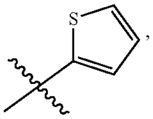, 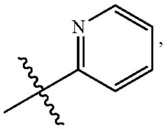,
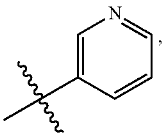, 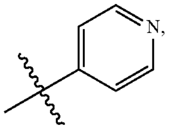, 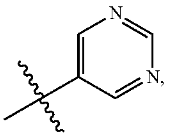,
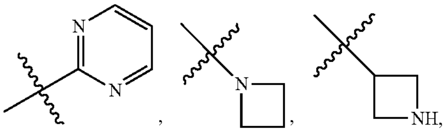, 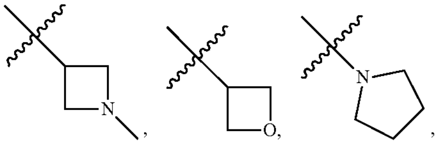, 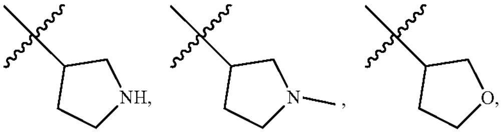, -continued
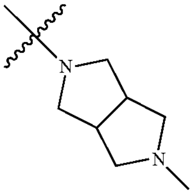, 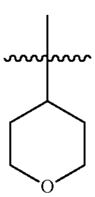, 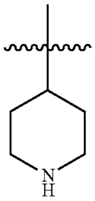, 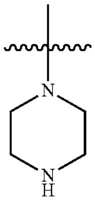,
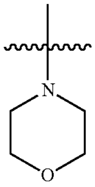, 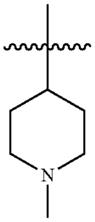, 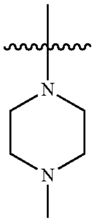, or 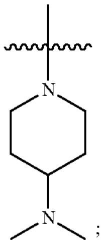;
preferably, $R^3$ is —H, -D, —F, —Cl, —$OCH_3$, —CN,
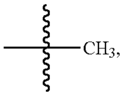 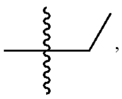, 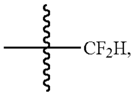 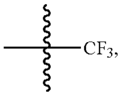
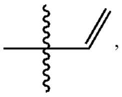, 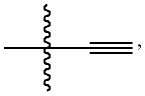, or 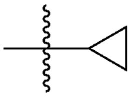;
more preferably, $R^3$ is —H, —F, $OCH_3$, $CH_3$,
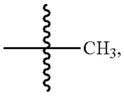 or 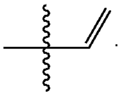.
In another preferred embodiment, in general formula (1), structural unit
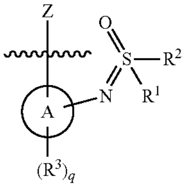
is:
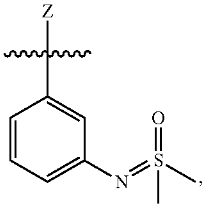, 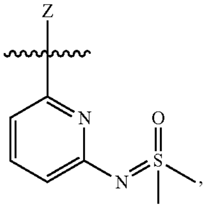,
-continued
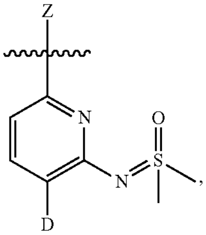, 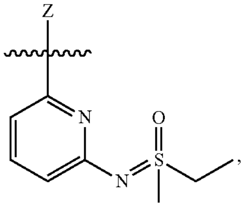,
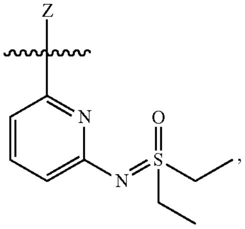,
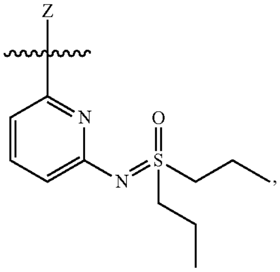,
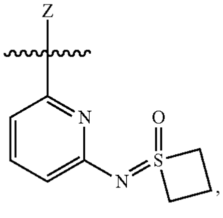, 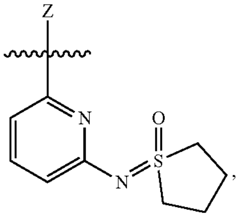,
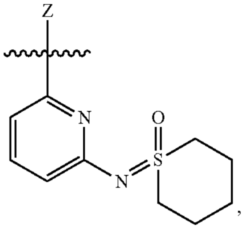, 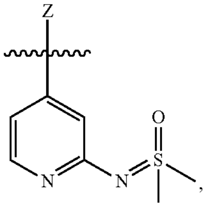,
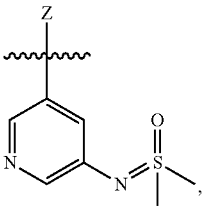, 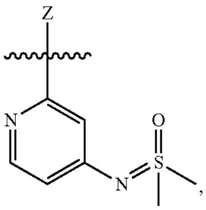,
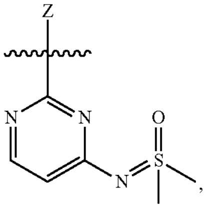, 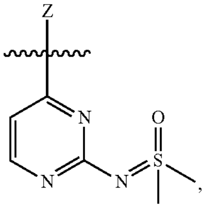, -continued
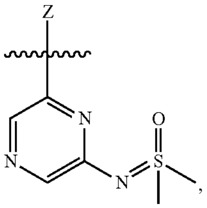
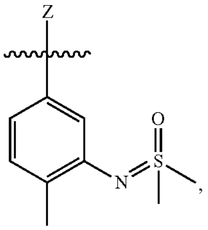
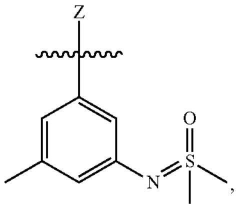
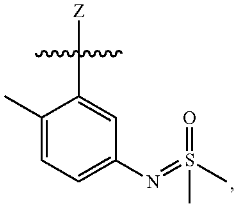
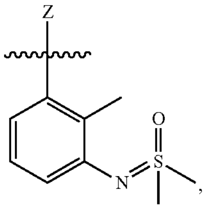
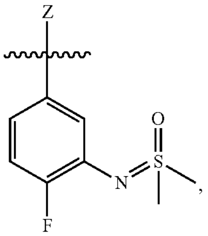
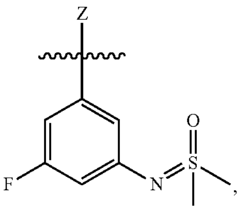
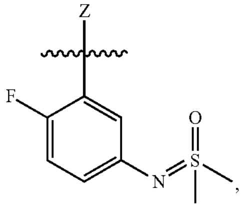
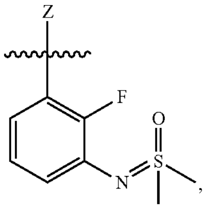
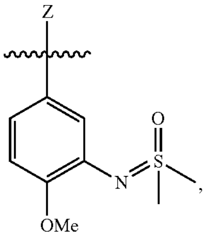
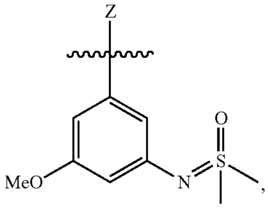
-continued
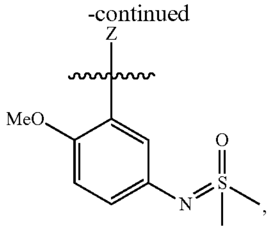
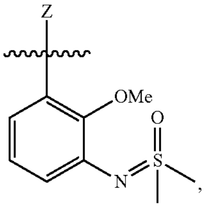
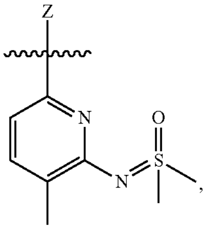
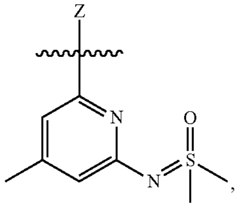
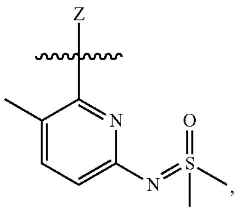
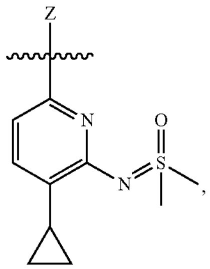
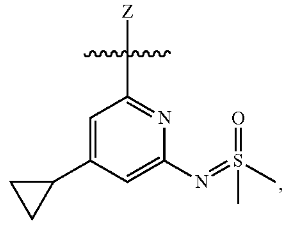
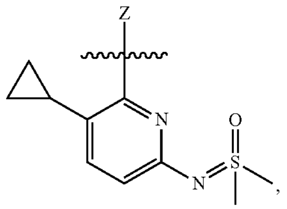
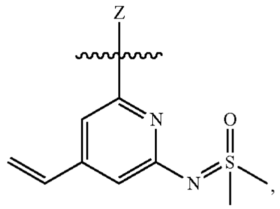

-continued
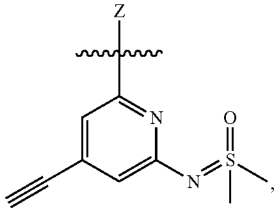
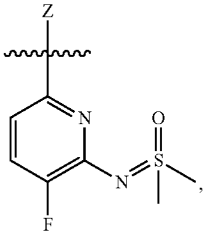
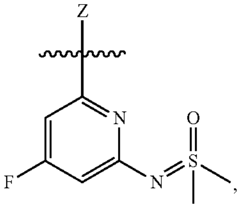
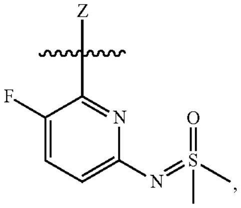
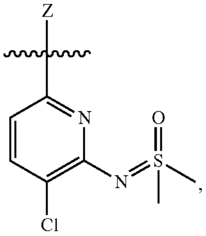
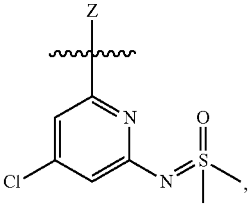
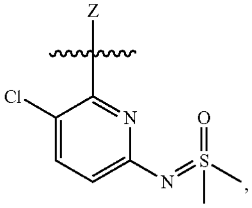
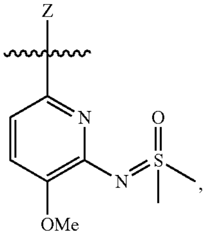
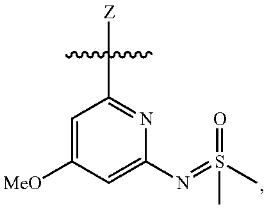
-continued
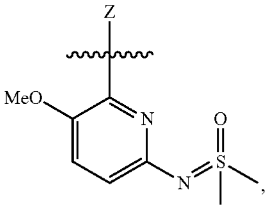
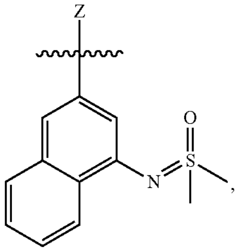
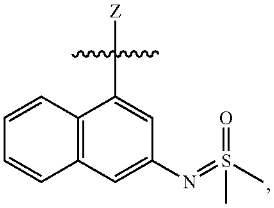
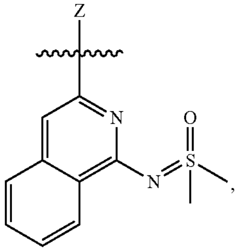
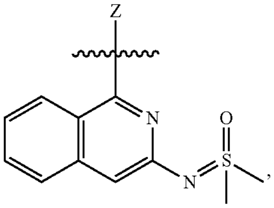
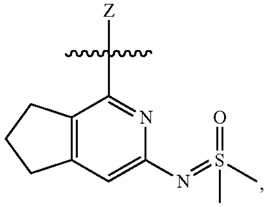
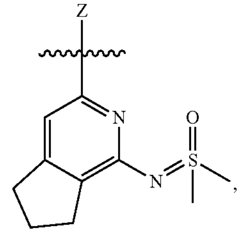

-continued
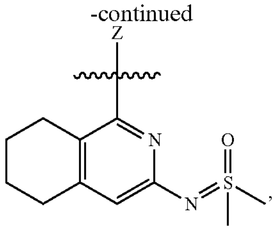
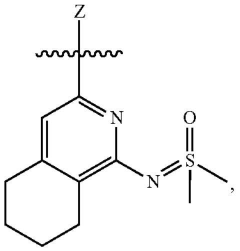
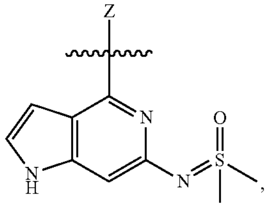
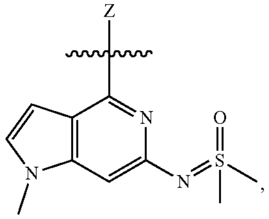
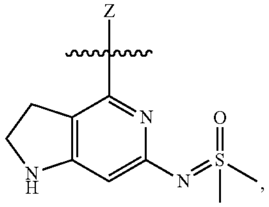
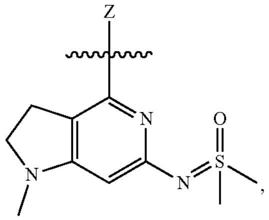
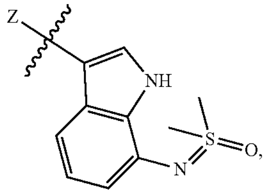
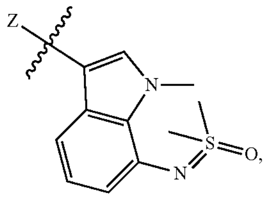
-continued
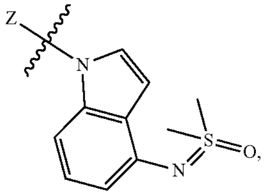
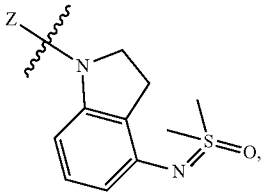
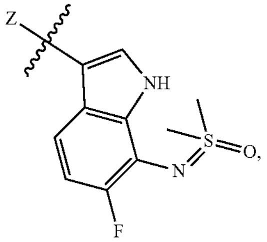
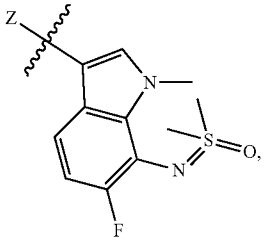
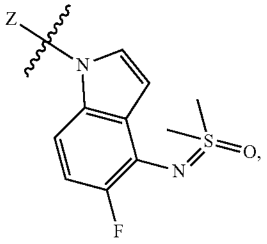
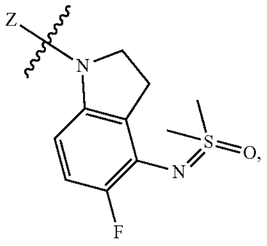
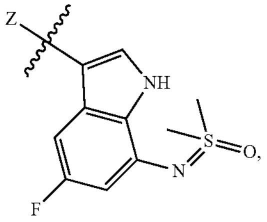

-continued
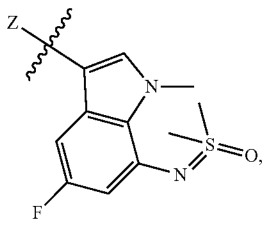
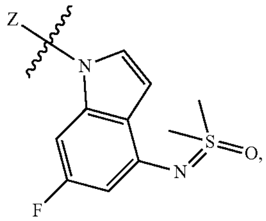
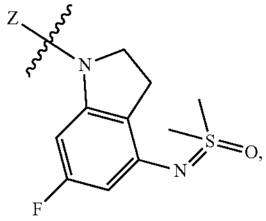
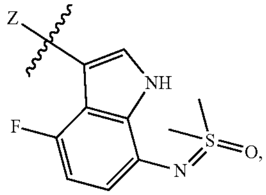
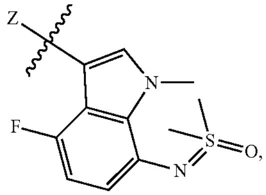
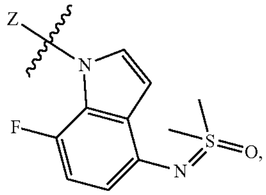
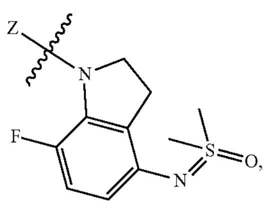
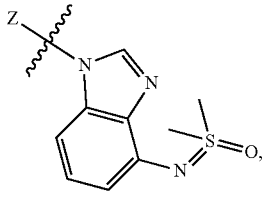
-continued
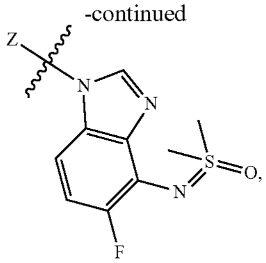
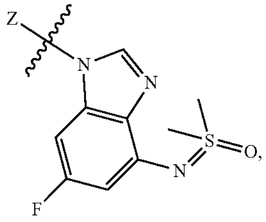
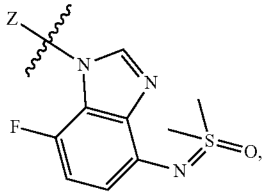
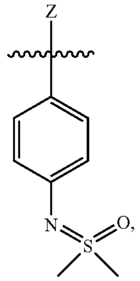
or
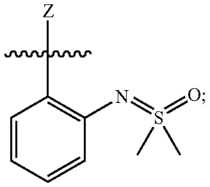
preferably
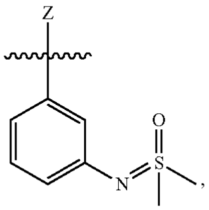
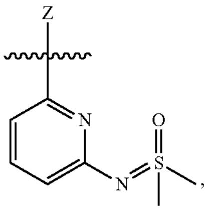
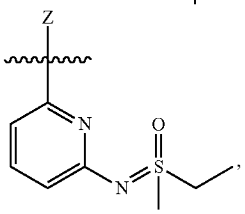
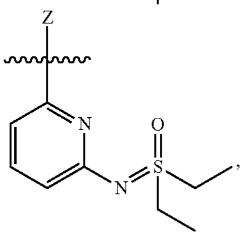

-continued
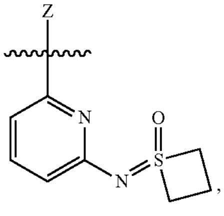,
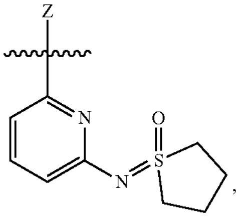,
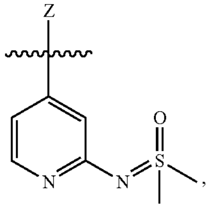,
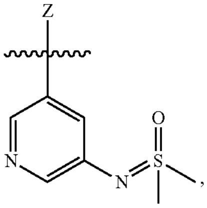,
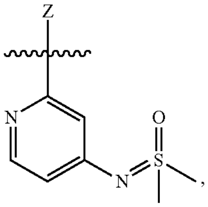,
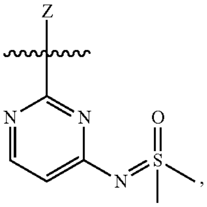,
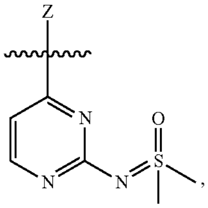,
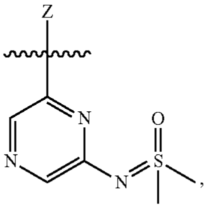,
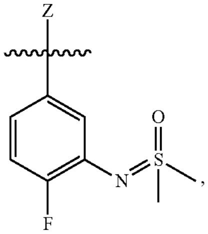,
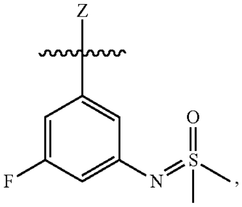,
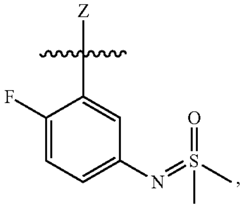,
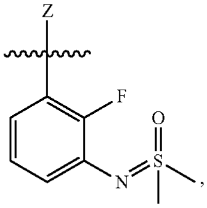,
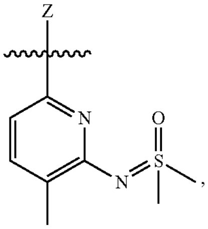,
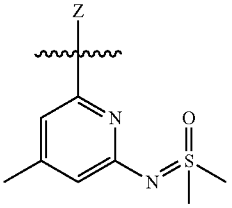,
-continued
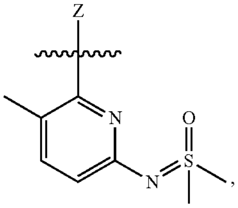,
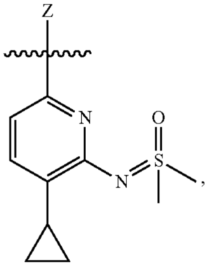,
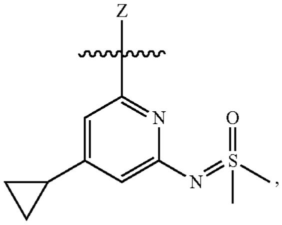,
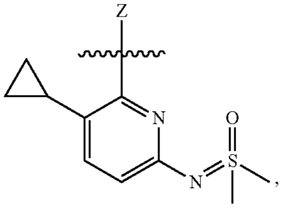,
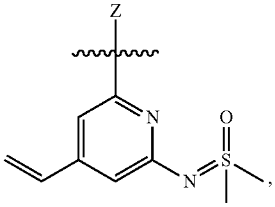,
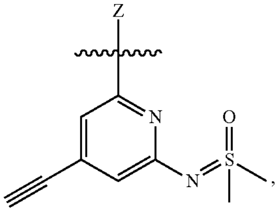,
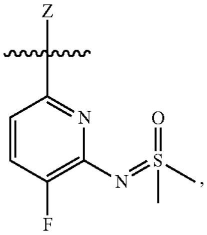,
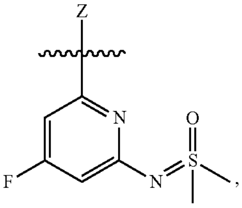,
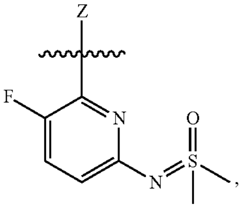,
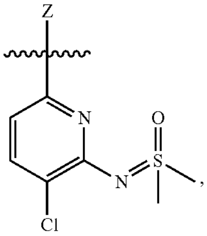,
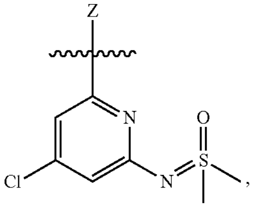,
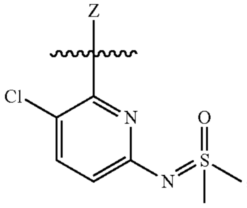,
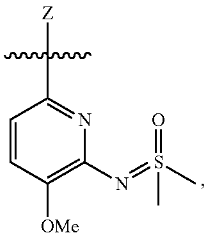,
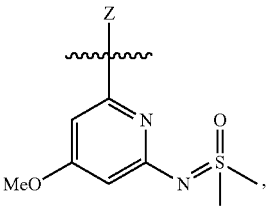, -continued
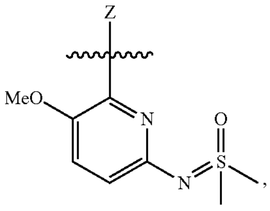
,
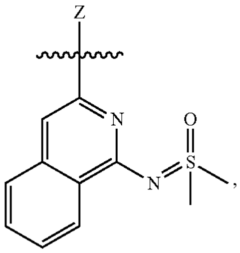
,
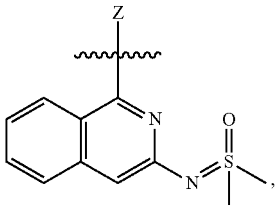
,
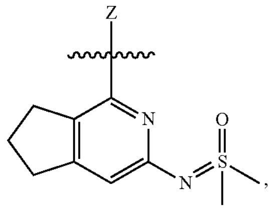
,
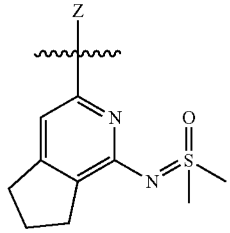
,
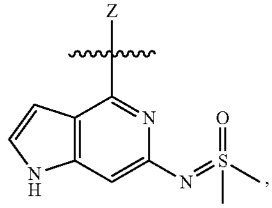
,
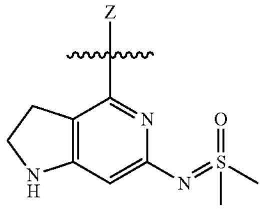
,
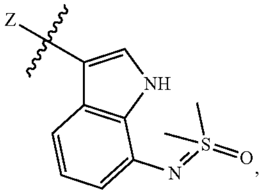
,
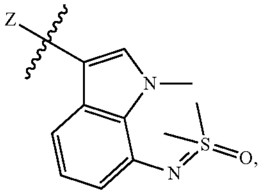
,
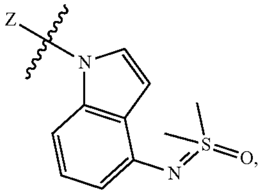
,
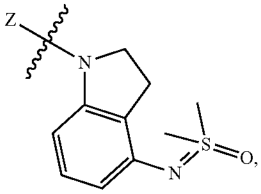
,
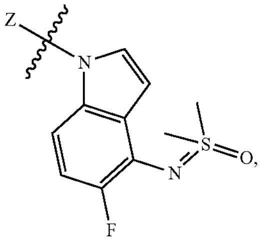
,
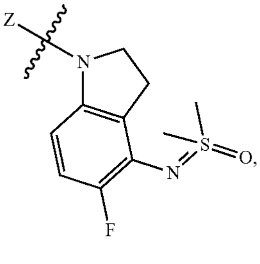
,
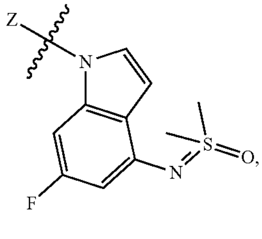
,
-continued
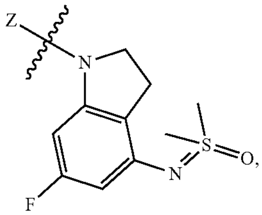
,
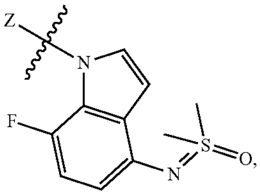
,
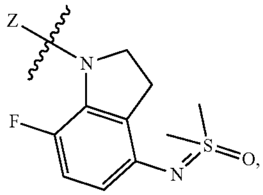
,
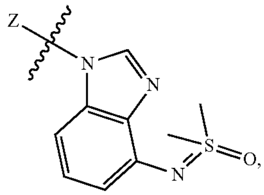
,
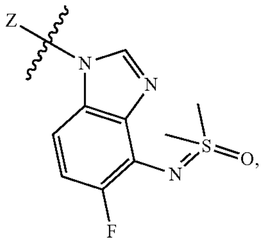
,
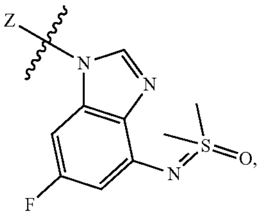
,
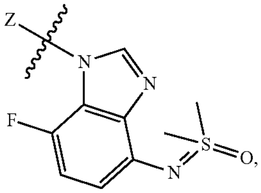
, or
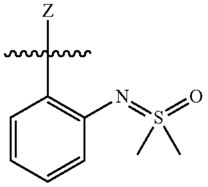
;
more preferably
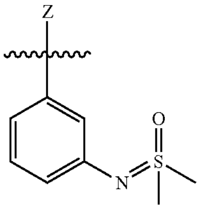
,
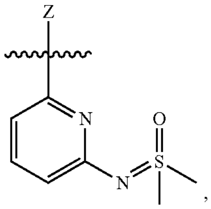
,
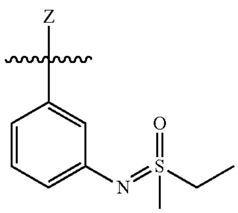
,
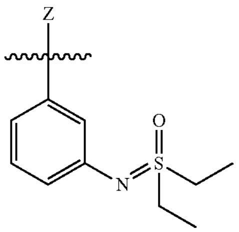
,
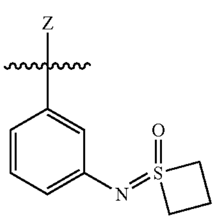
,
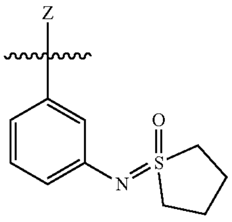
, -continued
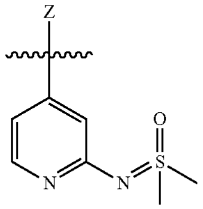,
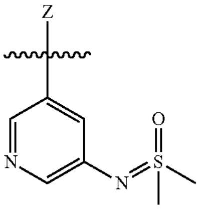,
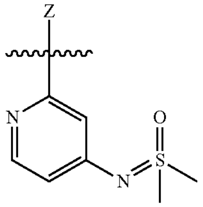,
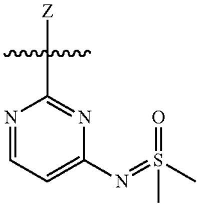,
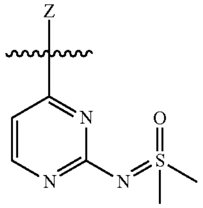,
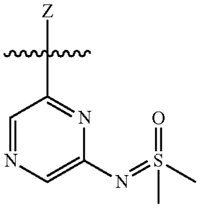,
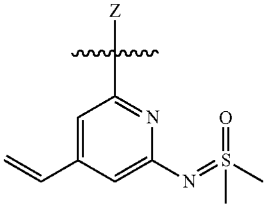,
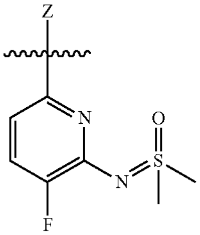,
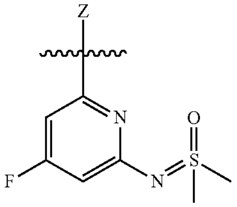,
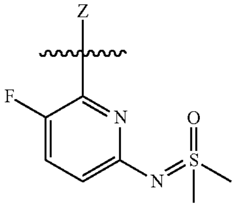,
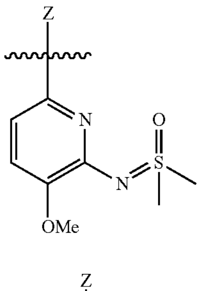,
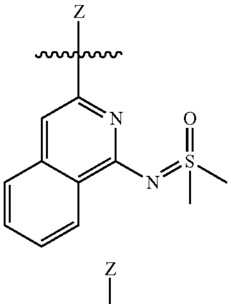,
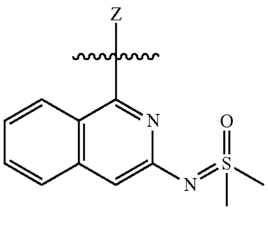,
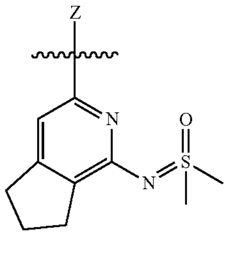,
-continued
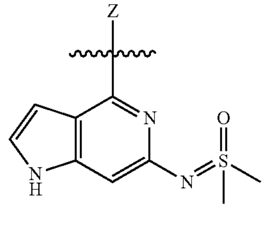,
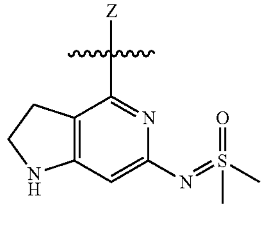,
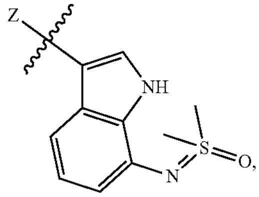
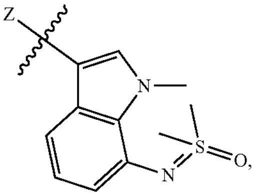
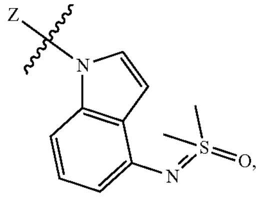
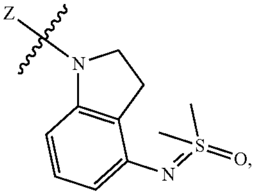
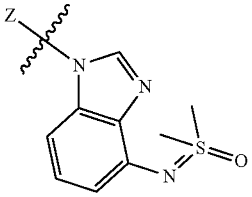
or
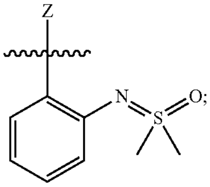
more preferably
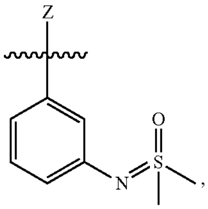,
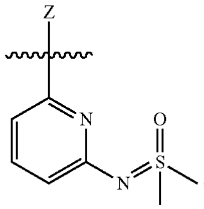,
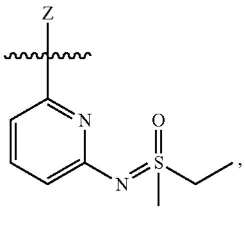,
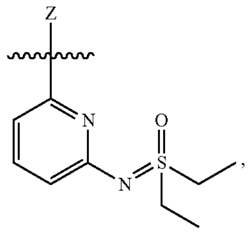,
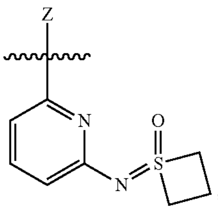,
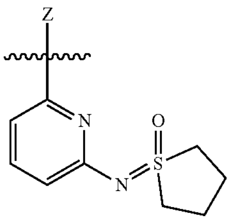, -continued

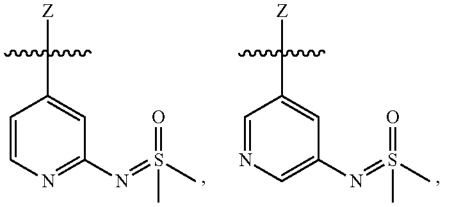

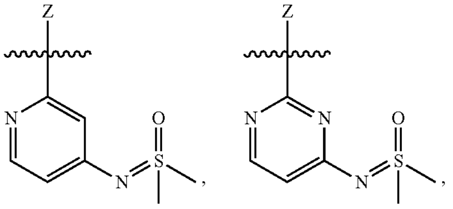

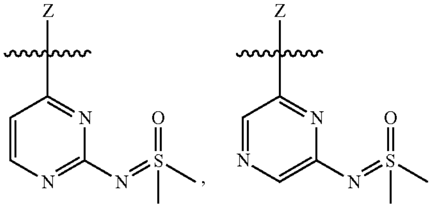

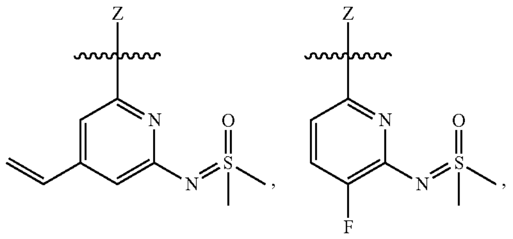

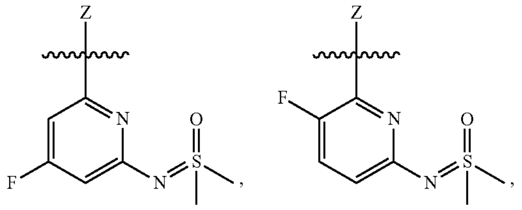

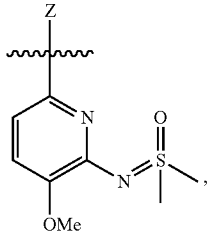

or

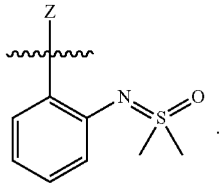

In another preferred embodiment, in general formula (1), ring B is (C6-C10) aryl or 5- to 10-membered heteroaryl.

In another preferred embodiment, in general formula (1), ring B is:

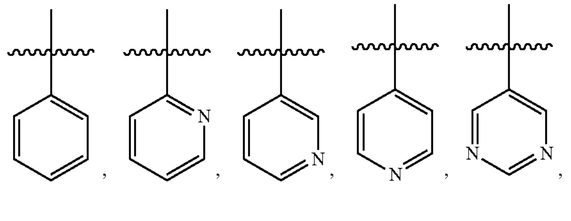

-continued

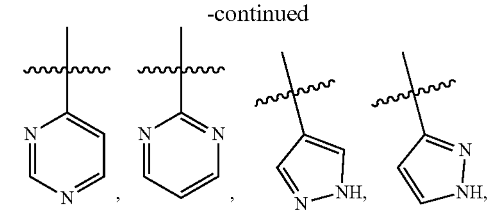

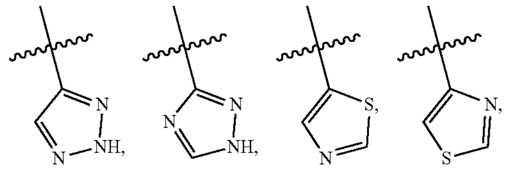

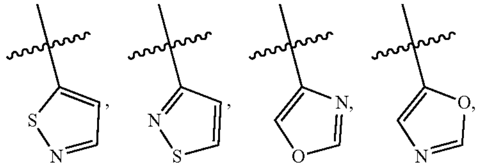

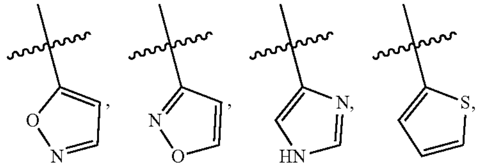

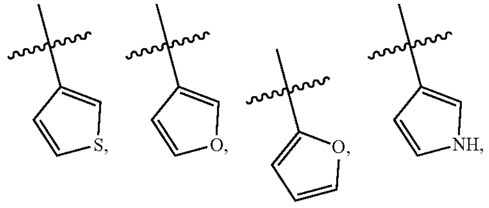

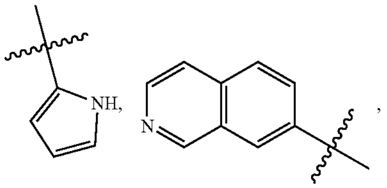

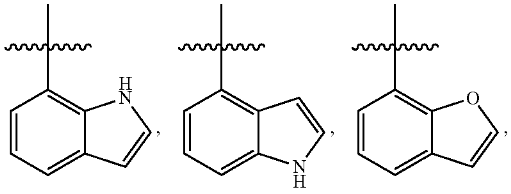

or

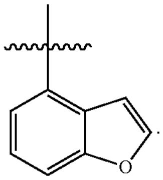

In another preferred embodiment, in general formula (1), each $R^4$ is independently —H, —F, —Cl, —Br, —I, —OH, $—CH_2OR^{11}$, $—(CH_2)_2OR^{11}$, $—(CH_2)_{30}R^{11}$, $—OR^{11}$, $—CH_2NR^{11}R^{12}$, $—(CH_2)_2NR^{11}R^{12}$, $—(CH_2)_3NR^{11}R^{12}$, $—NR^{11}R^{12}$, —CN, $—O(CH_2)_2NR^{11}R^{12}$, $—N(R^{12})(CH_2)_2NR^{11}R^{12}$, $—C(O)NR^{11}R^{12}$, $—NR^{12}C(O)R^{11}$, $—NR^{12}S(O)_2R^{11}$, $—S(O)_2R^{11}$, $—SR^{11}$, $—S(O)_2NR^{11}R^{12}$, (C1-C4) alkyl, (C1-C4) haloalkyl, (C2-C4) alkenyl, (C2-C4) alkynyl, (C3-C6) cycloalkyl, (C1-C4) alkoxy, $—CH_2$-4- to 11-membered heterocycloalkyl, 4- to 11-membered heterocycloalkyl, 5- to 9-membered heteroaryl, or (C6-C10) aryl, wherein the (C1-C4) alkyl, (C1-C4) haloalkyl, (C2-C4) alkenyl, (C2-C4) alkynyl, (C3-C6) cycloalkyl, (C1-C4) alkoxy, —$CH_2$-4- to 11-membered heterocycloalkyl, 4- to 11-membered heterocycloalkyl, 5- to 9-membered heteroaryl, or (C6-C10) aryl may be optionally substituted with 1, 2, 3, or 4 of the following groups: —H, —F, —Cl, —Br, —I, —OH, —$CH_2OCH_3$, —$(CH_2)_2OCH_3$, —$OCH_3$, —$OCH_2CH_3$, —$OCH(CH_3)_2$, —$CH_2N(CH_3)_2$, —$(CH_2)_2N(CH_3)_2$, —$N(CH_3)_2$, —CN, —$O(CH_2)_2N(CH_3)_2$, —NH—$(CH_2)_2N(CH_3)_2$, —$N(CH_3)$—$(CH_2)_2N(CH_3)_2$,

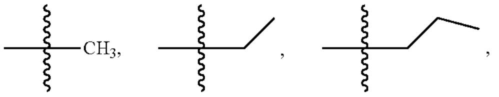
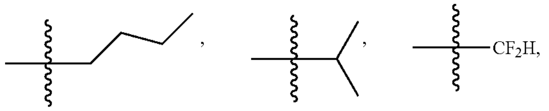
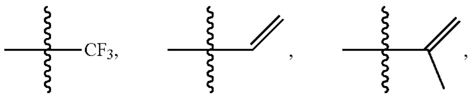
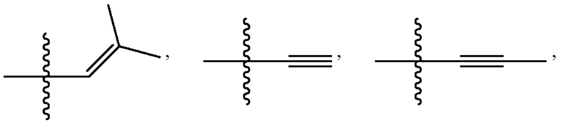
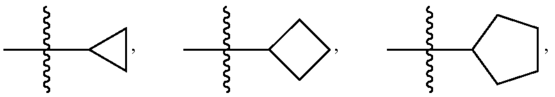
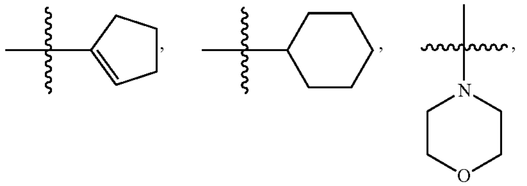
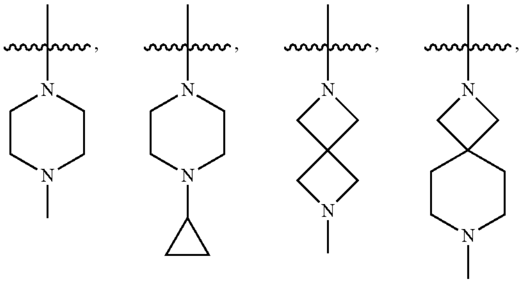
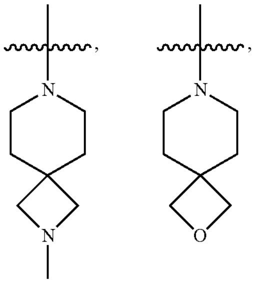

and

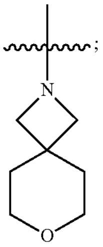

or two adjacent $R^4$ on ring B, along with the atoms connected thereto, are capable of forming 5- to 7-membered heterocycloalkyl or (C5-C7) cycloalkyl, wherein the heterocycloalkyl and cycloalkyl may be optionally substituted with 1, 2, 3, or 4 of the following groups: —H, —F, —Cl, —Br, —I, —OH, —$CH_2OCH_3$, —$(CH_2)_2OCH_3$, —$(CH_2)_{20}H$, —$OCH_3$, —$OCH_2CH_3$, —$OCH(CH_3)_2$, —$CH_2N(CH_3)_2$, —$(CH_2)_2N(CH_3)_2$, —$N(CH_3)_2$, —CN, —$O(CH_2)_2N(CH_3)_2$, —NH—$(CH_2)_2N(CH_3)_2$, —$N(CH_3)$—$(CH_2)_2N(CH_3)_2$, —$C(O)CH_3$, —$C(O)NH_2$, —$C(O)N(CH_3)_2$, —$S(O)_2CH_3$, —$SCH_3$, —$S(O)_2NH_2$, —$S(O)_2N(CH_3)_2$,

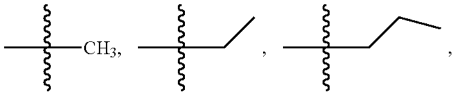
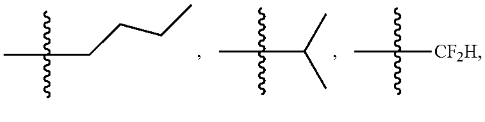
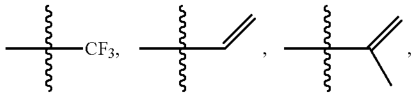
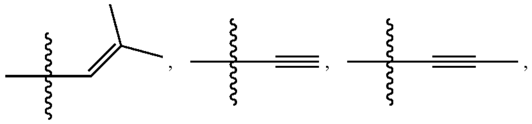
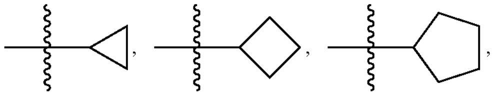
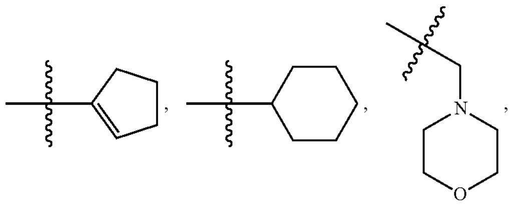
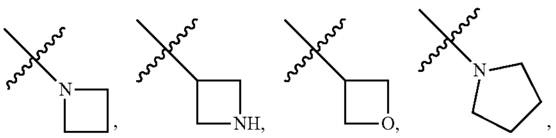
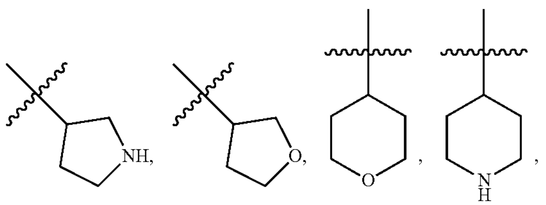
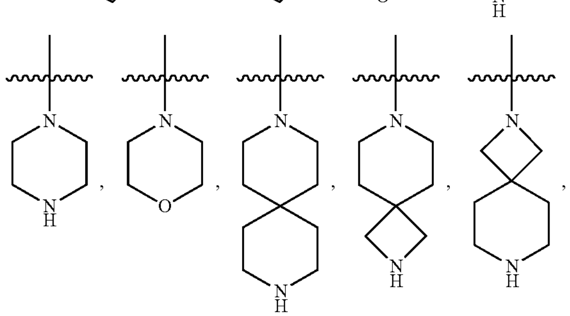

-continued
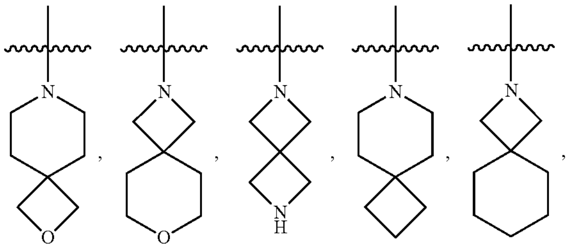
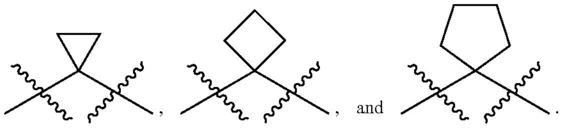
In another preferred embodiment, in general formula (1), each $R^4$ is independently —H, —F, —Cl, —Br, —I, —OH, $—CH_2OCH_3$, $—(CH_2)_2OCH_3$, $—(CH_2)_3OCH_3$, $—CH_2OH$, $—(CH_2)_{20}H$, $—(CH_2)_{30}H$, $—CH_2NH_2$, $—(CH_2)_2NH_2$, $—(CH_2)_3NH_2$, $—OCH_3$, $—OCH_2CH_3$, $—OCH(CH_3)_2$, $—OCF_3$, $—OCF_2H$, $—CH_2N(CH_3)_2$, $—(CH_2)_2N(CH_3)_2$, $—N(CH_3)_2$, —CN, $—O(CH_2)_2N(CH_3)_2$, $—NH—(CH_2)_2N(CH_3)_2$, $—N(CH_3)—(CH_2)_2N(CH_3)_2$, $—C(O)NH_2$, $—C(O)N(CH_3)_2$, $—S(O)_2CH_3$, $—SCH_3$, $—S(O)_2NH_2$, $—S(O)_2N(CH_3)_2$,
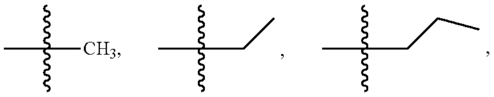
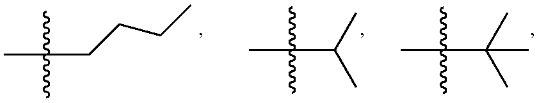
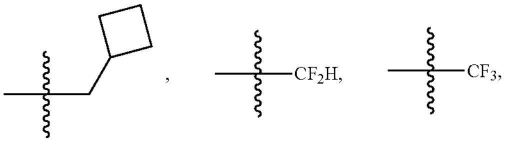
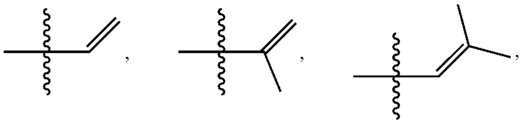
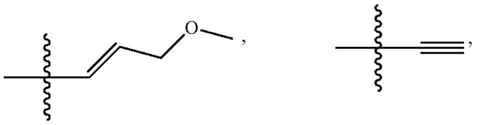
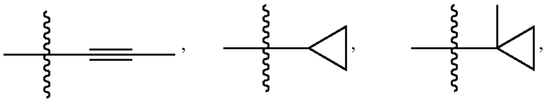
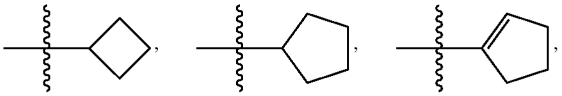
-continued
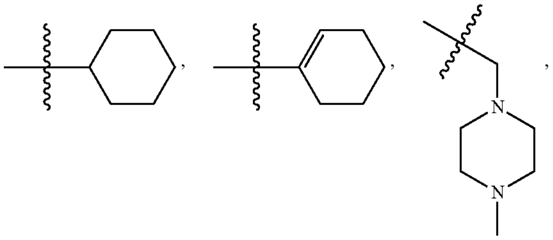
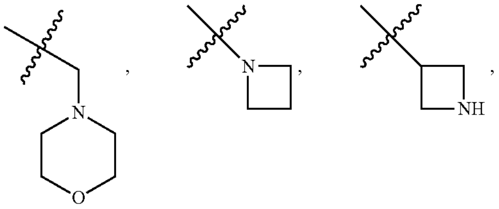
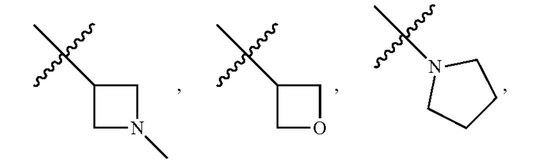
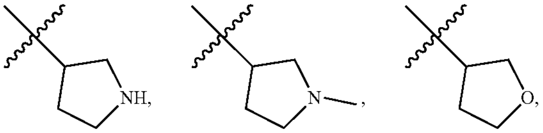
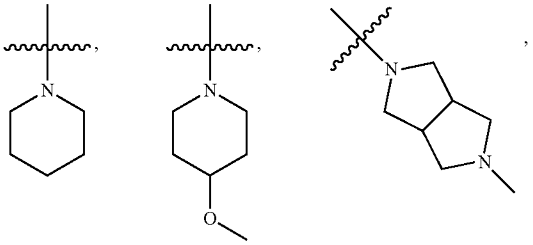
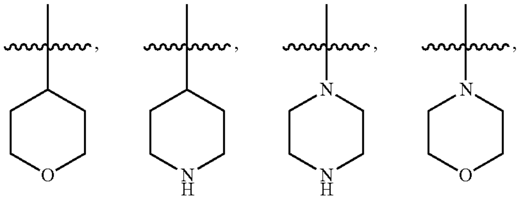
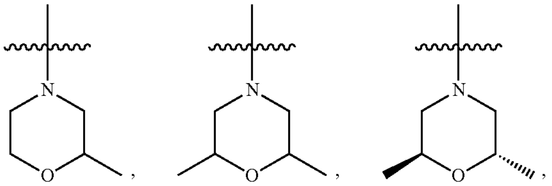
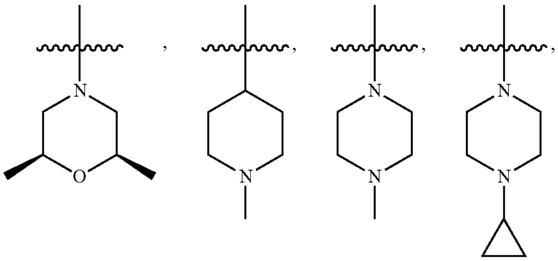

-continued
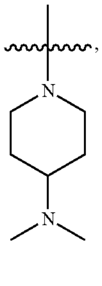, 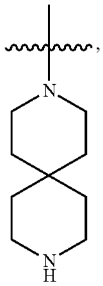, 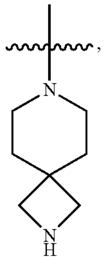, 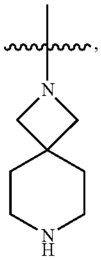, 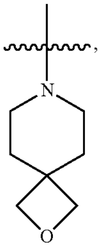, 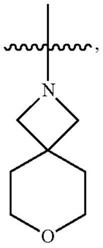, 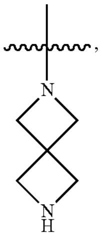, 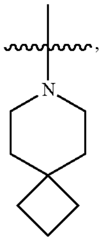, 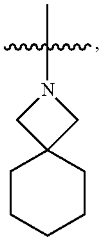, 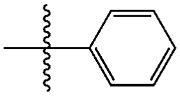, 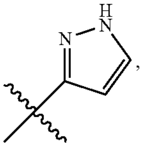, 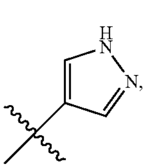, 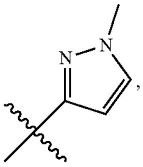, 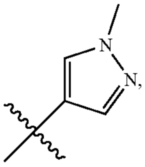, 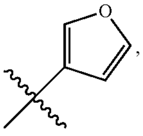, 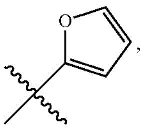, 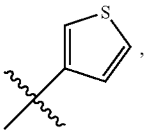, 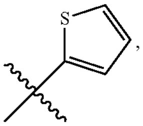, 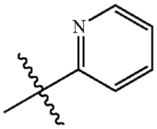, 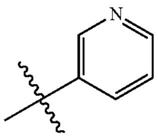, 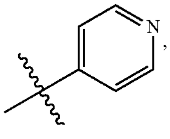, 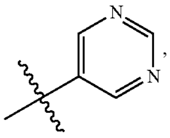, 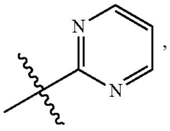,
-continued
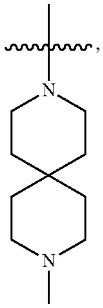, 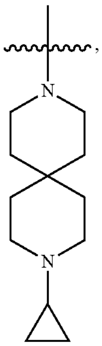, 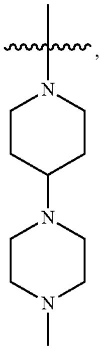, 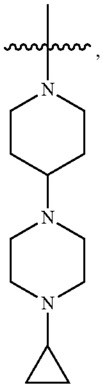, 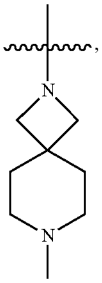, 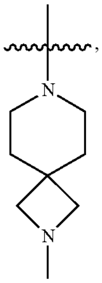, 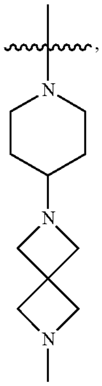, 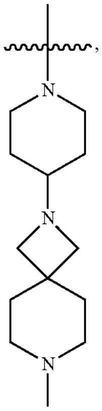 or 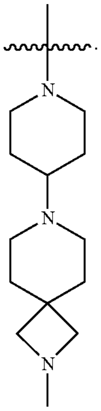.
In another preferred embodiment, in general formula (1), each $R^4$ is independently
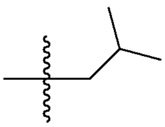 and 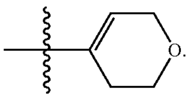.
In another preferred embodiment, in general formula (1), $R^4$ is preferably —H, —F, —Cl, —Br, —I, $—CH_2OCH_3$, $—(CH_2)_2OCH_3$, $—(CH_2)_3OCH_3$, $—CH_2OH$, $—(CH_2)_{20}H$, $—(CH_2)_{30}H$, $—CH_2NH_2$, $—(CH_2)_2NH_2$, $—(CH_2)_3NH_2$, $—OCH_3$, $—OCH_2CH_3$, $—OCH(CH_3)_2$, $—OCF_3$, $—OCF_2H$, $—CH_2N(CH_3)_2$, $—N(CH_3)_2$, —CN, $—SCH_3$,

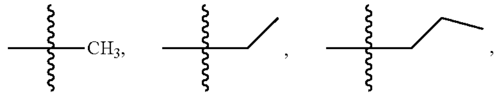
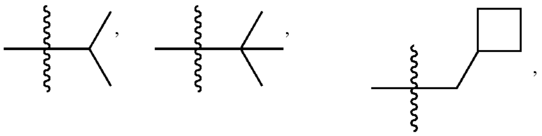
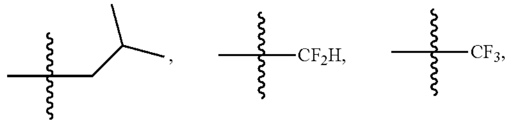
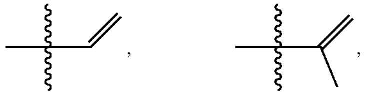
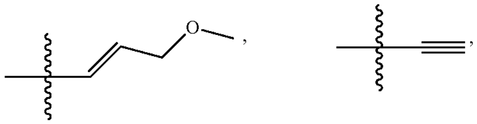
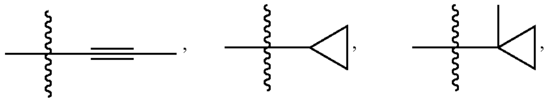
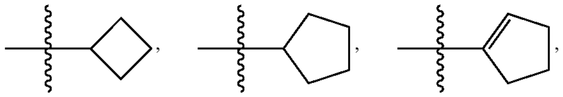
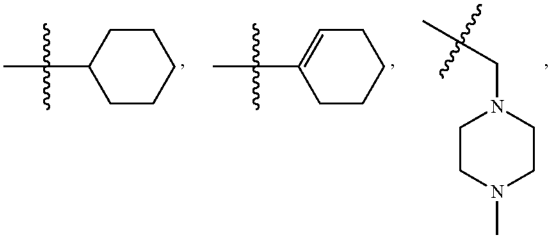
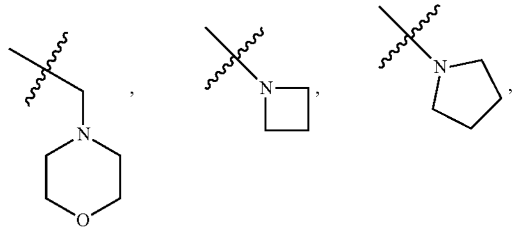
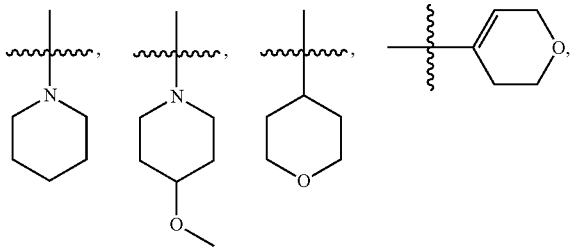
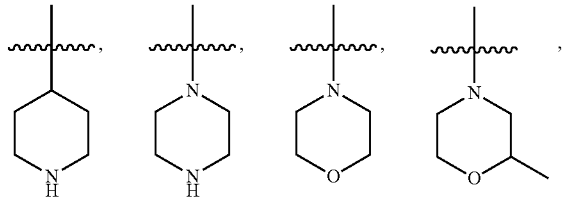
-continued
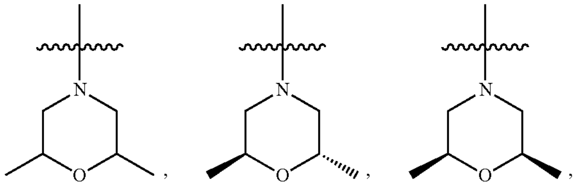
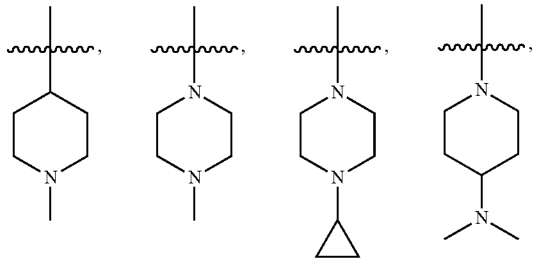
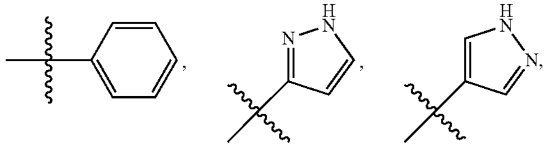
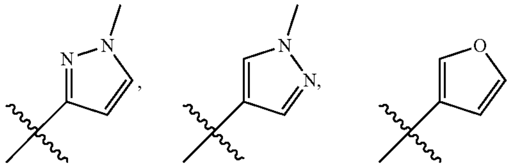
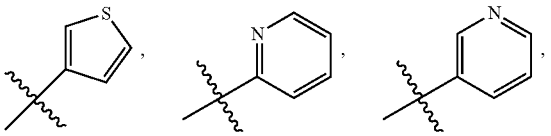
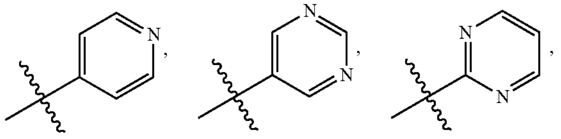
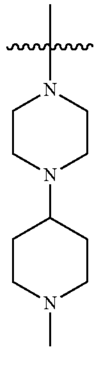
or
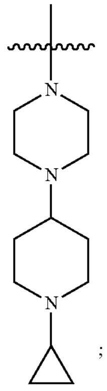
;
more preferably, $R^4$ is —H, —F, —Cl, —Br, —I, —$CH_2OCH_3$, —$(CH_2)_2OCH_3$, —$(CH_2)_3OCH_3$, —$CH_2OH$, —$(CH_2)_{20}H$, —$(CH_2)_{30}H$, —$CH_2NH_2$, —$(CH_2)_2NH_2$, —$(CH_2)_3NH_2$, —$OCH_3$, —$OCH_2CH_3$—$OCH(CH_3)_2$—$CH_2N(CH_3)_2$, —$N(CH_3)_2$, —CN,

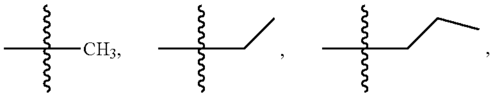
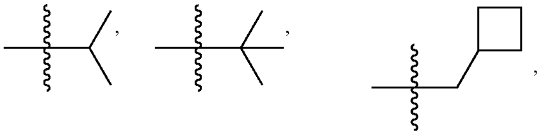
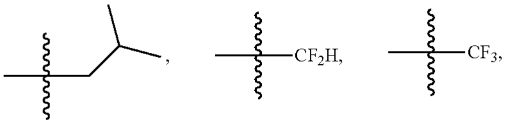
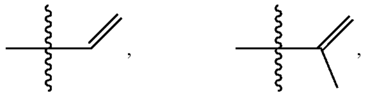
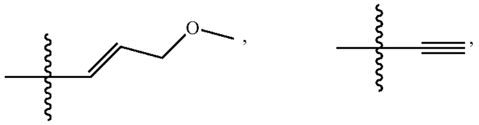
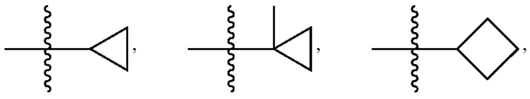
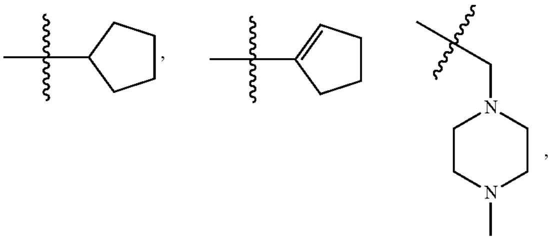
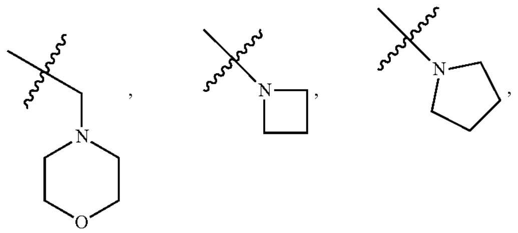
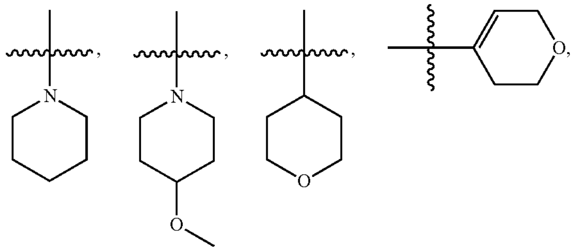
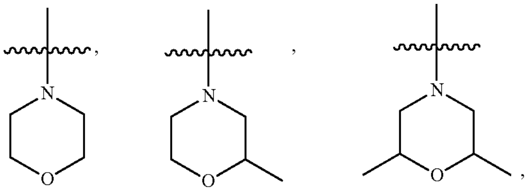
-continued
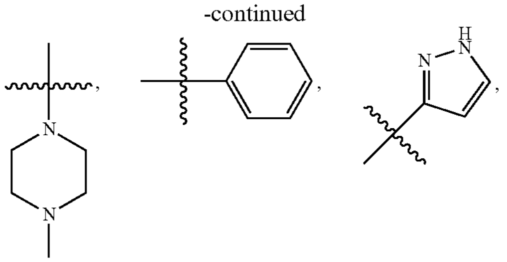
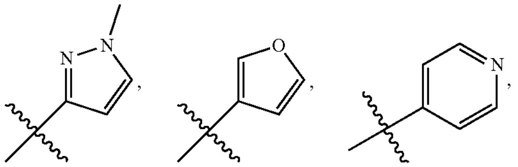
or
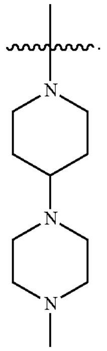
In another preferred embodiment, in general formula (1), two adjacent $R^4$ on ring B, along with the atoms connected thereto, are capable of forming 5- to 7-membered heterocycloalkyl wherein the heterocycloalkyl is:
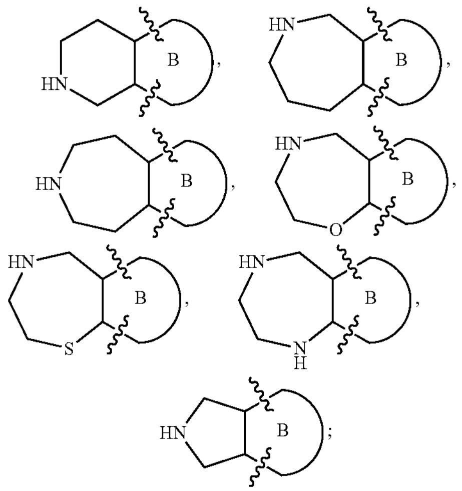
or two adjacent $R^4$ on ring B, along with the atoms connected thereto, are capable of forming (C5-C7 cycloalkyl, wherein the (C5-C7) cycloalkyl is:
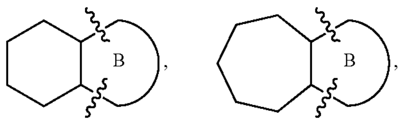
or -continued

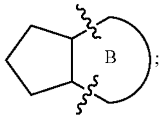;

wherein the 5- to 7-membered heterocycloalkyl and the (C5-C7) cycloalkyl may be optionally substituted with 1, 2, 3, or 4 of the following groups: —H, —F, —Cl, —Br, —I, —OH, —$CH_2OCH_3$, —$(CH_2)_2OCH_3$, —$(CH_2)_{20}H$, —$OCH_3$, —$OCH_2CH_3$, —$OCH(CH_3)_2$, —$CH_2N(CH_3)_2$, —$(CH_2)_2N(CH_3)_2$, —$N(CH_3)_2$, —CN, —$O(CH_2)_2N(CH_3)_2$, —NH—$(CH_2)_2N(CH_3)_2$, —$N(CH_3)$—$(CH_2)_2N(CH_3)_2$, —$C(O)CH_3$, —$C(O)NH_2$, —$C(O)N(CH_3)_2$, —$S(O)_2CH_3$, —$SCH_3$, —$S(O)_2NH_2$, —$S(O)_2N(CH_3)_2$,

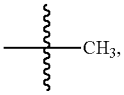, 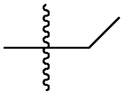, 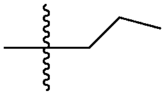,

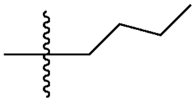, 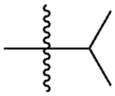, 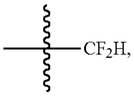,

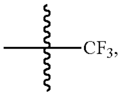, 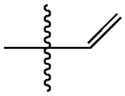, 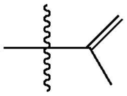,

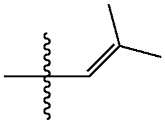, 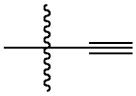, 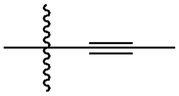,

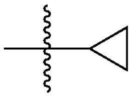, 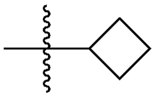, 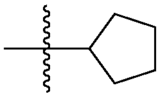,

-continued

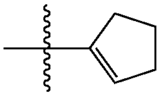, 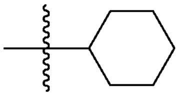, 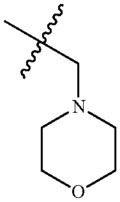,

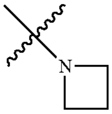, 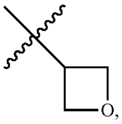, 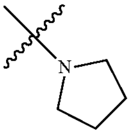, 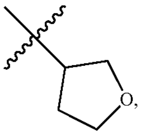,

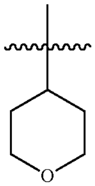, 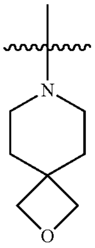, 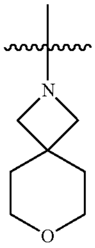, 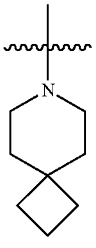, 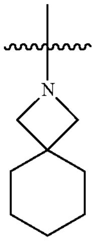,

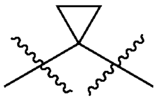, 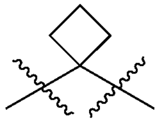, and 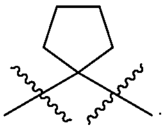.

In another preferred embodiment, in general formula (1), structural unit

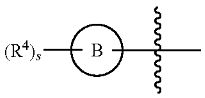

is:

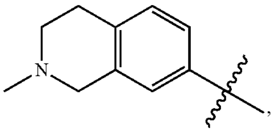, 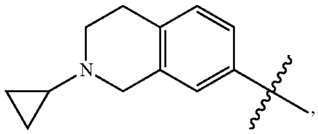, 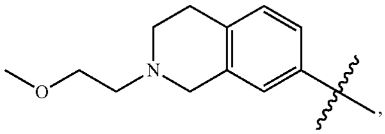,

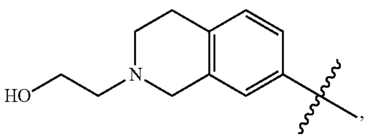, 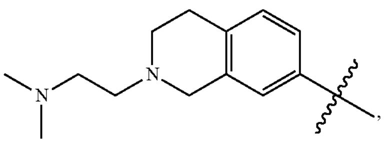, 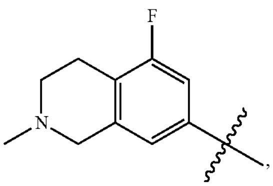,

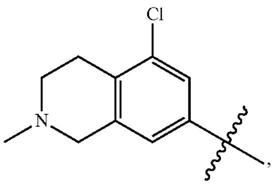, 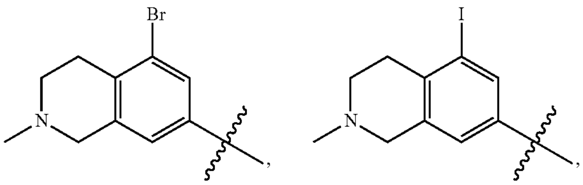,

-continued
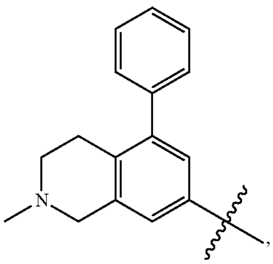,
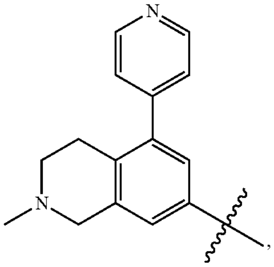,
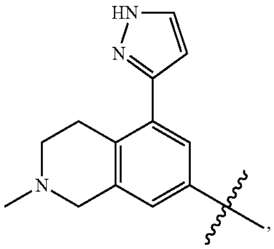,
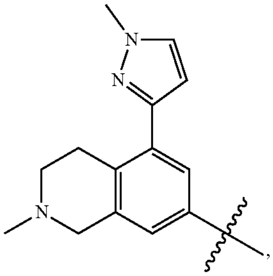,
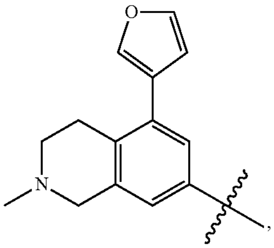,
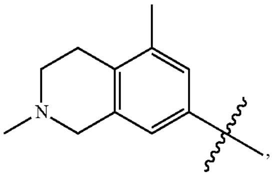,
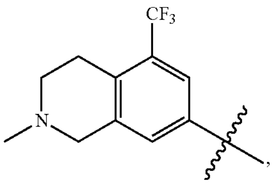,
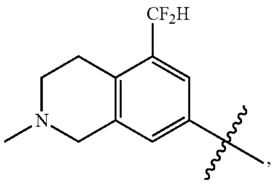,
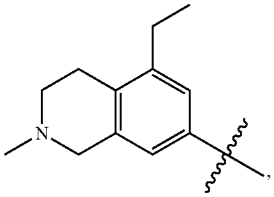,
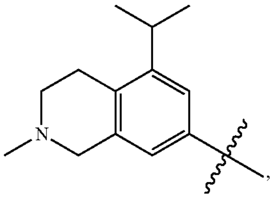,
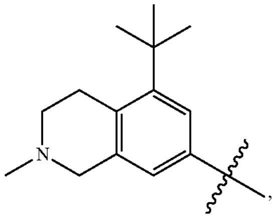,
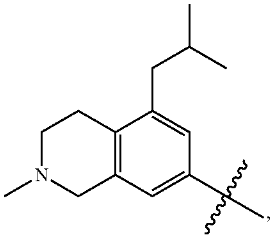,
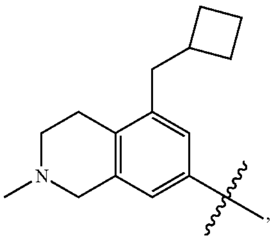,
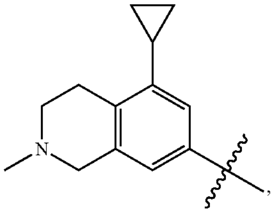,
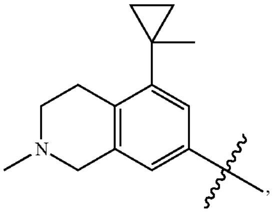,
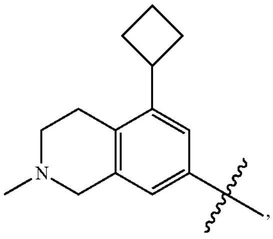,
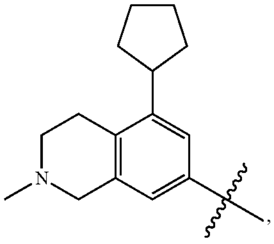,
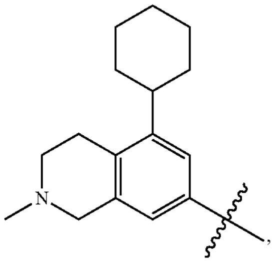, -continued
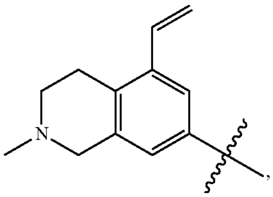,
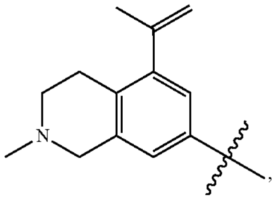,
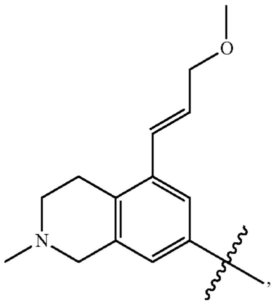,
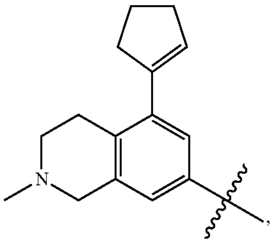,
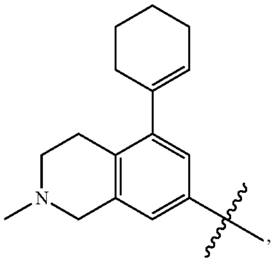,
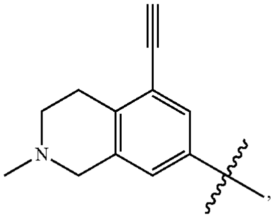,
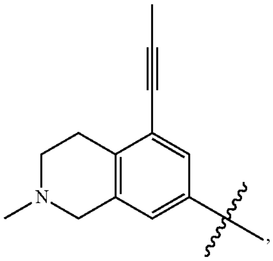,
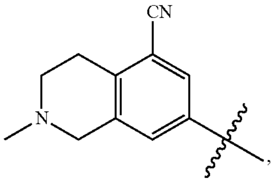,
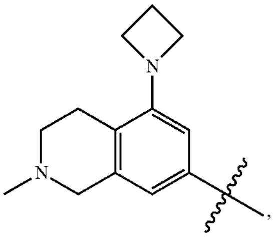,
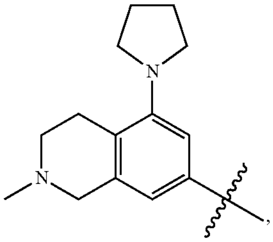,
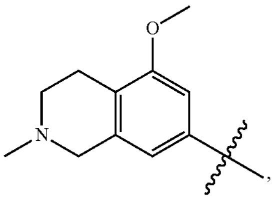,
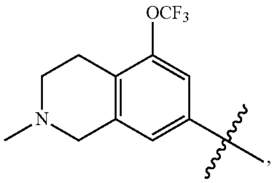,
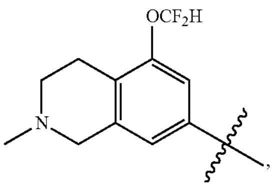,
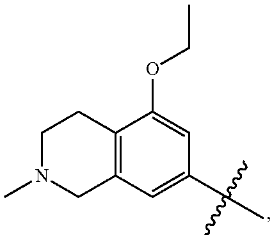,
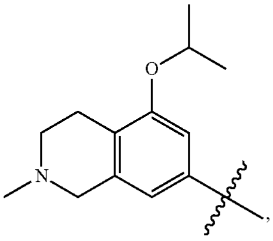,
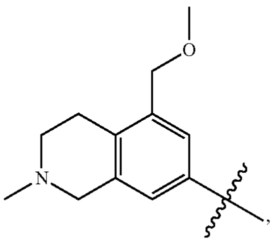,
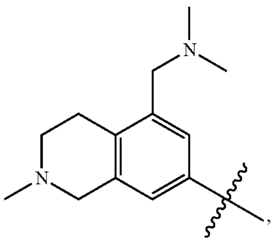,
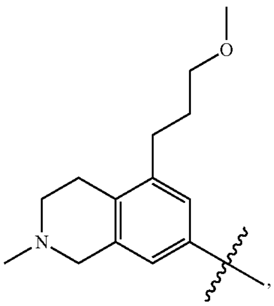, -continued
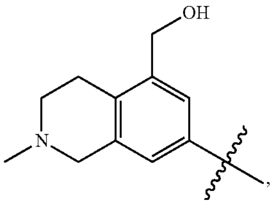,
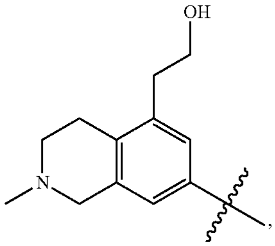,
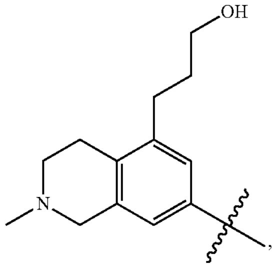,
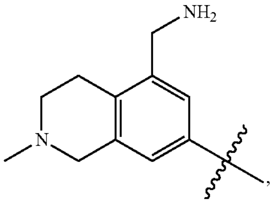,
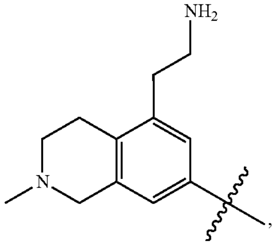,
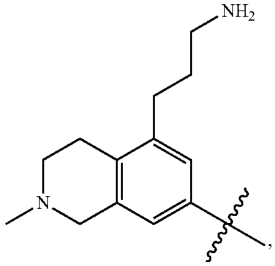,
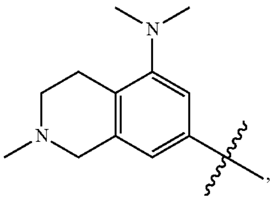,
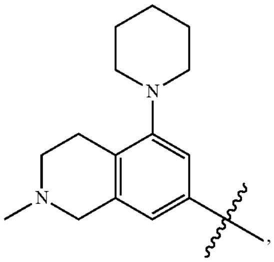,
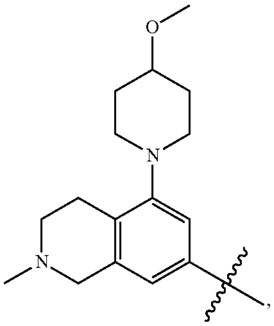,
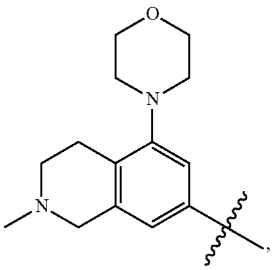,
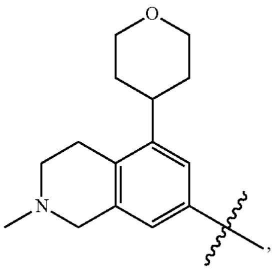,
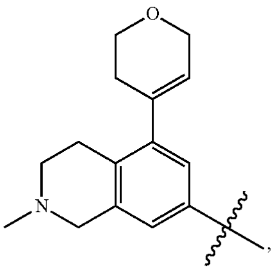,
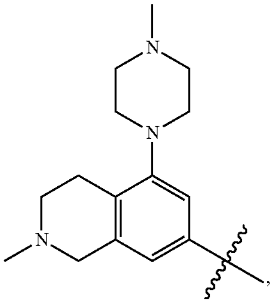,
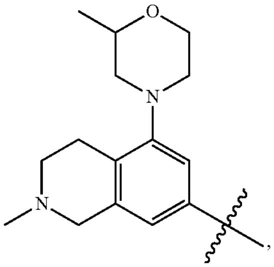,
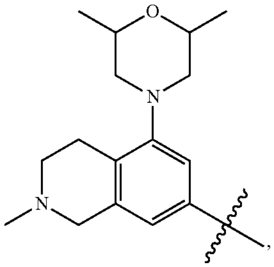,
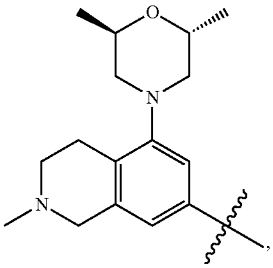,
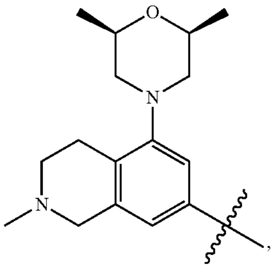,
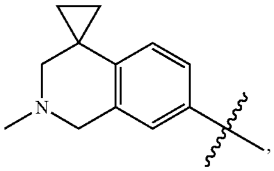, -continued
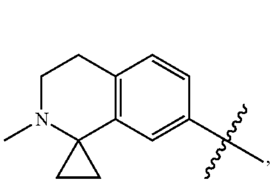,
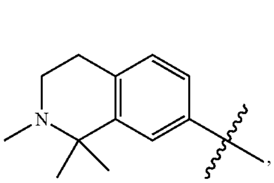,
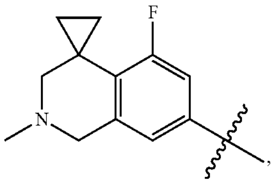,
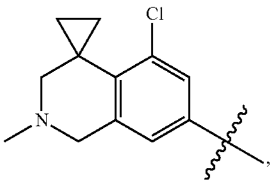,
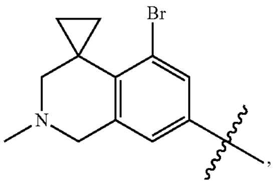,
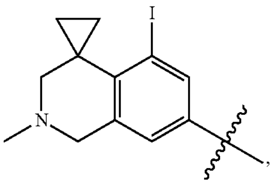,
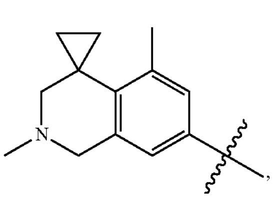,
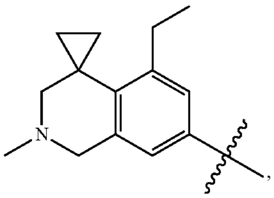,
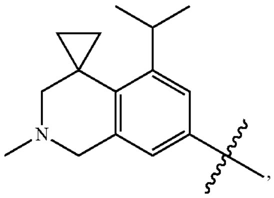,
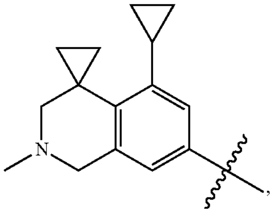,
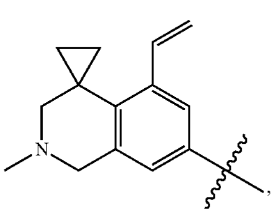,
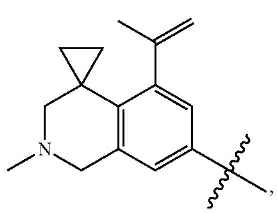,
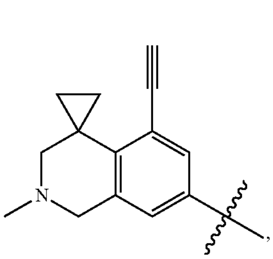,
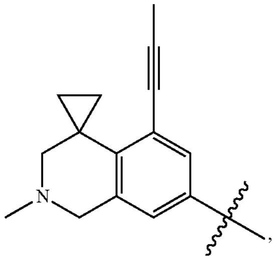,
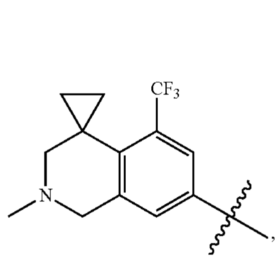,
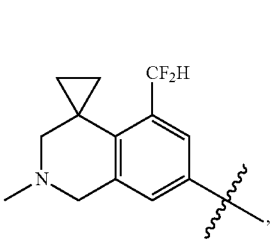,
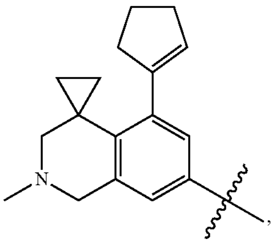,
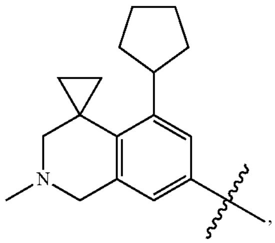,
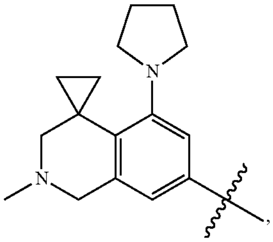,
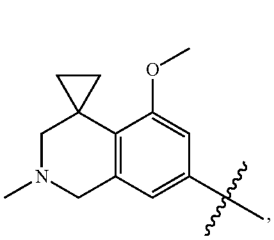,
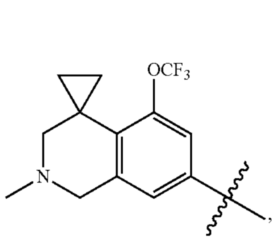, -continued
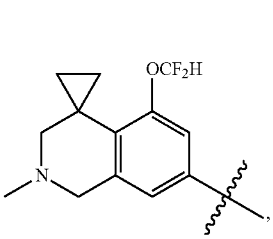, 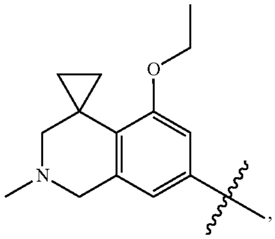, 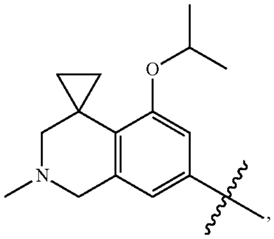,
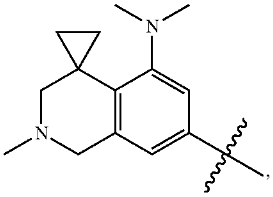, 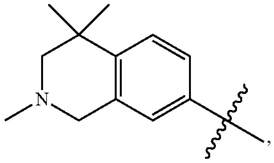, 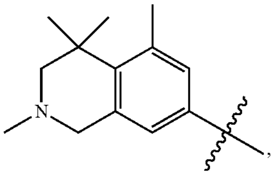,
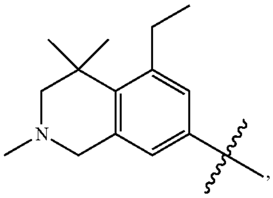, 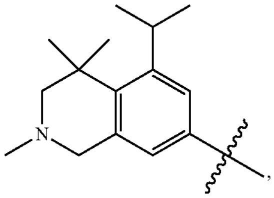, 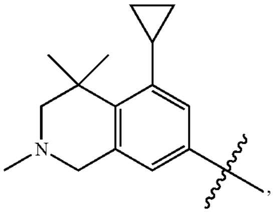,
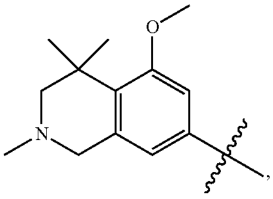, 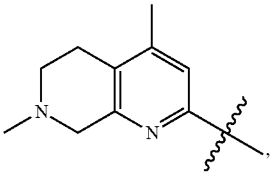, 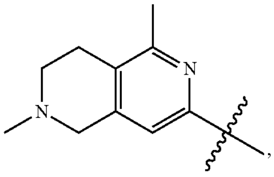,
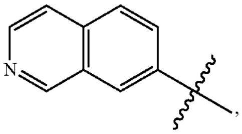, 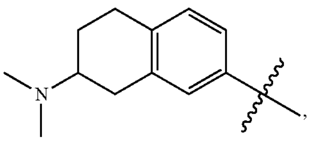, 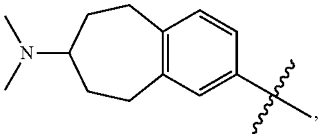,
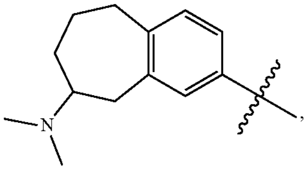, 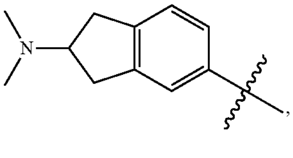, 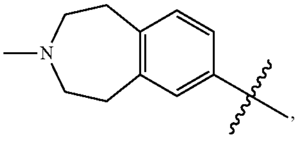,
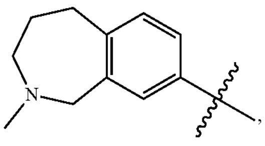, 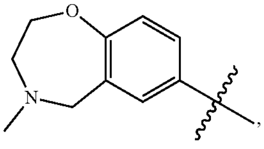, 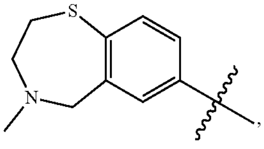,
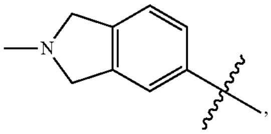,
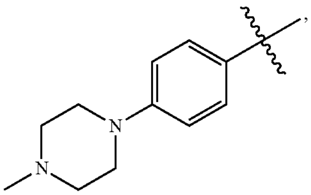, 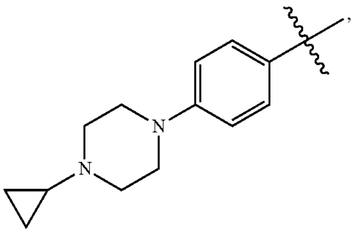, -continued
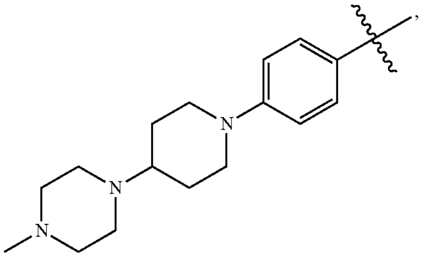,
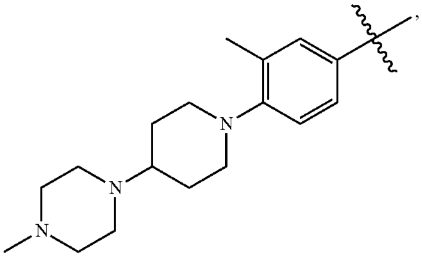,
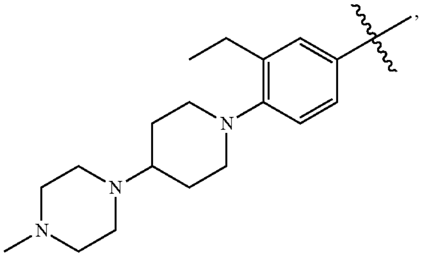,
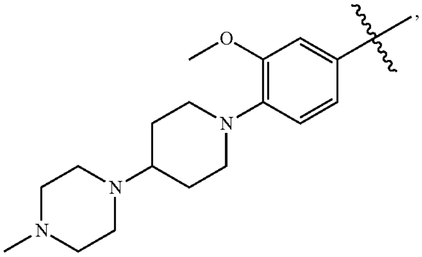,
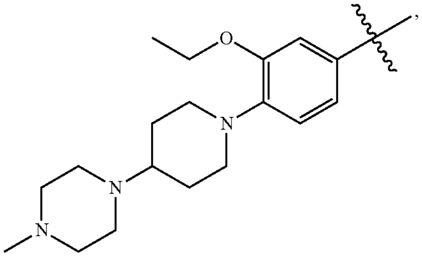,
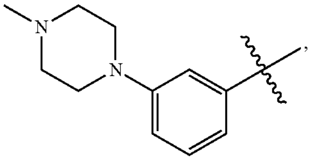,
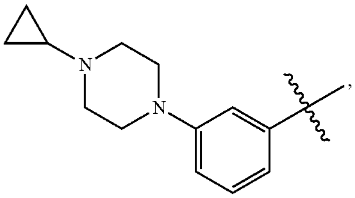,
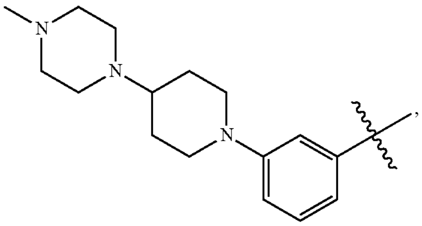,
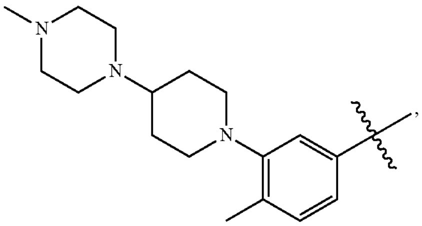,
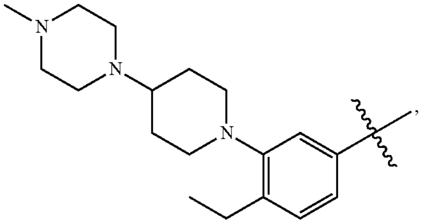,
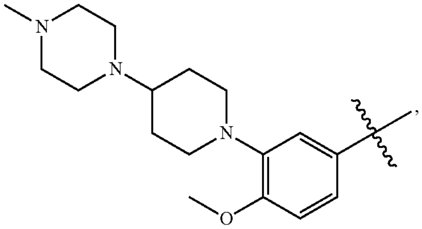, or
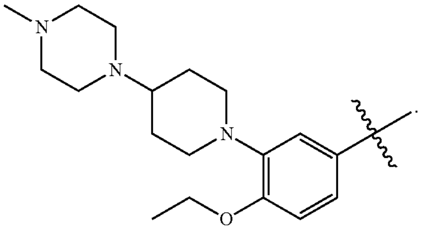.

In another preferred embodiment, in general formula (1), structural unit
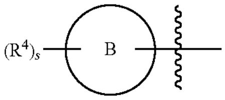
is:
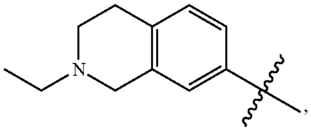
,
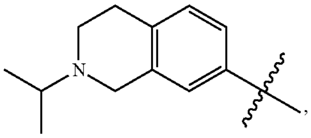
,
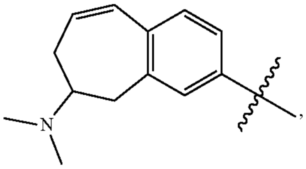
, or
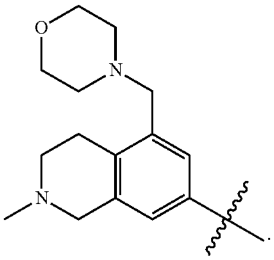
.
In another preferred embodiment, in general formula (1), structural unit
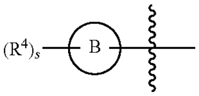
is:
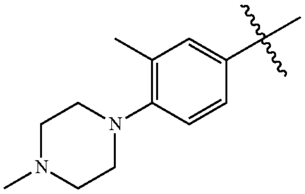
,
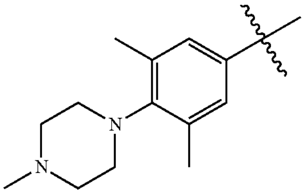
,
-continued
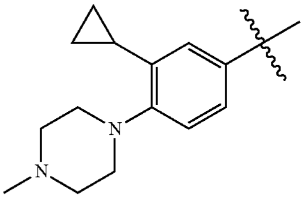
,
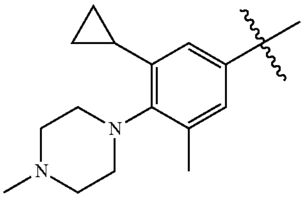
,
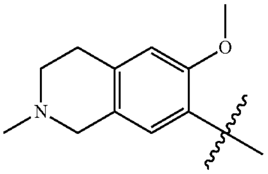
,
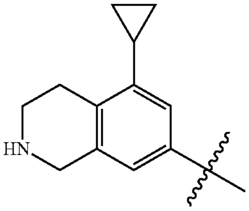
,
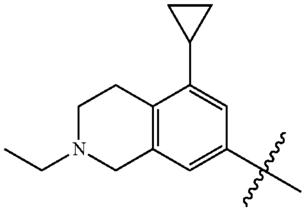
,
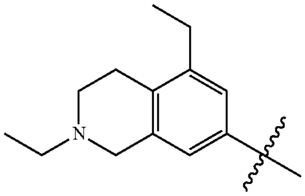
,
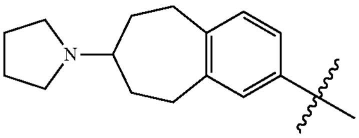
,
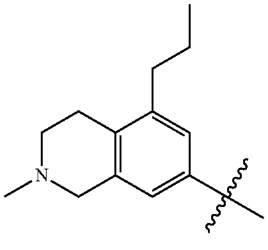
, or
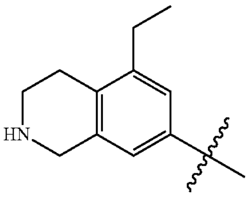
.
In another preferred embodiment in general formula (1), structural unit
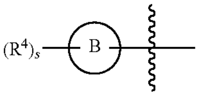

is preferably:
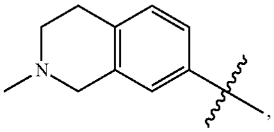,
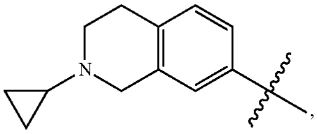,
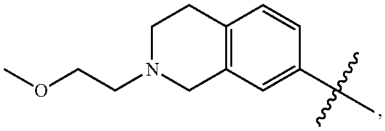,
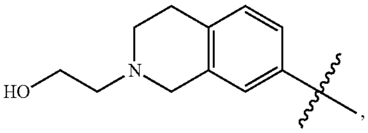,
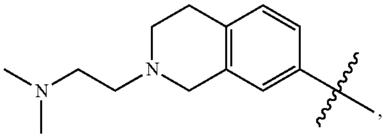,
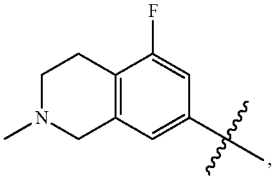, 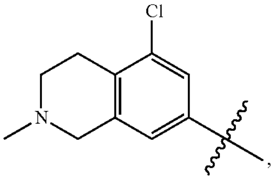,
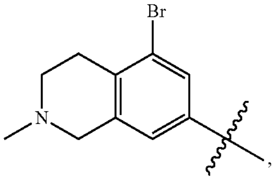, 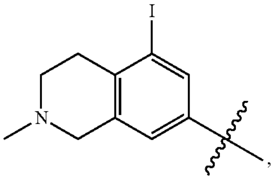,
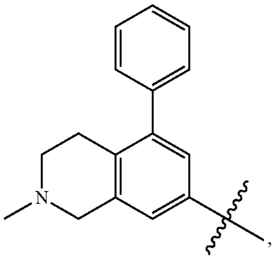, 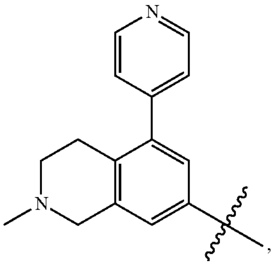,
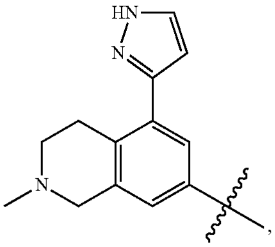, 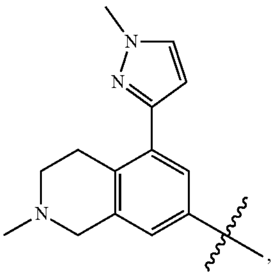,
-continued
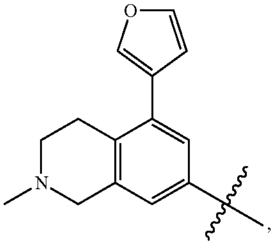, 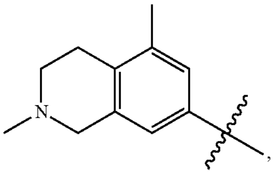,
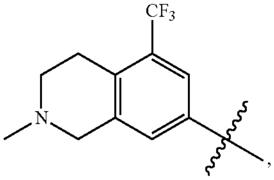, 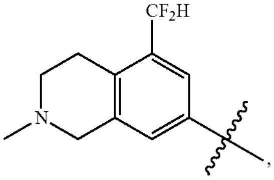,
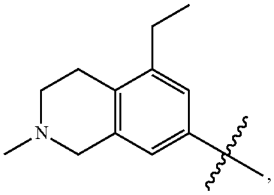, 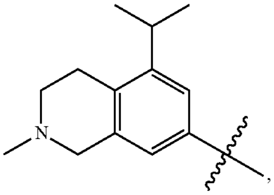,
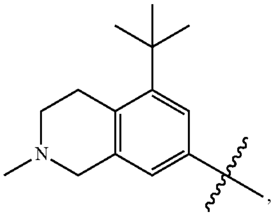, 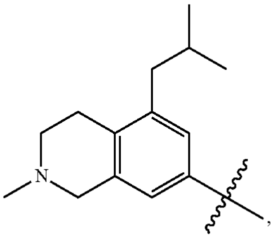,
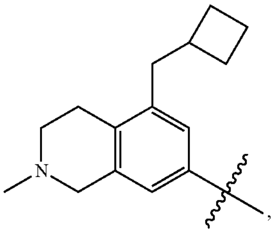, 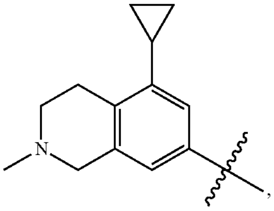,
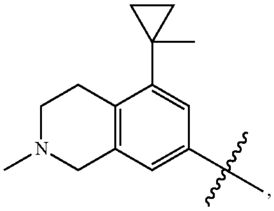, 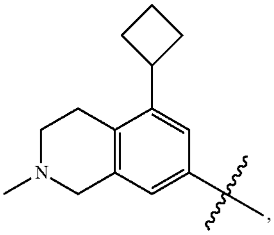,
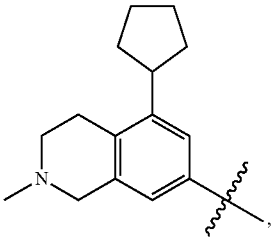, 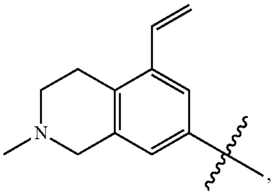, -continued
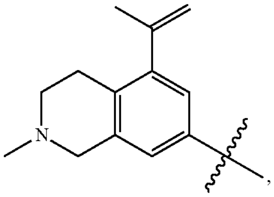,
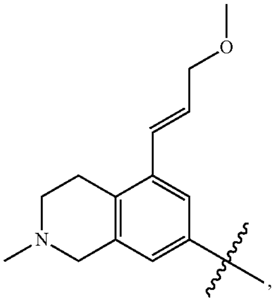, 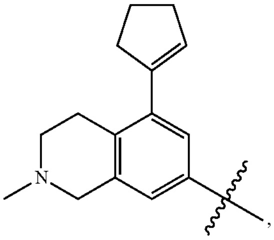,
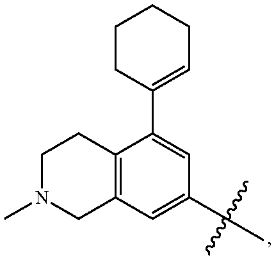, 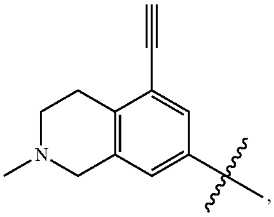,
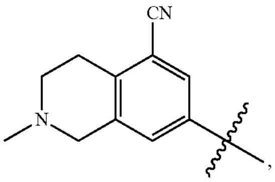, 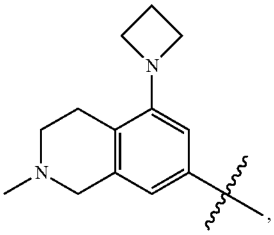,
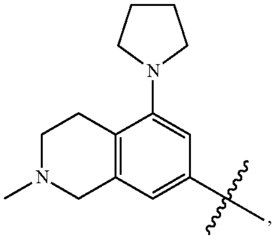, 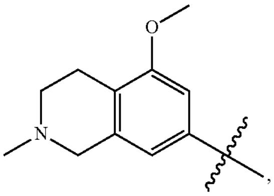,
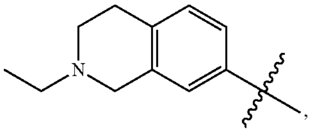,
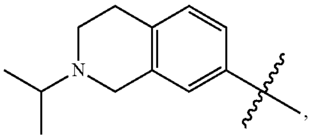,
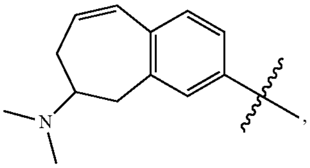,
-continued
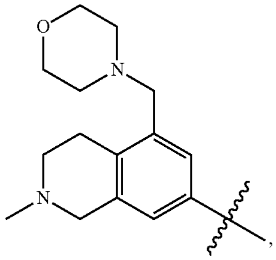,
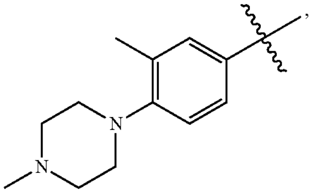,
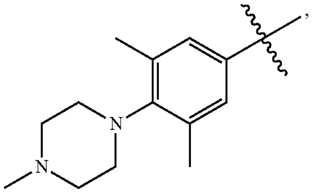,
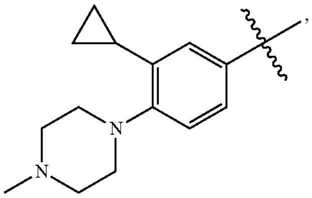,
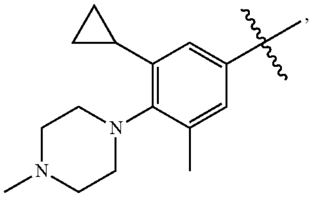,
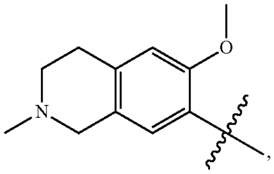, 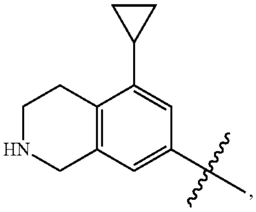,
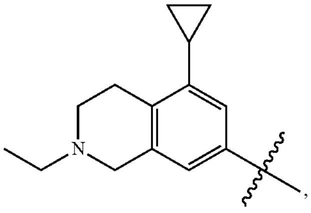,
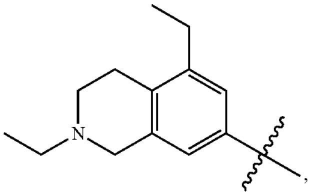, -continued
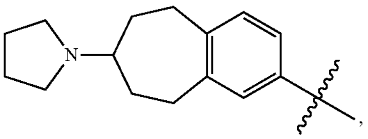,
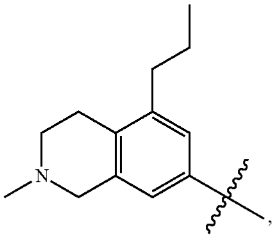, 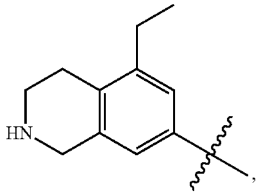,
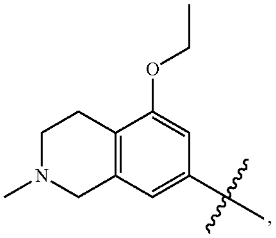, 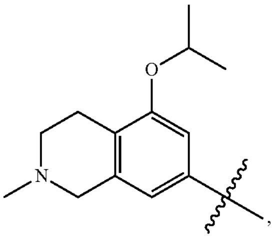,
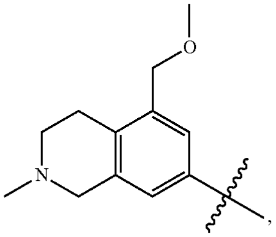, 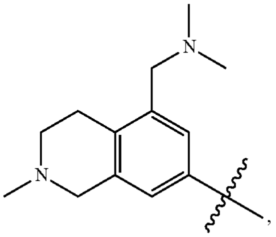,
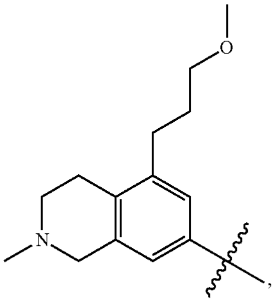, 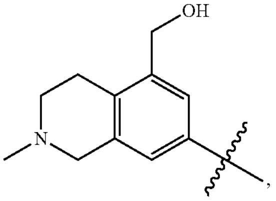,
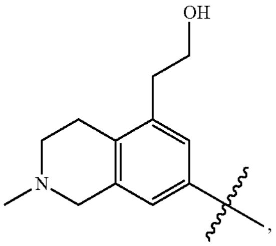, 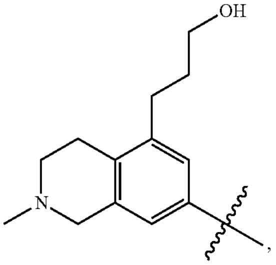,
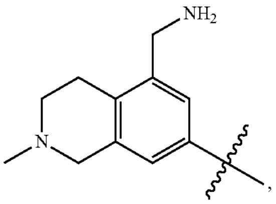, 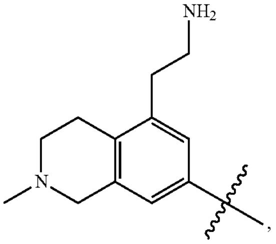,
-continued
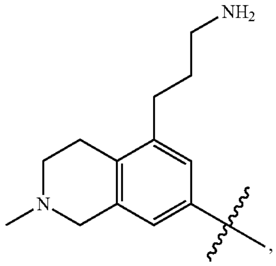 [SMILES: *c1cc(CCCN)c2c(c1)CN(C)CC2],
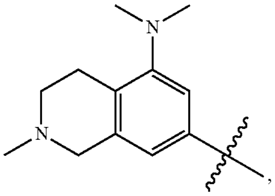, 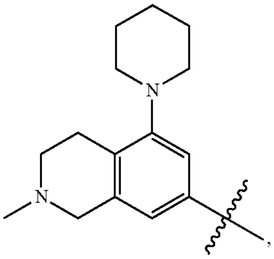,
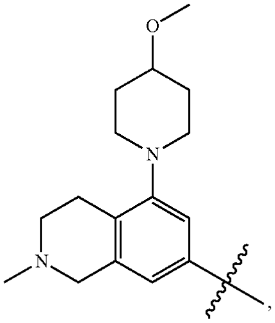, 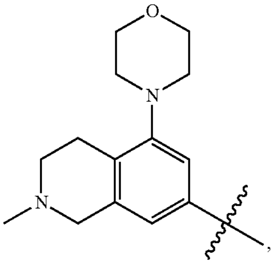,
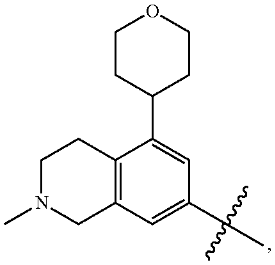, 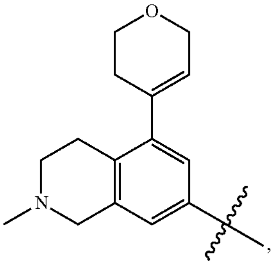,
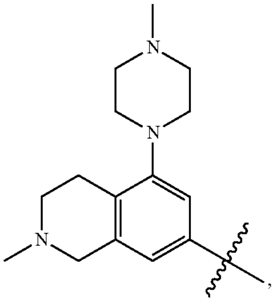, 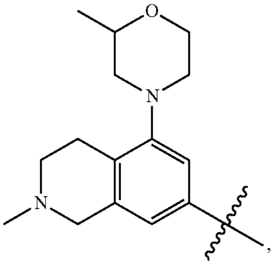,
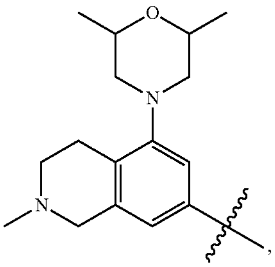, 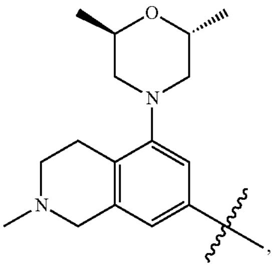, -continued
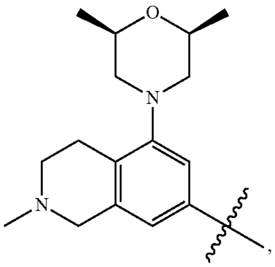,
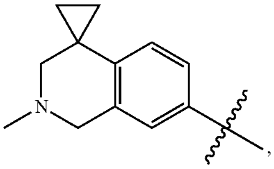,
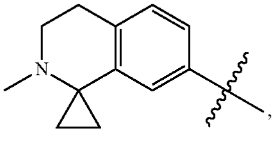,
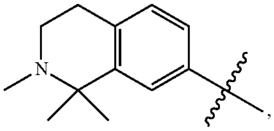,
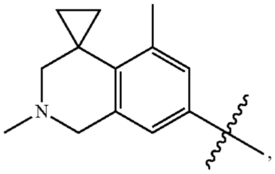,
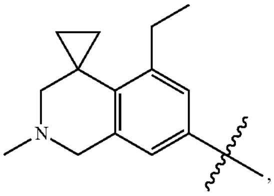,
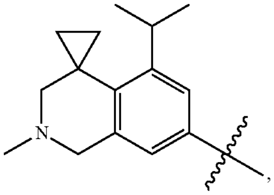,
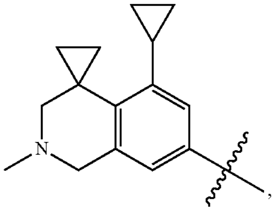,
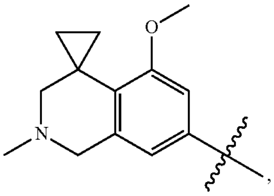,
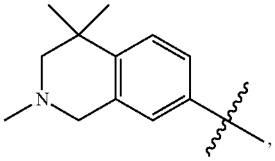,
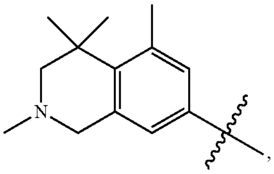,
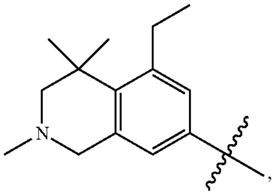,
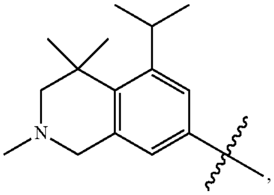,
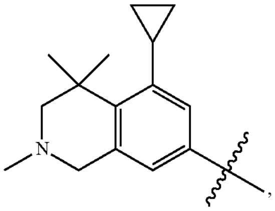,
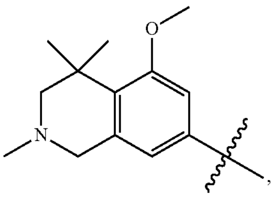,
-continued
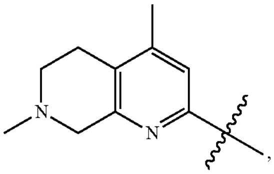,
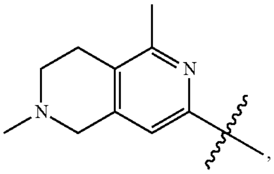,
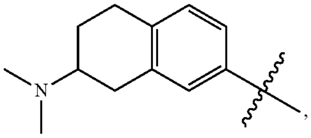,
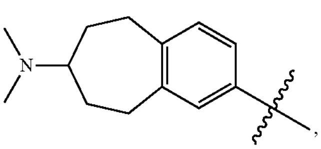,
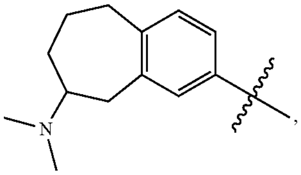,
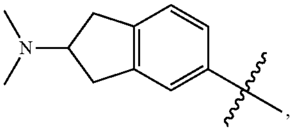,
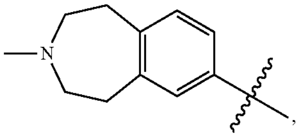,
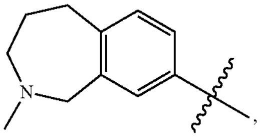,
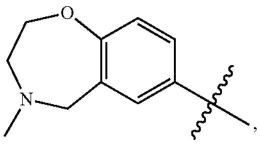,
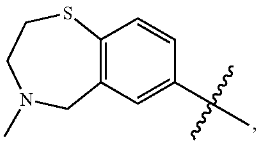,
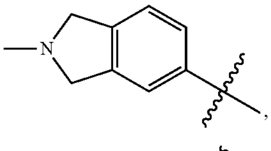,
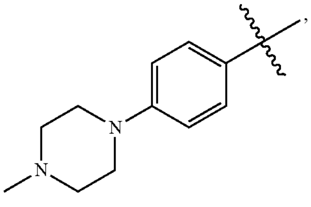, or
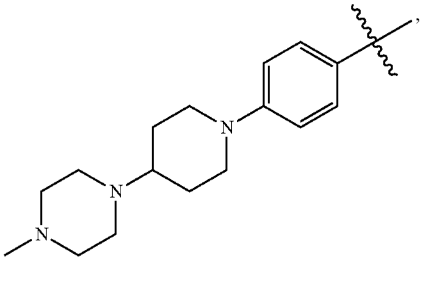

-continued
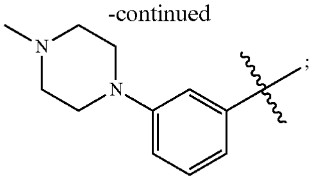;
more preferably
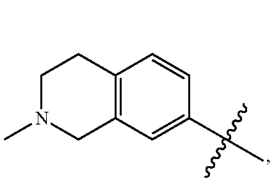, 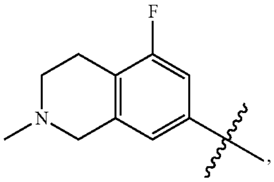, 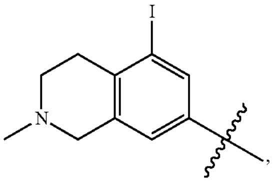,
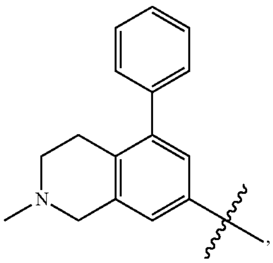, 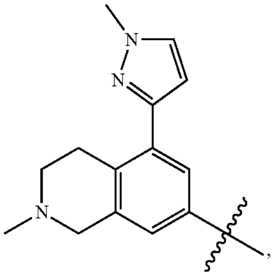, , 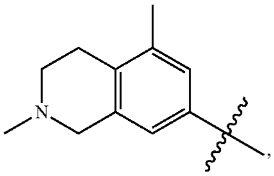,
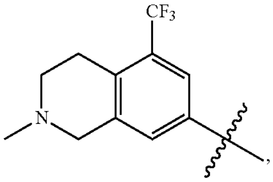, 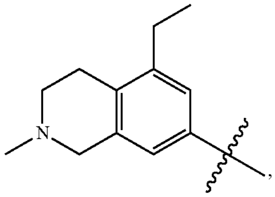, 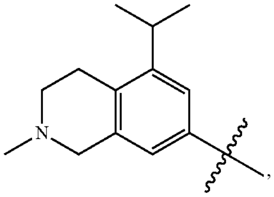,
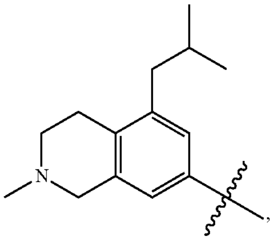, 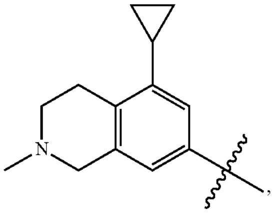, 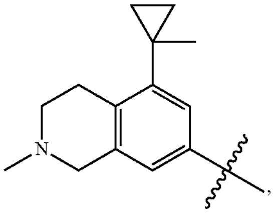,
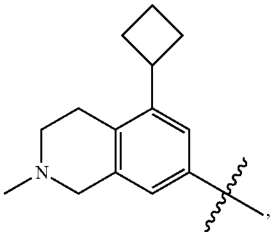, 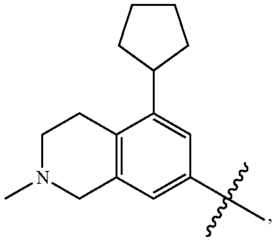, 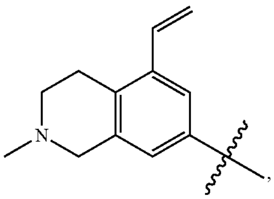,
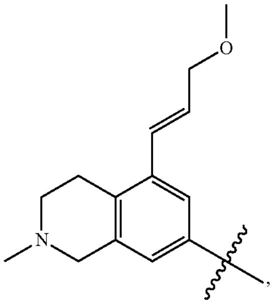, 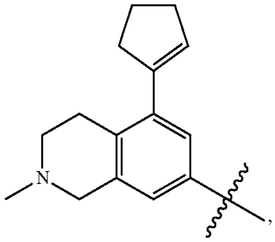, 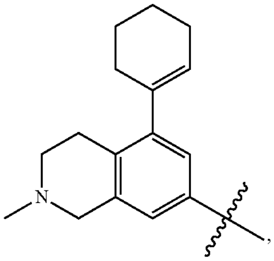, -continued
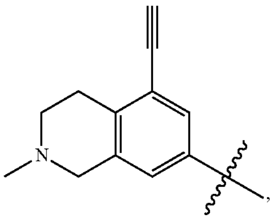
,
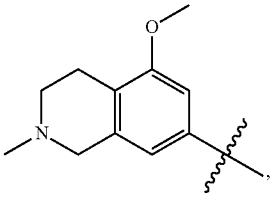
,
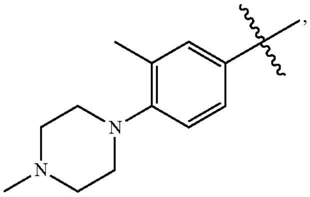
,
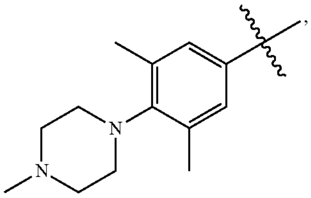
,
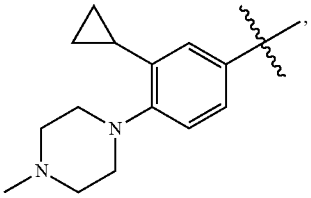
,
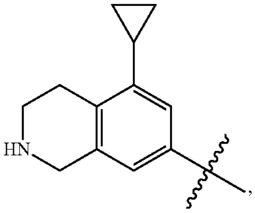
,
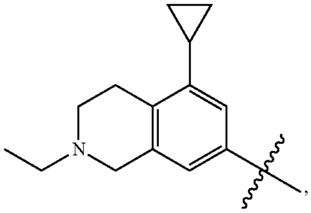
,
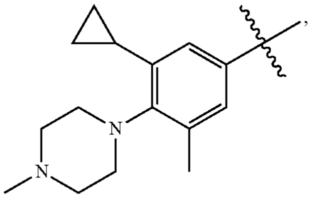
,
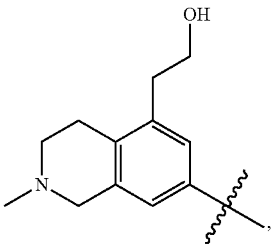
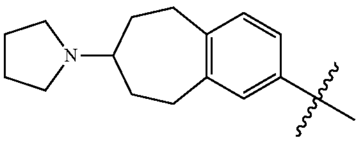
,
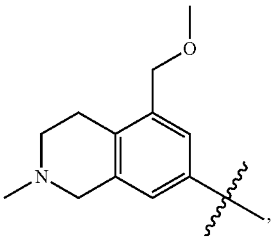
,
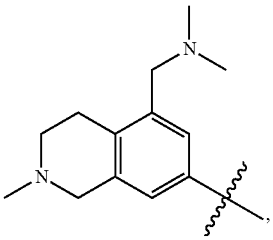
,
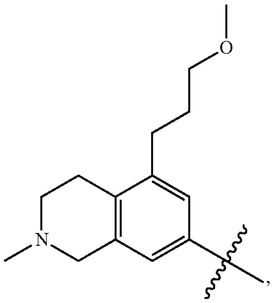
,
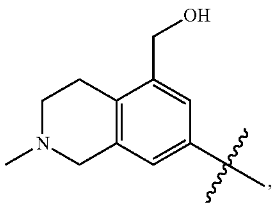
, -continued
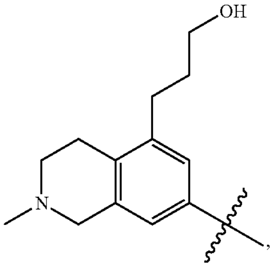,
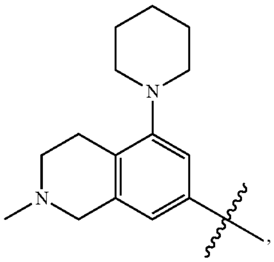,
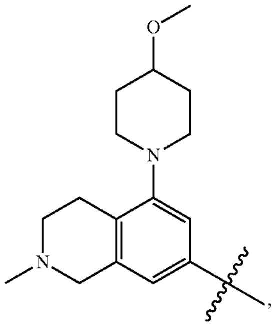,
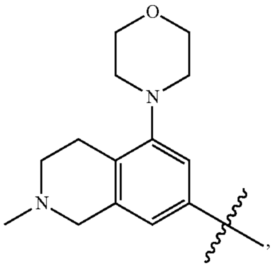,
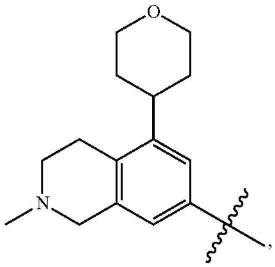,
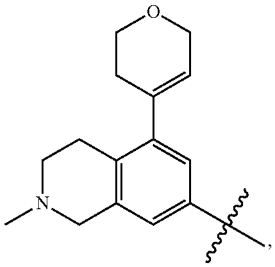,
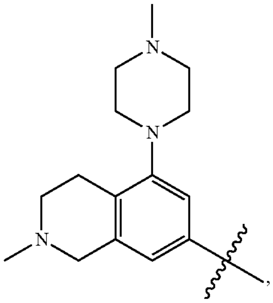,
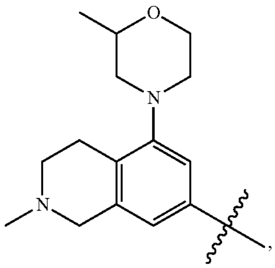,
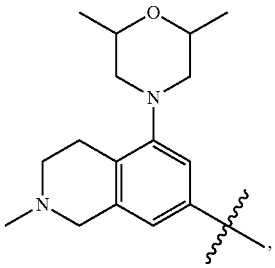,
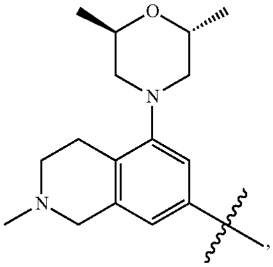,
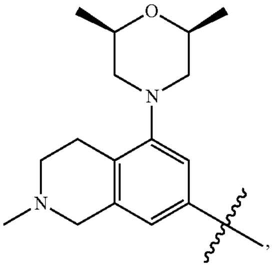,
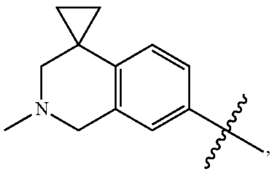,
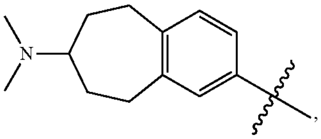,
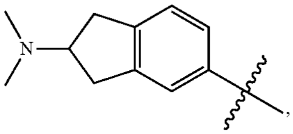,
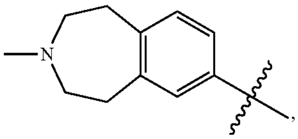,
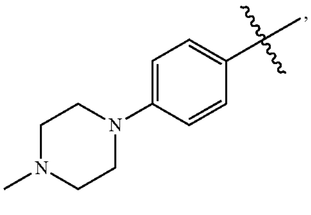,
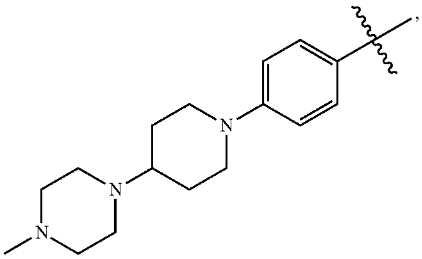, or -continued

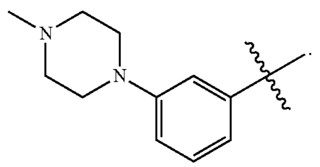

In some embodiments of the present invention, the present invention provides a compound of general formula (2), or an isomer, a crystalline form, a pharmaceutically acceptable salt, a hydrate or a solvate thereof:

(2)

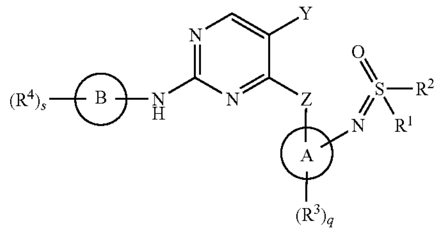

wherein A, B, Y, Z, $R^1$, $R^2$, $R^3$, $R^4$, q, and s are as defined above and are exemplified in the

DETAILED DESCRIPTION

In some embodiments of the present invention, the present invention provides a compound of general formula (3a) or general formula (3b), or an isomer, a crystalline form, a pharmaceutically acceptable salt, a hydrate or a solvate thereof:

(3a)

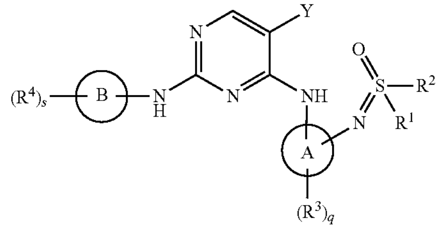

(3b)

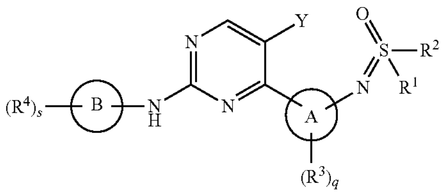

wherein A, B, Y, $R^1$, $R^2$, $R^3$, $R^4$, q, and s are as defined above and are exemplified in the detailed description.

In some embodiments of the present invention, the present invention provides a compound of general formula (4), or an isomer, a crystalline form, a pharmaceutically acceptable salt, a hydrate or a solvate thereof:

(4)

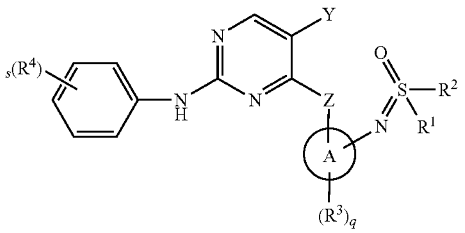

wherein A, Y, Z, $R^1$, $R^2$, $R^3$, $R^4$, q, and s are as defined above and are exemplified in the detailed description.

In some embodiments of the present invention, the present invention provides a compound of general formula (5a) or general formula (5b), or an isomer, a crystalline form, a pharmaceutically acceptable salt, a hydrate or a solvate thereof:

(5a)

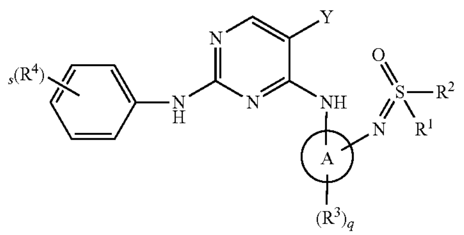

(5b)

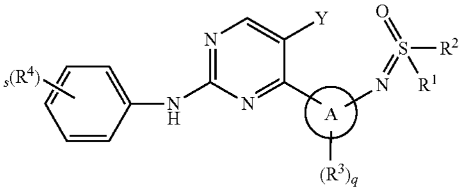

wherein A, Y, $R^1$, $R^2$, $R^3$, $R^4$, q, and s are as defined above and are exemplified in the detailed description.

In some embodiments of the present invention, the present invention provides a compound of general formula (6), or an isomer, a crystalline form, a pharmaceutically acceptable salt, a hydrate or a solvate thereof:

(6)

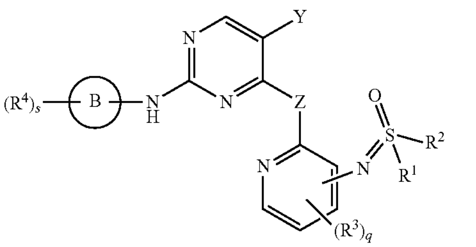

wherein B, Y, Z, $R^1$, $R^2$, $R^3$, $R^4$, q, and s are as defined above and are exemplified in the detailed description.

In some embodiments of the present invention, the present invention provides a compound of general formula (7a), general formula (7b), general formula (7c), general formula (7d), general formula (7e), general formula (7f) or general formula (7g), or an isomer, a crystalline form, a pharmaceutically acceptable salt, a hydrate or a solvate thereof:

(7a)

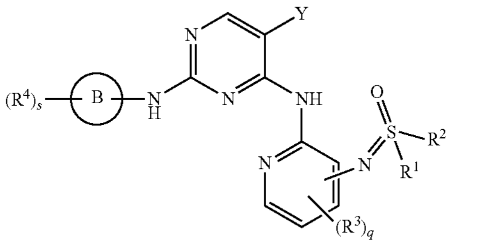

(7b)

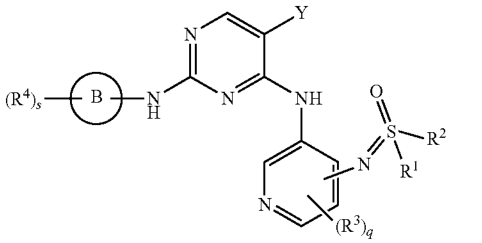

(7c)

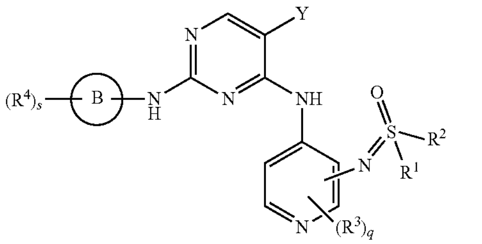

(7d)

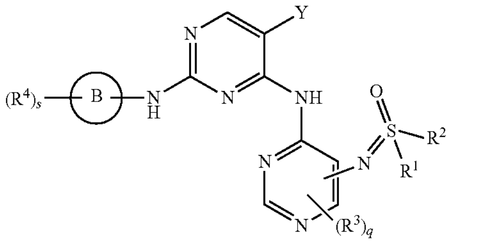

-continued (7e)

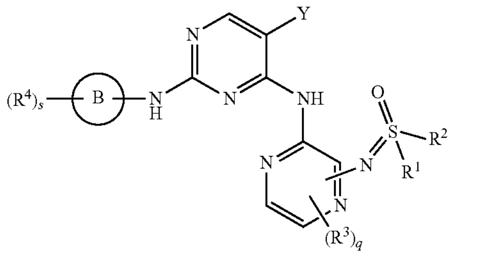

(7f)

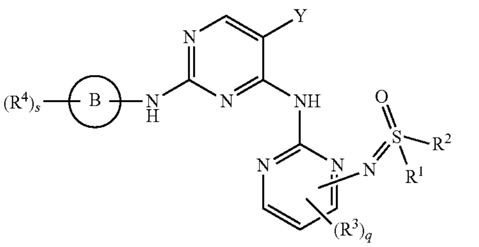

(7g)

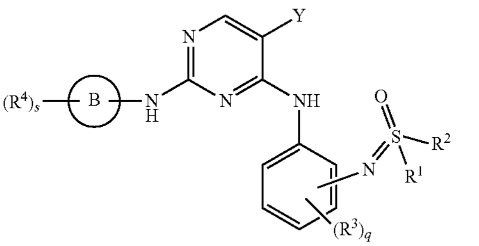

wherein B, Y, $R^1$, $R^2$, $R^3$, $R^4$, q, and s are as defined above and are exemplified in the detailed description.

In some embodiments of the present invention, the present invention provides a compound of general formula (8a), general formula (8b), general formula (8c), general formula (8d), general formula (8e), general formula (8f) or general formula (8g), or an isomer, a crystalline form, a pharmaceutically acceptable salt, a hydrate or a solvate thereof:

(8a)

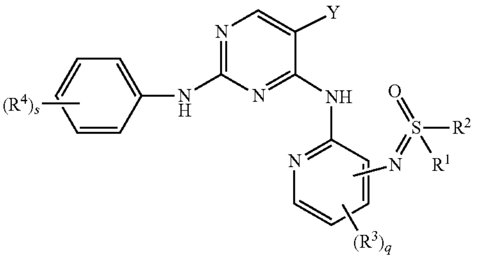

(8b)

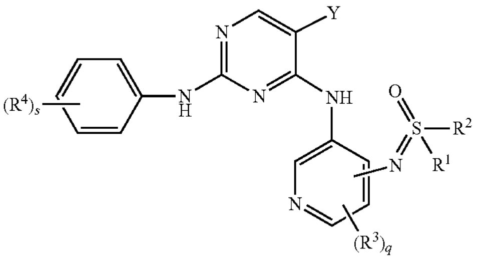

-continued
(8c)
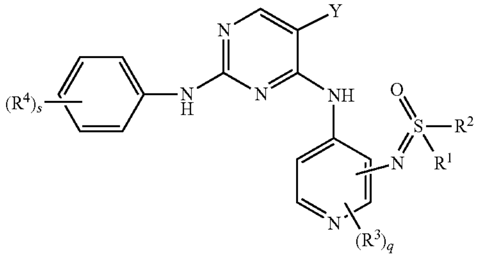
(8d)
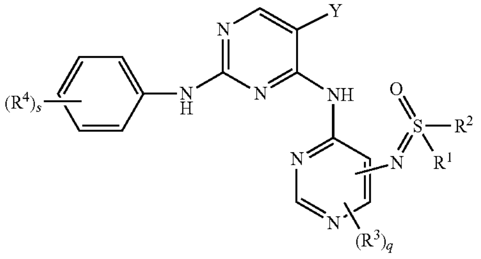
(8e)
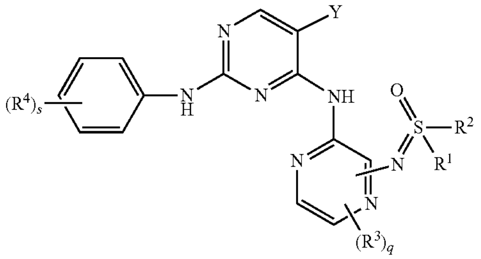
(8f)
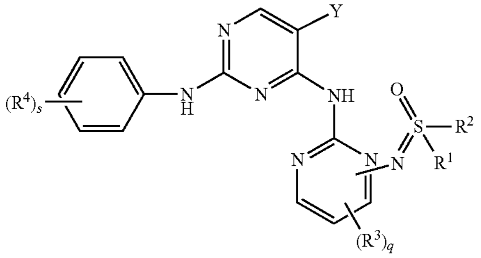
(8g)
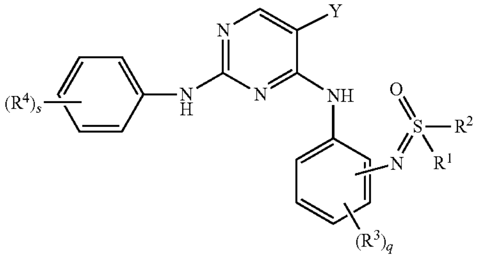
wherein Y, $R^1$, $R^2$, $R^3$, $R^4$, q, and s are as defined above and are exemplified in the detailed description.
In various different embodiments of the present invention, the compound of general formula (1_) has one of the following structures:
1
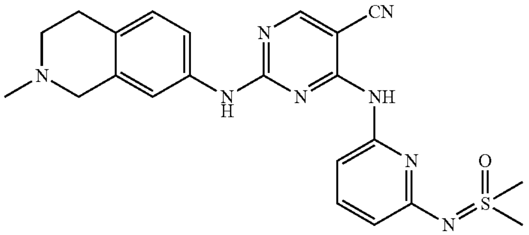
2
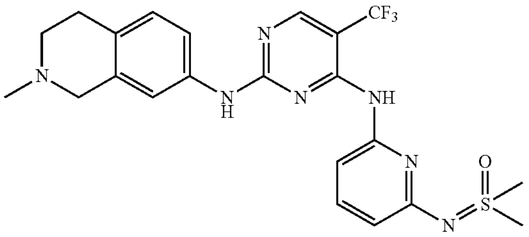
3
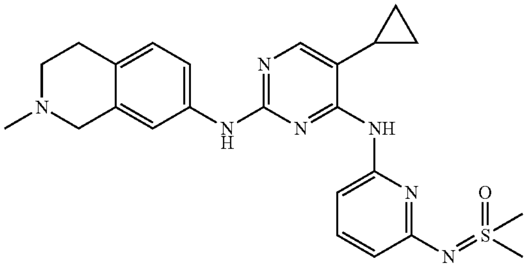
4
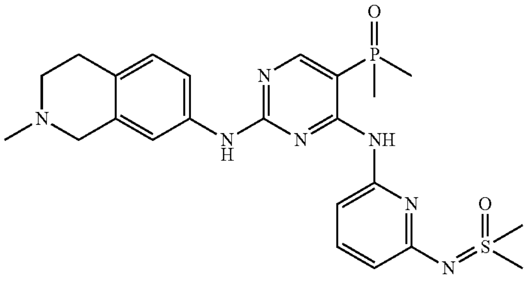
5
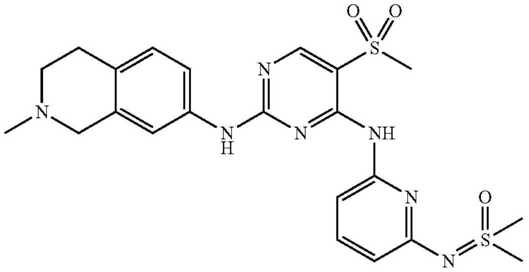

-continued
6
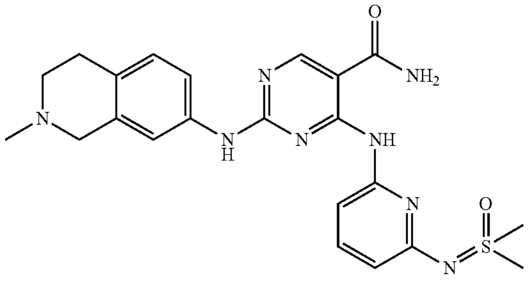
7
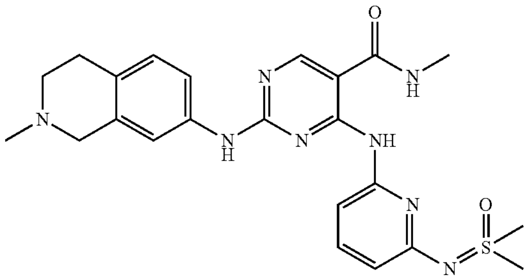
8
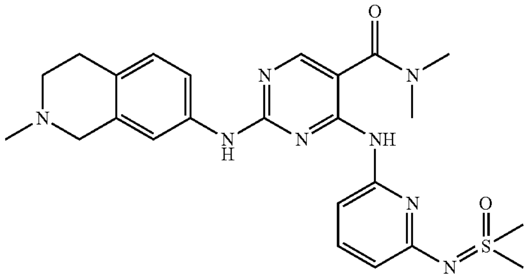
9
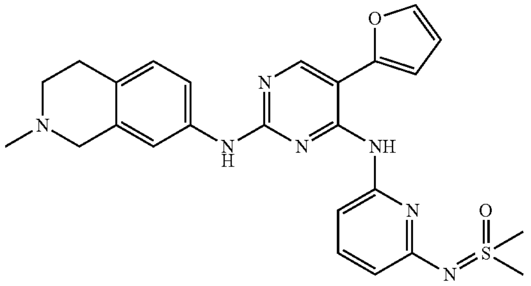
10
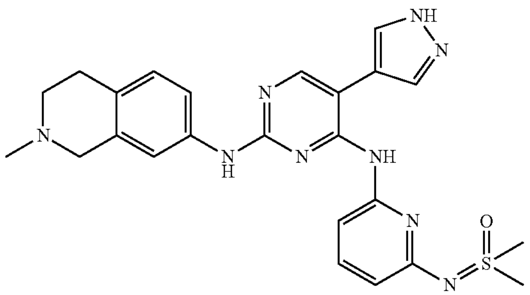
-continued
11
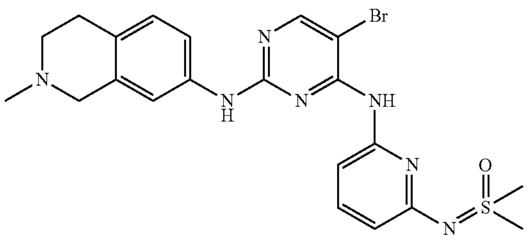
12
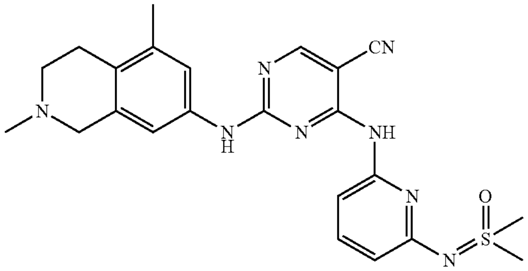
13
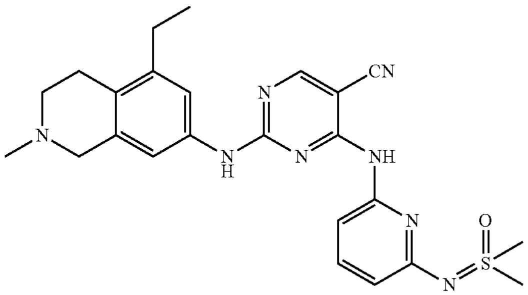
14
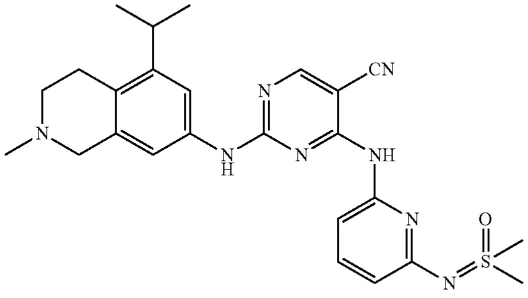
15
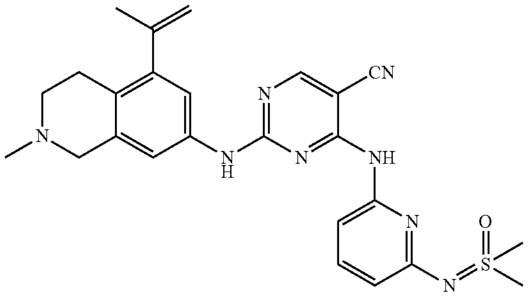

-continued
16
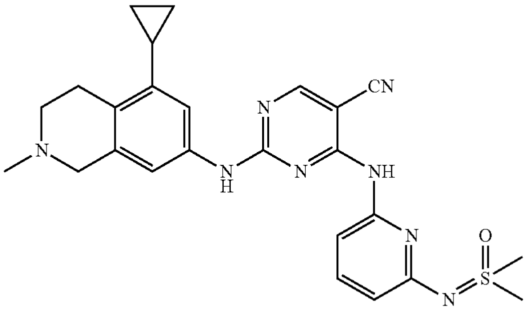
17
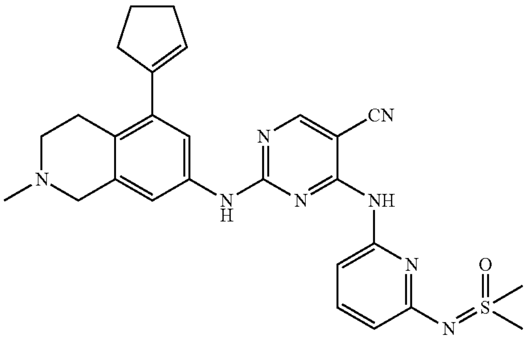
18
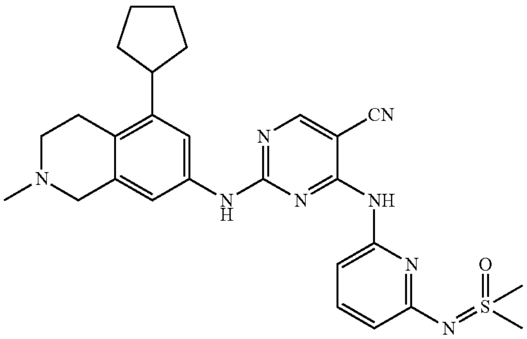
19
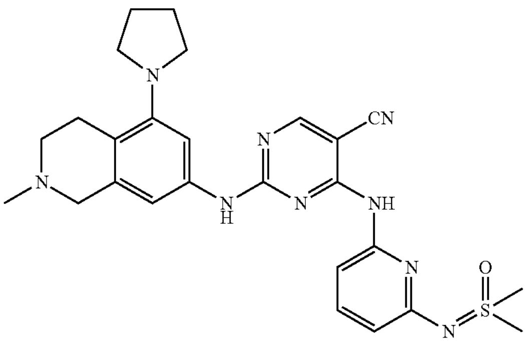
-continued
20
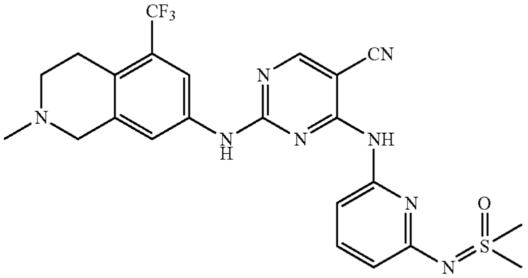
21
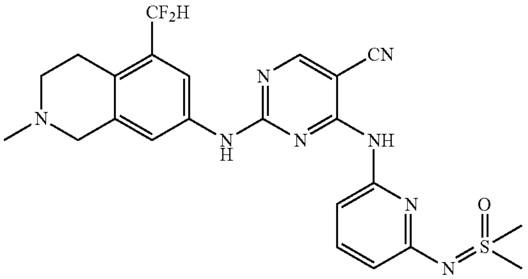
22
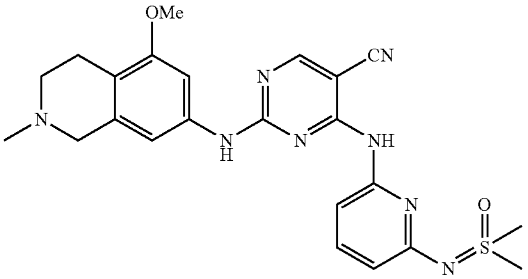
23
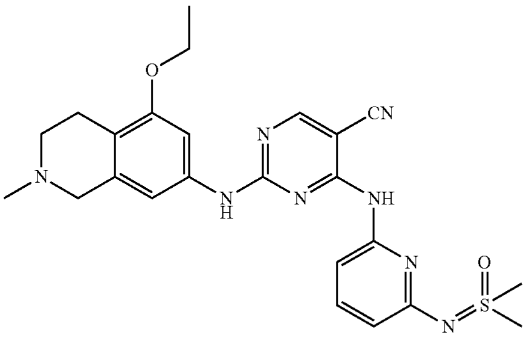
24
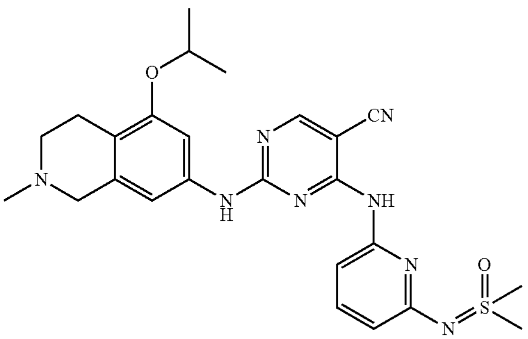

-continued
25
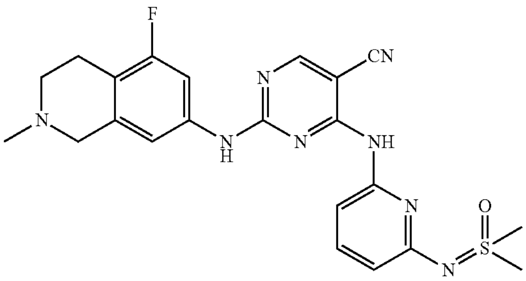
26
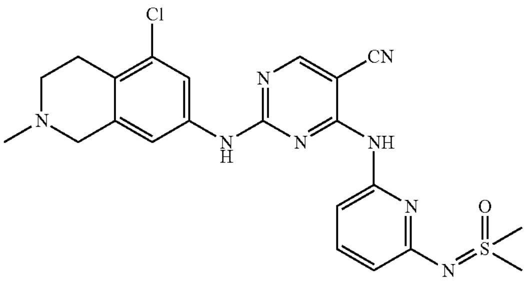
27
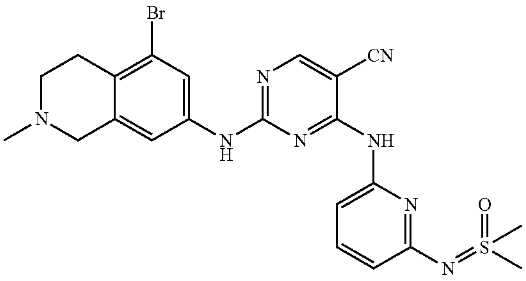
28
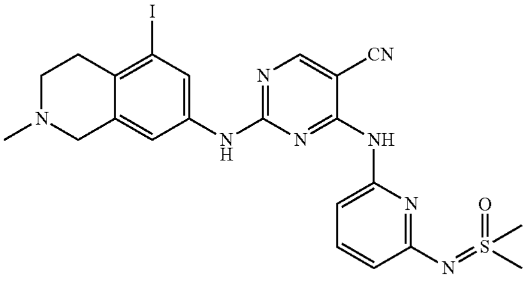
29
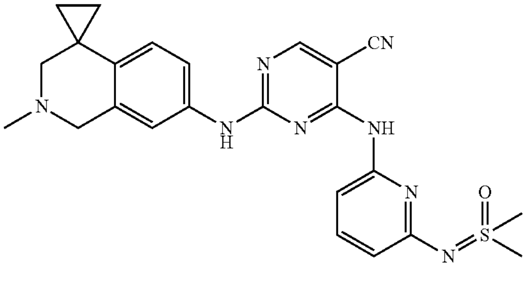
-continued
30
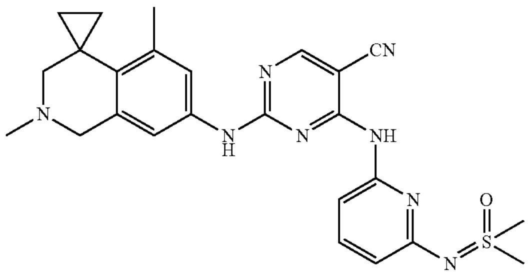
31
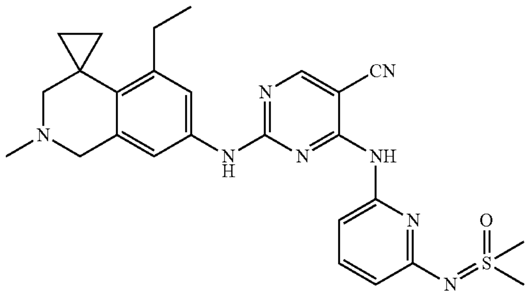
32
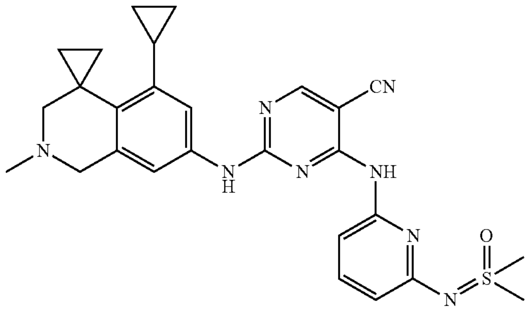
33
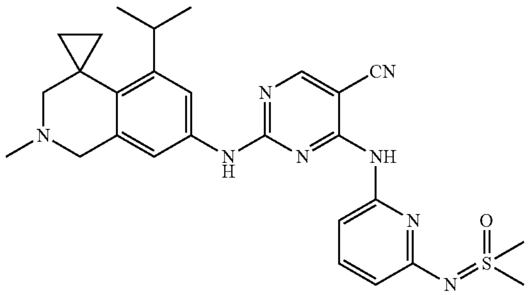
34
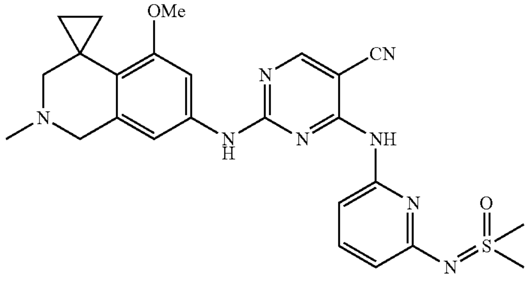

-continued
35
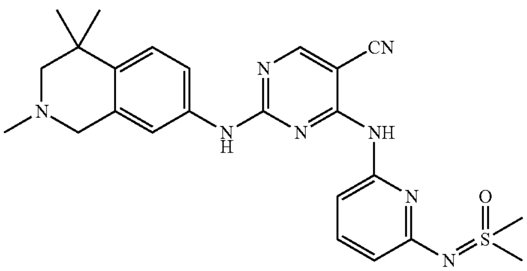
36
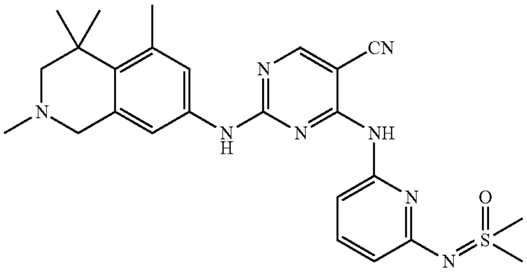
37
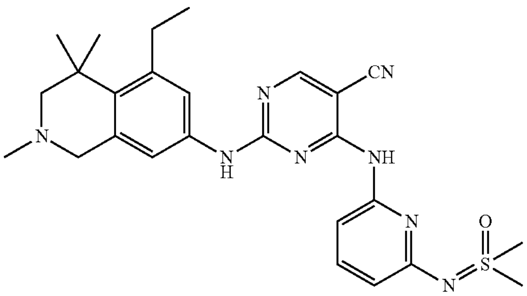
38
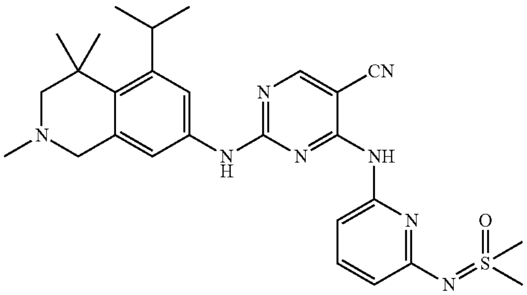
39
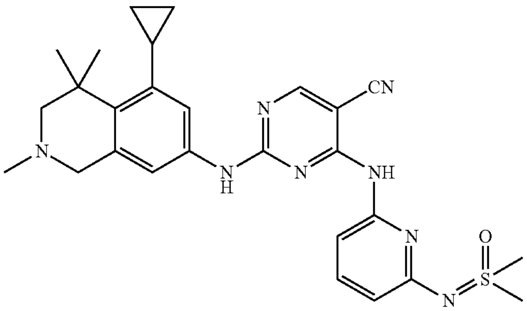
-continued
40
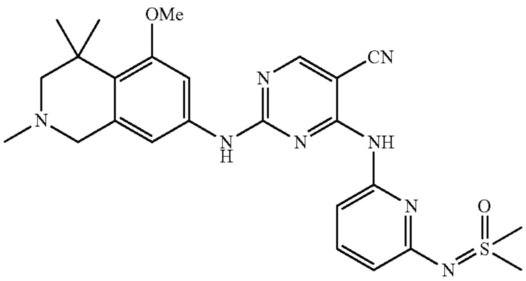
41
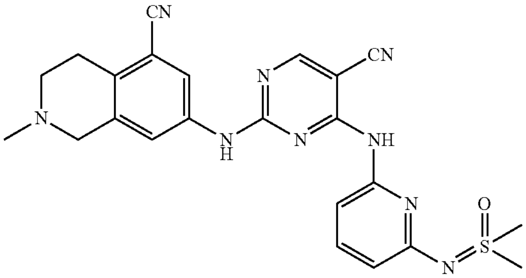
42
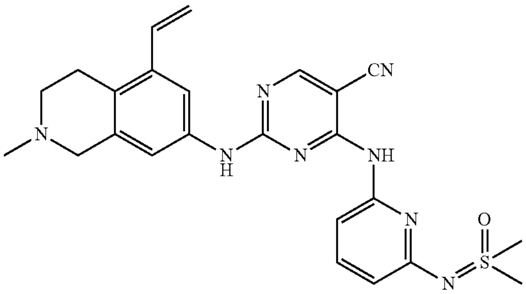
43
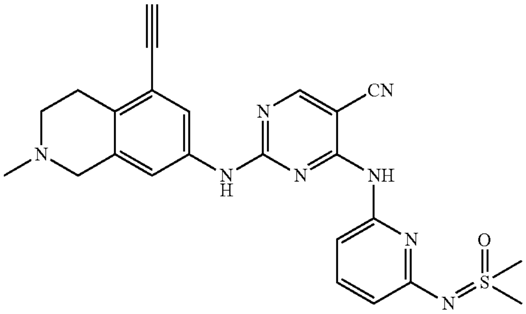
44
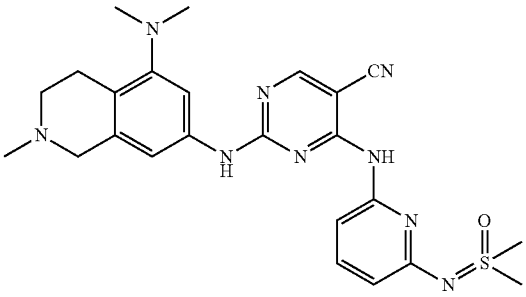

-continued
45
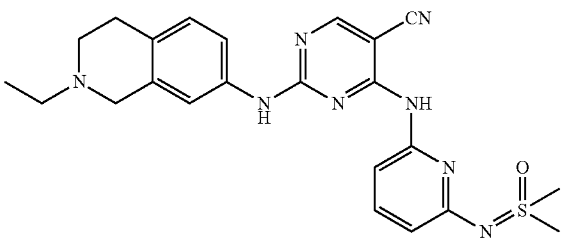
46
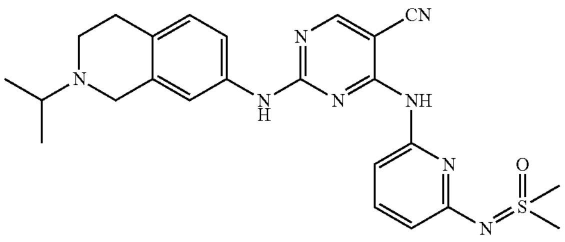
47
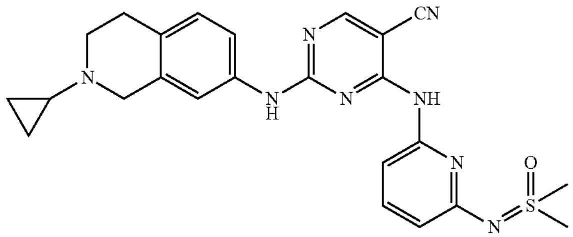
48
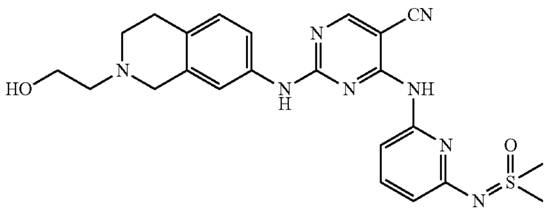
49
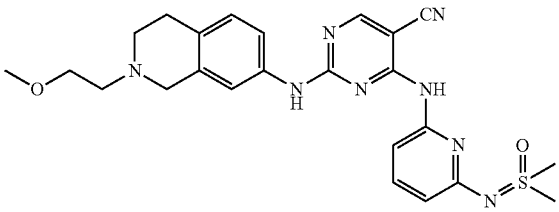
50
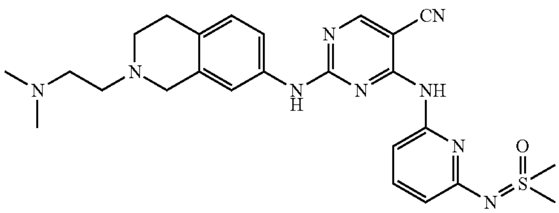
-continued
51
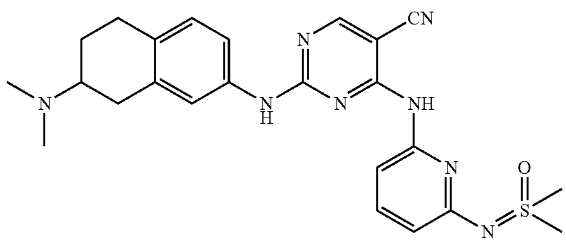
52
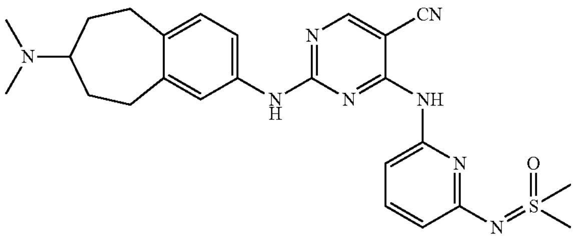
53
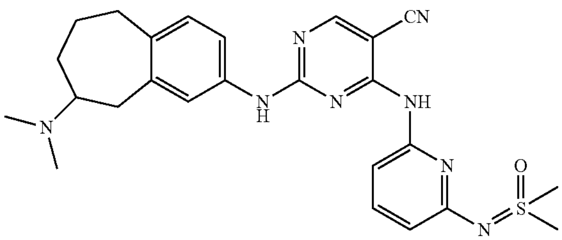
54
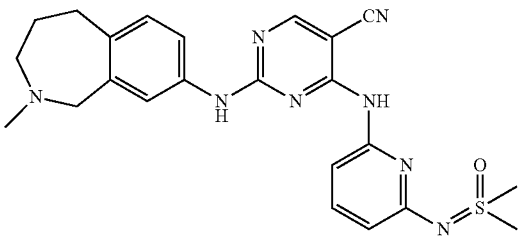
55
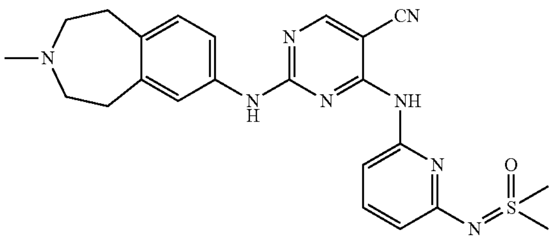
56
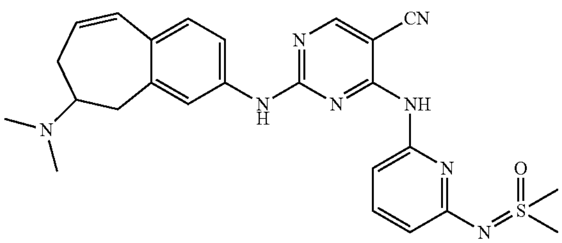

-continued
57
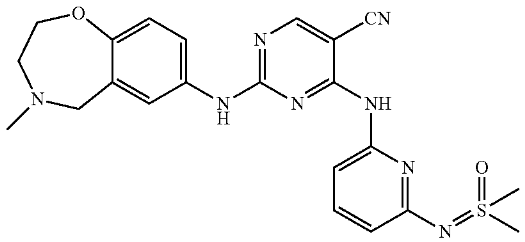
58
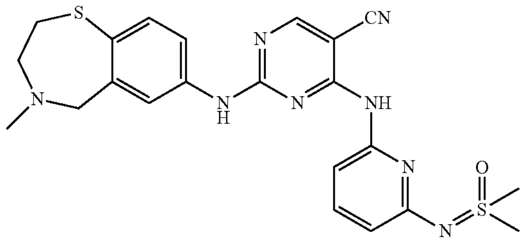
59
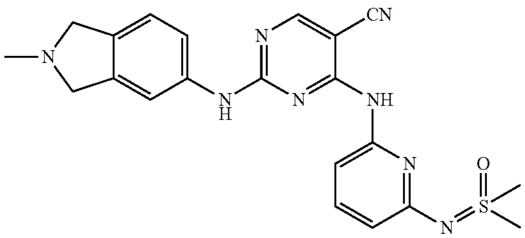
60
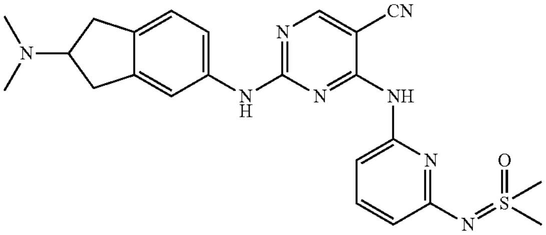
61
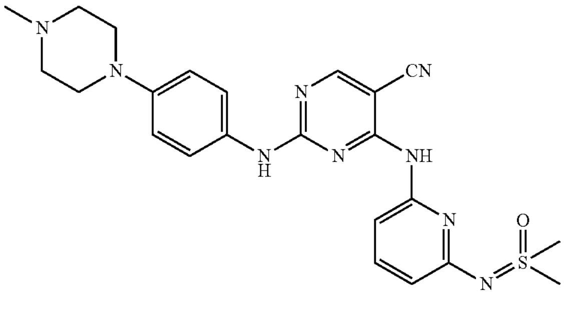
-continued
62
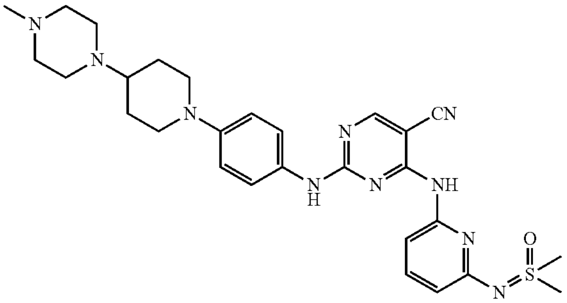
63
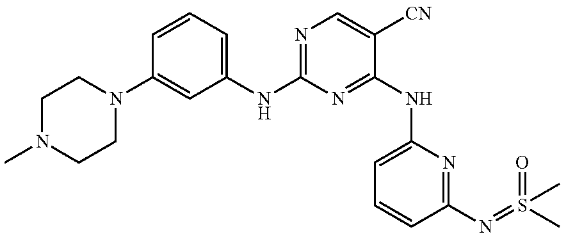
64
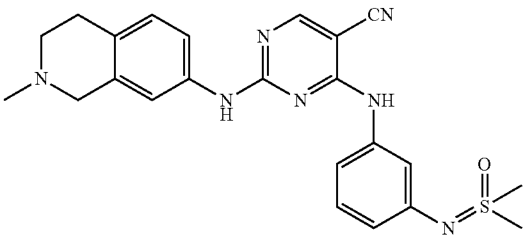
65
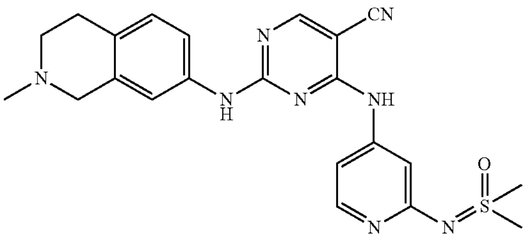
66
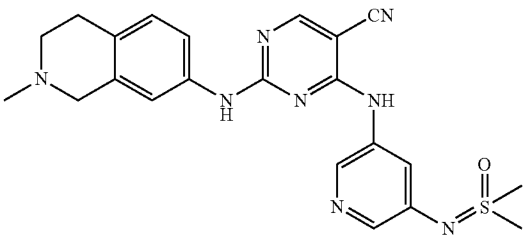
67
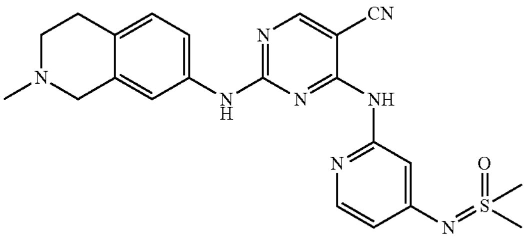

-continued
68
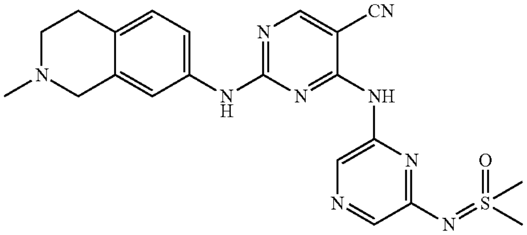
69
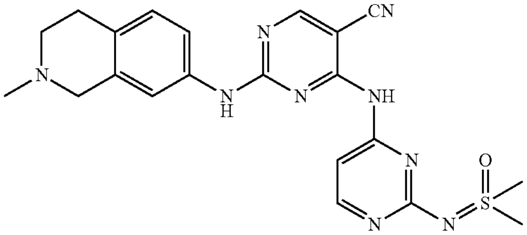
70
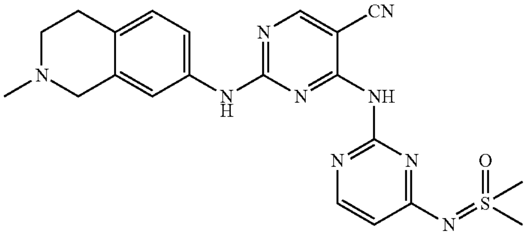
71
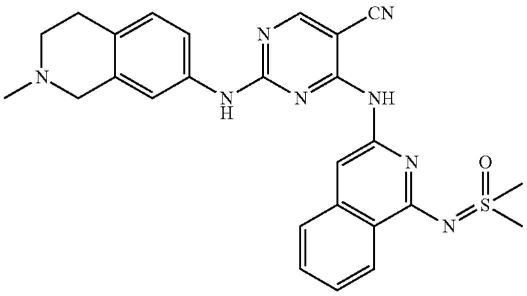
72
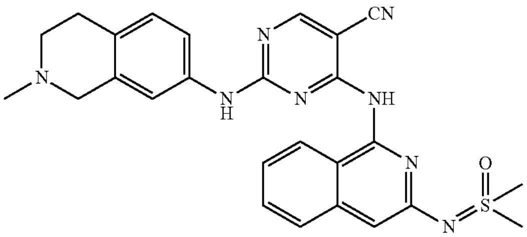
-continued
73
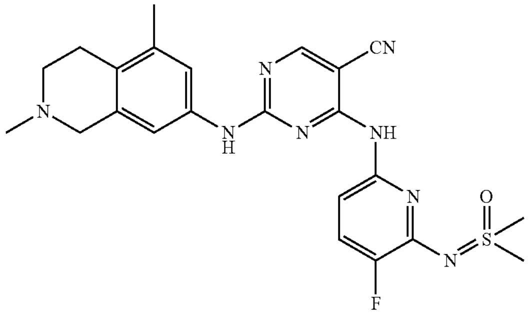
74
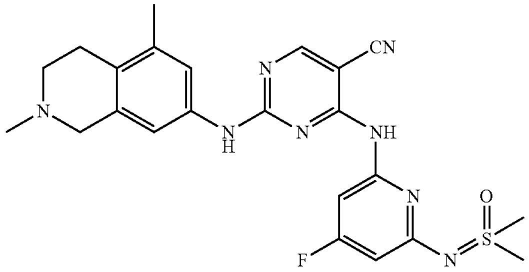
75
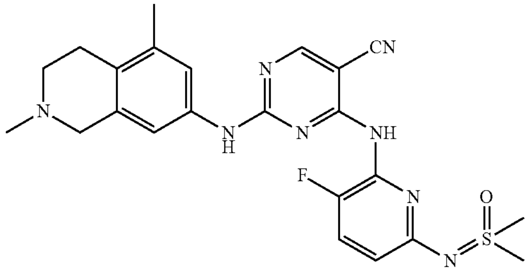
76
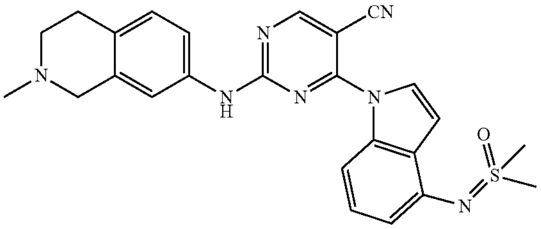
77
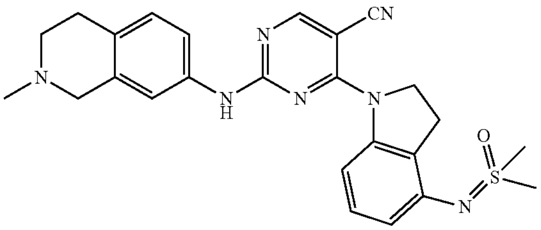

-continued
78
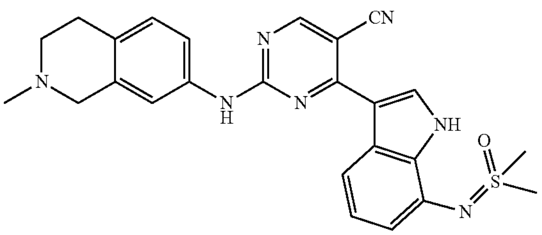
79
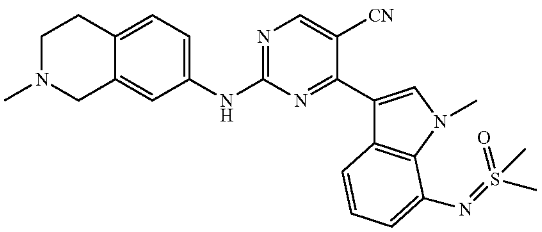
80
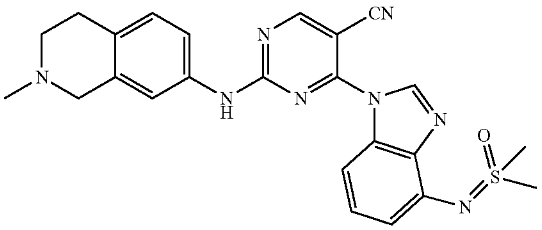
81
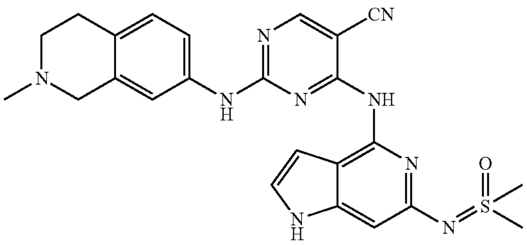
82
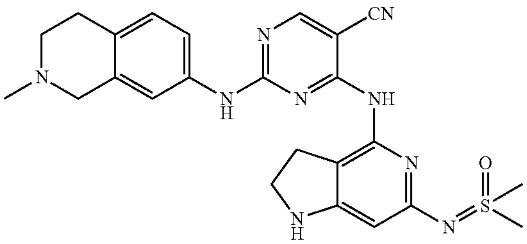
83
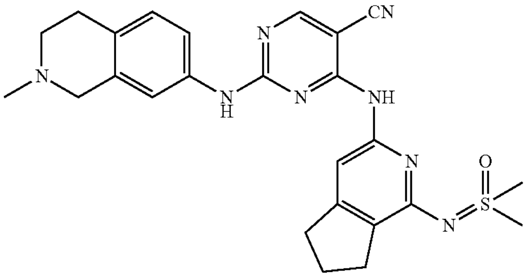
-continued
84
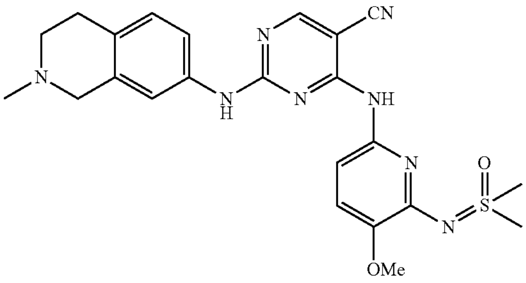
85
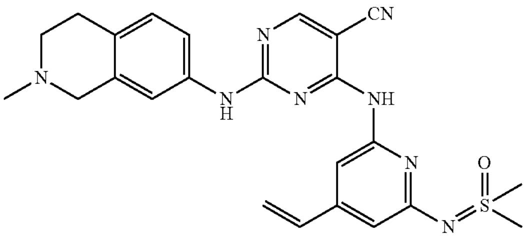
86
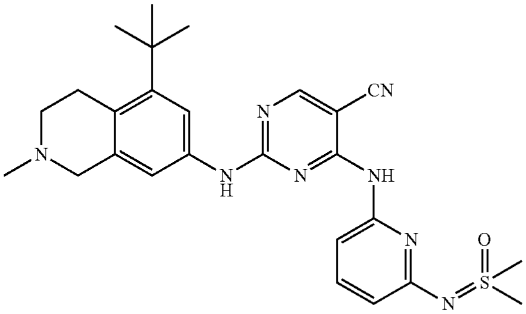
87
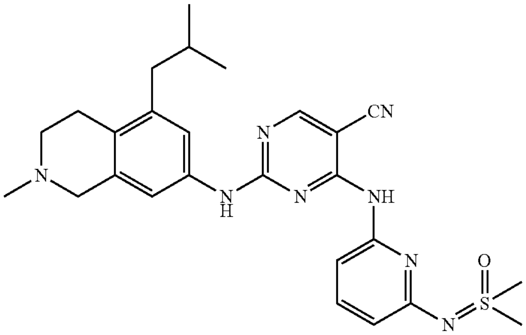
88
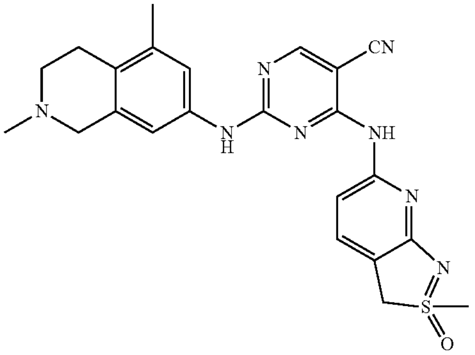

-continued
89
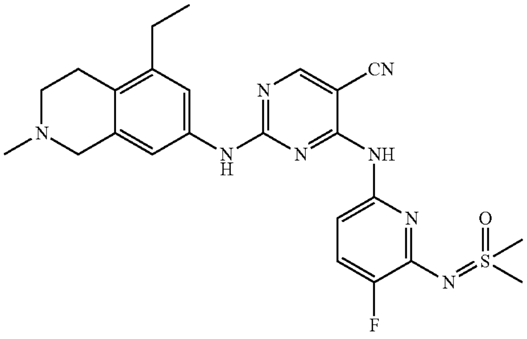
90
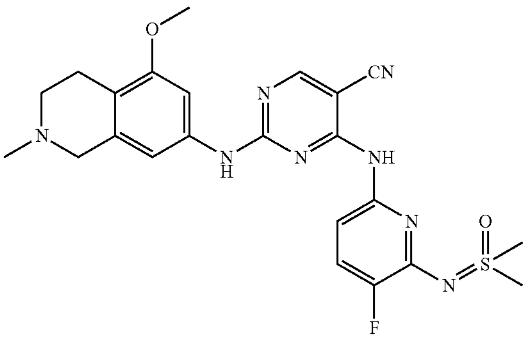
91
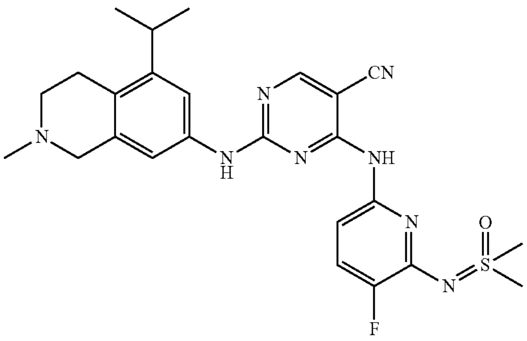
92
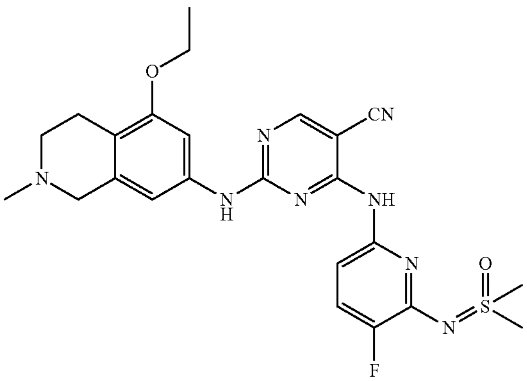
-continued
93
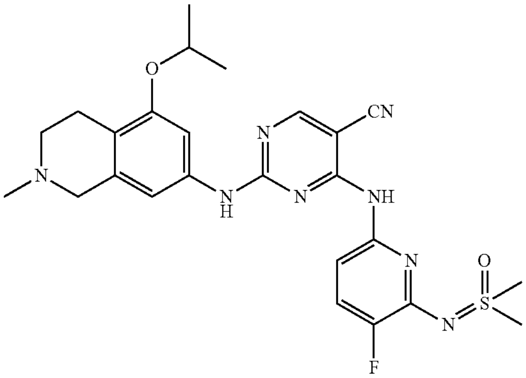
94
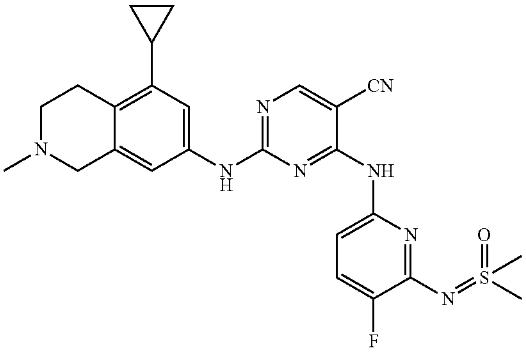
95
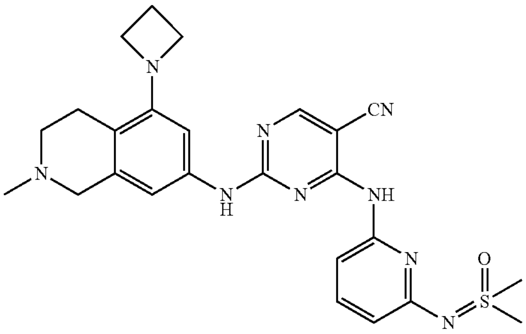
96
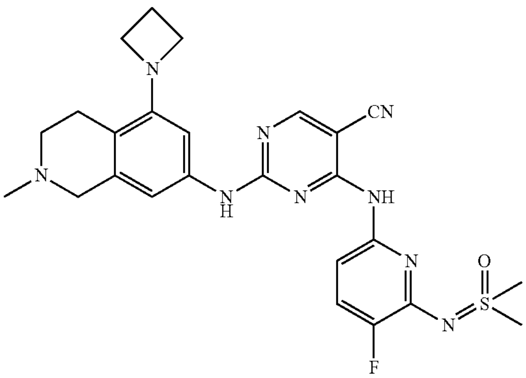

-continued
97
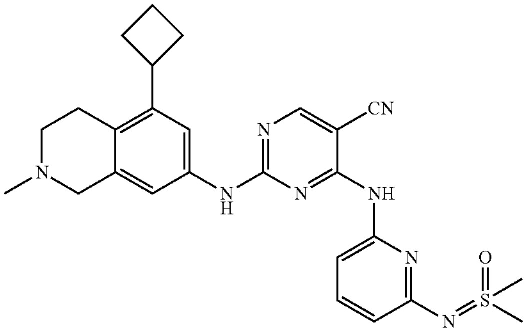
98
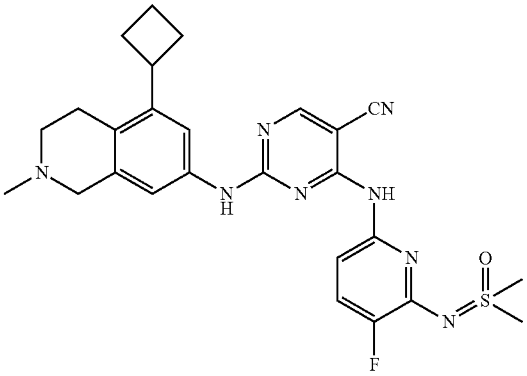
99
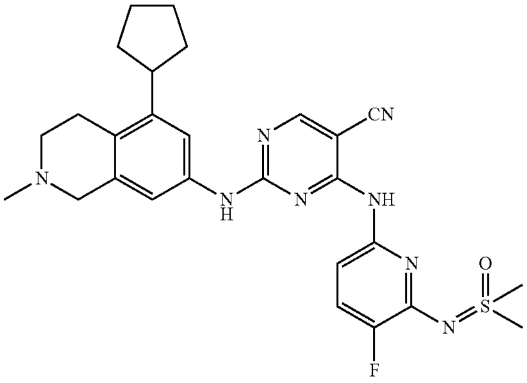
100
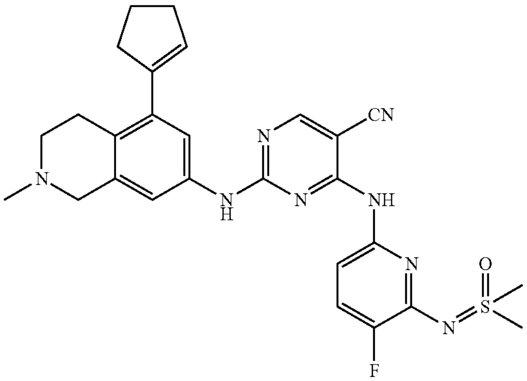
-continued
101
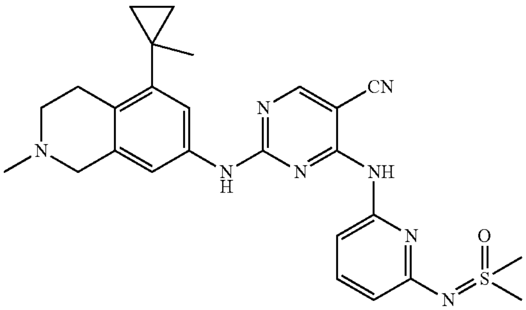
102
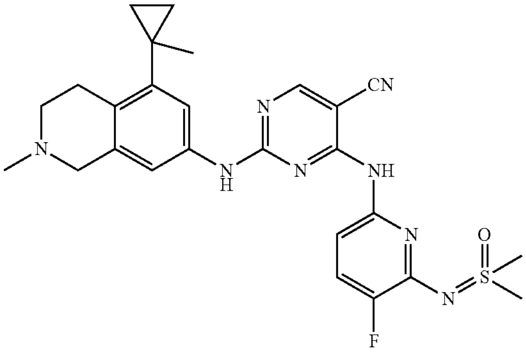
103
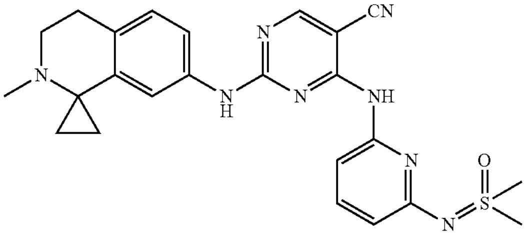
104
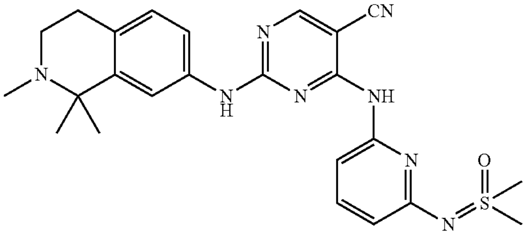
105
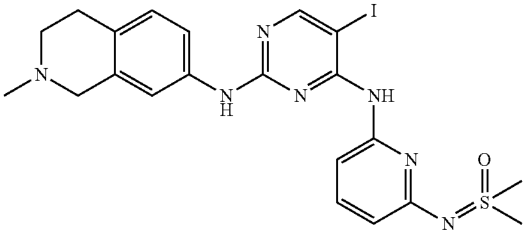

-continued
106
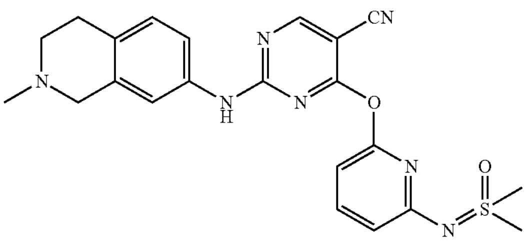
107
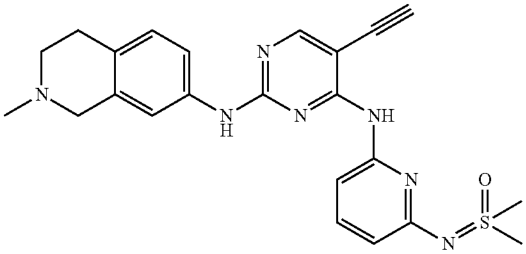
108
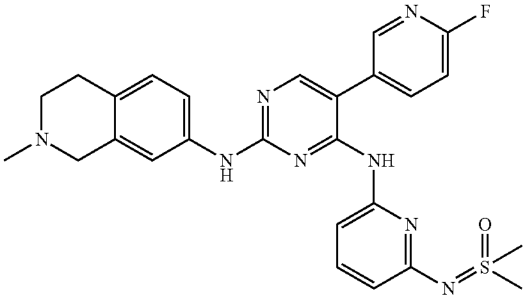
109
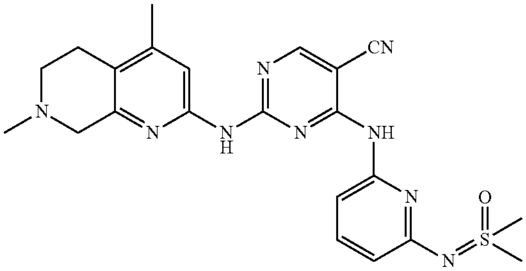
110
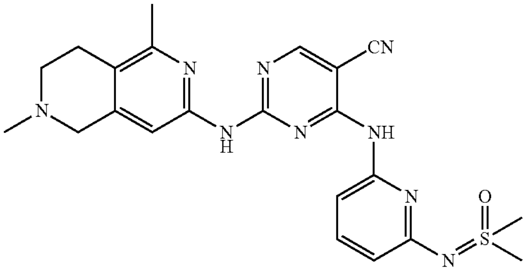
-continued
111
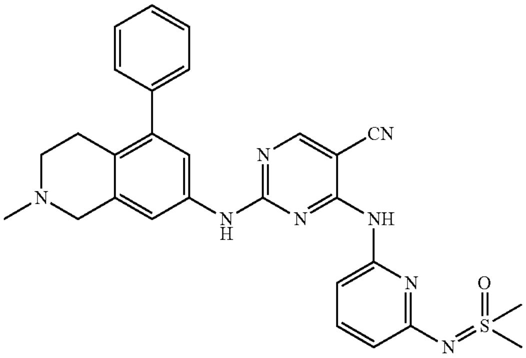
112
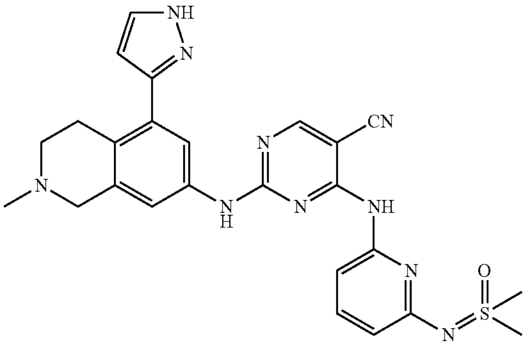
113
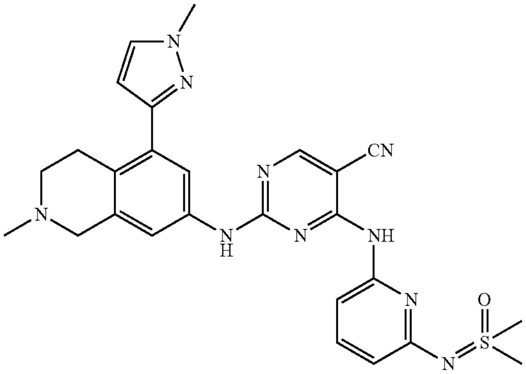
114
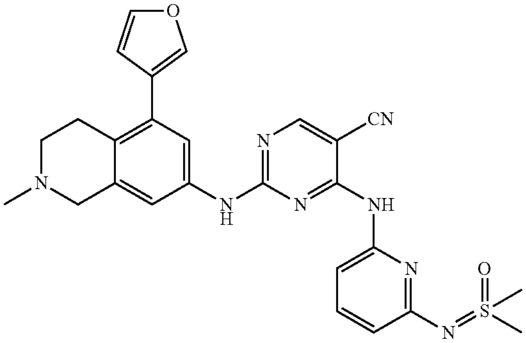

-continued
115
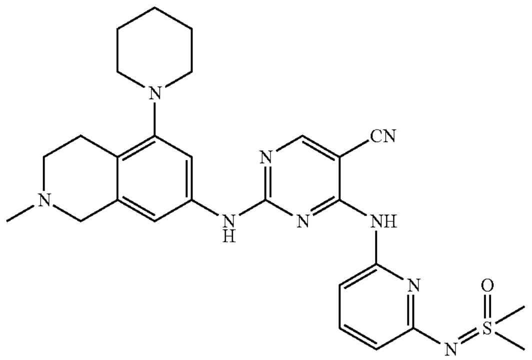
116
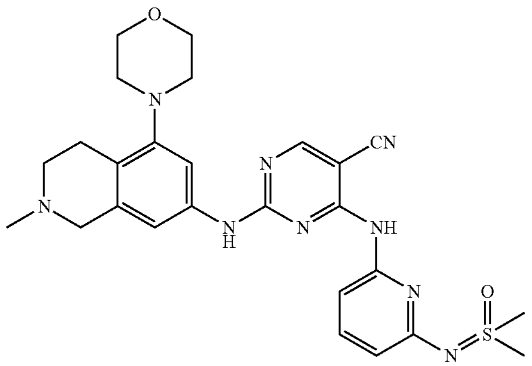
117
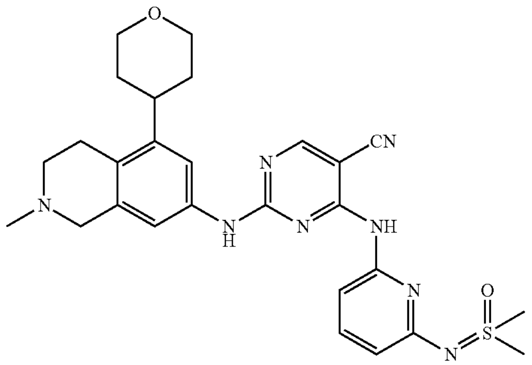
118
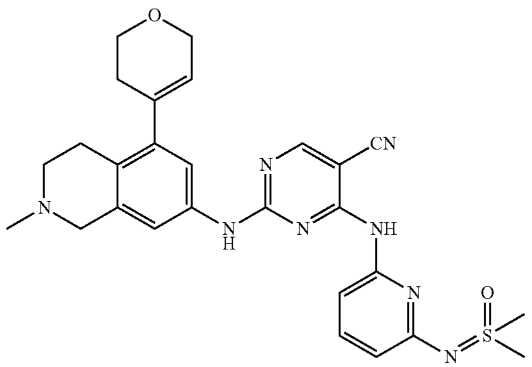
-continued
119
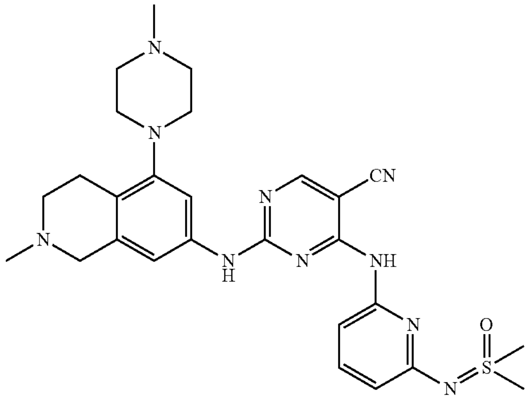
120
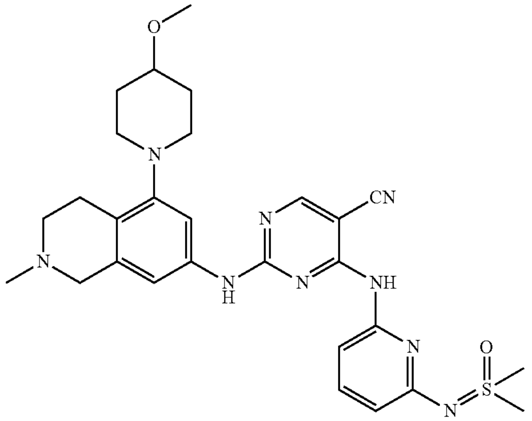
121
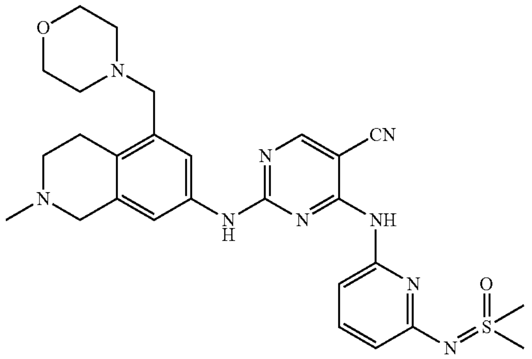
122
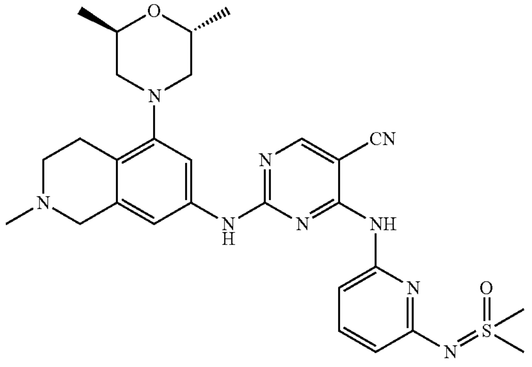

123
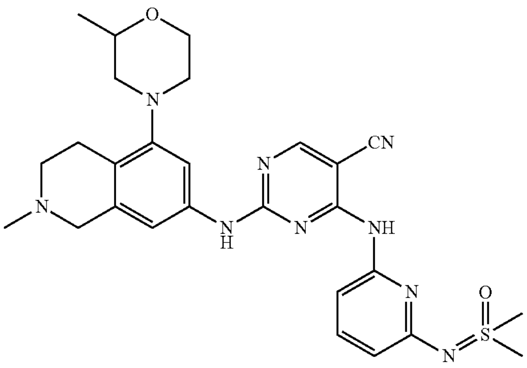
124
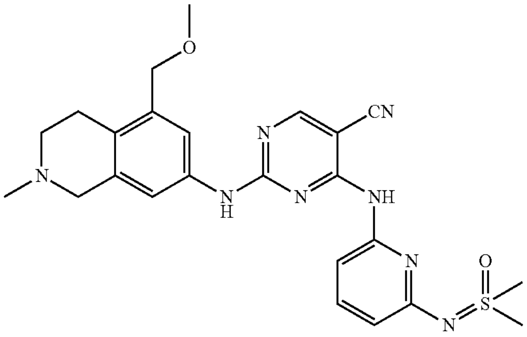
125
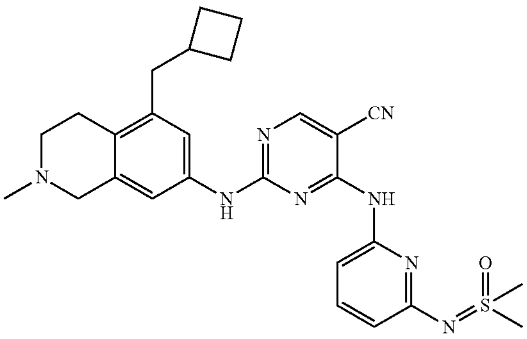
126
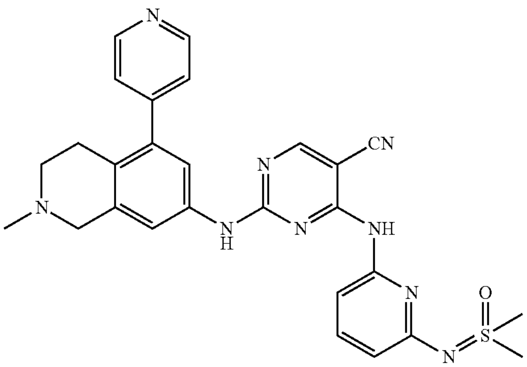
127
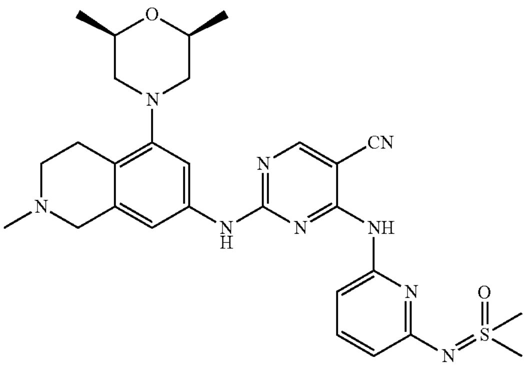
128
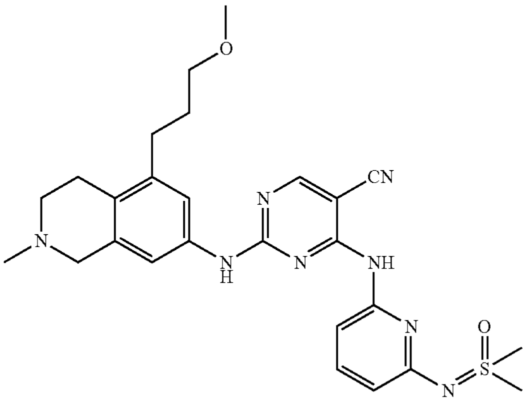
129
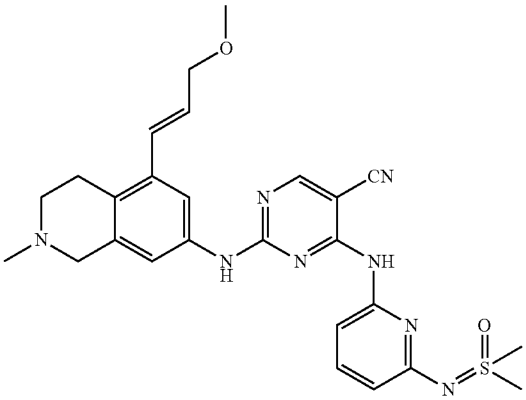
130
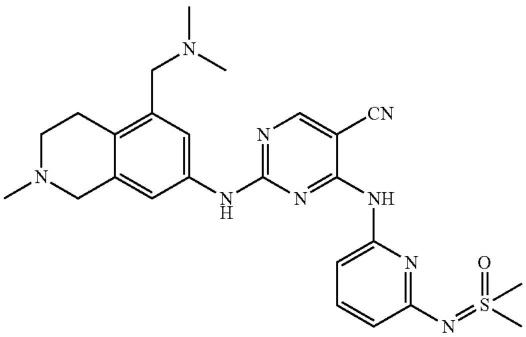

-continued
131
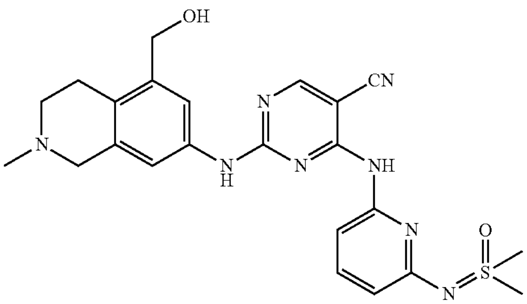
132
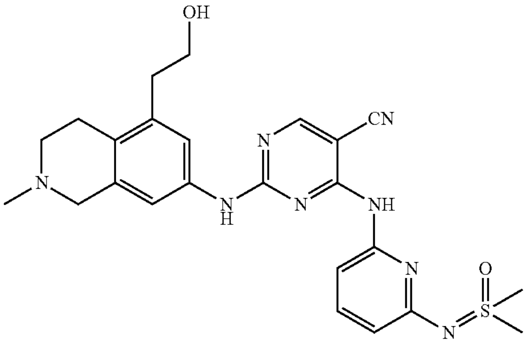
133
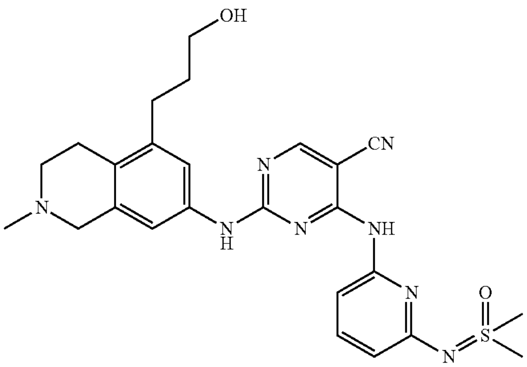
134
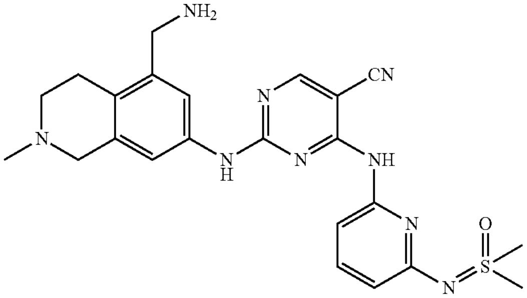
-continued
135
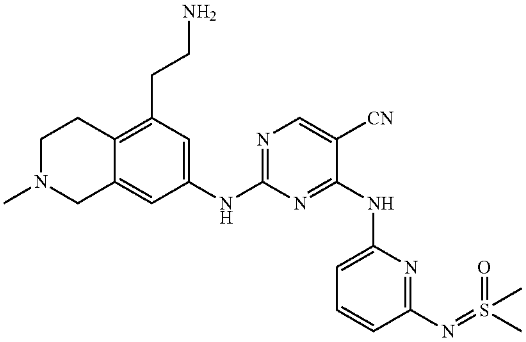
136
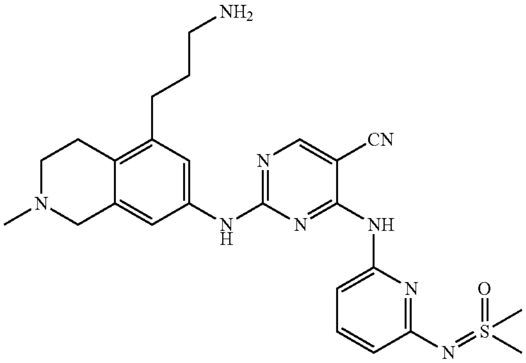
137
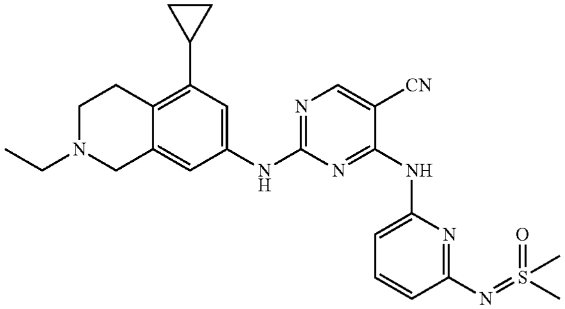
138
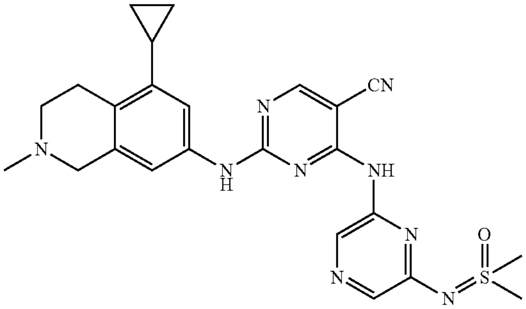

-continued
139
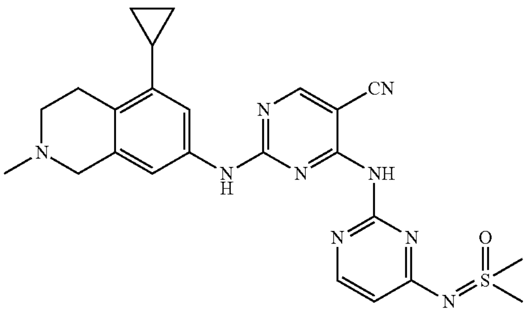
140
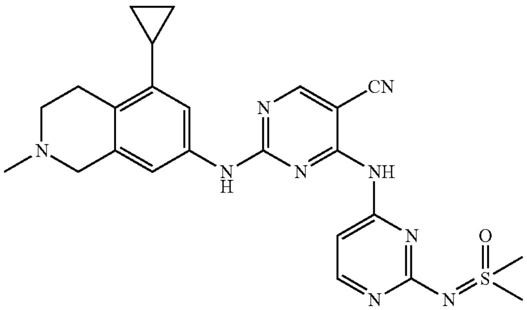
141
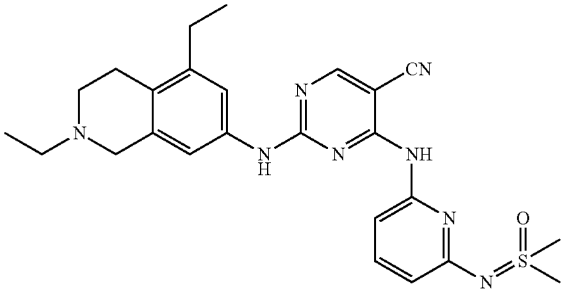
142
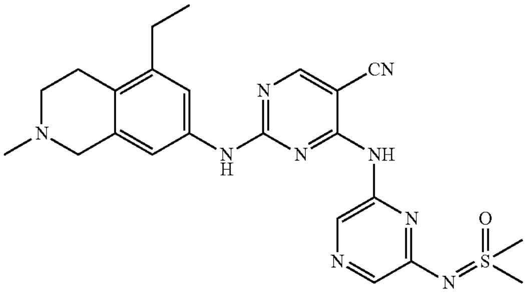
143
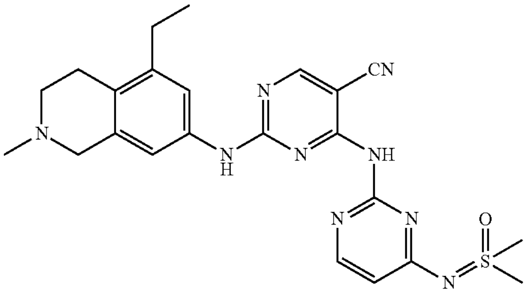
-continued
144
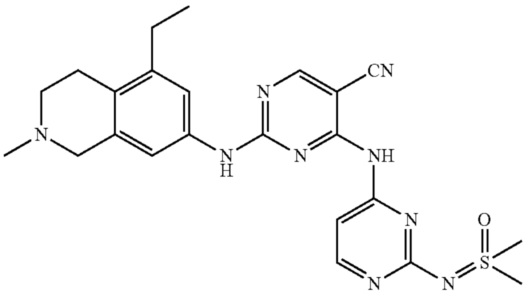
145
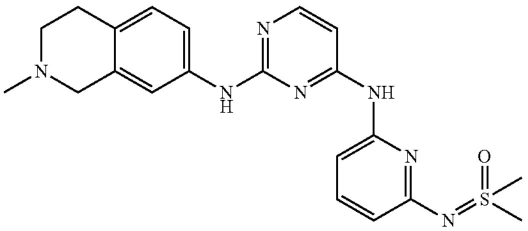
146
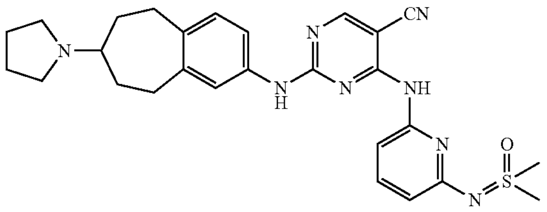
147
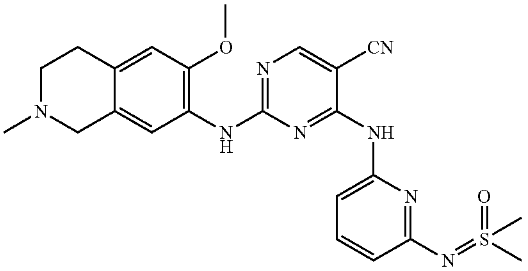
148
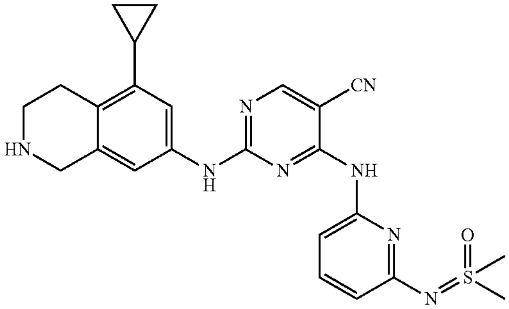

-continued
149
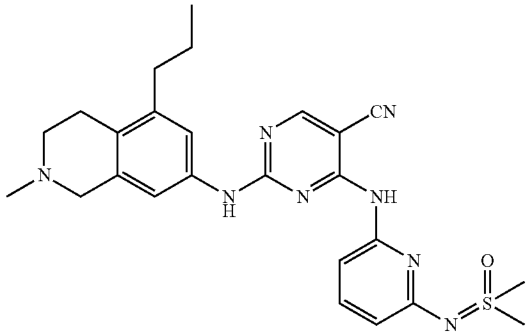
150
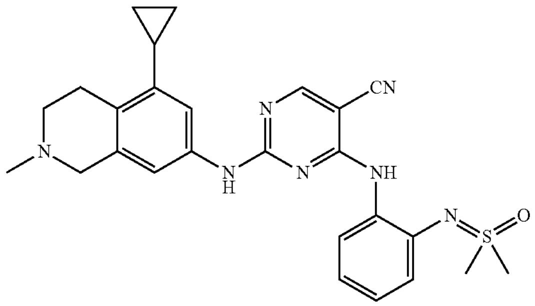
151
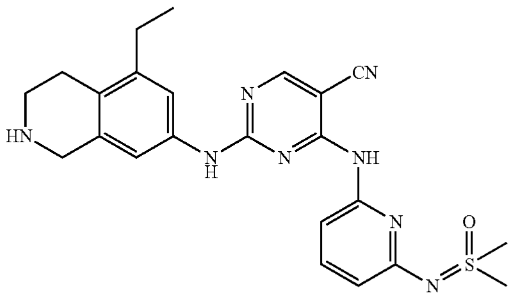
152
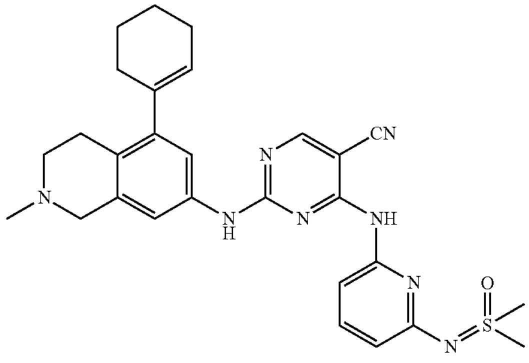
-continued
153
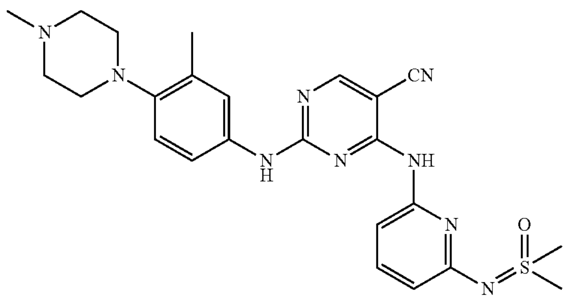
154
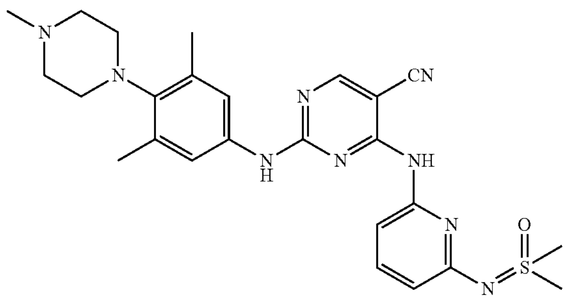
155
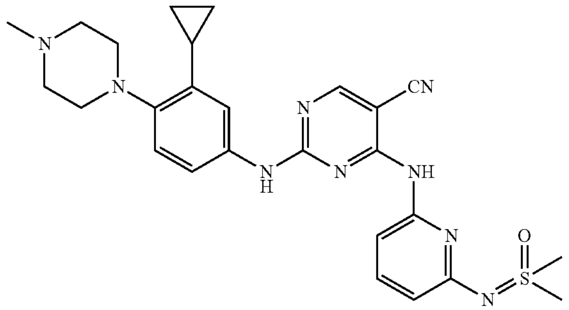
156
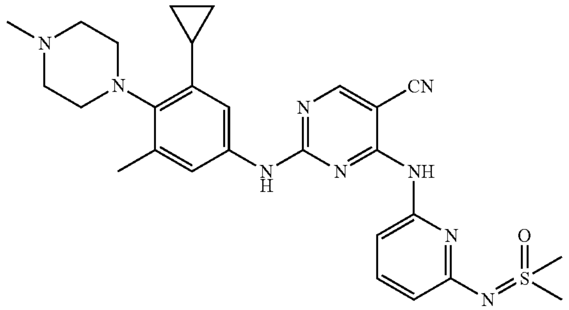
157
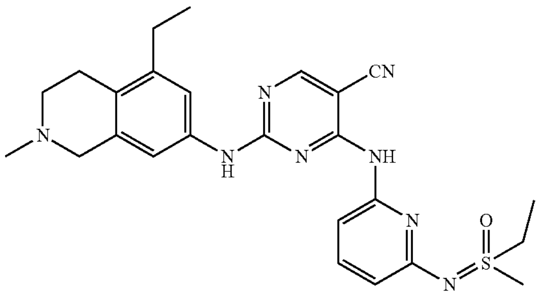

-continued

158

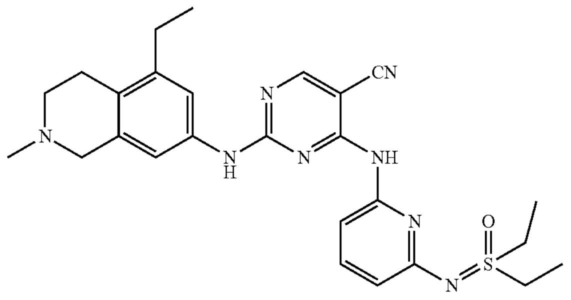

159

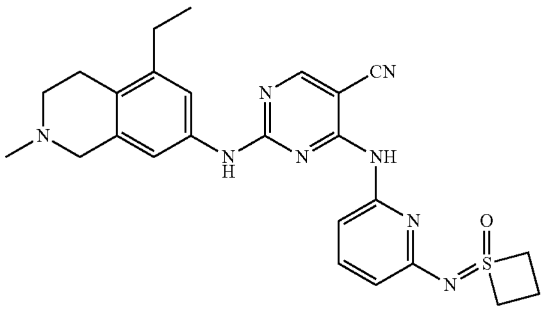

160

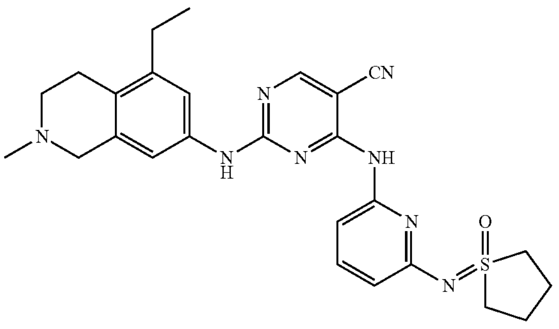

The present invention is further intended to provide a pharmaceutical composition comprising a pharmaceutically acceptable carrier, diluent and/or excipient, and the compound of general formula (1) or the isomer, the crystalline form, the pharmaceutically acceptable salt, the hydrate or the solvate thereof disclosed herein as an active ingredient.

The present invention is still further intended to provide use of the compound of general formula (1) or the isomer, the crystalline form, the pharmaceutically acceptable salt, the hydrate or the solvate thereof disclosed herein, or the above pharmaceutical composition in preparing a medicament for treating, regulating, or preventing a disease related to Wee-1 protein kinase.

The present invention is even further intended to provide a method for treating, regulating, or preventing a disease related to Wee-1 protein kinase, comprising: administering to a subject a therapeutically effective amount of the compound of general formula (1) or the isomer, the crystalline form, the pharmaceutically acceptable salt, the hydrate or the solvate disclosed herein, or the above pharmaceutical composition.

Through synthesis and careful studies of various classes of novel compounds with Wee-1 protein kinase inhibitory effects, the inventors have discovered that the compound of general formula (1) has surprisingly strong Wee-1 protein kinase inhibitory activity.

It should be understood that both the above general description and the following detailed description of the present invention are exemplary and explanatory, and are intended to provide further explanation of the present invention claimed.

Synthesis of Compound

Methods for preparing the compound of general formula (1) disclosed herein are specifically described below, which, however, are not intended to limit the present invention in any way. The compound of general formula (1) described above may be synthesized using standard synthetic techniques or well-known techniques in combination with the methods described herein. In addition, solvents, temperatures, and other reaction conditions mentioned herein may vary. Starting materials for the synthesis of the compounds may be obtained synthetically or commercially. The compounds described herein and other related compounds having various substituents may be synthesized using well-known techniques and starting materials, including the methods found in March, Advanced Organic Chemistry, 4th Ed., (Wiley 1992); Carey and Sundberg, Advanced Organic Chemistry, 4th Ed., Vols. A and B (Plenum 2000, 2001); and Green and Wuts, Protective Groups in Organic Synthesis, 3rd Ed., (Wiley 1999). General methods for preparing a compound can be changed by using appropriate reagents and conditions for introducing different groups into the formulas provided herein.

In one aspect, the compounds described herein are prepared according to methods well known in the art. However, the conditions involved in the methods, such as reactants, solvent, base, amount of the compound used, reaction temperature, and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention further provides a method for preparing the compound of general formula (1), wherein the compound of general formula (1) may be prepared by the following general reaction scheme 1, 2, 3, or 4:

General Reaction Scheme 1

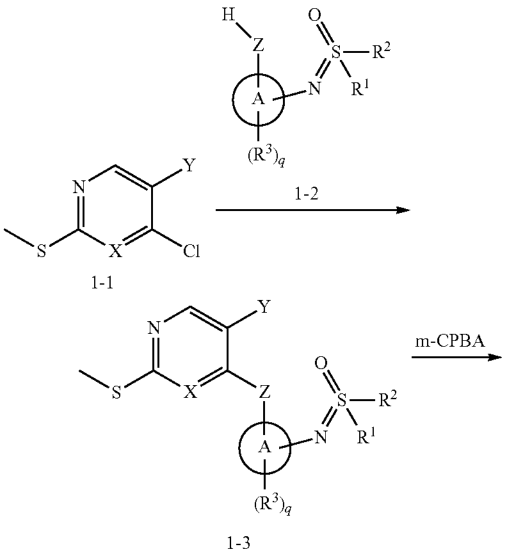

-continued

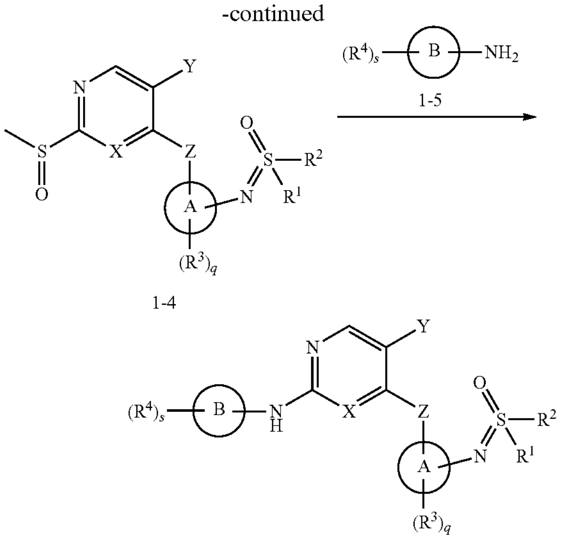

1-4

1-6

Embodiments of the compound of the general formula (1) may be prepared according to general reaction scheme 1, wherein $R^1$, $R^2$, $R^3$, $R^4$, X, Y, Z, s, q, and rings A and B are as defined above, H represents hydrogen, N represents nitrogen, Cl represents chlorine, S represents sulfur, and O represents oxygen. As shown in general reaction scheme 1, compounds 1-1 and 1-2 are subjected to a substitution reaction under alkaline conditions to generate compound 1-3, compound 1-3 reacts with m-CPBA to generate compound 1-4, and compounds 1-4 and 1-5 are subjected to a substitution reaction to generate target compound 1-6.

General Reaction Scheme 2

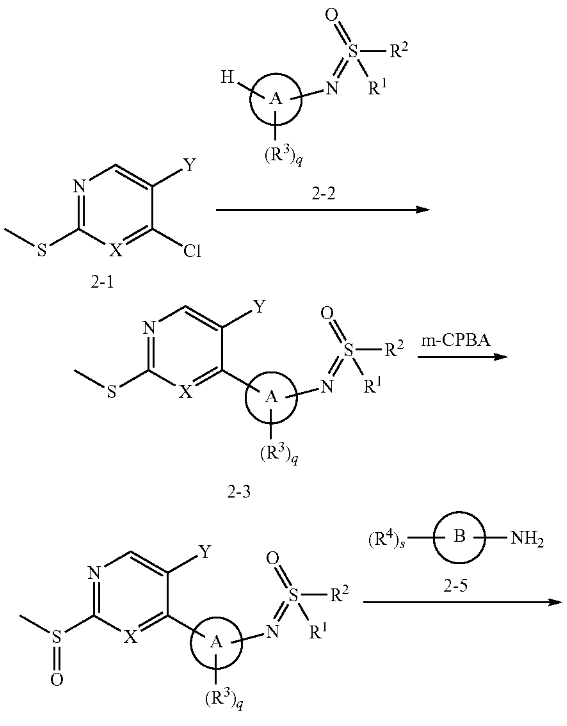

2-1

2-3

2-4

-continued

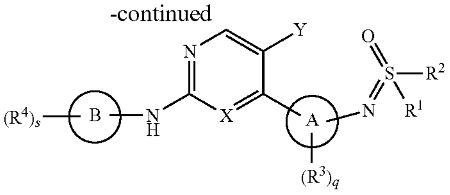

2-6

Embodiments of the compound of the general formula (1) may be prepared according to general reaction scheme 2, wherein $R^1$, $R^2$, $R^3$, $R^4$, X, Y, s, q, and rings A and B are as defined above, H represents hydrogen, N represents nitrogen, Cl represents chlorine, S represents sulfur, and O represents oxygen. As shown in general reaction scheme 2, compounds 2-1 and 2-2 are subjected to a substitution reaction under alkaline conditions to generate compound 2-3, compound 2-3 reacts with m-CPBA to generate compound 2-4, and compounds 2-4 and 2-5 are subjected to a substitution reaction to generate target compound 2-6.

General Reaction Scheme 3

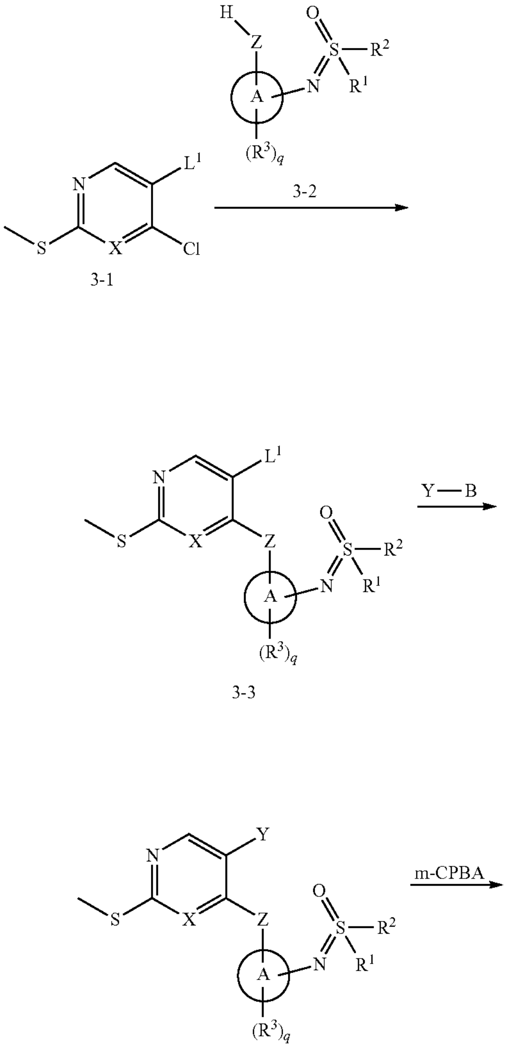

3-1

3-3

3-4

-continued

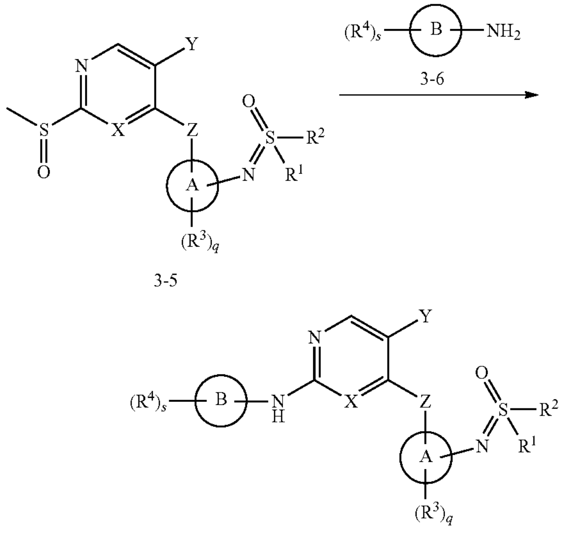

3-7

Embodiments of the compound of the general formula (1) may be prepared according to general reaction scheme 3, wherein $R^1$, $R^2$, $R^3$, $R^4$, X, Y, Z, s, q, and rings A and B are as defined above, H represents hydrogen, N represents nitrogen, Cl represents chlorine, S represents sulfur, O represents oxygen, B represents boronic acid, a boronic ester or a trifluoroborate, and $L^1$ represents bromine or iodine. As shown in general reaction scheme 3, compounds 3-1 and 3-2 are subjected to a substitution reaction under alkaline conditions to generate compound 3-3, compounds 3-3 and Y—B are subjected to a coupling reaction to generate target compound 3-4, compound 3-4 reacts with m-CPBA to generate compound 3-5, and compounds 3-5 and 3-6 are subjected to a substitution reaction to generate target compound 3-7.

General Reaction Scheme 4

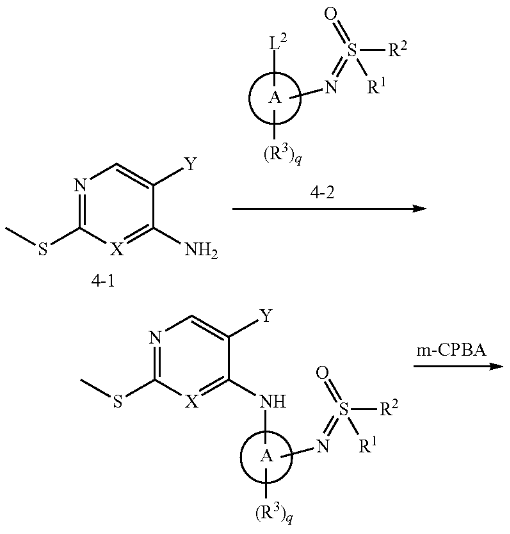

4-3

-continued

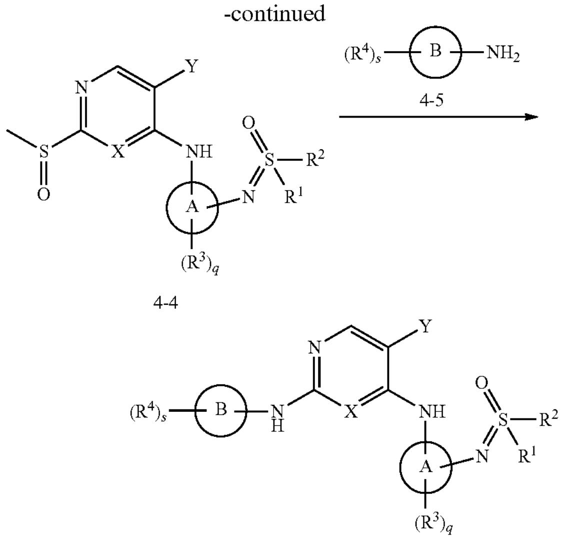

4-6

Embodiments of the compound of the general formula (1) may be prepared according to general reaction scheme 4, wherein $R^1$, $R^2$, $R^3$, $R^4$, X, Y, s, q, and rings A and B are as defined above, H represents hydrogen, N represents nitrogen, Cl represents chlorine, S represents sulfur, O represents oxygen, and $L^2$ represents bromine or chlorine. As shown in general reaction scheme 4, compounds 4-1 and 4-2 are subjected to a substitution reaction under alkaline conditions to generate compound 4-3, compound 4-3 reacts with m-CPBA to generate compound 4-4, and compounds 4-4 and 4-5 are subjected to a substitution reaction to generate target compound 4-6.

Further Forms of Compounds

"Pharmaceutically acceptable" herein refers to a substance, such as a carrier or diluent, that will not lead to loss of biological activity or properties in a compound and is relatively non-toxic. For example, when an individual is given a substance, such substance will not cause undesired biological effects or interact with any component contained therein in a deleterious manner.

The term "pharmaceutically acceptable salt" refers to a form of a compound that does not cause significant irritation to the organism receiving the administration or eliminate the biological activity and properties of the compound. In certain specific aspects, the pharmaceutically acceptable salt is obtained by subjecting the compound of general formula (1) to a reaction with acids, e.g., inorganic acids such as hydrochloric acid, hydrobromic acid, hydrofluoric acid, sulfuric acid, phosphoric acid, nitric acid, phosphoric acid and the like, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluenesulfonic acid and the like, and acidic amino acids such as aspartic acid, glutamic acid and the like.

It should be understood that references to pharmaceutically acceptable salts include solvent addition forms or crystalline forms, especially solvates or polymorphs. A solvate contains either stoichiometric or non-stoichiometric amount of solvent and is selectively formed during crystallization in a pharmaceutically acceptable solvent such as water and ethanol. Hydrates are formed when the solvent is water, or alcoholates are formed when the solvent is ethanol. The solvates of the compound of general formula (1) are conveniently prepared or formed according to methods described herein. For example, hydrates of the compound of general formula (1) are conveniently prepared by recrystallization in a mixed solvent of water/organic solvent, wherein the organic solvent used includes, but is not limited to, tetrahydrofuran, acetone, ethanol, or methanol. Furthermore, the compounds described herein may be present in either a non-solvated form or a solvated form. In general, the solvated forms are considered equivalent to the non-solvated forms for purposes of the compounds and methods provided herein.

In other specific examples, the compound of general formula (1) is prepared in different forms including, but not limited to, amorphous, pulverized, and nanoparticle forms. In addition, the compound of general formula (1) includes crystalline forms, but may also be polymorphs. Polymorphs include different lattice arrangements of the same elements of a compound. Polymorphs generally have different X-ray diffraction spectra, infrared spectra, melting points, density, hardness, crystalline forms, optical and electrical properties, stability, and solubility. Different factors such as recrystallization solvent, crystallization rate, and storage temperature may lead to a single dominant crystalline form.

In another aspect, the compound of general formula (1) may have a chiral center and/or axial chirality, and thus may be present in the form of a racemate, a racemic mixture, a single enantiomer, a diastereomeric compound, a single diastereomer, and a cis-trans isomer. Each chiral center or axial chirality will independently produce two optical isomers, and all possible optical isomers, diastereomeric mixtures, and pure or partially pure compounds are included within the scope of the present invention. The present invention is meant to include all such isomeric forms of these compounds.

The compound of the present invention may contain unnatural proportions of atomic isotopes at one or more of the atoms that constitute the compound. For example, the compound may be labeled with radioactive isotopes, such as tritium ($^3H$), iodine-125 ($^{125}I$), and C-14 ($^{14}C$). For another example, deuterium can be used to substitute a hydrogen atom to form a deuterated compound. The bond formed by deuterium and carbon is stronger than that formed by common hydrogen and carbon, and compared with an undeuterated medicament, the deuterated medicament generally has the advantages of reduced adverse effects, increased medicament stability, enhanced efficacy, prolonged in vivo half-life, and the like. All isotopic variations of the compound of the present invention, whether radioactive or not, are intended to be encompassed within the scope of the present invention.

Terminology

Unless otherwise stated, the terms used in the present application, including those in the specification and claims, are defined as follows. It must be noted that in the specification and the appended claims, the singular forms "a" and "an" include plural meanings unless clearly indicated otherwise. Unless otherwise stated, conventional methods for mass spectrometry, nuclear magnetic resonance spectroscopy, HPLC, protein chemistry, biochemistry, recombinant DNA techniques, and pharmacology are used. As used herein, "or" or "and" refers to "and/or" unless otherwise stated.

Unless otherwise specified, "alkyl" refers to a saturated aliphatic hydrocarbon group, including linear and branched groups containing 1 to 6 carbon atoms. Lower alkyls containing 1 to 4 carbon atoms, such as methyl, ethyl, propyl, 2-propyl, n-butyl, isobutyl, or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, $CF_3(CH_3)CH$, $^iPr$, $^nPr$, $^iBu$, $^nBu$, and $^tBu$.

Unless otherwise specified, "alkenyl" refers to an unsaturated aliphatic hydrocarbon group containing carbon-carbon double bonds, including linear or branched groups containing 1 to 14 carbon atoms. Lower alkenyls containing 1 to 4 carbon atoms, such as vinyl, 1-propenyl, 1-butenyl, or 2-methylpropenyl, are preferred.

Unless otherwise specified, "alkynyl" refers to an unsaturated aliphatic hydrocarbon group containing carbon-carbon triple bonds, including linear and branched groups containing 1 to 14 carbon atoms. Lower alkynyls containing 1 to 4 carbon atoms, such as ethynyl, 1-propynyl, or 1-butynyl, are preferred.

Unless otherwise specified, "cycloalkyl" refers to a non-aromatic hydrocarbon ring system (monocyclic, bicyclic, or polycyclic), and partially unsaturated cycloalkyl may be referred to as "cycloalkenyl" if the carbocyclic ring contains at least one double bond, or "cycloalkynyl" if the carbocyclic ring contains at least one triple bond. The cycloalkyl may include monocyclic or polycyclic groups and spiro rings (e.g., having 2, 3, or 4 fused rings). In some embodiments, the cycloalkyl is monocyclic. In some embodiments, the cycloalkyl is monocyclic or bicyclic.

The ring carbon atoms of the cycloalkyl may optionally be oxidized to form an oxo or sulfido group. The cycloalkyl further includes cycloalkylene. In some embodiments, the cycloalkyl contains 0, 1, or 2 double bonds. In some embodiments, the cycloalkyl contains 1 or 2 double bonds (partially unsaturated cycloalkyl). In some embodiments, the cycloalkyl may be fused to aryl, heteroaryl, cycloalkyl, and heterocycloalkyl. In some embodiments, the cycloalkyl may be fused to aryl, cycloalkyl, and heterocycloalkyl. In some embodiments, the cycloalkyl may be fused to aryl and heterocycloalkyl. In some embodiments, the cycloalkyl may be fused to aryl and cycloalkyl. Examples of cycloalkyl include cyclopropyl, cyclobutyl, cyclopentyl, cyclohexyl, cycloheptyl, cyclopentenyl, cyclohexenyl, cyclohexadienyl, cycloheptatrienyl, norcamphanyl, norpinanyl, norcarnyl, bicyclo[1.1.1]pentyl, bicyclo[2.1.1]hexyl, and the like.

Unless otherwise specified, "alkoxy" refers to an alkyl group that bonds to the rest of the molecule through an ether oxygen atom. Representative alkoxy groups are those having 1-6 carbon atoms, such as methoxy, ethoxy, propoxy, isopropoxy, butoxy, isobutoxy, sec-butoxy, and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^{i-}PrO$, $^{n-}PrO$, $^{i-}BuO$, $^{n-}BuO$, and $^{t-}BuO$.

Unless otherwise specified, "aryl" refers to an aromatic hydrocarbon group, which is monocyclic or polycyclic; for example, a monocyclic aryl ring may be fused to one or more carbocyclic aromatic groups. Examples of aryl include, but are not limited to, phenyl, naphthyl, and phenanthryl.

Unless otherwise specified, "aryloxy" refers to an aryl group that bonds to the rest of the molecule through an ether oxygen atom. Examples of the aryloxy include, but are not limited to, phenoxy and naphthoxy.

Unless otherwise specified, "arylene" refers to a divalent aryl defined as above. Examples of arylene include, but are not limited to, phenylene, naphthylene, and phenanthrylene.

Unless otherwise specified, "heteroaryl" refers to an aromatic group containing one or more heteroatoms (O, S, or N), and the "heteroaryl" is monocyclic or polycyclic. For example, a monocyclic heteroaryl ring is fused to one or more carbocyclic aromatic groups or other monocyclic heterocycloalkyl groups. Examples of heteroaryl include, but are not limited to, pyridyl, pyridazinyl, imidazolyl, pyrimidinyl, pyrazolyl, triazolyl, pyrazinyl, quinolinyl, isoquinolinyl, furanyl, thienyl, isoxazolyl, thiazolyl, oxazolyl, isothiazolyl, pyrrolyl, indolyl, benzimidazolyl, benzofuranyl, benzothiazolyl, benzothienyl, benzoxazolyl, benzopyridyl, pyrrolopyrimidinyl, 1H-pyrrolo[3,2-b]pyridyl, 1H-pyrrolo[2,3-c]pyridyl, 1H-pyrrolo[3,2-c]pyridyl, 1H-pyrrolo[2,3-b]pyridyl,

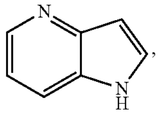,
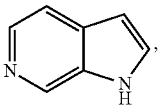,
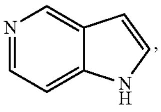, and
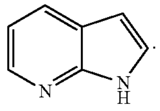.

Unless otherwise specified, "heteroarylene" refers to a divalent heteroaryl defined as above.

Unless otherwise specified, "heterocycloalkyl" refers to a non-aromatic ring or ring system, which may optionally contain one or more alkenylene as part of the ring structure, having at least one heteroatom ring member independently selected from boron, phosphorus, nitrogen, sulfur, oxygen, and phosphorus. Partially unsaturated heterocycloalkyl may be referred to as "heterocycloalkenyl" if the heterocycloalkyl contains at least one double bond, or "heterocycloalkynyl" if the heterocycloalkyl contains at least one triple bond. The heterocycloalkyl may include monocyclic, bicyclic, spiro ring, or polycyclic systems (e.g., having two fused or bridged rings). In some embodiments, the heterocycloalkyl is a monocyclic group having 1, 2, or 3 heteroatoms independently selected from nitrogen, sulfur, and oxygen. The ring carbon atoms and heteroatoms of the heterocycloalkyl may optionally be oxidized to form oxo or sulfido groups or other oxidized bonds (e.g., C(O), S(O), C(S) or $S(O)_2$, N-oxides, etc.), or the nitrogen atoms may be quaternized. The heterocycloalkyl may be attached via a ring carbon atom or a ring heteroatom. In some embodiments, the heterocycloalkyl contains 0 to 3 double bonds. In some embodiments, the heterocycloalkyl contains 0 to 2 double bonds. Also included in the definition of heterocycloalkyl are moieties having one or more aromatic rings fused to (i.e., sharing a bond with) the heterocycloalkyl ring, for example, benzo-derivatives of piperidine, morpholine, azepin, thienyl, or the like. Heterocycloalkyl containing a fused aromatic ring may be attached via any ring atom, including ring atoms of the fused aromatic ring. Examples of heterocycloalkyl include, but are not limited to, azetidinyl, azepinyl, dihydrobenzofuranyl, dihydrofuranyl, dihydropyranyl, N-morpholinyl, 3-oxa-9-azaspiro[5.5]undecyl, 1-oxa-8-azaspiro[4.5]decyl, piperidinyl, piperazinyl, oxopiperazinyl, pyranyl, pyrrolidinyl, quininyl, tetrahydrofuranyl, tetrahydropyranyl, 1,2,3,4-tetrahydroquinolinyl, tropanyl, 4,5,6,7-tetrahydrothiazolo[5,4-c]pyridinyl, 4,5,6,7-tetrahydro-1H-imidazo[4,5-c]pyridine, N-methylpiperidinyl, tetrahydroimidazolyl, pyrazolidinyl, butyrolactam, valerolactam, imidazolidinonyl, hydantoinyl, dioxolanyl, phthalimidyl, pyrimidine-2,4(1H,3H)-dione, 1,4-dioxanyl, morpholinyl, thiomorpholinyl, thiomorpholinyl-S-oxide, thiomorpholinyl-S,S-oxide, piperazinyl, pyranyl, pyridonyl, 3-pyrrolinyl, thiopyranyl, pyronyl, tetrahydrothienyl, 2-azaspiro[3.3]heptanyl, indolinyl,

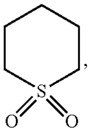,
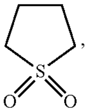,
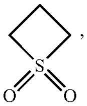,
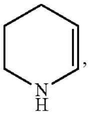,
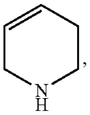,
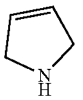, and
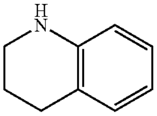.

Unless otherwise specified, "heterocycloalkylene" refers to a divalent heterocycloalkyl as defined above.

Unless otherwise specified, "halogen" (or halo) refers to fluorine, chlorine, bromine, or iodine.

The term "halo" (or "halogenated") before a group name indicates that the group is partially or fully halogenated, that is, substituted in any combination with F, Cl, Br, or I, preferably with F or Cl.

"Optional" or "optionally" means that the subsequently described event or circumstance may, but does not necessarily, occur, and the description includes instances where the event or circumstance occurs and instances where it does not.

The substituent "$—O—CH_2—O—$" means that two oxygen atoms in the substituent are linked to two adjacent carbon atoms in the heterocycloalkyl, aryl, or heteroaryl, for example:

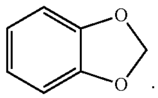.

When the number of a linker group is 0, such as $—(CH_2)_0—$, it means that the linker group is a single bond.

When one of the variables is selected from a chemical bond, it means that the two groups linked by this variable are linked directly. For example, when L in X-L-Y represents a chemical bond, it means that the structure is actually X-Y The term "-membered ring" includes any cyclic structure. The term "membered" refers to the number of backbone atoms that form a ring. For example, cyclohexyl, pyridyl, pyranyl, and thiopyranyl are six-membered rings, and cyclopentyl, pyrrolyl, furanyl, and thienyl are five-membered rings.

The term "moiety" refers to a specific portion or functional group of a molecule. Chemical moiety is generally considered to be a chemical entity contained in or attached to a molecule. Unless otherwise stated, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) or a straight dashed bond ( ). Unless otherwise stated, a single bond or a double bond is represented by .

Specific Pharmaceutical and Medical Terminology

The term "acceptable", as used herein, means that a formulation component or an active ingredient does not unduly adversely affect a general therapeutic target's health.

The terms "treatment," "treatment course," and "therapy", as used herein, include alleviating, inhibiting, or ameliorating a symptom or condition of a disease; inhibiting the development of complications; ameliorating or preventing underlying metabolic syndrome; inhibiting the development of a disease or symptom, e.g., controlling the progression of a disease or condition; alleviating a disease or symptom; leading to disease or symptom regression; and alleviating a complication caused by a disease or symptom, or preventing or treating a sign caused by a disease or symptom. As used herein, a compound or pharmaceutical composition, when administered, can ameliorate a disease, symptom, or condition, which particularly refers to ameliorating the severity, delaying the onset, slowing the progression, or reducing the duration of the disease. Fixed or temporary administration, or continuous or intermittent administration, may be attributed to or associated with the administration.

The "active ingredient" refers to the compound of general formula (1), and pharmaceutically acceptable inorganic or organic salts of the compound of general formula (1). The compounds of the present invention may contain one or more asymmetric centers (chiral center or axial chirality) and thus occur in the form of a racemate, racemic mixture, single enantiomer, diastereomeric compound, and single diastereomer. Asymmetric centers that may be present depend on the nature of the various substituents on the molecule. Each of these asymmetric centers will independently produce two optical isomers, and all possible optical isomers, diastereomeric mixtures, and pure or partially pure compounds are included within the scope of the present invention. The present invention is meant to include all such isomeric forms of these compounds.

The terms such as "compound", "composition", "agent", or "medicine or medicament" are used interchangeably herein and all refer to a compound or composition that, when administered to an individual (human or animal), is capable of inducing a desired pharmacological and/or physiological response by local and/or systemic action.

The term "administered, administering, or administration" refers herein to the direct administration of the compound or composition, or the administration of a prodrug, derivative, analog, or the like of the active compound.

Although the numerical ranges and parameters defining the broad scope of the present invention are approximations, the related numerical values set forth in the specific examples have been present herein as precisely as possible. Any numerical value, however, inherently contains a standard deviation necessarily resulting from certain methods of testing. Herein, "about" generally means that the actual value is within a particular value or range±10%, 5%, 1%, or 0.5%. Alternatively, the term "about" indicates that the actual numerical value falls within the acceptable standard error of a mean, as considered by those skilled in the art. All ranges, quantities, numerical values, and percentages used herein (e.g., to describe an amount of a material, a length of time, a temperature, an operating condition, a quantitative ratio, and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At the very least, these numerical parameters should be understood as the significant digits indicated or the numerical value obtained using conventional rounding rules.

Unless otherwise defined in the specification, the scientific and technical terms used herein have the same meaning as commonly understood by those skilled in the art. Furthermore, nouns in their singular forms used in the specification encompass their plural forms, unless contradicted by context; nouns in their plural forms used also encompass their singular forms.

Therapeutic Use

The present invention provides use of the compound of general formula (1) or the pharmaceutical composition of the present invention in inhibiting Weel kinase and, therefore, use in treating one or more disorders associated with Wee 1 kinase activity. Therefore, in certain embodiments, the present invention provides a method for treating Weel kinase-mediated disorders, which comprises the step of administering to a patient in need the compound disclosed herein or the pharmaceutically acceptable composition thereof.

In some embodiments, a method for treating cancer is provided, comprising administering to an individual in need an effective amount of any aforementioned pharmaceutical composition comprising the compound of structural general formula (1). In some embodiments, the compound of general formula (1) may be used in combination with an additional anti-cancer drug. In some embodiments, the compound of general formula (1) may be used in combination with gemcitabine. In some embodiments, the cancer is mediated by Weel kinase. In other embodiments, the cancer is a hematologic cancer and a solid tumor, including, but not limited to, hematologic malignancies (leukemias, lymphomas, and myelomas including multiple myeloma, myelodysplastic syndrome and myeloproliferative family syndrome), and solid tumors (carcinomas such as prostate, breast, lung, colon, pancreas, kidney, ovary and soft tissue cancers, osteosarcoma, and interstitial tumors), and the like.

Route of Administration

The compound and the pharmaceutically acceptable salt thereof disclosed herein can be prepared into various formulations comprising a safe and effective amount of the compound or the pharmaceutically acceptable salt thereof disclosed herein, and a pharmaceutically acceptable excipient or carrier, wherein the "safe and effective amount" means that the amount of the compound is sufficient to significantly improve the condition without causing serious adverse effects. The safe and effective amount of the compound is determined according to the age, condition, course of treatment, and other specific conditions of a treated subject.

The "pharmaceutically acceptable excipient or carrier" refers to one or more compatible solid or liquid fillers or gel substances that are suitable for human use and must be of sufficient purity and sufficiently low toxicity. "Compatible" means that the components of the composition are capable of intermixing with the compound of the present invention and with each other, without significantly diminishing the pharmaceutical efficacy of the compound. Examples of pharmaceutically acceptable excipients or carriers include cellulose and its derivatives (e.g., sodium carboxymethylcellulose, sodium ethylcellulose, or cellulose acetate), gelatin, talc, solid lubricants (e.g., stearic acid or magnesium stearate), calcium sulfate, vegetable oil (e.g., soybean oil, sesame oil, peanut oil, or olive oil), polyols (e.g., propylene glycol, glycerol, mannitol, or sorbitol), emulsifiers (e.g., Tween®), wetting agents (e.g., sodium lauryl sulfate), colorants, flavoring agents, stabilizers, antioxidants, preservatives, pyrogen-free water, etc. When the compound of the present invention is administered, it may be administered orally, rectally, parenterally (intravenously, intramuscularly, or subcutaneously), or topically.

Solid dosage forms for oral administration include capsules, tablets, pills, pulvises, and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol, and silicic acid; (b) binders, such as hydroxymethyl cellulose, alginate, gelatin, polyvinylpyrrolidone, sucrose, and acacia; (c) humectants, such as glycerol; (d) disintegrants, such as agar, calcium carbonate, potato or tapioca starch, alginic acid, certain complex silicates, and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets, and pills, the dosage forms may further comprise buffers.

Solid dosage forms such as tablets, dragees, capsules, pills, and granules can be prepared using coatings and shells such as enteric coatings and other materials well known in the art. They may comprise opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups, and elixirs. In addition to the active compound, the liquid dosage form may comprise inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, peanut oil, corn germ oil, olive oil, castor oil and sesame oil, or mixtures of these substances.

Besides such inert diluents, the composition may further comprise adjuvants, such as wetting agents, emulsifiers, suspending agents, sweeteners, flavoring agents, and perfuming agents. Suspensions, in addition to the active compound, may comprise suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may comprise physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents, or excipients include water, ethanol, polyols, and suitable mixtures thereof.

Dosage forms for topical administration of the compound of the present invention include ointments, pulvises, patches, sprays, and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds. When the pharmaceutical composition is used, a safe and effective amount of the compound of the present invention is administered to a mammal (such as a human) to be treated, wherein the dose is a pharmaceutically effective dose.

For a human of 60 kg, the daily dose of administration is usually 1-2000 mg, preferably 50-1000 mg. In determining a specific dose, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent, or similar purpose. Thus, unless otherwise expressly stated, the features disclosed herein are merely general examples of equivalent or similar features.

DETAILED DESCRIPTION

Various specific aspects, features, and advantages of the compounds, methods, and pharmaceutical compositions described above will be set forth in detail in the following description, which will make the content of the present invention very clear. It should be understood that the detailed description and examples below describe specific embodiments for reference only. After reading the description of the present invention, those skilled in the art can make various changes or modifications to the present invention, and such equivalents also fall within the scope of the present invention defined herein.

In all examples, $^1$H-NMR spectra were recorded with a Vian Mercury 400 nuclear magnetic resonance spectrometer, and chemical shifts are expressed in δ (ppm); silica gel for separation was 200-300 mesh silica gel if not specified, and the ratio of the eluents was volume ratio.

The following abbreviations are used in the present invention: $(Boc)_2O$ for di-tert-butyl dicarbonate; $CDCl_3$ for deuterated chloroform; CSA for camphor-10-sulfonic acid (O); EtOAc for ethyl acetate; Hexane for n-hexane; HPLC for high-performance liquid chromatography; MeCN for acetonitrile; DCE for 1,2-dichloroethane; DCM for dichloromethane; DIPEA for diisopropylethylamine; 1,4-Dioxane for 1,4-dioxane; DMF for N,N-dimethylformamide; DMAP for 4-(dimethylamino)pyridine; DMSO for dimethyl sulfoxide; h for hour; IPA for isopropanol; min for minute; $K_2CO_3$ for potassium carbonate; KOAc for potassium acetate; $K_3PO_4$ for potassium phosphate; min for minute; MeOH for methanol; MS for mass spectrometry; MsOH for methanesulfonic acid; m-CPBA for m-chloroperoxybenzoic acid; n-BuLi for n-butyllithium; NMR for nuclear magnetic resonance; NIS for iodosuccinimide; Pd/C for palladium carbon; $Pd(PPh_3)_4$ for tetrakis(triphenylphosphine)palladium; $Pd_2(dba)_3$ for tris(dibenzylideneacetone)dipalladium(O); PE for petroleum ether; RuPhos Pd $G_3$ for (2-dicyclohexylphosphino-2',6'-diisopropoxy-1,1'-biphenyl)[2-(2'-amino-1,1'-biphenylyl)]palladium(II) methanesulfonate; SEMCl for 2-(trimethylsilyl)ethoxymethyl chloride; TBAB for tetrabutylammonium bromide; TBAB for tetrabutylammonium fluoride; TFA for trifluoroacetic acid; TfOH for trifluoromethanesulfonic acid; $T_3P$ for 1-propylphosphonic anhydride; XantPhos for 4,5-bis(diphenylphosphino)-9,9-dimethylxanthene; TLC for thin-layer chromatography; XPhos for 2-dicyclohexylphosphonium-2',4',6'-triisopropylbiphenyl; LC-MS for liquid chromatography-mass spectrometry; and RT for retention time.

Example 1: Synthesis of Compound 1

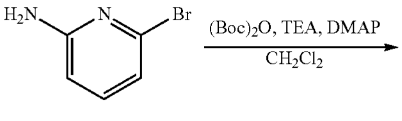

Int_1-1

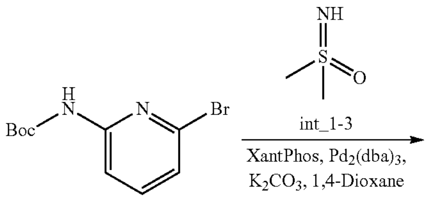

Int_1-2

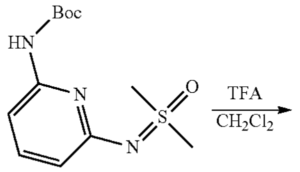

Int_1-4

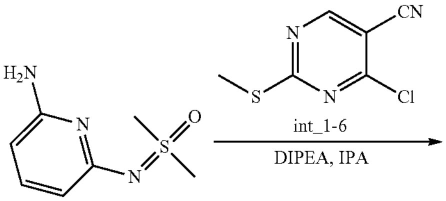

Int_1-5

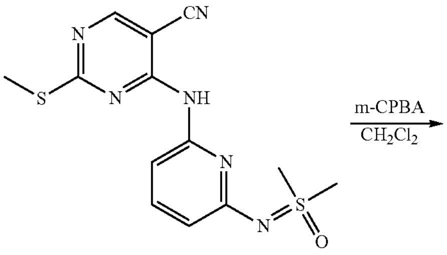

int_1-7

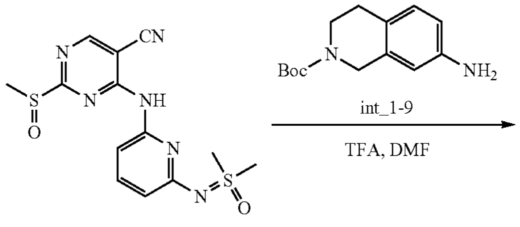

int_1-8

-continued

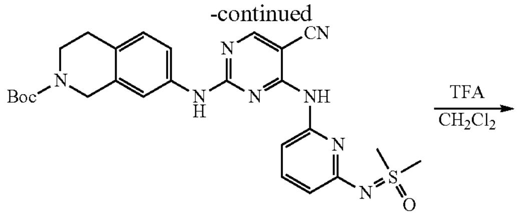

int_1-10

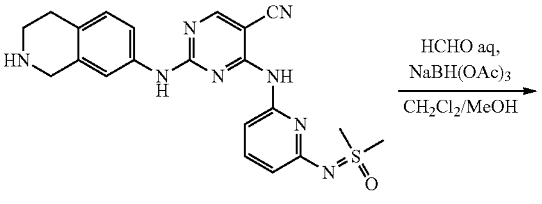

int_1-11

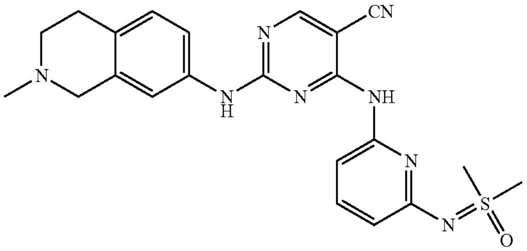

1

Step 1: Synthesis of Compound Int_1-2 int_1-2

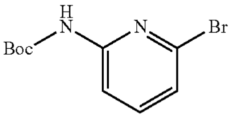

Int_1-1 (3.46 g, 20 mmol) was dissolved in dichloromethane (100 mL), and DIPEA (5.2 g, 40 mmol), DMAP (1.22 g, 10 mmol), and $(Boc)_2O$ (4.8 g, 22 mmol) were added. The mixture was incubated overnight at room temperature for reaction, until LC-MS indicated the completion of the reaction. The reaction mixture was diluted with dichloromethane (100 mL), washed with water (200 mL), washed with 2 N diluted HCl (100 mL), washed with an aqueous sodium bicarbonate solution (100 mL), washed with water (100 mL) and finally washed with a saturated brine (100 mL). The organic phase was dried over anhydrous sodium sulfate, filtered, and distilled at reduced pressure to give a pale brown gel as a crude product (4.0 g, 73% yield). The crude product was used directly in the next reaction.

ESI-MS m/z: 273 $[M+H]^+$.

Step 2: Synthesis of Compound Int_1-4 int_1-4

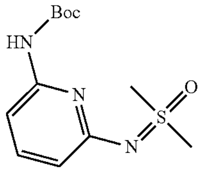

Int_1-2 (4 g, 14.6 mmol), int_1-3 (1.36 g, 14.6 mmol), cesium carbonate (7.14 g, 161 mmol), $Pd_2(dba)_3$ (668 mg, 0.73 mmol), and Xantphos (845 mg, 1.46 mmol) were dissolved in 1,4-dioxane (120 mL), and the mixture was incubated at 85° C. in nitrogen atmosphere overnight, until LC-MS indicated the completion of the reaction. The reaction solution was filtered and distilled at reduced pressure to give a crude product, and the crude product was subjected to column chromatography ($SiO_2$, DCM:MeOH=100:1 to 30:1) to give a pale yellow solid product (2.7 g, 65% yield).

ESI-MS m/z: 286 $[M+H]^+$

Step 3: Synthesis of Compound Int_1-5 int_1-5

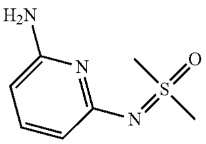

Int_1-4 (2.4 g, 8.41 mmol) was dissolved in dichloromethane (30 mL), and trifluoroacetic acid (10 mL) was added. The mixture was incubated overnight at room temperature for reaction, until LC-MS indicated the completion of the reaction. The reaction solution was directly concentrated at reduced pressure to give a pale yellow solid (1.6 g, 100% yield). The crude product was used directly in the next reaction.

ESI-MS m/z: 186 $[M+H]^+$

Step 4: Synthesis of Compound Int_1-7 int_1-7

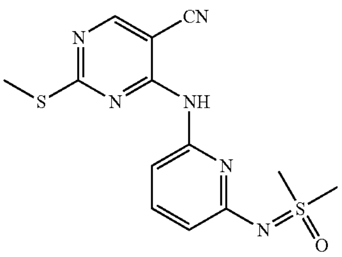

Int_1-6 (2 g, 10.8 mmol) and int_1-5 (3.2 g, 10.8 mmol) were dissolved in isopropanol (5 mL), and DIPEA (5.57 g, 43.1 mmol, 7.51 mL) was added. The reaction solution was heated to 50° C. and incubated overnight, until LC-MS indicated the completion of the reaction. The reaction solution was cooled to room temperature, and a white solid was precipitated and filtered to give a product. The product was dried to give a white solid (1.2 g, 33% yield).

$^1H$ NMR: (400 MHz, DMSO-$d_6$) δ 9.80 (s, 1H), 8.70 (s, 1H), 7.58 (t, J=7.9 Hz, 1H), 7.16 (d, J=7.8 Hz, 1H), 6.44 (d, J=7.9 Hz, 1H), 3.41 (s, 6H), 2.49 (s, 3H) ESI-MS m/z: 335 $[M+H]^+$

Step 5: Synthesis of Compound Int_1-8 int_1-8

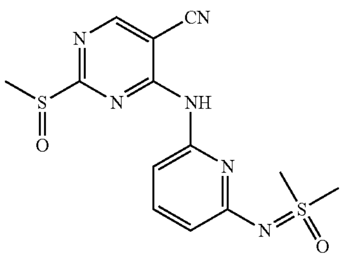

Int_1-7 (334 mg, 1.0 mmol) was dissolved in dichloromethane (40 mL), and m-CPBA (85%, 240 mg, 1.2 mmol) was added at room temperature. The mixture was stirred at room temperature for half an hour, until LC-MS indicated the completion of the reaction. The reaction solution was concentrated at reduced pressure to give a crude product (335 mg). The crude product was used directly in the next reaction.

ESI-MS m/z: 351 $[M+H]^+$

Step 6: Synthesis of Compound Int_1-10 int_1-10

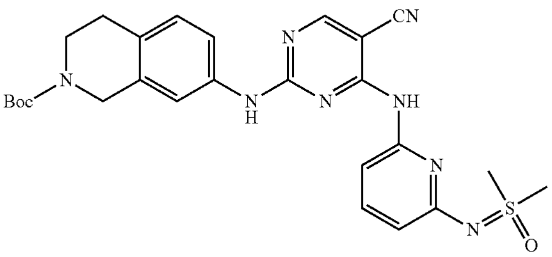

Int_1-8 (335 mg, 0.95 mmol) was dissolved in DMF (20 mL), and int_1-9 (298 mg, 1.2 mmol) and trifluoroacetic acid (115 mg, 1 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by column chromatography ($SiO_2$, DCM: MeOH=100:1 to 30:1) to give a white solid (160 mg, 31% yield).

ESI-MS m/z: 535 $[M+H]^+$

Step 7: Synthesis of Compound Int_1-11

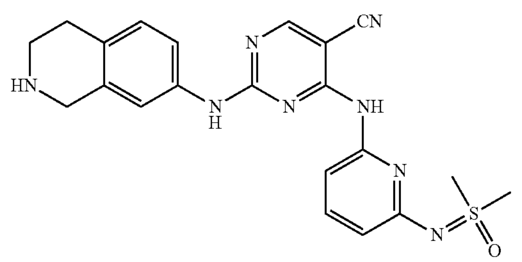

Int_1-10 (800 mg, 1.5 mmol) was dissolved in dichloromethane (80 mL), and trifluoroacetic acid (4.2 g, 37.4 mmol) was added. The mixture was incubated for 1 h at room temperature for reaction, until LC-MS indicated the completion of the reaction. The reaction solution was directly concentrated at reduced pressure to give a yellow solid (800 mg, crude product). The crude product was used directly in the next reaction.

ESI-MS m/z: 435 $[M+H]^+$

Step 8: Synthesis of Compound 1

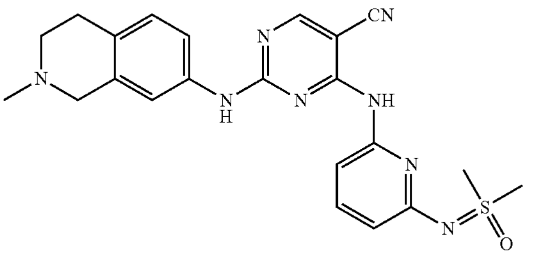

1

Int_1-11 (800 mg, 1.84 mmol) and DIPEA (4.8 g, 37.4 mmol) were dissolved in dichloromethane (10 mL) and methanol (10 mL), and an aqueous formaldehyde solution (37-40%, 1 mL) and sodium borohydride acetate (3.2 g, 15 mmol) were added. The mixture was incubated for 1 h at room temperature for reaction, until LC-MS indicated the completion of the reaction. Water (100 mL) was added to the reaction solution. The aqueous phase was extracted with ethyl acetate (100 mL×3), and the organic phase was dried over anhydrous sodium sulfate. The organic phase was concentrated at reduced pressure to give a crude product, and the crude product was subjected to column chromatography ($SiO_2$, DCM:MeOH=100:1 to 20:1) to give a pale yellow solid product (500 mg, 60% yield).

$^1$H NMR (400 MHz, Chloroform-d) δ 8.33 (s, 1H), 7.65 (d, J=9.3 Hz, 2H), 7.45 (s, 2H), 7.25 (d, J=2.2 Hz, 1H), 7.20-7.13 (m, 1H), 7.06 (d, J=8.2 Hz, 1H), 6.54 (d, J=7.9 Hz, 1H), 3.51 (s, 2H), 3.33 (s, 6H), 2.89 (t, J=6.0 Hz, 2H), 2.67 (t, J=5.9 Hz, 2H), 2.42 (s, 3H).

ESI-MS m/z: 449 $[M+H]^+$

Example 2: Synthesis of Compound 3

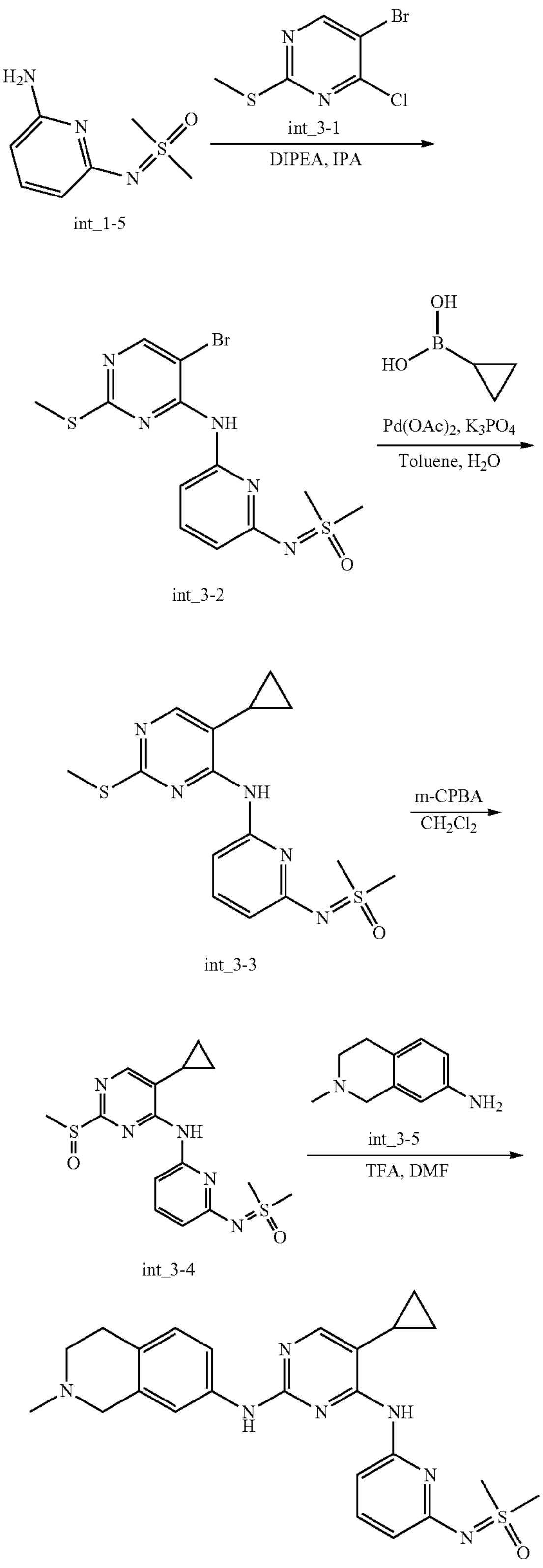

3

Step 1: Synthesis of Compound Int_3-2 int_3-2

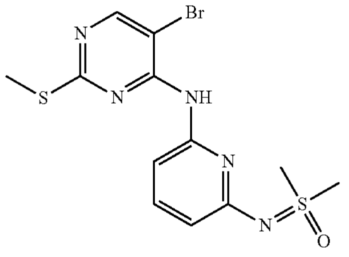

Int_3-1 (2 g, 8.35 mmol) and int_1-5 (1.55 g, 8.35 mmol) were dissolved in isopropanol (5 mL), and DIPEA (4.32 g, 33.4 mmol, 5.83 mL) was added. The reaction solution was heated to 80° C. and incubated overnight, until LC-MS indicated the completion of the reaction. The reaction solution was cooled to room temperature, concentrated by rotary evaporation, and purified by column chromatography to give a pale yellow solid (1.5 g, 46.3% yield).

ESI-MS m/z: 388 $[M+H]^+$

Step 2: Synthesis of Compound Int_3-3 int_3-3

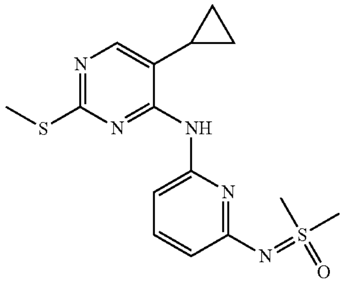

Int_3-2 (100 mg, 0.26 mmol), cyclopropylboronic acid (45 mg, 0.52 mmol), potassium phosphate (166 mg, 0.78 mmol) were dissolved in a mixed solvent of toluene (7.5 mL) and water (0.5 mL). The mixture was purged with argon three times before palladium acetate (7 mg, 0.03 mmol) and tricyclohexylphosphine (17 mg, 0.06 mmol) were added. In argon atmosphere, the mixture was heated to 100° C. and stirred for 16 h, until LC-MS indicated the completion of the reaction. The reaction solution was cooled to room temperature, concentrated by rotary evaporation, and purified by column chromatography to give a pale yellow solid (61 g, 67.1% yield).

ESI-MS m/z: 350 $[M+H]^+$

Step 3: Synthesis of Compound Int_3-4 int_3-4

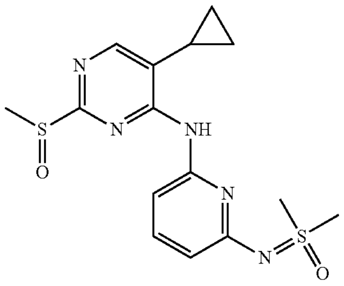

Int_3-3 (500 mg, 1.43 mmol) was dissolved in dichloromethane (40 mL), and m-CPBA (85%, 348.6 mg, 1.72 mmol) was added at room temperature. The mixture was stirred at room temperature for half an hour, until LC-MS indicated the completion of the reaction. The reaction solution was concentrated at reduced pressure to give a crude product (335 mg). The crude product was used directly in the next reaction.

ESI-MS m/z: 366 $[M+H]^+$

Step 4: Synthesis of Compound 3

3

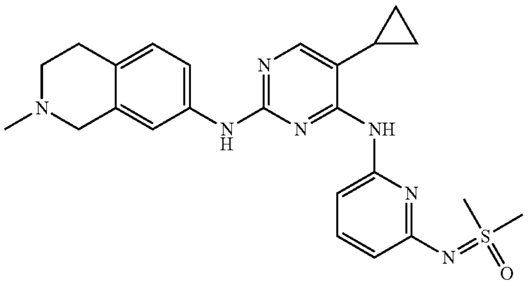

Int_3-4 (100 mg, 0.273 mmol) was dissolved in DMF (5 mL), and int_3-5 (45 mg, 0.28 mmol) and trifluoroacetic acid (456 mg, 4.0 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by reverse-phase preparative chromatography to give a white solid (80 mg, 63% yield).

$^1H$ NMR (400 MHz, Chloroform-d) δ 7.92 (s, 1H), 7.87 (d, J=8.0 Hz, 1H), 7.64 (s, 1H), 7.49 (t, J=7.9 Hz, 1H), 7.33 (d, J=2.2 Hz, 1H), 7.20 (dd, J=8.1, 2.3 Hz, 1H), 7.02 (d, J=8.2 Hz, 1H), 6.89 (s, 1H), 6.51 (d, J=7.8 Hz, 1H), 3.54 (s, 2H), 3.34 (s, 6H), 2.87 (t, J=5.9 Hz, 2H), 2.68 (t, J=5.9 Hz, 2H), 2.43 (s, 3H), 1.57 (td, J=7.9, 4.0 Hz, 1H), 1.04-0.91 (m, 2H), 0.64-0.54 (m, 2H).

ESI-MS m/z: 464 $[M+H]^+$

Example 3: Synthesis of Compound 6

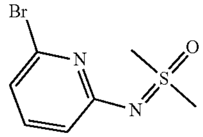

int_6-1

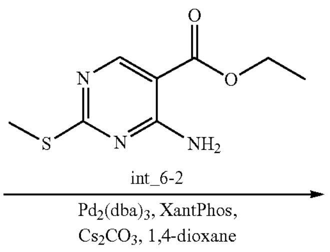

int_6-2

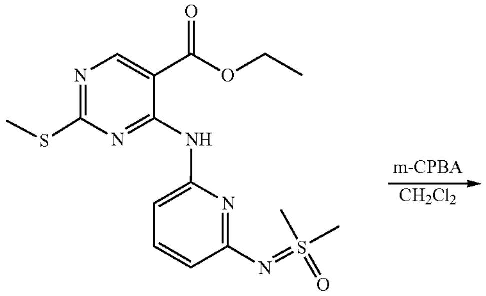

int_6-3

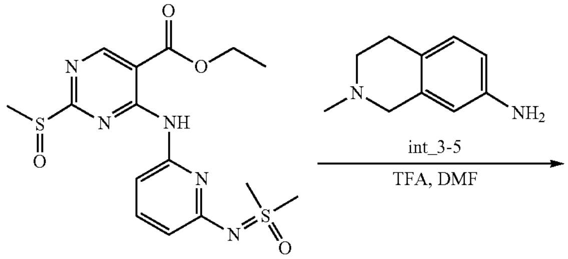

int_3-5 int_6-4

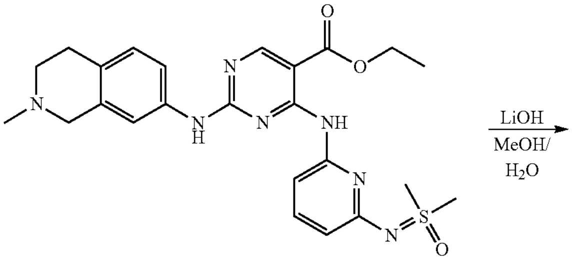

int_6-5

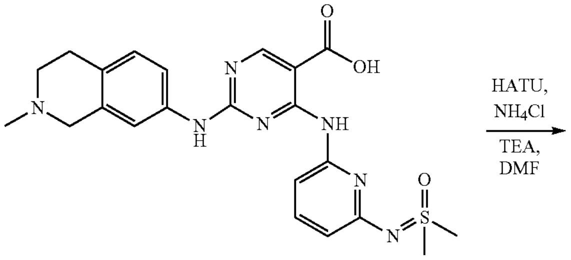

int_6-6

-continued

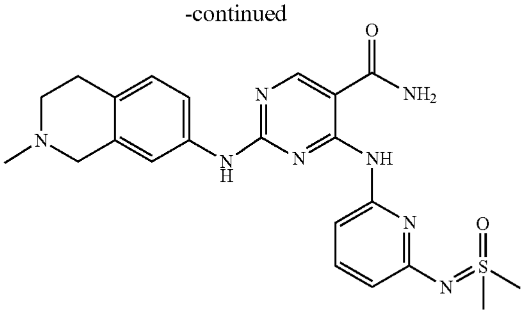

6

Step 1: Synthesis of Compound Int_6-3 int_6-3

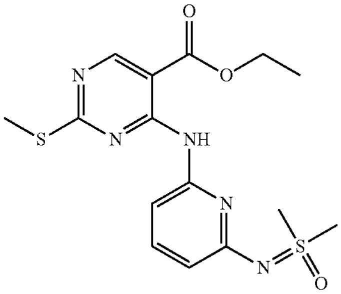

Int_6-1 (1.6 g, 6.4 mmol), int_6-2 (1.37 g, 6.4 mmol), cesium carbonate (4.17 g, 12.8 mmol), $Pd_2(dba)_3$ (586 mg, 0.64 mmol), and Xantphos (741 mg, 1.28 mmol) were dissolved in 1,4-dioxane (100 mL), and the mixture was incubated at 85° C. overnight, until LC-MS indicated the completion of the reaction. The reaction solution was filtered and distilled at reduced pressure to give a crude product, and the crude product was subjected to column chromatography ($SiO_2$, DCM:MeOH=100:1 to 30:1) to give a pale yellow solid product (1.2 g, 49% yield).

ESI-MS m/z: 382 $[M+H]^+$

Step 2: Synthesis of Compound Int_6-4 int_6-4

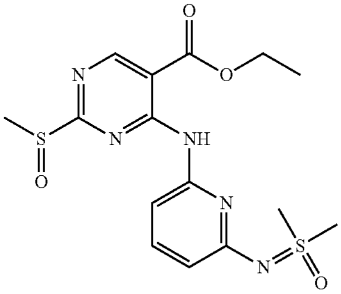

Int_6-4 (1.2 g, 3.15 mmol) was dissolved in dichloromethane (80 mL), and m-CPBA (85%, 893.3 mg, 4.4 mmol) was added at room temperature. The mixture was stirred at room temperature for half an hour, until LC-MS indicated the completion of the reaction. The reaction solution was washed with aqueous sodium bicarbonate (100 mL×2). The aqueous phase was extracted with ethyl acetate (100 mL×3), and the organic phase was dried over anhydrous sodium sulfate. The organic phase was concentrated at reduced pressure to give a crude product (1.1 g). The crude product was used directly in the next reaction.

ESI-MS m/z: 398 $[M+H]^+$

Step 3: Synthesis of Compound Int_6-5 int_6-5

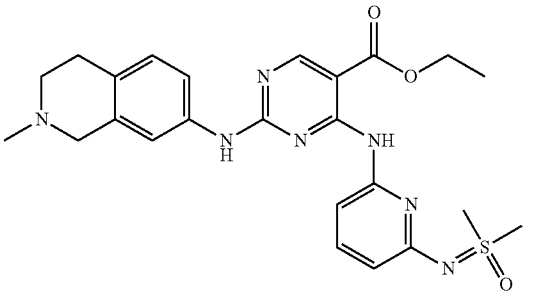

Int_6-4 (1.3 g, 3.15 mmol) was dissolved in DMF (50 mL), and int_3-5 (767.4 mg, 4.73 mmol) and trifluoroacetic acid (718 mg, 6.3 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by preparative column chromatography ($SiO_2$, DCM:MeOH=100:1 to 30:1) to give a white solid (1.1 g, 70% yield).

LC-MS: 496 $[M+H]^+$

Step 4: Synthesis of Compound Int_6-6 int_6-6

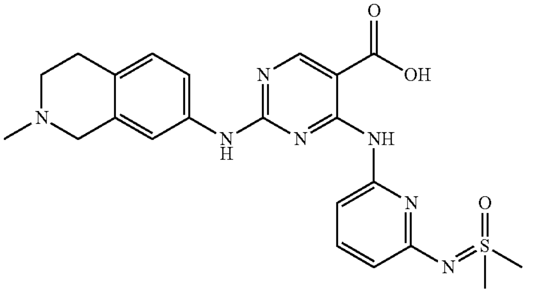

Int_6-5 (580 mg, 1.07 mmol) was dissolved in methanol (50 mL), and lithium hydroxide (675 mg, 16.06 mmol) was added. The mixture was incubated for 5 h at room temperature for reaction, until LC-MS indicated the completion of the reaction. The mixture was adjusted to pH 5-6 with dilute hydrochloric acid and concentrated at reduced pressure to remove the solvent, thus giving a crude product. The crude product was purified by reverse-phase column chromatography to give a yellow powder (500 mg, 91% yield).

ESI-MS m/z: 468 $[M+H]^+$

Step 5: Synthesis of Compound 6

6

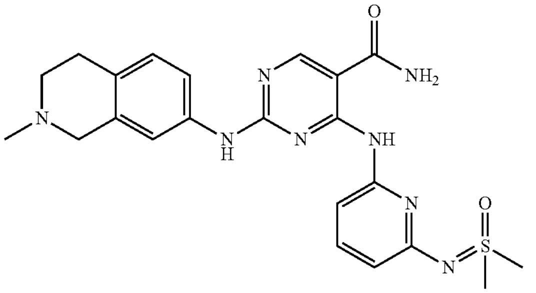

Int_6-6 (93 mg, 0.2 mmol) was dissolved in DMF (10 mL), and ammonium chloride (22 mg, 0.4 mmol), TEA (0.2 mL), and HATU (152 mg, 0.4 mmol) were added. The mixture was stirred overnight at room temperature for reaction, until LC-MS indicated the completion of the reaction. The solvent was removed by concentration at reduced pressure to give a crude product. The crude product was purified by preparative HPLC to give an off-white solid (40 mg, 43% yield).

$^1H$ NMR (400 MHz, DMSO-$d_6$) δ 11.71 (s, 1H), 9.57 (s, 1H), 8.67 (s, 1H), 7.88 (d, J=72.4 Hz, 2H), 7.41 (dd, J=8.7, 5.1 Hz, 2H), 7.30 (s, 2H), 6.99 (d, J=8.3 Hz, 1H), 6.29 (d, J=7.9 Hz, 1H), 3.40 (s, 2H), 3.34 (s, 6H), 2.73 (t, J=5.9 Hz, 2H), 2.56 (t, J=5.9 Hz, 2H), 2.29 (s, 3H).

ESI-MS m/z: 467 $[M+H]^+$

Example 4: Synthesis of Compound 7

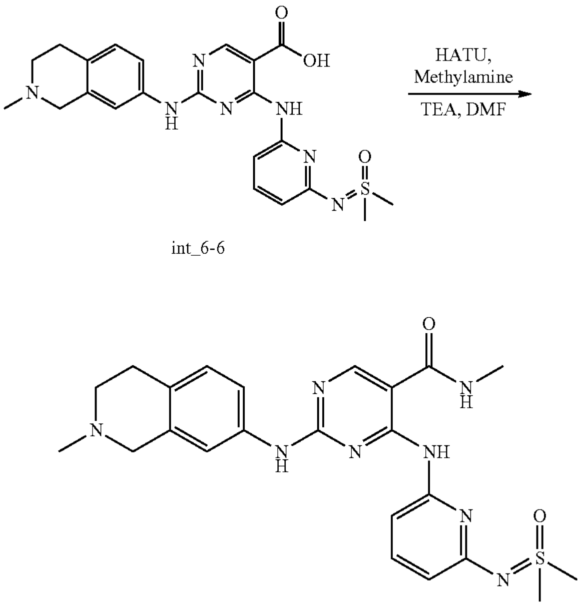

int_6-6

7

Step 1: Synthesis of Compound 7

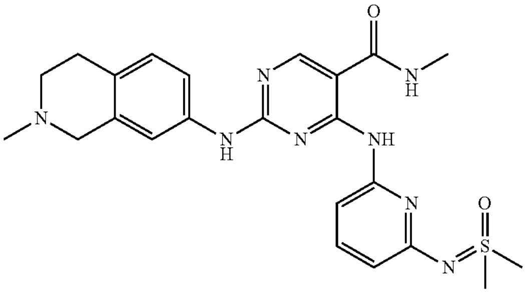

7

Int_6-6 (80 mg, 0.17 mmol) was dissolved in DMF (10 mL), and methylamine hydrochloride (12 mg, 0.17 mmol), TEA (34 mg, 0.34 mmol), and HATU (129 mg, 0.34 mmol) were added.

The mixture was stirred overnight at room temperature for reaction, until LC-MS indicated the completion of the reaction. The solvent was removed by concentration at reduced pressure to give a crude product. The crude product was purified by preparative HPLC to give an off-white solid (8 mg, 7% yield).

$^1$H NMR (400 MHz, Chloroform-d) δ 11.06 (s, 1H), 8.27 (s, 1H), 7.70 (d, J=8.0 Hz, 1H), 7.41 (t, J=8.0 Hz, 1H), 7.30 (d, J=2.2 Hz, 1H), 7.20 (d, J=8.2 Hz, 1H), 7.09-7.01 (m, 2H), 6.47 (dd, J=7.9, 0.8 Hz, 1H), 6.21 (d, J=5.2 Hz, 1H), 3.52 (s, 2H), 3.39 (s, 6H), 2.98 (d, J=4.8 Hz, 3H), 2.88 (t, J=6.0 Hz, 2H), 2.68 (t, J=6.0 Hz, 2H), 2.43 (s, 3H).

ESI-MS m/z: 481 $[M+H]^+$

Example 5: Synthesis of Compound 8

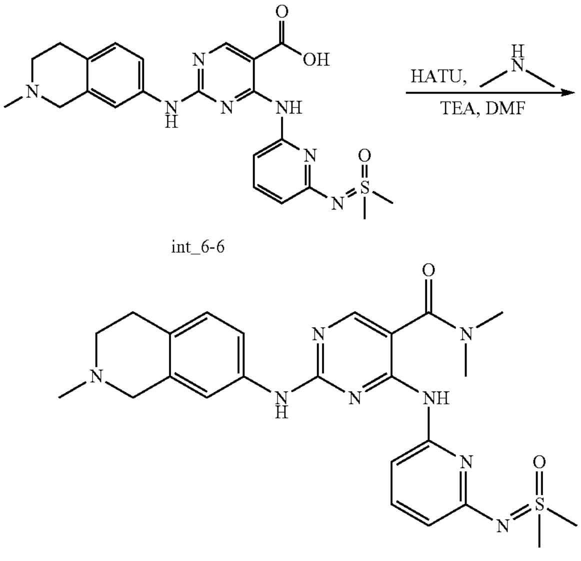

int_6-6

8

Step 1: Synthesis of Compound 8

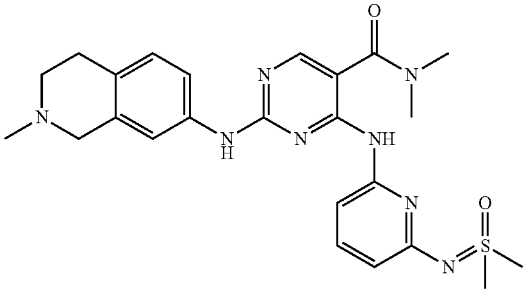

8

Int_6-6 (80 mg, 0.17 mmol) was dissolved in DMF (10 mL), and a solution of dimethylamine in tetrahydrofuran (2.0 M, 0.09 mL, 0.17 mmol), TEA (34 mg, 0.34 mmol), and HATU (129 mg, 0.34 mmol) were added. The mixture was stirred overnight at room temperature for reaction, until LC-MS indicated the completion of the reaction. The solvent was removed by concentration at reduced pressure to give a crude product. The crude product was purified by preparative HPLC to give an off-white solid (61 mg, 56% yield).

$^1$H NMR (400 MHz, Chloroform-d) δ 9.44 (s, 1H), 8.12 (s, 1H), 7.70 (d, J=8.0 Hz, 1H), 7.44 (t, J=7.9 Hz, 1H), 7.32 (d, J=2.3 Hz, 1H), 7.23-7.17 (m, 2H), 7.05 (d, J=8.2 Hz, 1H), 6.47 (d, J=7.8 Hz, 1H), 3.52 (s, 2H), 3.35 (s, 6H), 3.10 (s, 6H), 2.88 (t, J=5.9 Hz, 2H), 2.67 (t, J=5.9 Hz, 2H), 2.42 (s, 3H).

ESI-MS m/z: 495 $[M+H]^+$

Example 6: Synthesis of Compound 9

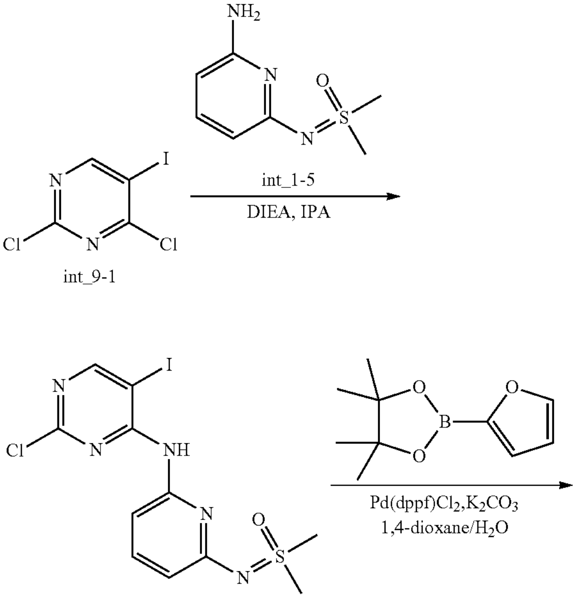

int_9-1 int_9-2

-continued

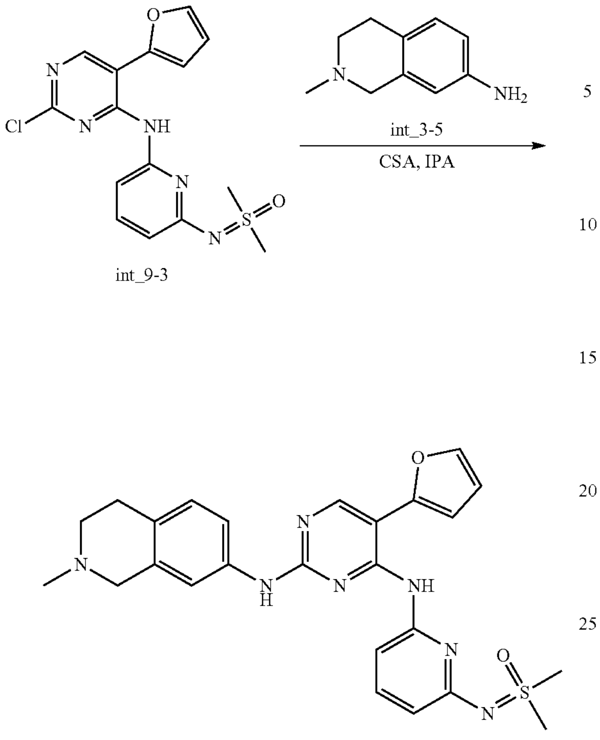

int_9-3

9

Step 1: Synthesis of Compound Int_9-2 int_9-2

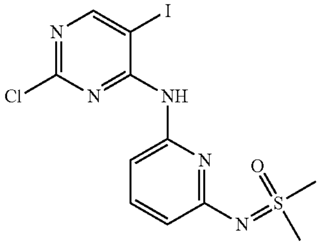

Int_9-1 (1.48 g, 5.4 mmol), int_1-5 (1.0 g, 4 mmol), and DIPEA (2.82 mL, 16.2 mmol) were dissolved in isopropanol (15 mL), and the mixture was heated to 60° C. and stirred overnight, until LC-MS indicated the completion of the reaction. The reaction solution was concentrated by rotary evaporation, and the crude product was purified by reverse-phase preparative HPLC to give a pale yellow solid (300 mg, 13% yield).

ESI-MS m/z: 424 $[M+H]^+$

Step 2: Synthesis of Compound Int_9-3 int_9-3

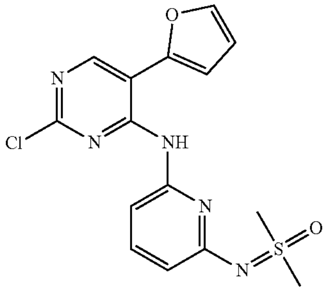

Int_9-2 (84 mg, 0.2 mmol), 2-(furan-2-yl)-4,4,5,5-tetramethyl-1,3,2-dioxolane (46 mg, 0.24 mmol), potassium carbonate (56 mg, 0.4 mmol), and Pd(dppf)$Cl_2$ (14 mg, 0.02 mmol) were dissolved in a mixed solvent of 1,4-dioxane (4 mL) and water (0.4 mL). In argon atmosphere, the mixture was heated to 80° C. and stirred for reaction for 16 h, until LC-MS indicated the completion of the reaction. The reaction solution was concentrated by rotary evaporation, and the crude product was purified by reverse-phase preparative HPLC to give an orange solid (40 mg, 55% yield).

ESI-MS m/z: 364 $[M+H]^+$

Step 3: Synthesis of Compound 9

9

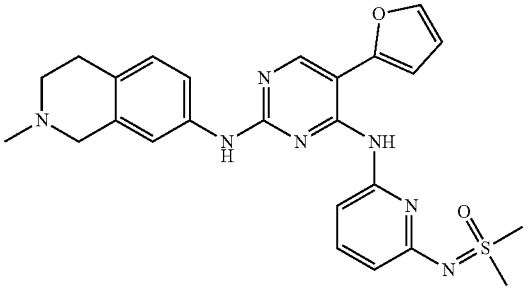

Int_9-2 (40 mg, 0.11 mmol) was dissolved in DMF (50 mL), and int_3-5 (18 mg, 0.11 mmol) and CSA (51 mg, 0.22 mmol) were added. The reaction solution was heated to 80° C. and stirred for 16 h, until LC-MS indicated the completion of the reaction. The reaction solution was cooled to room temperature and concentrated at reduced pressure to give a crude product. The crude product was purified by preparative HPLC to give a white solid (50 mg, 93% yield).

$^1$H NMR (400 MHz, Chloroform-d) δ 8.32 (d, J=21.4 Hz, 2H), 7.79 (d, J=8.0 Hz, 1H), 7.49 (dd, J=16.8, 8.9 Hz, 2H), 7.36 (s, 1H), 7.05 (d, J=9.3 Hz, 2H), 6.51 (s, 3H), 3.57 (d, J=9.5 Hz, 2H), 3.34 (d, J=6.9 Hz, 6H), 2.91 (t, J=5.9 Hz, 2H), 2.73 (t, J=5.8 Hz, 3H), 2.47 (s, 4H).

ESI-MS m/z: 490 $[M+H]^+$

Example 7: Synthesis of Compound 11

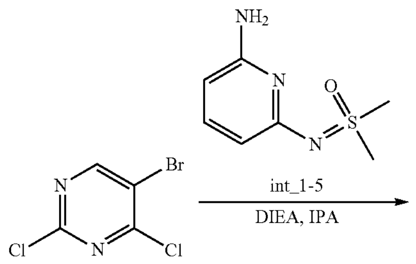

int_11-1

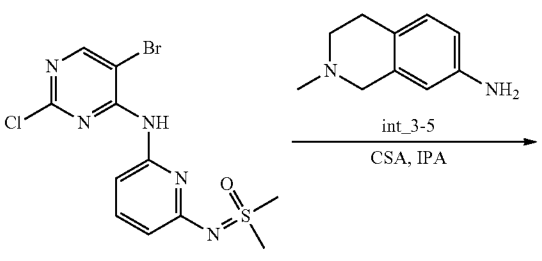

int_11-2

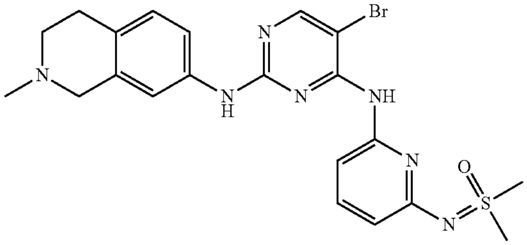

11

Step 1: Synthesis of Compound Int_11-2 int_11-2

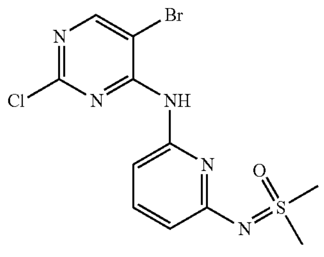

Int_11-1 (1.45 g, 6.4 mmol), int_1-5 (1.3 g, 7 mmol), and DIPEA (2.82 mL, 16.2 mmol) were dissolved in isopropanol (30 mL), and the mixture was heated to 80° C. and stirred overnight, until LC-MS indicated the completion of the reaction. The reaction solution was concentrated by rotary evaporation, and the crude product was purified by reverse-phase preparative HPLC to give a pale yellow solid (1.7 g, 71% yield).

ESI-MS m/z: 376 $[M+H]^+$

Step 2: Synthesis of Compound 11

11

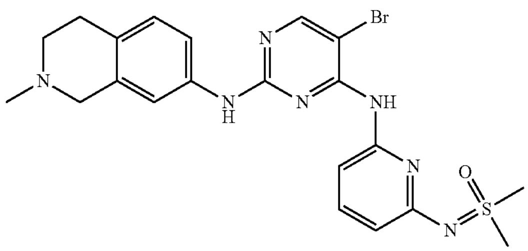

Int_11-2 (600 mg, 1.59 mmol) was dissolved in DMF (30 mL), and int_3-5 (258 mg, 1.59 mmol) and CSA (743 mg, 3.2 mmol) were added. The reaction solution was heated to 85° C. and stirred for 16 h, until LC-MS indicated the completion of the reaction. The reaction solution was cooled to room temperature and concentrated at reduced pressure to give a crude product. The crude product was purified by preparative HPLC to give a white solid (510 mg, 64% yield).

$^1$H NMR (400 MHz, Chloroform-d) δ 8.15 (s, 1H), 7.74 (d, J=8.0 Hz, 1H), 7.55 (s, 1H), 7.48 (t, J=8.0 Hz, 1H), 7.28 (d, J=2.3 Hz, 1H), 7.19 (dd, J=8.1, 2.3 Hz, 1H), 7.04 (d, J=8.2 Hz, 1H), 6.93 (s, 1H), 6.53 (d, J=7.8 Hz, 1H), 3.53 (s, 2H), 3.35 (s, 6H), 2.88 (t, J=5.9 Hz, 2H), 2.68 (t, J=5.9 Hz, 2H), 2.43 (s, 3H).

ESI-MS m/z: 502 $[M+H]^+$

Example 8: Synthesis of Compound 12

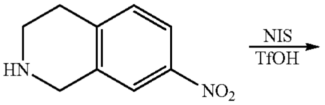

int-12-1-1

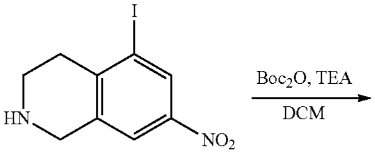

int_12-1-2

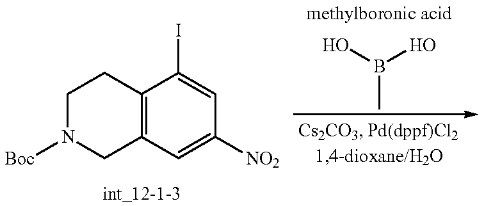

int_12-1-3

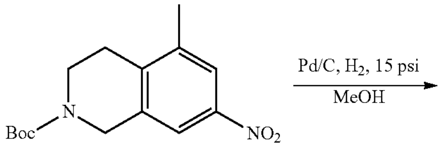

int_12-1-4

-continued

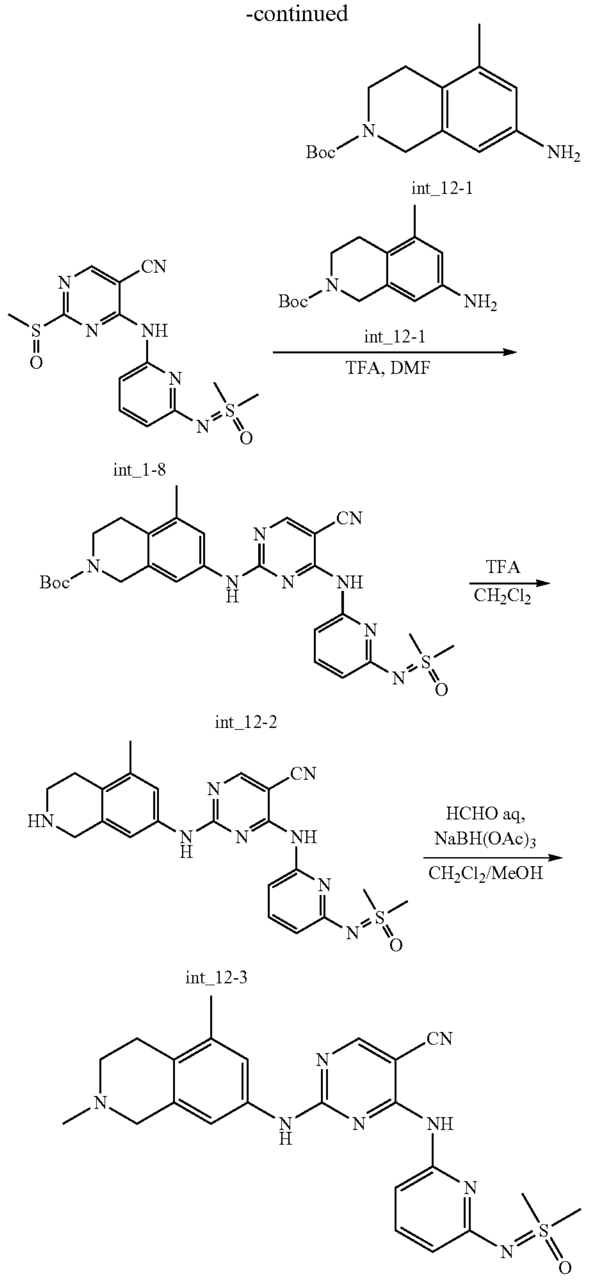

int_12-1 int_1-8 int_12-2 int_12-3

12

Step 1: Synthesis of Compound Int_12-1-2 int_12-1-2

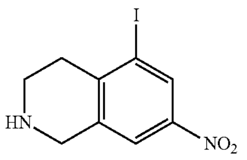

Int_12-1-1 hydrochloride (10.0 g, 46.10 mmol) was dissolved in TfOH (50.0 mL), and in nitrogen atmosphere, NIS (15.7 g, 69.88 mmol) was added at 0° C. The reaction solution was stirred at room temperature for 16 h, until LC-MS indicated the completion of the reaction. The reaction solution was cooled to room temperature, poured into ice water, adjusted to pH 8-9 with a dilute NaOH solution, and filtered to give a black solid int_12-1-2 (14 g, 46.0 mmol, crude product). The crude product was directly used for the next reaction.

ESI-MS m/z: 305 $[M+H]^+$

Step 2: Synthesis of Compound Int_12-1-3 int_12-1-3

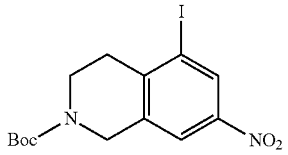

Int_12-1-2 (14.0 g, 46.0 mmol) and $(Boc)_2O$ (25.1 g, 115 mmol, 26.4 mL) were dissolved in DCM (200 mL), and TEA (14.0 g, 138 mmol, 19.2 mL) was added at room temperature. The reaction solution was stirred at room temperature for 16 h, until LC-MS indicated the completion of the reaction. Water (100 mL) was added to the reaction solution. The aqueous phase was extracted with dichloromethane (150 mL×3), and the organic phase was dried over anhydrous sodium sulfate. The organic phase was concentrated at reduced pressure to give a crude product (1.1 mg). The crude product was purified by preparative column chromatography ($SiO_2$, EtOAc/PE=0/1 to 1/9) to give a white solid (10 g, 53.7% yield).

ESI-MS m/z: 349 $[M+H]^+$

Step 3: Synthesis of Compound Int_12-1-4 int_12-1-4

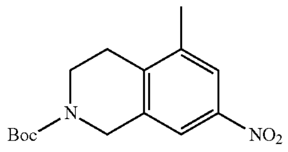

Int_12-1-3 (6.00 g, 14.8 mmol), methylboronic acid (8.90 g, 148.4 mmol), an aqueous cesium carbonate solution (2 M, 14.8 mL), and $Pd(dppf)Cl_2 \cdot CH_2Cl_2$ (1.2 g, 1.5 mmol) were dissolved in a mixed solvent of 1,4-dioxane (100 mL). In argon atmosphere, the mixture was heated to 100° C. and stirred for reaction for 5 h, until LC-MS indicated the completion of the reaction. The reaction solution was concentrated by rotary evaporation, and the crude product was purified by preparative column chromatography ($SiO_2$, EtOAc/PE=0/1 to 1/9) to give a white solid (2.5 g, 57.6% yield).

$^1H$ NMR: (400 MHz, DMSO-$d_6$) δ 7.92 (br d, J=8.5 Hz, 2H), 4.61 (br s, 2H), 3.61 (t, J=5.9 Hz, 2H), 2.75 (t, J=5.9 Hz, 2H), 2.32 (s, 3H), 1.48-1.37 (m, 9H)

ESI-MS m/z: 237 $[M+H]^+$

Step 4: Synthesis of Compound Int_12-1 int_12-1

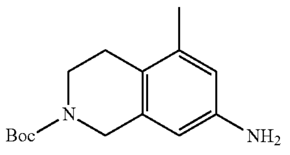

Int_12-1-4 (2.30 g, 7.80 mmol) was dissolved in methanol (40.0 mL), and 10% Pd/C (230 mg) was added. In hydrogen atmosphere (15.0 Psi.), the reaction solution was incubated at room temperature for 16 h, until LC-MS indicated the completion of the reaction. The reaction solution was filtered to give a filtrate, and the filtrate was concentrated at reduced pressure to give a yellow gel (2.00 g, 96.9% yield).

$^1$H NMR (400 MHz, DMSO-$d_6$) δ=6.28 (d, J=1.6 Hz, 1H), 6.14 (s, 1H), 5.75 (s, 1H), 4.77 (s, 2H), 4.31 (br s, 2H), 3.51 (t, J=6.0 Hz, 2H), 2.48-2.44 (m, 2H), 2.04 (s, 3H), 1.41 (s, 9H)

ESI-MS m/z: 207 $[M+H]^+$

Step 5: Synthesis of Compound Int_12-2 int_12-2

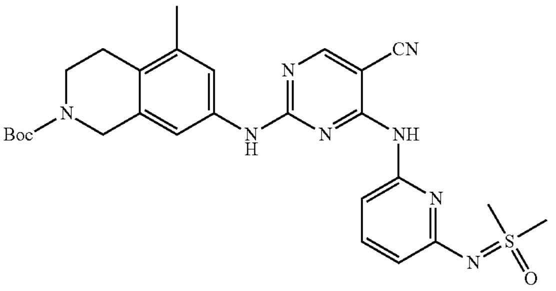

lp;3p

Int_1-8 (1.05 g, 3 mmol) was dissolved in DMF (100 mL), and int_12-1 (787 mg, 3 mmol) and trifluoroacetic acid (342 mg, 3 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by column chromatography ($SiO_2$, DCM: MeOH=100:1 to 30:1) to give a yellow solid (1.2 g, 87% yield).

ESI-MS m/z: 549 $[M+H]^+$

Step 6: Synthesis of Compound Int_12-3 int_12-3

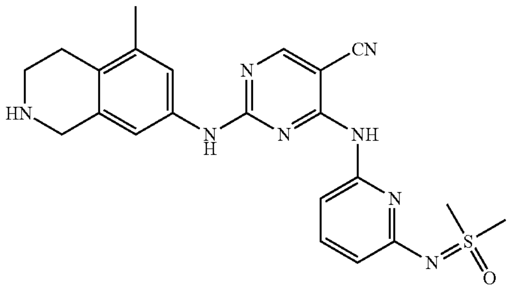

Int_12-2 (1.2 g, 2.19 mmol) was dissolved in dichloromethane (100 mL), and trifluoroacetic acid (6.24 g, 54.7 mmol) was added. The mixture was incubated for 1 h at room temperature for reaction, until LC-MS indicated the completion of the reaction. The reaction solution was directly concentrated at reduced pressure to give a yellow solid (1 g, crude product). The crude product was used directly in the next reaction.

ESI-MS m/z: 449 $[M+H]^+$

Step 7: Synthesis of Compound 12

12

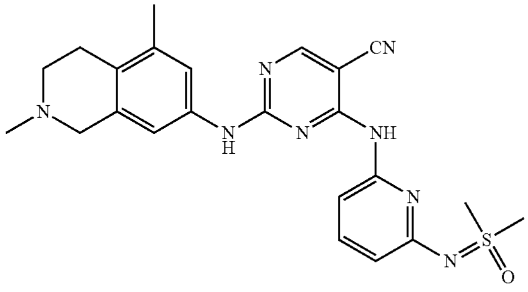

Int_12-3 (1 g, 2.23 mmol) and DIPEA (6.5 g, 50 mmol) were dissolved in dichloromethane (20 mL) and methanol (20 mL), and an aqueous formaldehyde solution (37-40%, 2 mL) and sodium borohydride acetate (3.4 g, 16 mmol) were added. The mixture was incubated for 1 h at room temperature for reaction, until LC-MS indicated the completion of the reaction. Water (100 mL) was added to the reaction solution. The aqueous phase was extracted with ethyl acetate (100 mL×3), and the organic phase was dried over anhydrous sodium sulfate. The organic phase was concentrated at reduced pressure to give a crude product, and the crude product was subjected to column chromatography ($SiO_2$, DCM:MeOH=100:1 to 20:1) to give a pale yellow solid product (700 mg, 92% yield).

$^1$H NMR (400 MHz, DMSO-$d_6$) δ 9.96 (brs, 1H), 9.27 (brs, 1H), 8.54 (s, 1H), 7.54 (t, J=7.9 Hz, 1H), 7.36 (d, J=2.2 Hz, 1H), 7.28-7.15 (m, 2H), 6.42 (d, J=8.0 Hz, 1H), 4.13 (s, 2H), 3.35 (s, 9H), 2.83 (d, J=4.8 Hz, 4H), 2.11 (s, 3H).

ESI-MS m/z: 463 $[M+H]^+$

Example 9: Synthesis of Compound 13

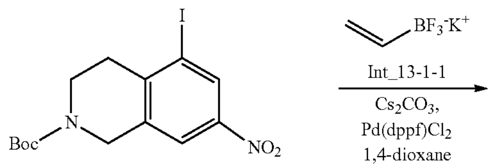

Int_12-1-3

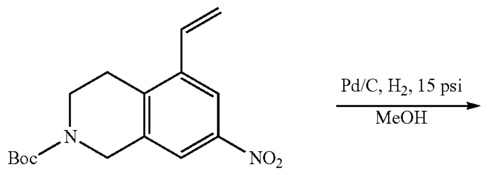

Int_13-1-2

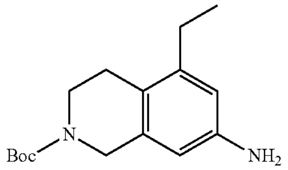

Int_13-1

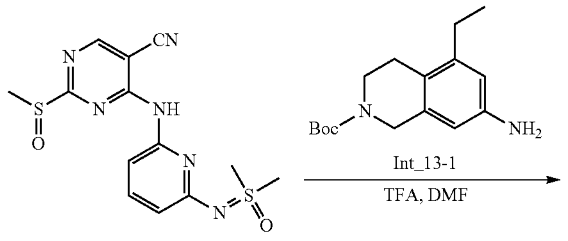

Int_1-8

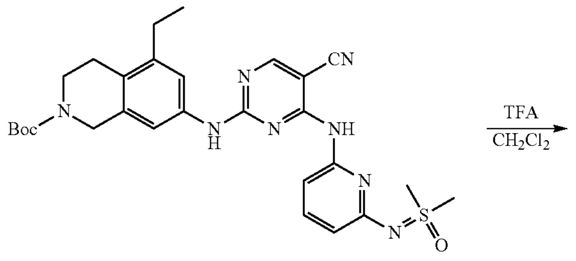

Int_13-2

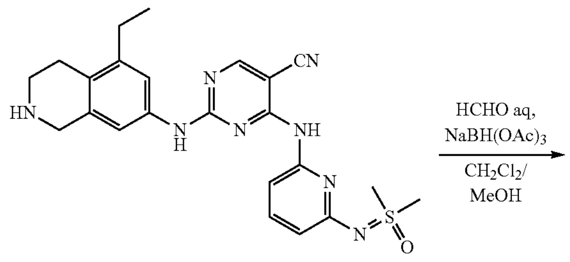

Int_13-3

-continued

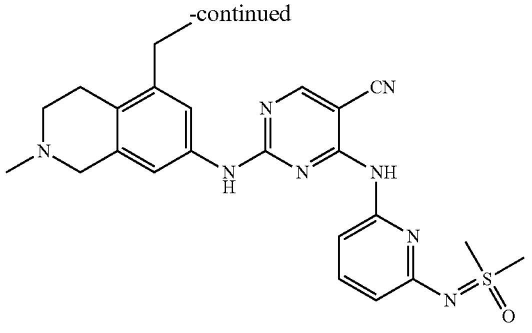

13

Step 1: Synthesis of Compound Int_13-1-2 int_13-1-2

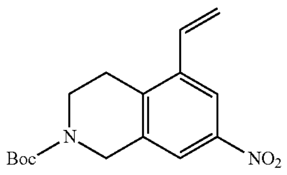

Int_12-1-3 (3.00 g, 7.42 mmol), int_13-1-1 (4.97 g, 37.1 mmol), an aqueous cesium carbonate solution (2.00 M, 7.42 mL), and $Pd(dppf)Cl_2 \cdot CH_2Cl_2$ (606 mg, 742 μmol) were dissolved in 1,4-dioxane (40 mL). In argon atmosphere, the mixture was heated to 100° C. and stirred for reaction for 5 h, until LC-MS indicated the completion of the reaction. The reaction solution was concentrated by rotary evaporation, and the crude product was purified by preparative column chromatography ($SiO_2$, EtOAc/PE=0/1 to 1/9) to give a white solid (1.2 g, 53.1% yield).

ESI-MS m/z: 249 $[M+H]^+$

Step 2: Synthesis of Compound Int_13-1 int_13-1

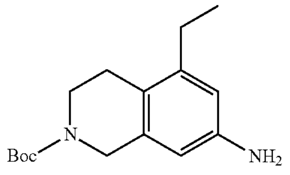

Int_13-1-2 (1.00 g, 3.29 mmol) was dissolved in methanol (40.0 mL), and 10% Pd/C (100 mg) was added. In hydrogen atmosphere (15.0 Psi.), the reaction solution was incubated at room temperature for 16 h, until LC-MS indicated the completion of the reaction. The reaction solution was filtered to give a filtrate, and the filtrate was concentrated at reduced pressure to give a yellow gel (600 mg, 61% yield).

$^1H$ NMR (400 MHz, DMSO-$d_6$) δ 6.30 (d, J=2.0 Hz, 1H), 6.15 (br s, 1H), 4.81 (s, 2H), 4.31 (br s, 2H), 3.49 (br t, J 5.9 Hz, 2H), 2.41 (q, J 7.5 Hz, 2H), 1.41 (s, 9H), 1.07 (t, J=7.5 Hz, 3H)

ESI-MS m/z: 221 $[M+H]^+$

Step 3: Synthesis of Compound Int_13-2 int_13-2

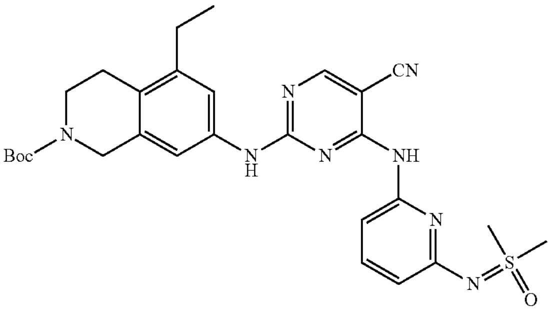

Int_1-8 (100 mg, 0.281 mmol) was dissolved in DMF (5 mL), and int_13-1 (79 mg, 0.281 mmol) and trifluoroacetic acid (63.9 mg, 0.56 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by column chromatography ($SiO_2$, DCM: MeOH=100:1 to 30:1) to give a yellow solid (34 mg, 21.5% yield).

ESI-MS m/z: 563 $[M+H]^+$

Step 4: Synthesis of Compound Int_13-3 int_13-3

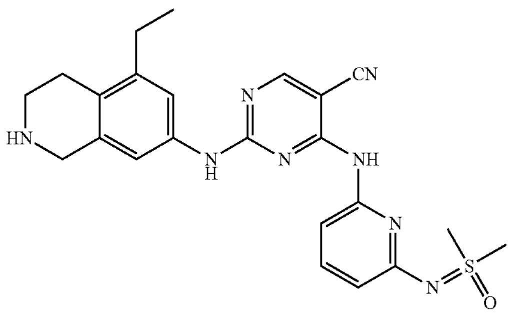

Int_13-2 (34 mg, 0.06 mmol) was dissolved in dichloromethane (5 mL), and trifluoroacetic acid (1 mL) was added. The mixture was incubated for 2 h at room temperature for reaction, until LC-MS indicated the completion of the reaction. The reaction solution was directly concentrated at reduced pressure to give a yellow solid (31 mg, crude product). The crude product was used directly in the next reaction.

ESI-MS m/z: 463 $[M+H]^+$

Step 5: Synthesis of Compound 13

13

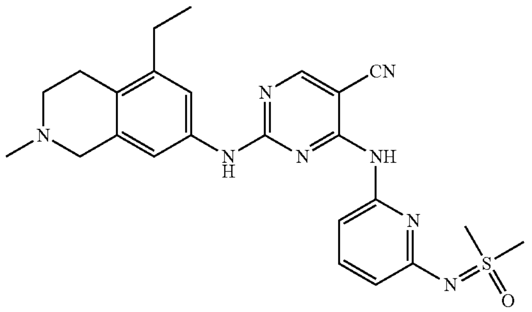

Int_13-3 (500 mg, 1.08 mmol) and DIPEA (3.2 g, 25 mmol) were dissolved in dichloromethane (10 mL) and methanol (10 mL), and an aqueous formaldehyde solution (37-40%, 1 mL) and sodium borohydride acetate (1.7 g, 8 mmol) were added. The mixture was incubated for 1 h at room temperature for reaction, until LC-MS indicated the completion of the reaction. Water (100 mL) was added to the reaction solution. The aqueous phase was extracted with ethyl acetate (100 mL×3), and the organic phase was dried over anhydrous sodium sulfate. The organic phase was concentrated at reduced pressure to give a crude product, and the crude product was subjected to column chromatography ($SiO_2$, DCM:MeOH=100:1 to 20:1) to give a white solid product (129 mg, 25% yield).

$^1H$ NMR (400 MHz, Chloroform-d) δ 8.36 (s, 1H), 7.76-7.59 (m, 2H), 7.43 (d, J=27.0 Hz, 2H), 7.18 (s, 1H), 7.07 (s, 1H), 6.56 (d, J=7.9 Hz, 1H), 3.55 (s, 2H), 3.36 (s, 6H), 2.83 (d, J=6.1 Hz, 2H), 2.73 (t, J=5.8 Hz, 2H), 2.58 (q, J=7.6 Hz, 2H), 2.45 (s, 3H), 1.18 (t, J=7.6 Hz, 3H).

ESI-MS m/z: 477 $[M+H]^+$

Example 10: Synthesis of Compound 16

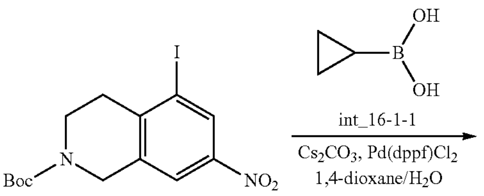

int_12-1-3

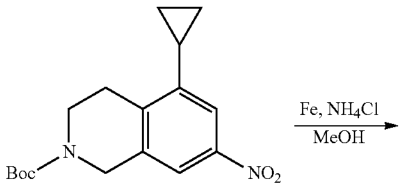

int_16-1-2

-continued

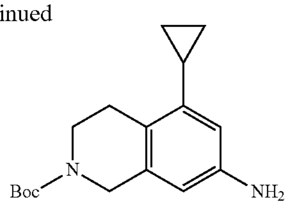

int_16-1

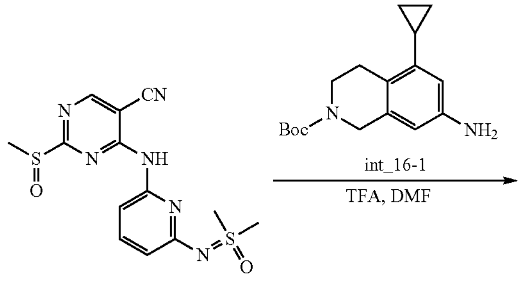

int_1-8

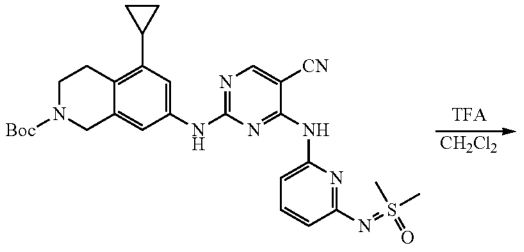

int_16-2

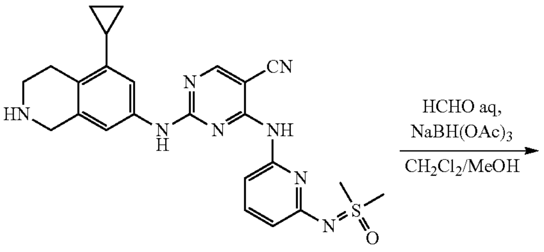

int_16-3

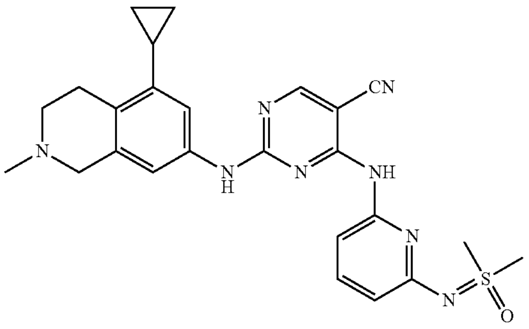

16

Step 1: Synthesis of Compound Int_16-1-2 int_16-1-2

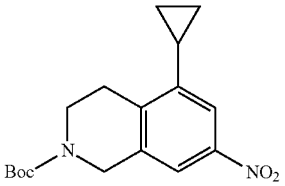

Int_12-1-3 (3.00 g, 7.42 mmol), int_16-1-1 (3.19 g, 37.1 mmol), cesium carbonate (4.84 g, 14.8 mmol), and Pd(dppf) $Cl_2 \cdot CH_2Cl_2$ (606 mg, 742 μmol) were dissolved in 1,4-dioxane (40 mL) and water (4 mL). In argon atmosphere, the mixture was heated to 100° C. and stirred for reaction for 5 h, until LC-MS indicated the completion of the reaction. The reaction solution was concentrated by rotary evaporation, and the crude product was purified by preparative column chromatography ($SiO_2$, EtOAc/PE=0/1 to 1/9) to give a white solid (1.4 g, 59.3% yield).

$^1$H NMR (400 MHz, DMSO-$d_6$) δ 7.95 (d, J=2.0 Hz, 1H), 7.62 (d, J=2.3 Hz, 1H), 4.62 (br s, 2H), 3.63 (br t, J=5.9 Hz, 2H), 2.98 (t, J=5.9 Hz, 2H), 2.04-1.94 (m, 1H), 1.47-1.35 (m, 9H), 1.05-0.93 (m, 2H), 0.74-0.62 (m, 2H)

Step 2: Synthesis of Compound Int_16-1 int_16-1

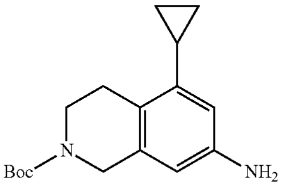

Int_16-1-2 (1.20 g, 3.77 mmol) was dissolved in methanol (20.0 mL) and water (20.0 mL), and $NH_4Cl$ (2.02 g, 37.7 mmol) and Fe powder (2.10 g, 37.7 mmol) were added. The reaction solution was heated to 80° C. and incubated for 5 h, until LC-MS indicated the completion of the reaction. The reaction solution was filtered to give a filtrate, and the filtrate was concentrated at reduced pressure to give a white solid (470 mg, 43.2% yield).

$^1$H NMR (400 MHz, DMSO-$d_6$) δ 6.18-6.08 (m, 2H), 4.79 (s, 2H), 4.32 (br s, 2H), 3.53 (br t, J=5.8 Hz, 2H), 2.69 (br t, J=6.0 Hz, 2H), 1.79-1.71 (m, 1H), 1.42 (s, 10H), 0.86-0.77 (m, 2H), 0.49-0.43 (m, 2H)

ESI-MS m/z: 233 $[M+H]^+$

Step 3: Synthesis of Compound Int_16-2 int_16-2

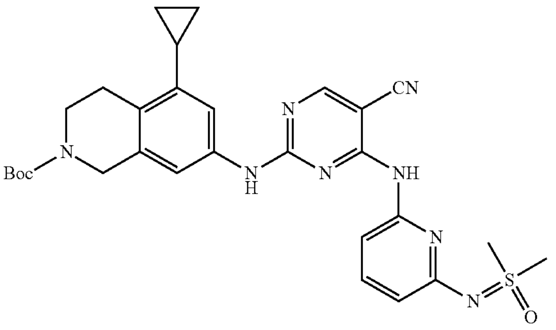

Int_1-8 (100 mg, 0.28 mmol) was dissolved in DMF (5 mL), and int_16-1 (81 mg, 0.28 mmol) and trifluoroacetic acid (63.9 mg, 0.56 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by column chromatography ($SiO_2$, DCM: MeOH=100:1 to 30:1) to give a yellow solid (60 mg, 37% yield).

ESI-MS m/z: 575 $[M+H]^+$

Step 4: Synthesis of Compound Int_16-3 int_16-3

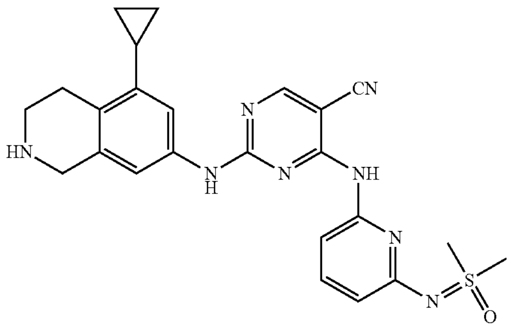

Int_16-2 (60 mg, 0.10 mmol) was dissolved in dichloromethane (2 mL), and trifluoroacetic acid (0.5 mL) was added. The mixture was incubated for 2 h at room temperature for reaction, until LC-MS indicated the completion of the reaction. The reaction solution was directly concentrated at reduced pressure to give a yellow solid (55 mg, crude product). The crude product was used directly in the next reaction.

ESI-MS m/z: 475 $[M+H]^+$

Step 5: Synthesis of Compound 16

16

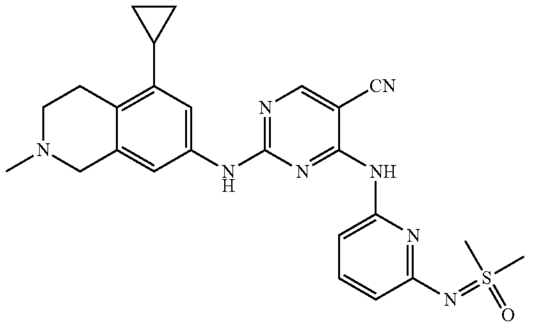

Int_16-3 (55 mg, 0.116 mmol) and DIPEA (298 mg, 2.3 mmol) were dissolved in dichloromethane (2 mL) and methanol (2 mL), and an aqueous formaldehyde solution (37-40%, 1 mL) and sodium borohydride acetate (600 mg, 2.83 mmol) were added. The mixture was incubated for 1 h at room temperature for reaction, until LC-MS indicated the completion of the reaction. The reaction solution was concentrated at reduced pressure to give a crude product, and the crude product was purified by preparative column HPLC to give a white solid product (40 mg, 70% yield).

$^1$H NMR (400 MHz, Chloroform-d) δ 8.35 (s, 1H), 7.69 (d, J=8.0 Hz, 1H), 7.51 (d, J=35.5 Hz, 3H), 7.16 (s, 1H), 6.88 (s, 1H), 6.56 (d, J=7.9 Hz, 1H), 3.53 (s, 2H), 3.36 (d, J=1.7 Hz, 6H), 2.98 (d, J=6.1 Hz, 2H), 2.75 (t, J=6.2 Hz, 2H), 2.46 (s, 3H), 1.82 (s, 1H), 0.88 (d, J=8.0 Hz, 2H), 0.56 (d, J=5.4 Hz, 2H).

ESI-MS m/z: 489 $[M+H]^+$

Example 11: Synthesis of Compound 19

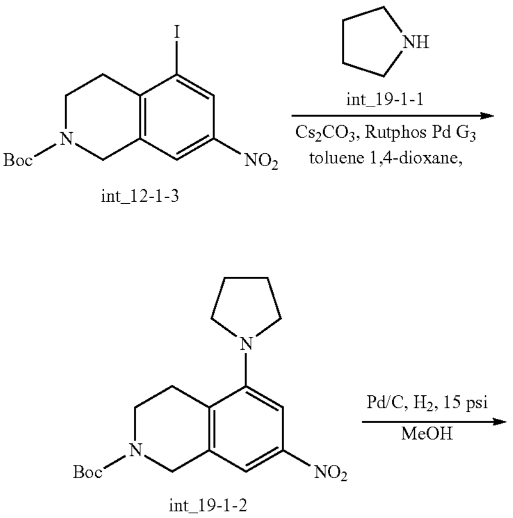

-continued

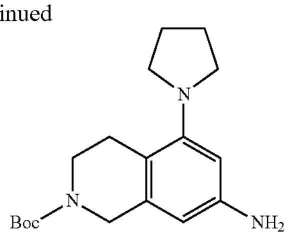

int_19-1

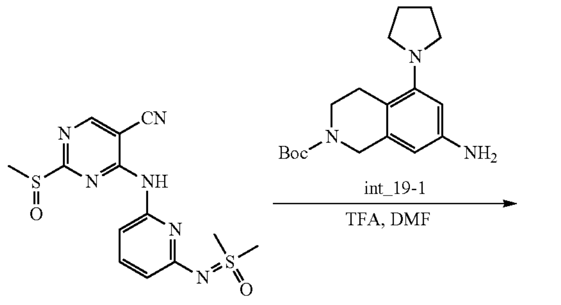

int_1-8

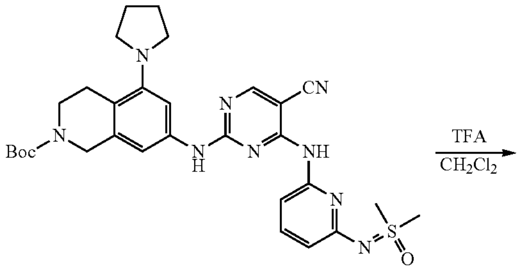

int_19-2

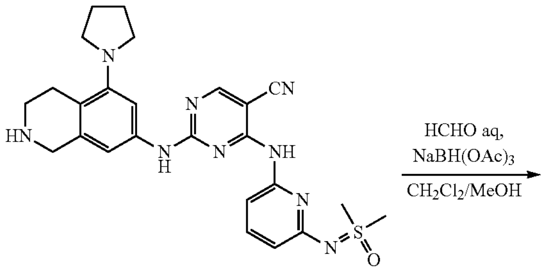

int_19-3

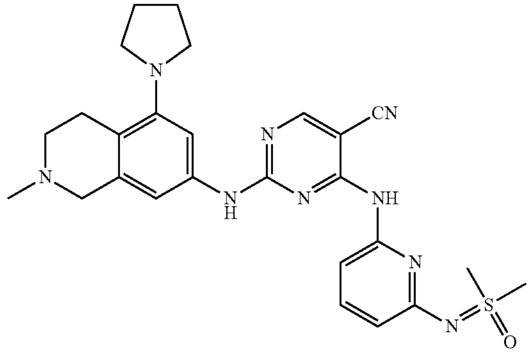

19

Step 1: Synthesis of Compound Int_19-1-2 int_19-1-2

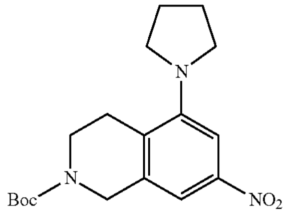

Int_12-1-3 (5.00 g, 12.4 mmol), int_19-1-1 (2.64 g, 37.1 mmol), cesium carbonate (8.06 g, 24.7 mmol), and RuPhos Pd $G_3$ (606 mg, 742 μmol) were dissolved in 1,4-dioxane (50 mL). In argon atmosphere, the mixture was heated to 100° C. and stirred for reaction for 5 h, until LC-MS indicated the completion of the reaction. The reaction solution was concentrated by rotary evaporation, and the crude product was purified by preparative column chromatography ($SiO_2$, EtOAc/PE=0/1 to 1/9) to give a white solid (1.7 g, 39.6% yield).

ESI-MS m/z: 348 $[M+H]^+$

Step 2: Synthesis of Compound Int_19-1 int_19-1

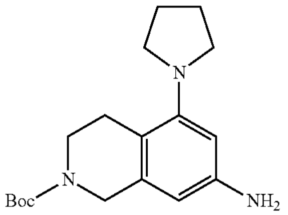

Int_19-1-2 (0.70 g, 2.01 mmol) was dissolved in methanol (40.0 mL), and 10% Pd/C (100 mg) was added. In hydrogen atmosphere (15.0 Psi.), the reaction solution was incubated at room temperature for 16 h, until LC-MS indicated the completion of the reaction. The reaction solution was filtered to give a filtrate, and the filtrate was concentrated at reduced pressure to give a white solid (410 mg, 63.5% yield).

$^1$H NMR (400 MHz, DMSO-$d_6$) δ 6.08 (d, J=2.0 Hz, 1H), 5.93 (s, 1H), 4.76 (s, 2H), 4.30 (br s, 2H), 3.44-3.37 (m, 2H), 2.99 (br t, J=6.2 Hz, 4H), 2.42 (br s, 1H), 1.89-1.79 (m, 4H), 1.65 (br s, 1H), 1.43 (s, 9H)

ESI-MS m/z: 318 $[M+H]^+$

Step 3: Synthesis of Compound Int_19-2 int_19-2

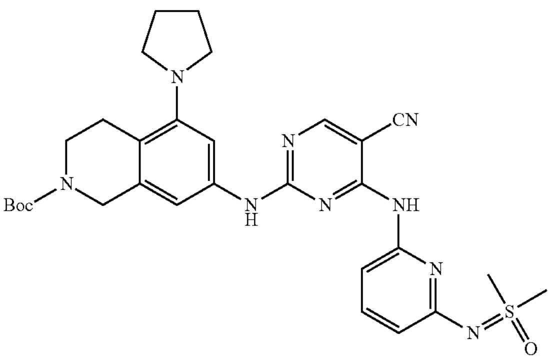

Int_1-8 (56 mg, 0.158 mmol) was dissolved in DMF (5 mL), and int_19-1 (50 mg, 0.158 mmol) and trifluoroacetic acid (64 mg, 0.631 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by column chromatography ($SiO_2$, DCM: MeOH=100:1 to 30:1) to give an orange solid (50 mg, 52.6% yield).

ESI-MS m/z: 604 $[M+H]^+$

Step 4: Synthesis of Compound Int_19-3 int_19-3

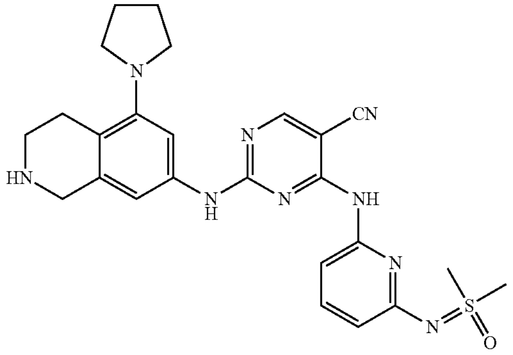

Int_19-2 (50 mg, 0.083 mmol) was dissolved in dichloromethane (5 mL), and trifluoroacetic acid (1 mL) was added. The mixture was incubated for 2 h at room temperature for reaction, until LC-MS indicated the completion of the reaction. The reaction solution was directly concentrated at reduced pressure to give a yellow solid (50 mg, crude product). The crude product was used directly in the next reaction.

ESI-MS m/z: 504 $[M+H]^+$

Step 5: Synthesis of Compound 19

19

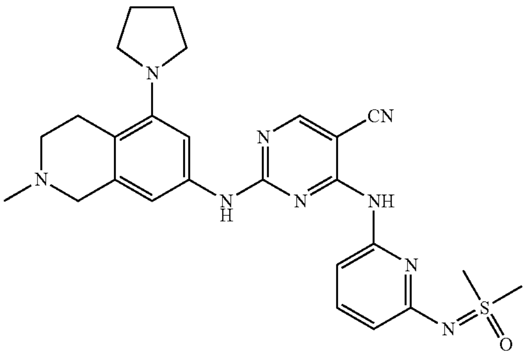

Int_19-3 (30 mg, 0.060 mmol) and DIPEA (298 mg, 2.3 mmol) were dissolved in dichloromethane (2 mL) and methanol (2 mL), and an aqueous formaldehyde solution (37-40%, 1 mL) and sodium borohydride acetate (200 mg, 0.95 mmol) were added. The mixture was incubated for 1 h at room temperature for reaction, until LC-MS indicated the completion of the reaction. The reaction solution was concentrated at reduced pressure to give a crude product, and the crude product was purified by preparative column HPLC to give a white solid product (5 mg, 16.2% yield).

$^1H$ NMR (400 MHz, Chloroform-d) δ 8.30 (s, 2H), 7.56 (d, J=18.1 Hz, 2H), 7.46 (d, J=9.7 Hz, 1H), 6.92 (d, J=2.0 Hz, 1H), 6.75 (s, 1H), 6.51 (d, J=7.8 Hz, 1H), 3.93 (s, 2H), 3.30 (s, 6H), 3.06 (d, J=12.4 Hz, 6H), 2.94 (d, J=6.0 Hz, 2H), 2.68 (s, 3H), 1.83 (d, J=6.3 Hz, 4H).

ESI-MS m/z: 518 $[M+H]^+$

Example 12: Synthesis of Compound 22

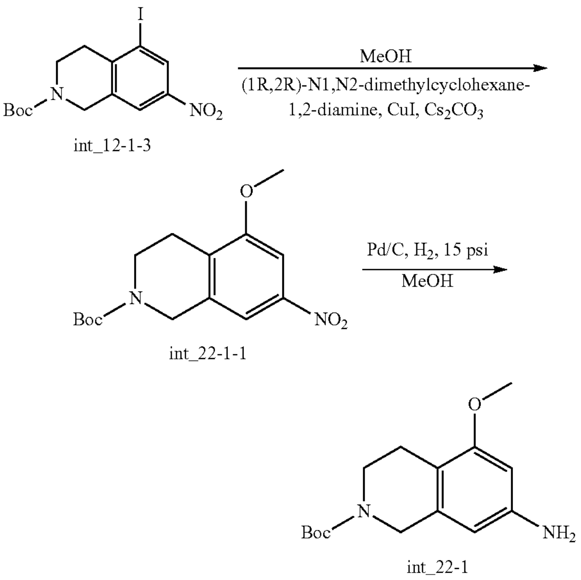

-continued

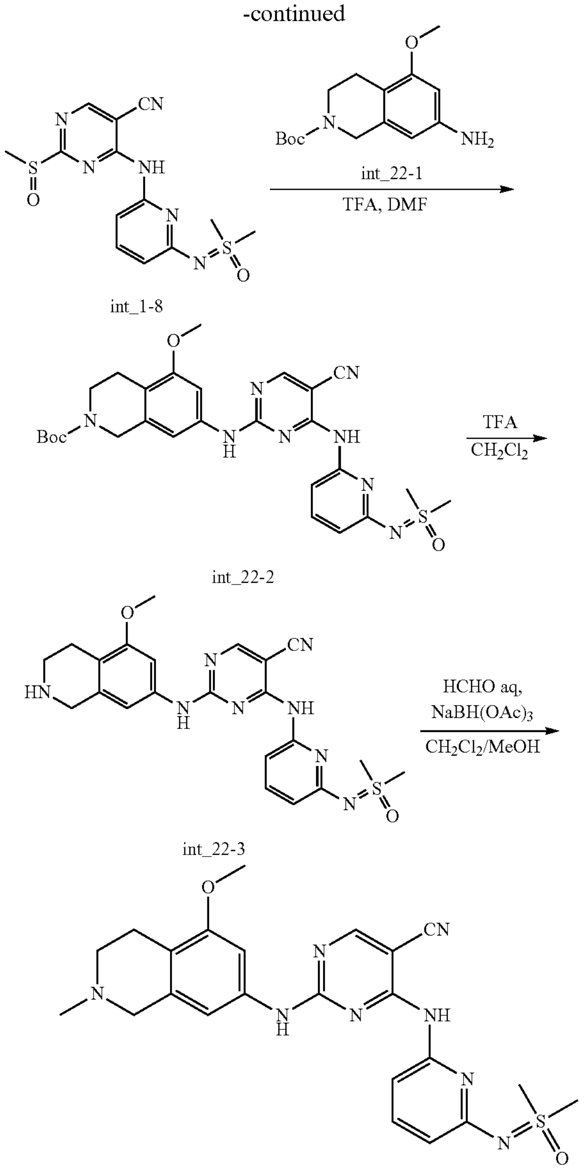

int_1-8 int_22-2 int_22-3

22

Step 1: Synthesis of Compound Int_22-1-1 int_22-1-1

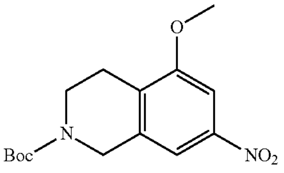

Int_12-1-3 (500 mg, 1.24 mmol), methanol (39.6 mg, 1.24 mmol), CuI (236 mg, 1.24 mmol), $Cs_2CO_3$ (806 mg, 2.47 mmol), and (1R,2R)—N1,N2-dimethylcyclohexane-1,2-diamine (175.96 mg, 1.24 mmol) were dissolved in methanol (8 mL). In nitrogen atmosphere, the mixture was heated to 110° C. with microwave and stirred for 1 h, until LC-MS indicated the completion of the reaction. The reaction solution was concentrated by rotary evaporation, and the crude product was purified by preparative column chromatography ($SiO_2$, EtOAc/PE=1/10) to give a white solid (420 mg, 27.5% yield).

$^1$H NMR (400 MHz, Chloroform-d) δ 7.67 (s, 1H), 7.55 (d, J=1.9 Hz, 1H), 4.64 (s, 2H), 3.94 (s, 3H), 3.68 (t, J=5.9 Hz, 2H), 2.82 (br t, J=5.8 Hz, 2H), 1.51 (s, 9H)

Step 2: Synthesis of Compound Int_22-1 int_22-1

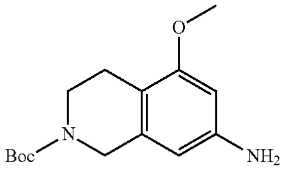

Int_22-1-1 (420 mg, 1.36 mmol) was dissolved in methanol (10.0 mL), and 10% Pd/C (100 mg) was added. In hydrogen atmosphere (15.0 Psi.), the reaction solution was incubated at room temperature for 16 h, until LC-MS indicated the completion of the reaction. The reaction solution was filtered to give a filtrate, and the filtrate was concentrated at reduced pressure to give a white gel (370 mg, 97.5% yield).

$^1$H NMR (400 MHz, Chloroform-d) δ 6.10 (br d, J=13.1 Hz, 2H), 4.47 (s, 2H), 3.79 (s, 3H), 3.61 (br s, 4H), 2.65 (br t, J=5.6 Hz, 2H), 1.50 (s, 9H)

ESI-MS m/z: 223 $[M+H]^+$

Step 3: Synthesis of Compound Int_22-2 int_22-2

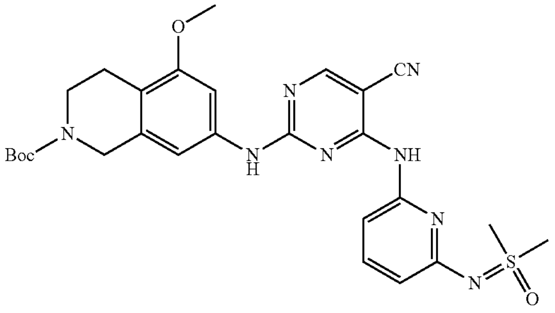

Int_1-8 (179 mg, 0.51 mmol) was dissolved in DMF (10 mL), and int_22-1 (212 mg, 0.76 mmol) and trifluoroacetic acid (114 mg, 1 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by column chromatography ($SiO_2$, DCM:MeOH=100:1 to 30:1) to give a pale yellow solid (250 mg, 87% yield).

ESI-MS m/z: 565 $[M+H]^+$

Step 4: Synthesis of Compound Int_22-3 int_22-3

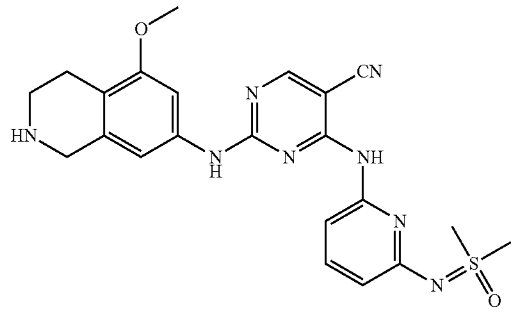

Int_22-2 (100 mg, 0.18 mmol) was dissolved in dichloromethane (5 mL), and trifluoroacetic acid (1 mL) was added. The mixture was incubated for 2 h at room temperature for reaction, until LC-MS indicated the completion of the reaction. The reaction solution was directly concentrated at reduced pressure to give a yellow solid (100 mg, crude product). The crude product was used directly in the next reaction.

ESI-MS m/z: 465 $[M+H]^+$

Step 5: Synthesis of Compound 22

22

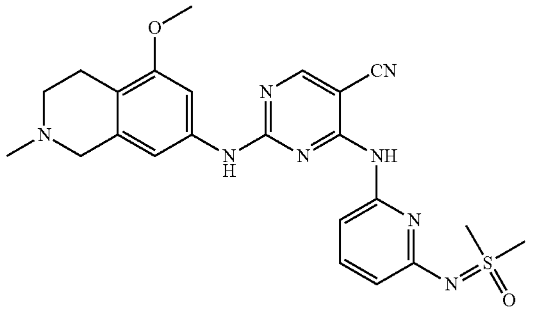

Int_22-3 (84 mg, 0.18 mmol) and DIPEA (298 mg, 2.3 mmol) were dissolved in dichloromethane (2 mL) and methanol (2 mL), and an aqueous formaldehyde solution (37-40%, 0.5 mL) and sodium borohydride acetate (500 mg, 2.36 mmol) were added. The mixture was incubated for 1 h at room temperature for reaction, until LC-MS indicated the completion of the reaction. The reaction solution was concentrated at reduced pressure to give a crude product, and the crude product was purified by preparative column HPLC to give a white solid product (45 mg, 52% yield).

$^1H$ NMR (400 MHz, Chloroform-d) δ 8.31 (s, 1H), 7.61 (d, J=18.0 Hz, 2H), 7.39 (s, 2H), 6.75 (s, 2H), 6.49 (d, J=7.7 Hz, 1H), 3.67 (s, 3H), 3.44 (s, 2H), 3.30 (s, 6H), 2.71 (s, 2H), 2.63 (s, 2H), 2.38 (s, 3H).

ESI-MS m/z: 479 $[M+H]^+$

Example 13: Synthesis of Compound 29

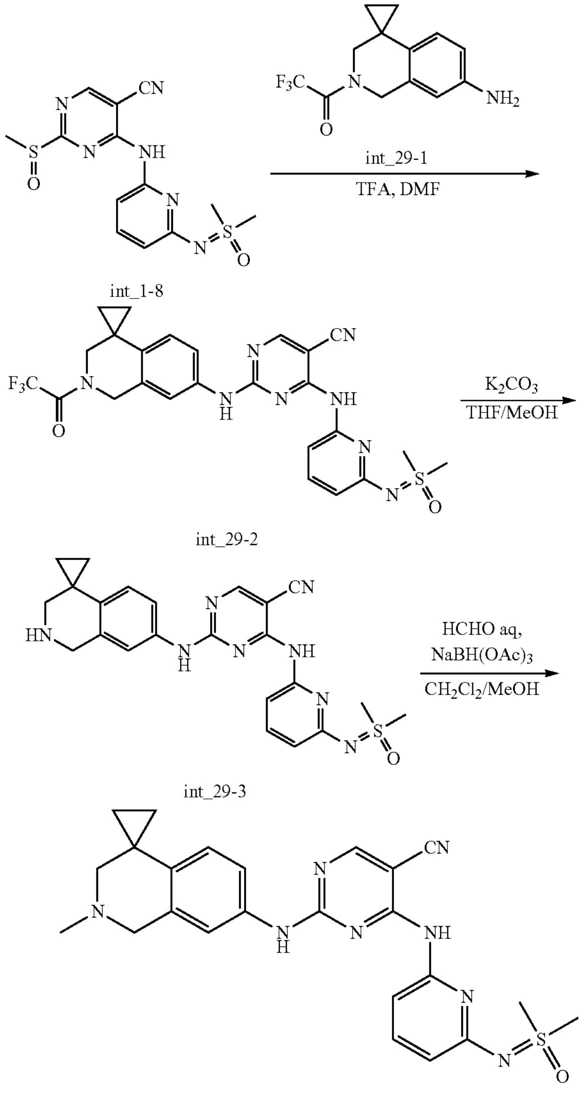

29

Step 1: Synthesis of Compound Int 29-2 int_29-2

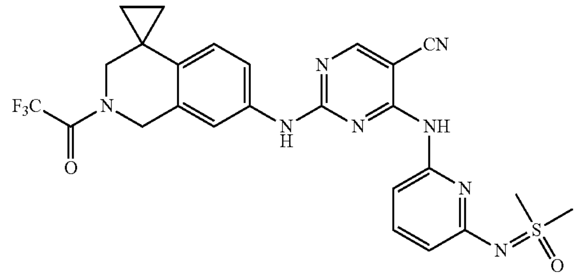

Int_1-8 (105 mg, 0.3 mmol) was dissolved in DMF (5 mL), and int_29-1 (81 mg, 0.3 mmol) and trifluoroacetic acid (34 mg, 0.3 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by column chromatography ($SiO_2$, DCM: MeOH=100:1 to 30:1) to give a pale yellow solid (56 mg, 33.5% yield).

ESI-MS m/z: 557 $[M+H]^+$

Step 2: Synthesis of Compound Int_29-3 int_29-3

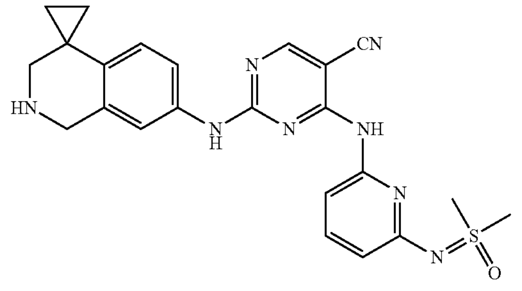

Int_29-2 (190 mg, 0.341 mmol) was dissolved in a mixture of methanol and THE (v/v=1:1, 15 mL), and potassium carbonate (48 mg, 0.341 mmol) was added. The mixture was incubated for 2 h at room temperature for reaction, until LC-MS indicated the completion of the reaction. The reaction solution was directly concentrated at reduced pressure to give a yellow solid (190 mg, crude product). The crude product was used directly in the next reaction.

ESI-MS m/z: 461 $[M+H]^+$

Step 3: Synthesis of Compound 29

29

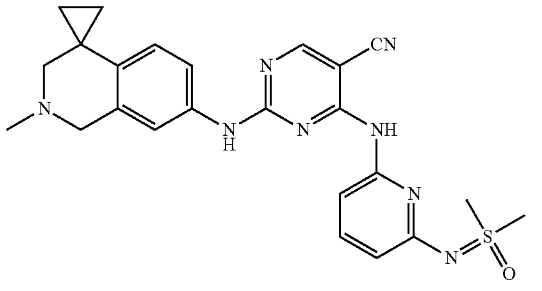

Int_29-3 (190 mg, 0.412 mmol) was dissolved in dichloromethane (5 mL) and methanol (5 mL), and an aqueous formaldehyde solution (37-40%, 1 mL) and sodium borohydride acetate (212 mg, 1 mmol) were added. The mixture was incubated for 1 h at room temperature for reaction, until LC-MS indicated the completion of the reaction. The reaction solution was concentrated at reduced pressure to give a crude product, and the crude product was purified by preparative column HPLC to give a yellow solid product (106 mg, 55% yield).

$^1H$ NMR (400 MHz, Chloroform-d) δ 8.32 (s, 1H), 7.79-7.55 (m, 3H), 7.44 (s, 1H), 7.24 (d, J=5.8 Hz, 1H), 7.17 (s, 1H), 6.63 (d, J=8.4 Hz, 1H), 6.54 (d, J=7.9 Hz, 1H), 3.64 (s, 2H), 3.34 (s, 6H), 2.52 (s, 2H), 2.42 (s, 3H), 0.99 (s, 2H), 0.91 (s, 2H).

ESI-MS m/z: 475 $[M+H]^+$

Example 14: Synthesis of Compound 42

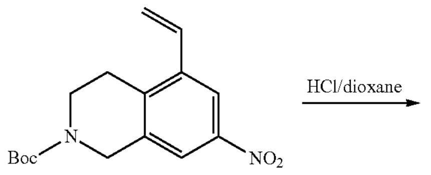

int_13-1-2

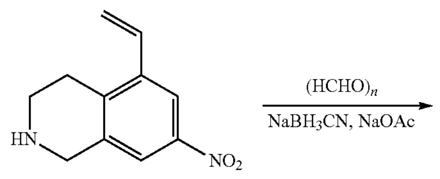

int_42-1-1

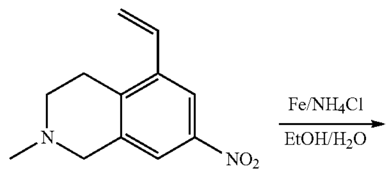

int_42-1-2

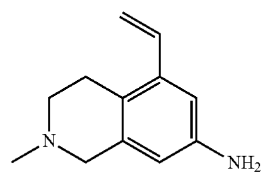

int_42-1

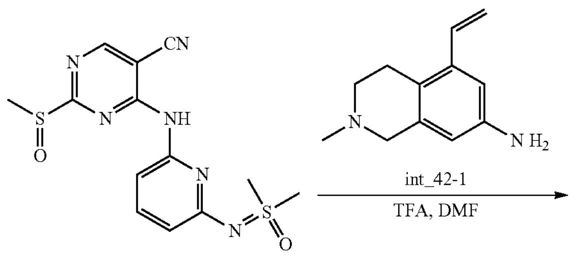

int_1-8

-continued

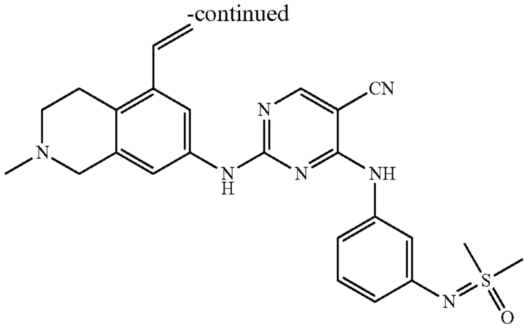

42

Step 1: Synthesis of compound int_42-1-1 int_42-1-1

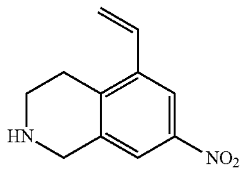

Int_13-1-2 (5.50 g, 18.1 mmol) was dissolved in 1,4-dioxane (50 mL), and an HCl/dioxane solution (4 M, 55.0 mL) was added. The reaction solution was stirred at room temperature for 2 h, until LC-MS indicated the completion of the reaction. The reaction solution was cooled to room temperature and concentrated at reduced pressure to give a crude product (4 g, 91.9% yield). The crude product was used directly in the next reaction.

ESI-MS m/z: 205 $[M+H]^+$

Step 2: Synthesis of Compound Int_42-1-2 int_42-1-2

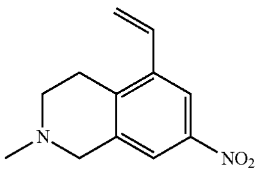

Int_42-1-1 (3.80 g, 18.6 mmol) was dissolved in methanol (40 mL), and NaOAc (3.05 g, 37.2 mmol), $NaBH_3CN$ (1.75 g, 27.9 mmol) and $(HCHO)_n$ (838 mg) were added. The reaction solution was heated to 50° C. and incubated for 4 h, until LC-MS indicated the completion of the reaction. Water (50 mL) was added to the reaction solution. The aqueous phase was extracted with ethyl acetate (50 mL×3), and the organic phase was dried over anhydrous sodium sulfate. The organic phase was concentrated at reduced pressure to give a crude product, and the crude product was subjected to column chromatography (ISCO®; 40 g Sepa Flash® Silica Flash Column, eluent of 0-50% ethyl acetate/petroleum ether gradient at 60 mL/min) to give a white solid (3.2 g, 78.8% yield).

$^1H$ NMR (400 MHz, Chloroform-d) δ 8.09 (d, J=2.0 Hz, 1H), 7.75 (d, J=1.6 Hz, 1H), 6.79 (dd, J=17.3, 11.0 Hz, 1H), 5.72 (d, J=17.3 Hz, 1H), 5.41 (d, J=11.0 Hz, 1H), 3.60 (s, 2H), 2.86-2.91 (m, 2H), 2.69-2.73 (m, 2H), 2.43 ppm (s, 3H)

Step 3: Synthesis of Compound Int_42-1 int_42-1

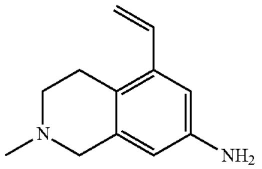

Int_42-1-2 (3.00 g, 13.7 mmol) was dissolved in ethanol (30.0 mL) and water (30.0 mL), and in nitrogen atmosphere, $NH_4Cl$ (4.41 g, 82.5 mmol) and Fe powder (4.61 g, 82.4 mmol) were added. The reaction solution was heated to 70° C. and incubated for 6 h, until LC-MS indicated the completion of the reaction. The reaction solution was filtered to give a filtrate, the filtrate was concentrated to give a crude product, and the crude product was subjected to column chromatography (ISCO®; 40 g Sepa Flash® Silica Flash Column, eluent of 0-60% ethyl acetate/petroleum ether gradient at 60 mL/min) to give a yellow solid (2.43 g, 93.9% yield).

$^1H$ NMR (400 MHz, DMSO-$d_6$) δ 6.82 (dd, J=17.3, 10.9 Hz, 1H), 6.72 (d, J=1.6 Hz, 1H), 6.27 (s, 1H), 5.57 (dd, J=17.3, 1.3 Hz, 1H), 5.28 (dd, J=10.9, 1.3 Hz, 1H), 4.13 (s, 2H), 3.34 (br s, 2H), 2.90 (br t, J=5.9 Hz, 2H), 2.80 ppm (s, 3H)

ESI-MS m/z: 189 $[M+H]^+$

Step 4: Synthesis of Compound 42

42

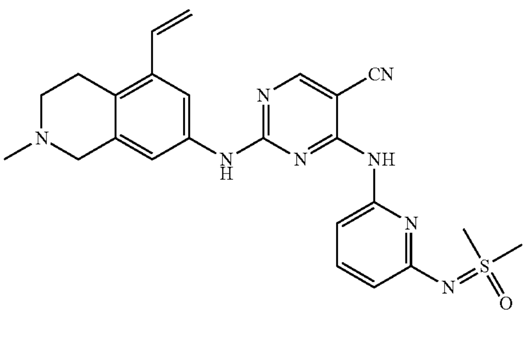

Int_1-8 (100 mg, 0.281 mmol) was dissolved in DMF (30 mL), and int_42-1 (54 mg, 0.281 mmol) and trifluoroacetic acid (113 mg, 1.1 mmol) were added. The reaction solution was heated to 80° C. and stirred for 16 h, until LC-MS indicated the completion of the reaction. The reaction solution was cooled to room temperature and concentrated at reduced pressure to give a crude product. The crude product was purified by preparative HPLC to give a white solid (3 mg, 2.3% yield).

ESI-MS m/z: 475 $[M+H]^+$

Example 15: Synthesis of Compound 43

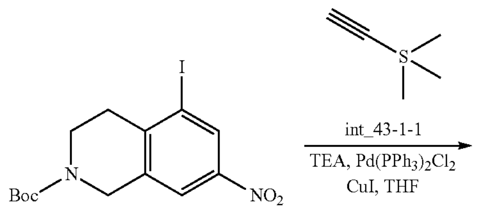

int_12-1-3

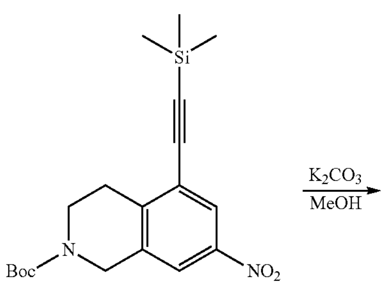

int_43-1-2

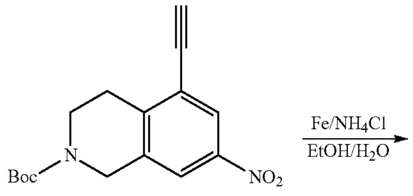

int_43-1-3

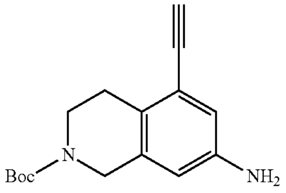

int_43-1

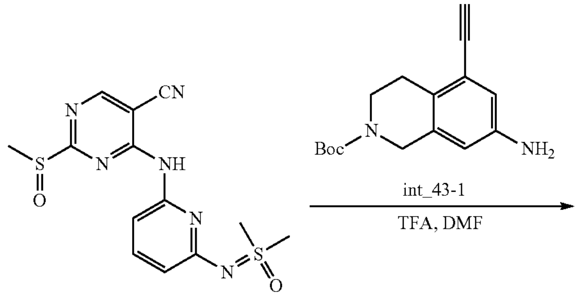

int_1-8

-continued

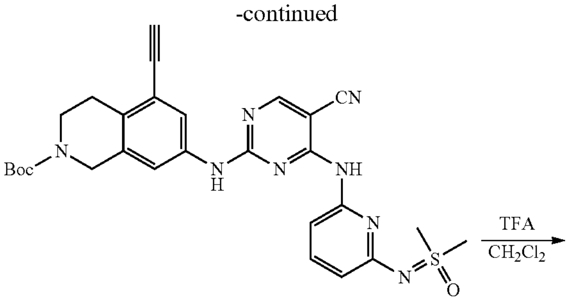

int_43-2

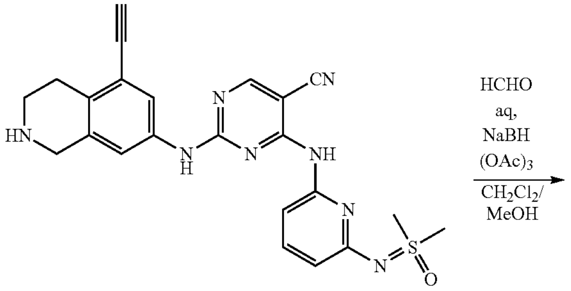

int_43-3

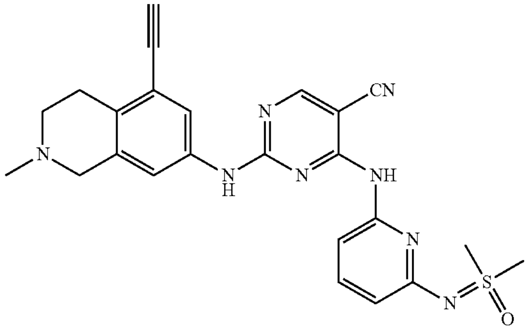

43

Step 1: Synthesis of Compound Int_43-1-2 int_43-1-2

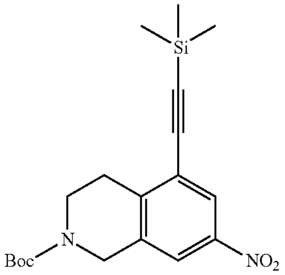

Int_12-1-3 (5.00 g, 12.4 mmol), int_43-1-1 (1.64 g, 16.7 mmol, 2.31 mL), CuI (141 mg, 742 mol), TEA (5.01 g, 49.5 mmol, 6.89 mL), and $Pd(PPh_3)_2Cl_2$ (434 mg, 618 μmol) were dissolved in 1,4-dioxane (40 mL)$_n$ In argon atmosphere, the mixture was heated to 70° C. and stirred for reaction for 1 h, until LC-MS indicated the completion of the reaction. Water (30 mL) was added to the reaction solution. The aqueous phase was extracted with ethyl acetate (50 mL×3), and the organic phase was dried over anhydrous sodium sulfate. The organic phase was concentrated at reduced pressure to give a crude product, and the crude product was subjected to column chromatography ($SiO_2$, EtOAc/PE=0/1 to 1/9) to give a yellow solid (3.5 g, 75.6% yield).

ESI-MS m/z: 319 $[M+H]^+$

Step 2: Synthesis of Compound Int_43-1-3 int_43-1-3

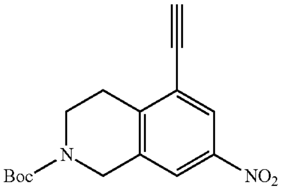

Int_43-1-2 (3.50 g, 9.35 mmol) was dissolved in methanol (50.0 mL), and $K_2CO_3$ (645 mg, 4.67 mmol) was added at 10° C. The reaction solution was warmed to room temperature and incubated for 5 h, until LC-MS indicated the completion of the reaction. Water (30 mL) was added to the reaction solution. The aqueous phase was extracted with dichloromethane (50 mL×3), and the organic phase was dried over anhydrous sodium sulfate. The organic phase was concentrated at reduced pressure to give a crude product, and the crude product was subjected to column chromatography ($SiO_2$, EtOAc/PE=0/1 to 1/9) to give a white solid (2.6 g, 92% yield).

$^1$H NMR (400 MHz, Chloroform-d) δ 8.14 (d, J=2.0 Hz, 1H), 7.90 (d, J=1.5 Hz, 1H), 4.59 (s, 2H), 3.64 (t, J=5.9 Hz, 2H), 3.37 (s, 1H), 2.98 (br t, J=5.8 Hz, 2H), 1.43 (s, 9H)

ESI-MS m/z: 247 $[M+H]^+$

Step 3: Synthesis of Compound Int_43-1 int_43-1

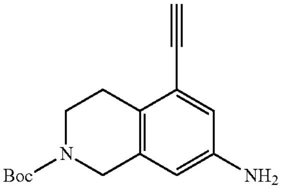

Int_43-1-3 (2.10 g, 6.95 mmol) was dissolved in ethanol (30.0 mL) and water (30.0 mL), and $NH_4Cl$ (3.72 g, 69.46 mmol) and Fe powder (3.88 g, 69.5 mmol) were added. The reaction solution was heated to 70° C. and incubated for 2 h, until LC-MS indicated the completion of the reaction. The reaction solution was filtered to give a filtrate, and the filtrate was concentrated. The aqueous phase was extracted with ethyl acetate (50 mL×3), and the organic phase was dried over anhydrous sodium sulfate. The organic phase was concentrated at reduced pressure to give a crude product, and the crude product was subjected to column chromatography ($SiO_2$, EtOAc/PE=0/1 to 1/9) to give a white solid (1 g, 52.9% yield). 1H NMR (400 MHz, DMSO-$d_6$) δ 6.58 (d, J=2.2 Hz, 1H), 6.38 (s, 1H), 5.07 (s, 2H), 4.33 (s, 2H), 4.22 (s, 1H), 3.51 (br t, J=5.8 Hz, 2H), 2.66 (t, J=5.9 Hz, 2H), 1.42 (s, 9H)

ESI-MS m/z: 217 $[M+H]^+$

Step 4: Synthesis of Compound Int_43-2 int_43-2

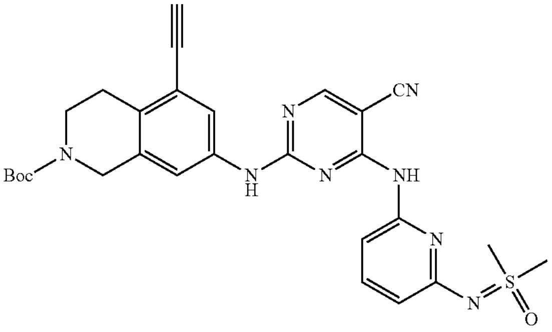

Int_1-8 (105 mg, 0.3 mmol) was dissolved in DMF (5 mL), and int_43-1 (82 mg, 0.299 mmol) and trifluoroacetic acid (34 mg, 0.3 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by column chromatography ($SiO_2$, DCM: MeOH=100:1 to 30:1) to give a yellow solid (65 mg, 62% yield).

ESI-MS m/z: 559 $[M+H]^+$

Step 5: Synthesis of Compound Int_43-3 int_43-3

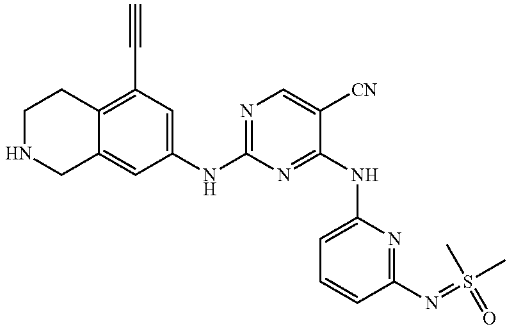

Int_43-2 (65 mg, 0.116 mmol) was dissolved in dichloromethane (5 mL), and trifluoroacetic acid (1 mL) was added. The mixture was incubated for 2 h at room temperature for reaction, until LC-MS indicated the completion of the reaction. The reaction solution was directly concentrated at reduced pressure to give a yellow solid (60 mg, crude product). The crude product was used directly in the next reaction.

ESI-MS m/z: 459 $[M+H]^+$

Step 6: Synthesis of Compound 43

43

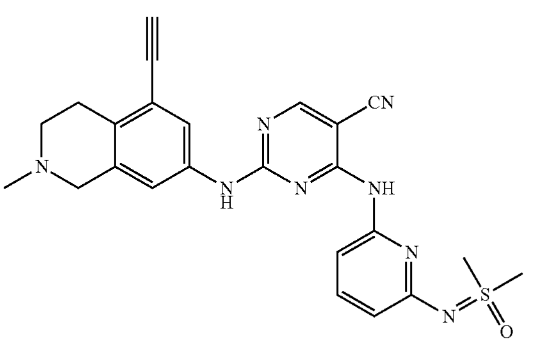

Int_43-3 (53 mg, 0.116 mmol) and DIPEA (298 mg, 2.3 mmol) were dissolved in dichloromethane (2 mL) and methanol (2 mL), and an aqueous formaldehyde solution (37-40%, 0.5 mL) and sodium borohydride acetate (50 mg, 0.24 mmol) were added. The mixture was incubated for 1 h at room temperature for reaction, until LC-MS indicated the completion of the reaction. The reaction solution was concentrated at reduced pressure to give a crude product, and the crude product was purified by preparative column HPLC to give a yellow solid product (32 mg, 58.6% yield).

$^1$H NMR (400 MHz, Chloroform-d) δ 8.31 (s, 1H), 7.61 (d, J=8.0 Hz, 1H), 7.57-7.44 (m, 3H), 7.25 (s, 1H), 7.12 (s, 1H), 6.51 (dd, J=7.9, 0.8 Hz, 1H), 3.45 (s, 2H), 3.30 (s, 6H), 3.22 (s, 1H), 2.94 (t, J=6.0 Hz, 2H), 2.66 (t, J=6.0 Hz, 2H), 2.39 (s, 3H).

ESI-MS m/z: 473 [M+H]$^+$

Example 16: Synthesis of Compound 52

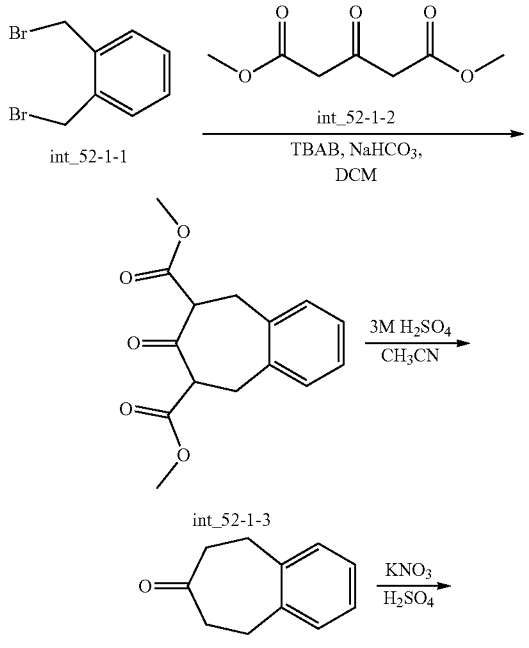

int_52-1-1
int_52-1-2
int_52-1-3
int_52-1-4

-continued

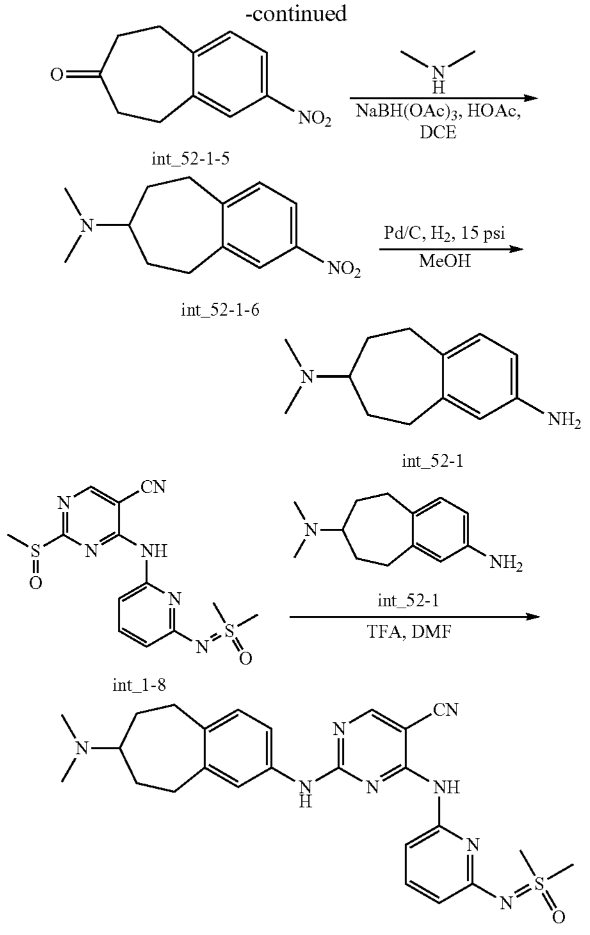

int_52-1-5
int_52-1-6
int_52-1
int_1-8
int_52-1

52

Step 1: Synthesis of compound int_52-1-3 int_52-1-3

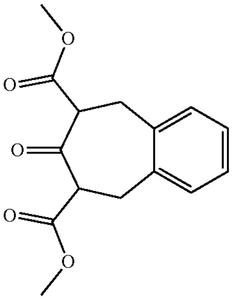

Int_52-1-1 (50 g, 189 mmol, 25.5 mL) and int_52-1-2 (49.5 g, 284 mmol, 40.9 mL) were dissolved in dichloromethane (400 mL), and TBAB (36.6 g, 113 mmol) and $NaHCO_3$ (1 M, 1000 mL) were added. The reaction solution was warmed to 40° C. and incubated for 16 h, until LC-MS indicated the completion of the reaction. Water (300 mL) was added to the reaction solution. The aqueous phase was extracted with dichloromethane (500 mL×3), and the organic phase was dried over anhydrous sodium sulfate. The organic phase was concentrated under reduced pressure to give a crude product (52 g, 99% yield) as a brown oil. The crude product was used directly in the next reaction.

$^1H$ NMR (400 MHz, Chloroform-d) δ 7.28-7.26 (m, 3H), 7.24 (s, 4H), 4.13 (q, J=7.3 Hz, 2H), 3.94 (dd, J=3.4, 8.9 Hz, 2H), 3.87-3.84 (m, 1H), 3.82-3.79 (m, 4H), 3.77-3.75 (m, 3H), 3.73-3.67 (m, 9H), 3.29-3.21 (m, 3H), 3.20-3.10 (m, 4H)

Step 2: Synthesis of Compound Int_52-1-4 int_52-1-4

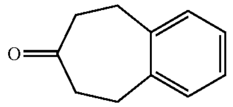

Int_52-1-3 (52 g, 188 mmol) was dissolved in acetonitrile (50 mL), and $H_2SO_4$ (3 M, 240.00 mL) was added. The reaction solution was heated to 100° C. and incubated for 16 h, until LC-MS indicated the completion of the reaction. Water (50 mL) was added to the reaction solution. The aqueous phase was extracted with ethyl acetate (300 mL×3), and the organic phase was dried over anhydrous sodium sulfate. The organic phase was concentrated at reduced pressure to give a crude product, and the crude product was purified by column chromatography (ISCO®; 220 g Sepa Flash® Silica Flash Column, eluent of 0-30% ethyl acetate/petroleum ether gradient at 80 mL/min) to give a white solid (25 g, 82.9% yield).

$^1H$ NMR (400 MHz, Chloroform-d) δ 7.20-7.09 (m, 4H), 2.89-2.77 (m, 4H), 2.63-2.45 (m, 4H)

Step 3: Synthesis of Compound Int_52-1-5 int_52-1-5

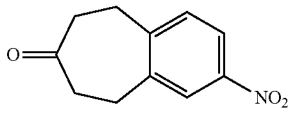

Int_52-1-4 (13 g, 81.1 mmol) was dissolved in $H_2SO_4$ (100 mL), and $KNO_3$ (9.02 g, 89.3 mmol) was added at −10° C. The reaction solution was incubated at −10° C. for 5 min, until LC-MS indicated the completion of the reaction. The reaction was poured into ice water (500 mL)$_n$ The aqueous phase was extracted with ethyl acetate (500 mL×3), and the organic phase was dried over anhydrous sodium sulfate. The organic phase was concentrated at reduced pressure to give a crude product, and the crude product was purified by column chromatography (ISCO®; 120 g Sepa Flash® Silica Flash Column, eluent of 0-30% ethyl acetate/petroleum ether gradient at 60 mL/min) to give a yellow solid (9 g, 54.1% yield).

$^1H$ NMR (400 MHz, Chloroform-d) δ 8.19-8.03 (m, 2H), 7.42 (d, J=8.3 Hz, 1H), 3.10-3.00 (m, 4H), 2.72-2.63 (m, 4H)

Step 4: Synthesis of Compound Int_52-1-6 int_52-1-6

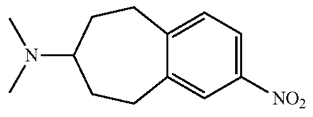

Int_52-1-5 (5 g, 24.4 mmol) and dimethylamine (2 M, 36.5 mL) were dissolved in DCE (50 mL), and HOAc (146 mg, 2.44 mmol, 139.4 μL) and $NaBH(OAc)_3$ (15.5 g, 73.1 mmol) were added at room temperature. The reaction solution was incubated at room temperature for 16 h, until LC-MS indicated the completion of the reaction. A saturated $NaHCO_3$ solution (150 mL) was added to the reaction solution. The aqueous phase was extracted with ethyl acetate (300 mL×3), and the organic phase was dried over anhydrous sodium sulfate. The organic phase was concentrated at reduced pressure to give a crude product, and the crude product was purified by column chromatography (ISCO®; 80 g Sepa Flash® Silica Flash Column, eluent of 0-10% MeOH (10% $NH_3 \cdot H_2O$)/DCM gradient at 60 mL/min) to give a white solid (3.7 g, 64.8% yield).

$^1H$ NMR (400 MHz, DMSO-$d_6$) δ 8.03 (d, J=2.4 Hz, 1H), 7.97 (dd, J=2.5, 8.3 Hz, 1H), 7.42 (d, J=8.3 Hz, 1H), 3.00 (dt, J=7.7, 13.4 Hz, 2H), 2.81-2.68 (m, 2H), 2.65-2.55 (m, 1H), 2.17 (s, 6H), 2.04-1.87 (m, 2H), 1.40-1.21 (m, 2H)

Step 5: Synthesis of Compound Int_52-1 int_52-1

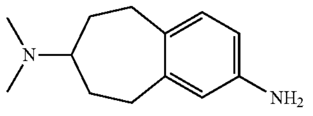

Int_52-1-6 (3.60 g, 15.4 mmol) was dissolved in methanol (20.0 mL), and 10% Pd/C (3 g, 15.4 mmol) was added. In hydrogen atmosphere (15.0 Psi.), the reaction solution was incubated at room temperature for 16 h, until LC-MS indicated the completion of the reaction. The reaction solution was filtered to give a filtrate, and the filtrate was concentrated at reduced pressure to give a white solid (2.5 g, 79.6% yield).

$^1H$ NMR (400 MHz, DMSO-$d_6$) δ 6.74 (d, J=8.0 Hz, 1H), 6.34 (d, J=2.3 Hz, 1H), 6.26 (dd, J=2.4, 7.9 Hz, 1H), 4.74 (br s, 2H), 2.63-2.52 (m, 3H), 2.48-2.41 (m, 2H), 2.20-2.06 (m, 6H), 2.01-1.77 (m, 2H), 1.33-1.07 (m, 2H)

ESI-MS m/z: 205 $[M+H]^+$

Step 6: Synthesis of Compound 52

52

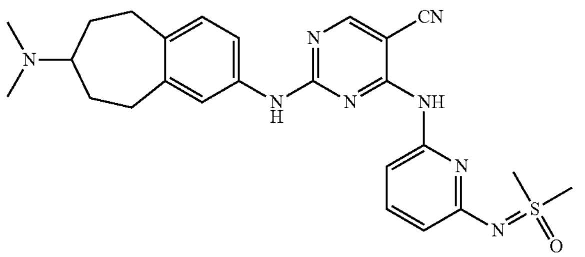

Int_1-8 (200 mg, 0.562 mmol) was dissolved in DMF (10 mL), and int_52-1 (115 mg, 0.562 mmol) and trifluoroacetic acid (226 mg, 2.2 mmol) were added. The reaction solution was heated to 80° C. and stirred for 16 h, until LC-MS indicated the completion of the reaction. The reaction solution was cooled to room temperature and concentrated at reduced pressure to give a crude product. The crude product was purified by preparative HPLC to give a white solid (71 mg, 15% yield).

$^1$H NMR (400 MHz, Chloroform-d) δ 8.34 (s, 1H), 7.69 (d, J=8.0 Hz, 1H), 7.60 (s, 1H), 7.44 (s, 1H), 7.35 (s, 1H), 7.18 (s, 1H), 7.08 (d, J=8.0 Hz, 1H), 6.54 (d, J=7.9 Hz, 1H), 3.34 (s, 6H), 2.90-2.55 (m, 5H), 2.26 (s, 6H), 2.12-2.01 (m, 2H), 1.36 (dd, J=12.4, 7.1 Hz, 2H).

ESI-MS m/z: 491 $[M+H]^+$

Example 17: Synthesis of Compound 55

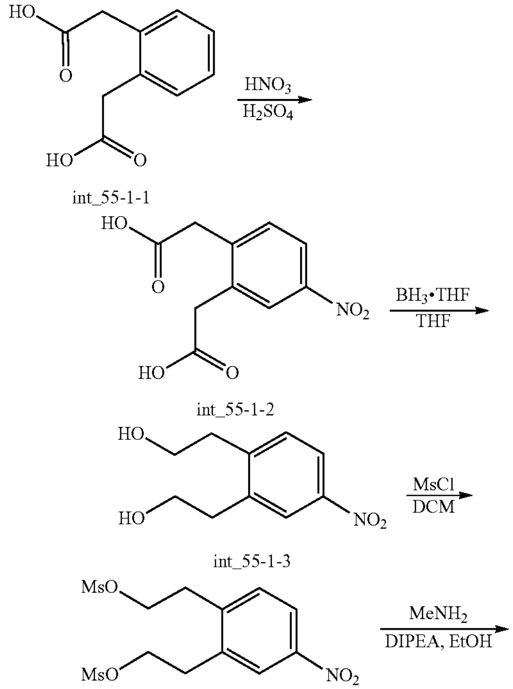

int_55-1-1 int_55-1-2 int_55-1-3 int_55-1-4

-continued

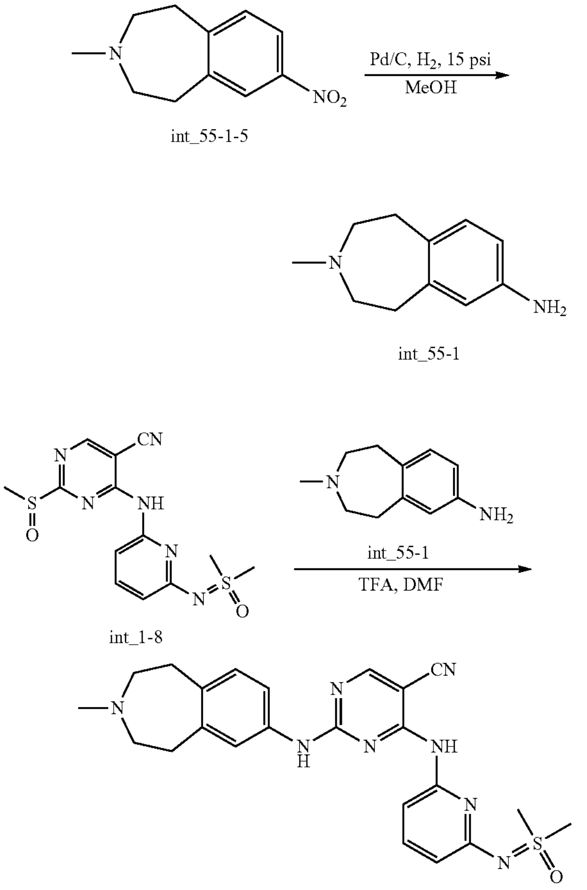

int_55-1-5 int_55-1 int_1-8

55

Step 1: Synthesis of Compound Int_55-1-2 int_55-1-2

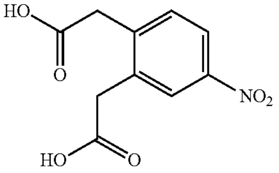

Int_55-1-1 (40.0 g, 205 mmol) was dissolved in $H_2SO_4$ (160 mL), and $HNO_3$ (20.9 g, 216 mmol, 14.9 mL, 65% purity) was added at 0° C. The reaction solution was incubated at 0° C. for 4 h, until LC-MS indicated the completion of the reaction. The reaction was poured into ice water (300 mL). The aqueous phase was extracted with ethyl acetate (500 mL×3), and the organic phase was dried over anhydrous sodium sulfate. The organic phase was concentrated under reduced pressure to give a crude product (32 g, 65% yield) as a yellow solid. The crude product was used directly in the next reaction.

$^1$H NMR (400 MHz, DMSO-$d_6$) δ 12.65 (br s, 2H), 8.18 (d, J=2.5 Hz, 1H), 8.10 (dd, J=8.3, 2.5 Hz, 1H), 7.55 (d, J=8.5 Hz, 1H), 3.80 (s, 2H), 3.77 ppm (s, 2H)

Step 2: Synthesis of Compound Int_55-1-3 int_55-1-3

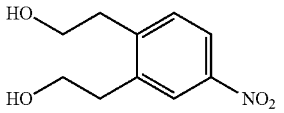

Int_55-1-2 (32.0 g, 133 mmol) was dissolved in THE (500 mL), and a $BH_3$·THF solution (1 M, 267 mL) was added at 0° C. The reaction solution was incubated at 0° C. for 4 h, until LC-MS indicated the completion of the reaction. Water (600 mL) was added to the reaction solution. The aqueous phase was extracted with ethyl acetate (500 mL×3), and the organic phase was dried over anhydrous sodium sulfate. The organic phase was concentrated at reduced pressure to give a crude product, and the crude product was purified by column chromatography (ISCO®; 220 g Sepa Flash® Silica Flash Column, eluent of 0-10% MeOH/DCM gradient at 80 mL/min) to give a yellow solid (17 g, 60.1% yield).

$^1$H NMR (400 MHz, DMSO-$d_6$) δ 8.07 (d, J=2.5 Hz, 1H), 7.99 (dd, J=8.5, 2.5 Hz, 1H), 7.47 (d, J=8.5 Hz, 1H), 4.82 (br s, 2H), 3.59-3.68 (m, 4H), 2.89 ppm (t, J=6.8 Hz, 4H)

Step 3: Synthesis of Compound Int_55-1-4 int_55-1-4

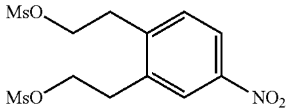

Int_55-1-3 (15 g, 71.0 mmol) and TEA (35.9 g, 355 mmol, 49.4 mL) were dissolved in DCM (400 mL), and MsCl (23.6 g, 206 mmol, 16 mL) was added at 0° C. The reaction solution was incubated at 0° C. for 3 h, until TLC indicated the completion of the reaction. Ice water (200 mL) was added to the reaction solution. The aqueous phase was extracted with dichloromethane (300 mL×3), and the organic phase was dried over anhydrous sodium sulfate. The organic phase was concentrated under reduced pressure to give a crude product (20 g, 76.7% yield). The crude product was used directly in the next reaction.

$^1$H NMR (400 MHz, Chloroform-d) δ 8.18-8.10 (m, 2H), 7.47 (d, J=8.3 Hz, 1H), 4.49 (q, J=6.7 Hz, 4H), 3.25 (t, J=6.8 Hz, 4H), 3.01 (d, J=5.5 Hz, 6H)

Step 4: Synthesis of Compound Int_55-1-5 int_55-1-5

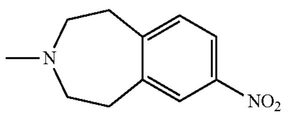

Int_55-1-4 (1 g, 2.72 mmol), methylamine (338 mg, 3.27 mmol, 30% purity), and DIPEA (879 mg, 6.80 mmol, 1.19 mL) were dissolved in ethanol (15 mL). The reaction solution was heated to 50° C. and incubated for 16 h, until LC-MS indicated the completion of the reaction. The reaction solution was concentrated at reduced pressure to give a crude product, and the crude product was purified by column chromatography ($SiO_2$, DCM/MeOH=10/1) to give a red oil (20 g, 76.7% yield).

$^1$H NMR (400 MHz, Chloroform-d) δ 8.04-7.98 (m, 2H), 7.28 (s, 1H), 7.26 (s, 1H), 3.13 (br s, 4H), 2.73 (br s, 4H), 2.48 (s, 3H)

Step 5: Synthesis of Compound Int_55-1 int_55-1

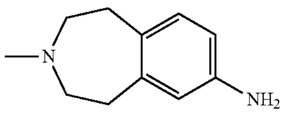

Int_55-1-5 (1 g, 4.85 mmol) was dissolved in methanol (20.0 mL), and 10% Pd/C (500 mg, 4.85 mmol) was added. In hydrogen atmosphere (15.0 Psi.), the reaction solution was incubated at room temperature for 16 h, until LC-MS indicated the completion of the reaction. The reaction solution was filtered to give a white solid (800 mg, 93.6% yield).

$^1$H NMR (400 MHz, Methanol-d4) δ 6.86 (d, J=7.8 Hz, 1H), 6.58-6.49 (m, 2H), 2.82 (br s, 4H), 2.57 (br s, 4H), 2.36 (s, 3H)

ESI-MS m/z: 177 $[M+H]^+$

Step 6: Synthesis of Compound 55

55

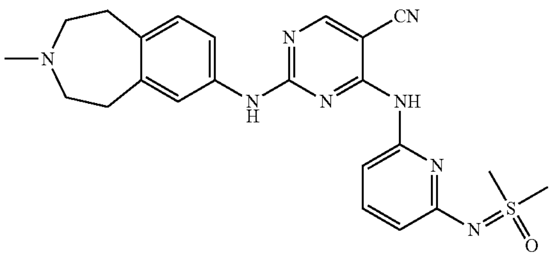

Int_1-8 (200 mg, 0.57 mmol) was dissolved in DMF (10 mL), and int_55-1 (99 mg, 0.562 mmol) and trifluoroacetic acid (226 mg, 2.2 mmol) were added. The reaction solution was heated to 80° C. and stirred for 16 h, until LC-MS indicated the completion of the reaction. The reaction solution was cooled to room temperature and concentrated at reduced pressure to give a crude product. The crude product was purified by preparative HPLC to give a white solid (42 mg, 16.2% yield).

$^1$H NMR (400 MHz, Chloroform-d) δ 8.34 (s, 1H), 7.62 (s, 2H), 7.23 (s, 1H), 7.23 (s, 2H), 7.06 (s, 2H), 6.55 (s, 1H), 3.34 (s, 6H), 3.13 (s, 4H), 2.91 (s, 4H), 2.60 (s, 3H).

ESI-MS m/z: 463 $[M+H]^+$

Example 18: Synthesis of Compound 60

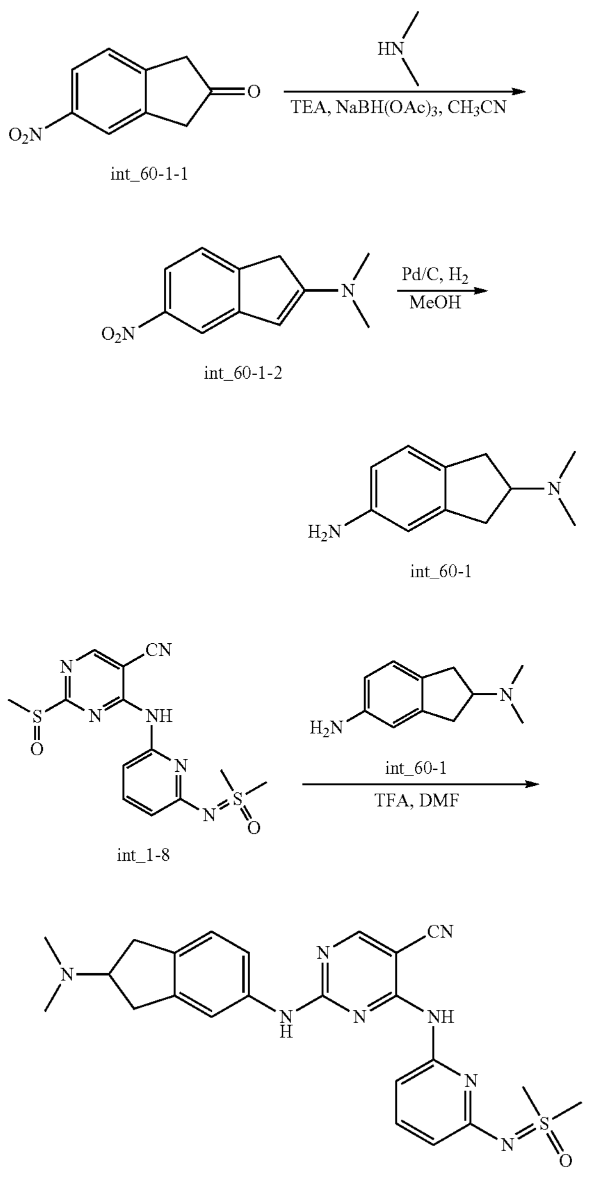

int_60-1-1, int_60-1-2, int_60-1, int_1-8, 60

Step 1: Synthesis of Compound Int_60-1-2 int_60-1-2

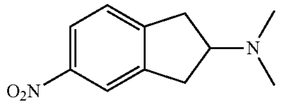

Int_60-1-1 (1.9 g, 10.7 mmol) was dissolved in acetonitrile (8 mL), and a solution of dimethylamine in tetrahydrofuran (2.0 M, 5.9 mL) and triethylamine (3.25 g, 32.1 mmol) was added. After 10 min of reaction, sodium borohydride acetate (6.8 g, 32.1 mmol) was added, and the reaction solution was stirred for reaction for 16 h, until LC-MS indicated the completion of the reaction. Water (100 mL) was added to the reaction solution. The aqueous phase was extracted with ethyl acetate (100 mL×3), and the organic phase was dried over anhydrous sodium sulfate. The organic phase was concentrated at reduced pressure to give a crude product, and the crude product was subjected to column chromatography ($SiO_2$, DCM:MeOH=100:1 to 20:1) to give a white solid (1.2 g, 55% yield).

ESI-MS m/z: 207 $[M+H]^+$

Step 2: Synthesis of Compound Int_60-1 int_60-1

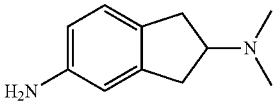

Int_60-1-2 (900 mg, 4.36 mmol) was dissolved in methanol (20.0 mL), and 10% Pd/C (150 mg) was added. In hydrogen atmosphere (15.0 Psi.), the reaction solution was incubated at room temperature for 16 h, until LC-MS indicated the completion of the reaction. The reaction solution was filtered to give a white solid (700 mg, 91% yield).

ESI-MS m/z: 177 $[M+H]^+$

Step 3: Synthesis of Compound 60

60

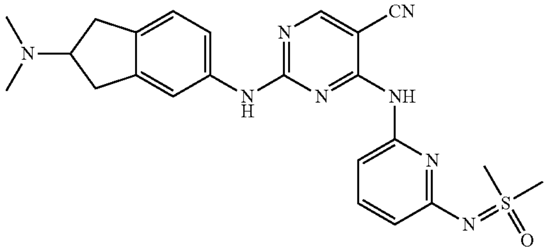

Int_1-8 (600 mg, 1.59 mmol) was dissolved in DMF (30 mL), and int_60-1 (258 mg, 1.46 mmol) and trifluoroacetic acid (365 mg, 3.2 mmol) were added. The reaction solution was heated to 85° C. and stirred for 16 h, until LC-MS indicated the completion of the reaction. The reaction solution was cooled to room temperature and concentrated at reduced pressure to give a crude product. The crude product was purified by preparative HPLC to give a white solid (530 mg, 72% yield).

$^1$H NMR (400 MHz, Chloroform-d) δ 8.35 (s, 1H), 7.68-7.59 (m, 2H), 7.45 (s, 2H), 7.33 (s, 1H), 7.22 (d, J=8.5 Hz, 1H), 7.15 (d, J=8.1 Hz, 1H), 6.56 (dd, J=7.9, 0.7 Hz, 1H), 3.35 (s, 6H), 3.35-3.25 (m, 1H), 3.15-2.98 (m, 4H), 2.43 (s, 6H).

ESI-MS m/z: 463 $[M+H]^+$

Example 19: Synthesis of Compound 61

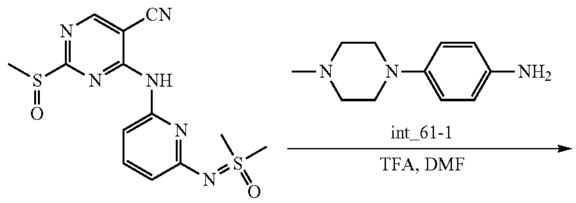

int_1-8

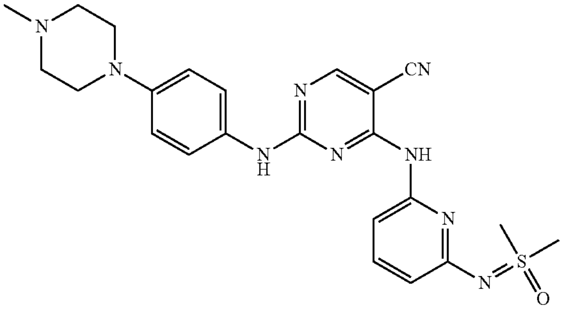

61

Step 1: Synthesis of Compound 61

61

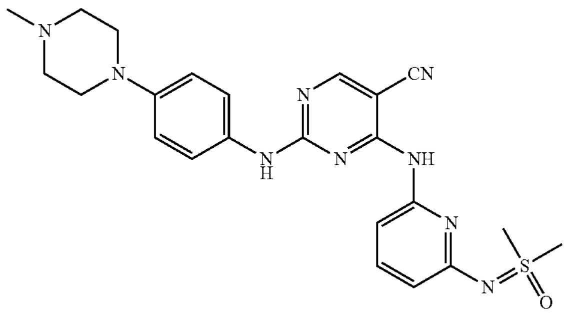

Int_1-8 (67 mg, 0.2 mmol) was dissolved in DMF (5 mL), and int_61-1 (57 mg, 0.3 mmol) and trifluoroacetic acid (92 mg, 0.8 mmol) were added. The reaction solution was heated to 85° C. and stirred for 16 h, until LC-MS indicated the completion of the reaction. The reaction solution was cooled to room temperature and concentrated at reduced pressure to give a crude product. The crude product was purified by preparative HPLC to give a white solid (38 mg, 39% yield).

$^1$H NMR (400 MHz, Chloroform-d) δ 8.32 (s, 1H), 7.62 (s, 2H), 7.36 (d, J=8.6 Hz, 4H), 6.91 (d, J=9.0 Hz, 2H), 6.53 (d, J=7.9 Hz, 1H), 3.33 (s, 6H), 3.24-3.16 (m, 4H), 2.58 (t, J=5.0 Hz, 4H), 2.35 (s, 3H).

ESI-MS m/z: 478 $[M+H]^+$

Example 20: Synthesis of Compound 62

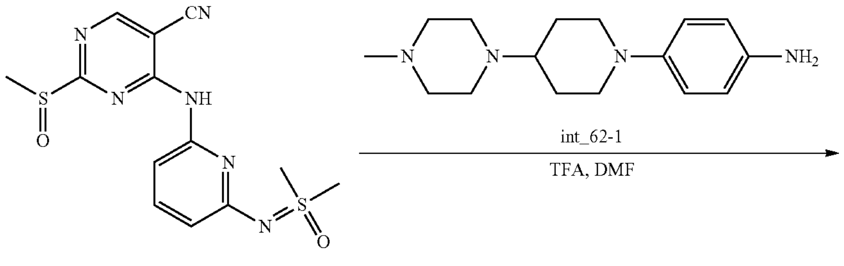

int_1-8

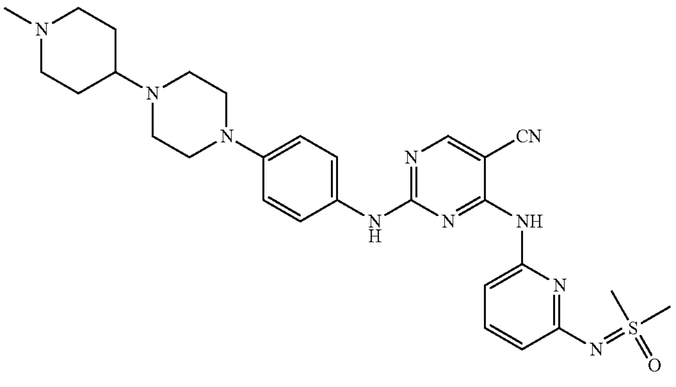

62

Step 1: Synthesis of Compound 62

62

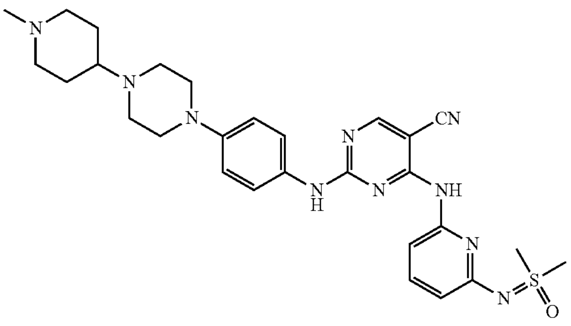

Int_1-8 (67 mg, 0.2 mmol) was dissolved in DMF (5 mL), and int_62-1 (55 mg, 0.2 mmol) and trifluoroacetic acid (115 mg, 1 mmol) were added. The reaction solution was heated to 85° C. and stirred for 16 h, until LC-MS indicated the completion of the reaction. The reaction solution was cooled to room temperature and concentrated at reduced pressure to give a crude product. The crude product was purified by preparative HPLC to give a white solid (40 mg, 35% yield).

$^1$H NMR (400 MHz, Chloroform-d) δ 8.31 (s, 1H), 7.66 (s, 2H), 7.33 (d, J=8.5 Hz, 4H), 6.90 (d, J=9.0 Hz, 2H), 6.53 (d, J=7.9 Hz, 1H), 3.70 (d, J=12.1 Hz, 2H), 3.33 (s, 6H), 2.75-2.66 (m, 2H), 2.63 (s, 4H), 2.45 (s, 4H), 2.40-2.32 (m, 1H), 2.28 (s, 3H), 1.94 (d, J=12.6 Hz, 2H), 1.66 (qd, J=12.1, 4.0 Hz, 2H).

ESI-MS m/z: 561 [M+H]$^+$

Example 21: Synthesis of Compound 63

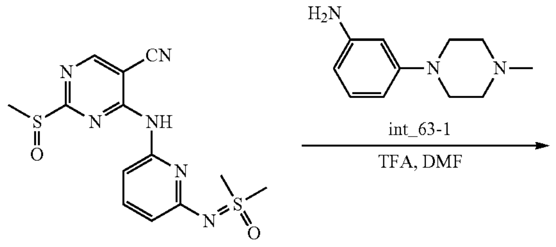

int_1-8

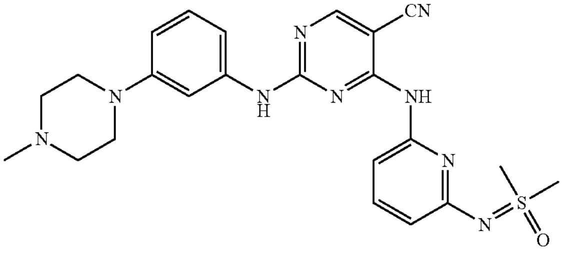

63

Step 1: Synthesis of Compound 63

63

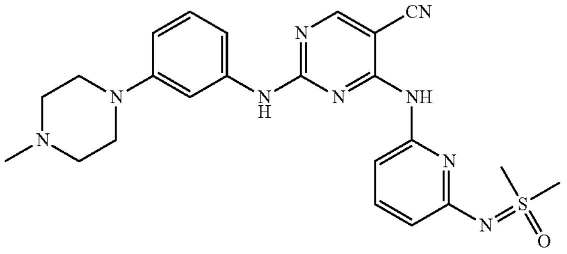

Int_1-8 (67 mg, 0.2 mmol) was dissolved in DMF (5 mL), and int_63-1 (39 mg, 0.2 mmol) and trifluoroacetic acid (92 mg, 0.8 mmol) were added. The reaction solution was heated to 85° C. and stirred for 16 h, until LC-MS indicated the completion of the reaction. The reaction solution was cooled to room temperature and concentrated at reduced pressure to give a crude product. The crude product was purified by preparative HPLC to give a white solid (10 mg, 17% yield).

$^1$H NMR (400 MHz, Chloroform-d) δ 8.36 (s, 1H), 7.68 (d, J=8.0 Hz, 1H), 7.62 (s, 1H), 7.46 (t, J=8.2 Hz, 1H), 7.41 (s, 1H), 7.21 (d, J=8.1 Hz, 1H), 7.13 (s, 1H), 6.97 (d, J=8.1 Hz, 1H), 6.70 (dd, J=8.4, 2.4 Hz, 1H), 6.54 (d, J=7.9 Hz, 1H), 3.34 (s, 6H), 3.27 (t, J=5.0 Hz, 4H), 2.70 (s, 4H), 2.44 (s, 3H).

ESI-MS m/z: 478 [M+H]$^+$

Example 22: Synthesis of Compound 64

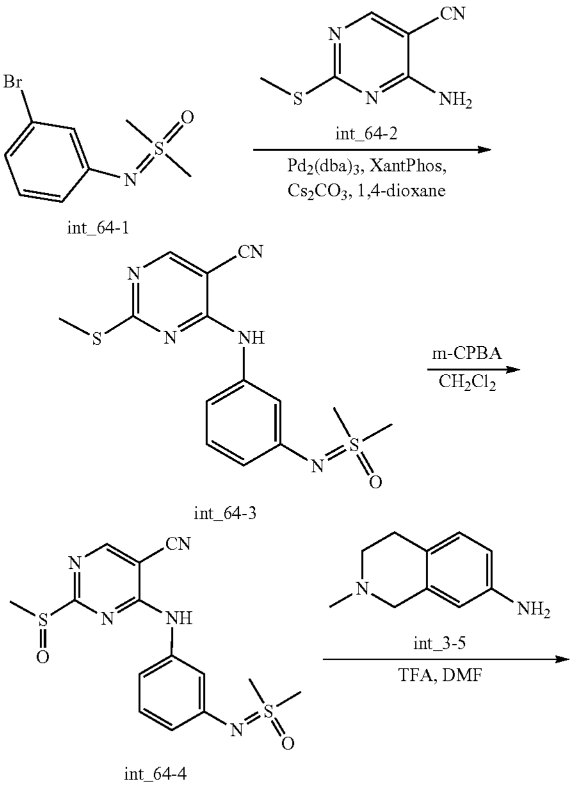

-continued

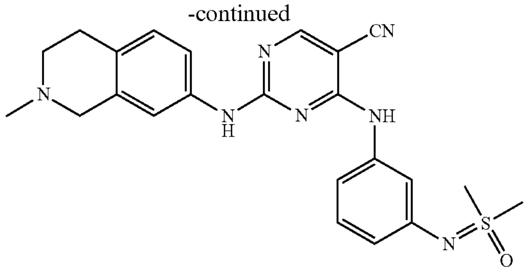

64

Step 1: Synthesis of Compound Int_64-3 int_64-3

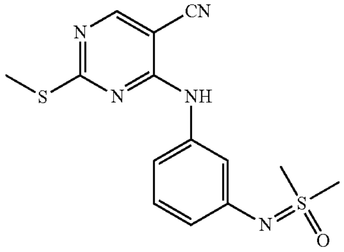

Int_64-1 (298 mg, 1.2 mmol), int_64-2 (200 mg, 1.2 mmol), cesium carbonate (782 mg, 2.4 mmol), $Pd_2(dba)_3$ (110 mg, 0.12 mmol), and Xantphos (138 mg, 0.24 mmol) were dissolved in 1,4-dioxane (20 mL), and the mixture was incubated at 85° C. overnight, until LC-MS indicated the completion of the reaction. The reaction solution was filtered and distilled at reduced pressure to give a crude product, and the crude product was subjected to column chromatography ($SiO_2$, DCM:MeOH=100:1 to 30:1) to give an orange solid product (130 mg, 33% yield).

ESI-MS m/z: 334 $[M+H]^+$

Step 2: Synthesis of Compound Int_64-4 int_64-4

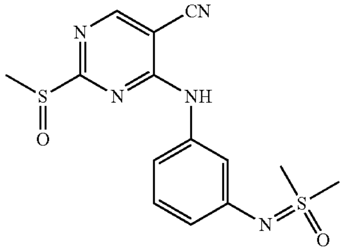

Int_64-3 (130 mg, 0.39 mmol) was dissolved in dichloromethane (15 mL), and m-CPBA (85%, 92 mg, 0.45 mmol) was added at room temperature. The mixture was stirred at room temperature for half an hour, until LC-MS indicated the completion of the reaction. The reaction solution was washed with aqueous sodium bicarbonate (50 mL×2). The aqueous phase was extracted with ethyl acetate (50 mL×3), and the organic phase was dried over anhydrous sodium sulfate. The organic phase was concentrated at reduced pressure to give a crude product (120 mg). The crude product was used directly in the next reaction.

ESI-MS m/z: 350 $[M+H]^+$

Step 3: Synthesis of Compound 64

64

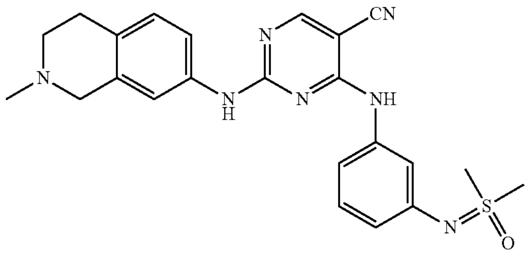

Int_64-4 (120 mg, 0.34 mmol) was dissolved in DMF (10 mL), and int_3-5 (95 mg, 0.59 mmol) and trifluoroacetic acid (158 mg, 1.56 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by preparative HPLC to give an orange solid (1.1 g, 70% yield).

$^1$H NMR (400 MHz, Chloroform-d) δ 8.27 (s, 1H), 7.49 (s, 1H), 7.23 (s, 2H), 7.07 (s, 2H), 6.98 (s, 1H), 6.94-6.76 (m, 1H), 3.63-3.31 (m, 2H), 3.10 (s, 5H), 2.83 (s, 2H), 2.63 (s, 2H), 2.40 (s, 3H).

LC-MS: 448 $[M+H]^+$

Example 23: Synthesis of Compound 77

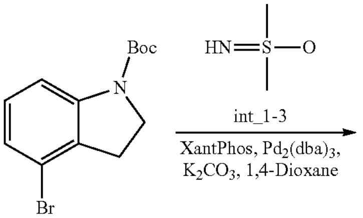

int_77-1

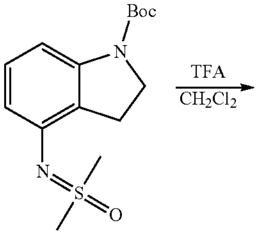

int_77-2

-continued

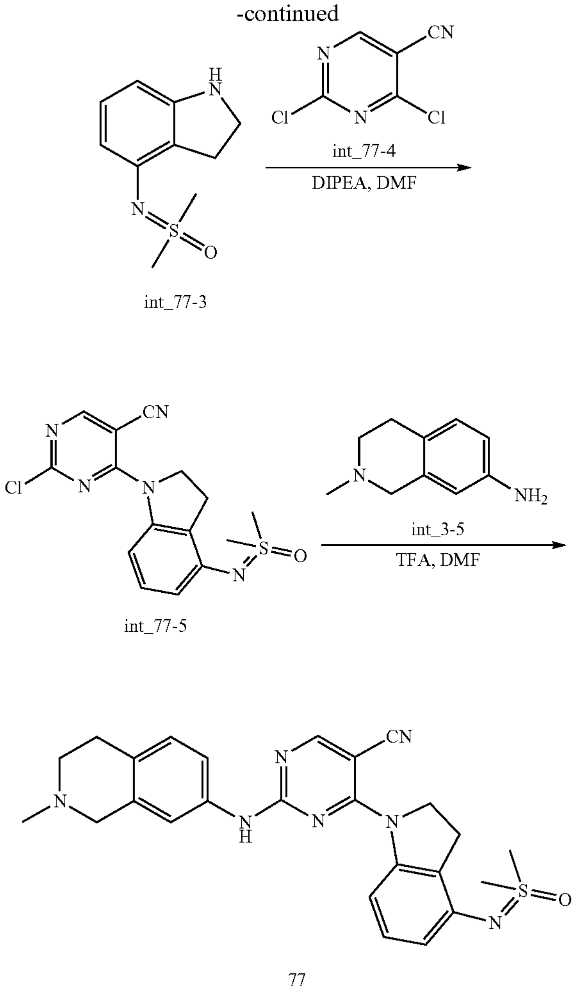

Step 1: Synthesis of Compound Int_77-2 int_77-2

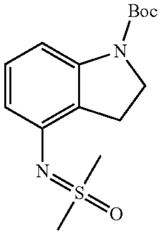

Int_77-1 (350 mg, 1.174 mmol), int_1-3 (110 mg, 1.174 mmol), cesium carbonate (574 mg, 1.761 mmol), $Pd_2(dba)_3$ (54 mg, 0.059 mmol), and Xantphos (68 mg, 0.117 mmol) were dissolved in 1,4-dioxane (15 mL), and the reaction solution was incubated at 80° C. overnight, until LC-MS indicated the completion of the reaction. The reaction solution was filtered and distilled at reduced pressure to give a crude product, and the crude product was purified by preparative HPLC to give a pale yellow solid product (374 mg, 89% yield).

ESI-MS m/z: 311 $[M+H]^+$

Step 3: Synthesis of Compound Int_77-3 int_77-3

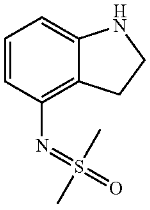

Int_77-2 (374 mg, 1.174 mmol) was dissolved in dichloromethane (15 mL), and trifluoroacetic acid (8 mL) was added. The mixture was incubated for 1 h at room temperature for reaction, until LC-MS indicated the completion of the reaction. The reaction solution was directly concentrated at reduced pressure to give a pale yellow solid (252 mg, crude product). The crude product was used directly in the next reaction.

ESI-MS m/z: 211 $[M+H]^+$

Step 4: Synthesis of Compound Int_77-5 int_77-5

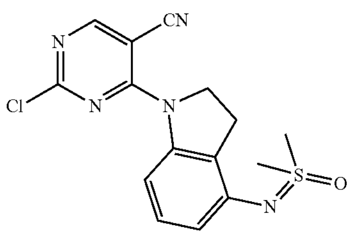

Int_77-3 (252 mg, 1.2 mmol) and int_77-4 (209 mg, 1.2 mmol) were dissolved in DMF (12 mL), and DIPEA (3.1 g, 24 mmol) was added. The reaction solution was heated to 50° C. and incubated overnight, until LC-MS indicated the completion of the reaction. The reaction solution was filtered and distilled at reduced pressure to give a crude product, and the crude product was purified by preparative HPLC to give a product (133 mg, 31.9% yield).

ESI-MS m/z: 348 $[M+H]^+$

Step 5: Synthesis of Compound 77

77

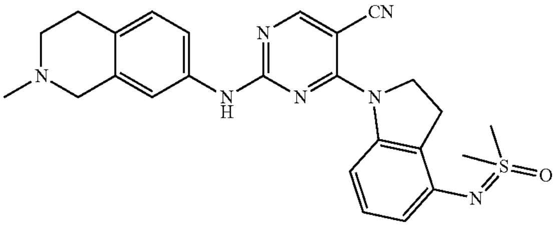

Int_77-5 (330 mg, 0.95 mmol) was dissolved in DMF (20 mL), and int_3-5 (162 mg, 1 mmol) and trifluoroacetic acid (342 mg, 3 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by preparative HPLC to give a white solid (150 mg, 33% yield).

$^1$H NMR (400 MHz, Chloroform-d) δ 8.37 (s, 1H), 7.67 (d, J=8.0 Hz, 1H), 7.28 (d, J=2.1 Hz, 1H), 7.22-7.13 (m, 1H), 7.06 (d, J=8.2 Hz, 1H), 6.97 (t, J=8.0 Hz, 1H), 6.85 (d, J=7.9 Hz, 1H), 4.45 (t, J=8.3 Hz, 2H), 3.52 (s, 2H), 3.16 (m, 8H), 2.90 (t, J=6.0 Hz, 2H), 2.70 (t, J=5.9 Hz, 2H), 2.44 (s, 3H).

ESI-MS m/z: 474 [M+H]$^+$

Example 24: Synthesis of Compound 78

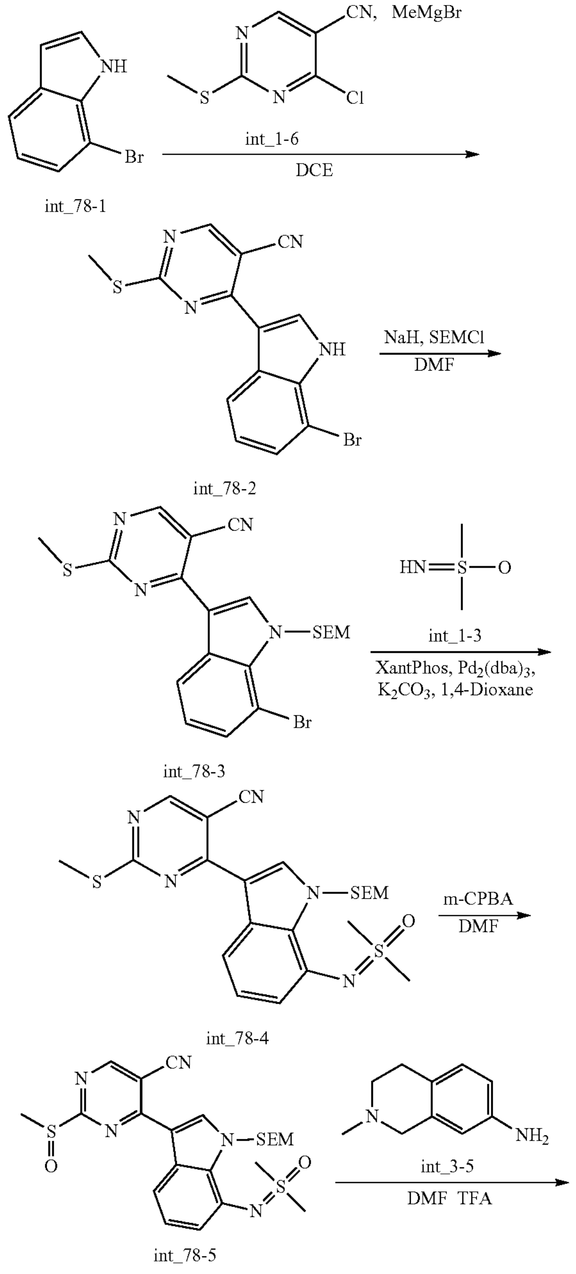

-continued

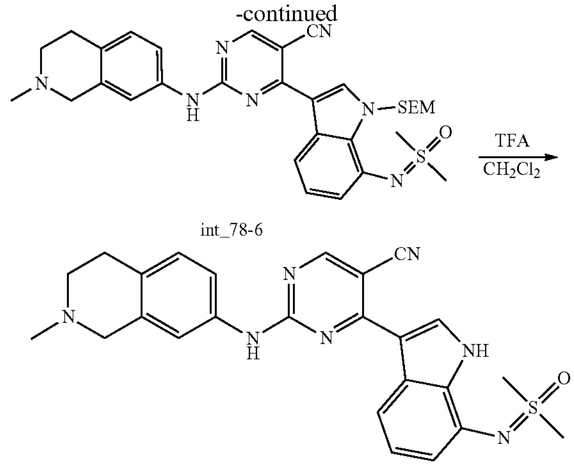

78

Step 1: Synthesis of Compound Int_78-2 int_78-2

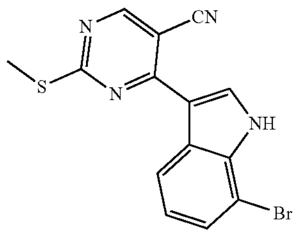

Int_78-1 (2.7 g, 13.77 mmol) was dissolved in DCE (60 mL), and in nitrogen atmosphere, a solution of methylmagnesium bromide in THE (3.0 M, 4.6 mL) was added at 0° C. The reaction solution was stirred for 30 min before int_1-6 (2.56 g, 13.77 mmol) was added, and then warmed to room temperature and stirred overnight, until LC-MS indicated the completion of the reaction. The reaction solution was poured into ice water, and a solid was precipitated and filtered to give a crude product (1.6 g, 34% yield). The crude product was used directly in the next reaction.

ESI-MS m/z: 345 [M+H]$^+$

Step 2: Synthesis of Compound Int_78-3 int_78-3

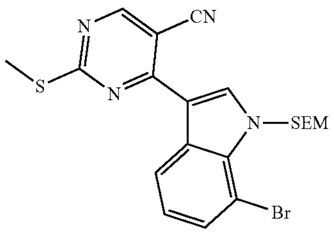

Int_78-2 (1 g, 2.9 mmol) was dissolved in DMF (50 mL), and in nitrogen atmosphere, NaH (60% in oil, 140 mg, 3.5 mmol) was added at 0° C. The mixture was stirred for 30 min before SEMCl (584 mg, 3.5 mmol) was added, and then warmed to room temperature and stirred overnight, until LC-MS indicated the completion of the reaction. The reaction solution was concentrated at reduced pressure to give a crude product. The crude product was purified by column chromatography ($SiO_2$, DCM:MeOH=100:1 to 20:1) to give a pale yellow solid (500 mg, 36% yield).

ESI-MS m/z: 475 $[M+H]^+$

Step 3: Synthesis of Compound Int_78-4 int_78-4

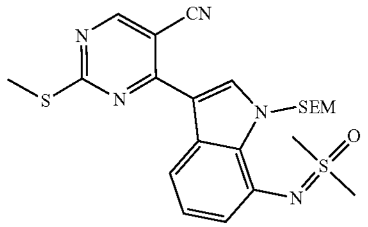

Int_78-3 (500 mg, 1.05 mmol), int_1-3 (587 mg, 6.32 mmol), cesium carbonate (855 mg, 2.63 mmol), $Pd_2(dba)_3$ (96 mg, 0.105 mmol) and Xantphos (73 mg, 0.126 mmol) were dissolved in DMF (20 mL), and the mixture was incubated at 85° C. in nitrogen atmosphere overnight, until LC-MS indicated the completion of the reaction. The reaction solution was filtered and distilled at reduced pressure to give a crude product, and the crude product was subjected to column chromatography ($SiO_2$, DCM:MeOH=100:1 to 20:1) to give a pale yellow solid product (500 mg, 97% yield).

ESI-MS m/z: 488 $[M+H]^+$

Step 4: Synthesis of Compound Int_78-5 int_78-5

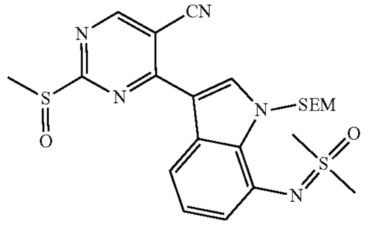

Int_78-3 (250 mg, 0.5 mmol) was dissolved in dichloromethane (20 mL), and m-CPBA (85%, 153 mg, 0.75 mmol) was added at room temperature. The mixture was stirred at room temperature for half an hour, until LC-MS indicated the completion of the reaction. Water (100 mL) was added to the reaction solution. The aqueous phase was extracted with dichloromethane (100 mL×3), and the organic phase was dried over anhydrous sodium sulfate. The organic phase was concentrated at reduced pressure to give a crude product (200 mg). The crude product was used directly in the next reaction.

ESI-MS m/z: 504 $[M+H]^+$

Step 5: Synthesis of Compound Int_78-6 int_78-6

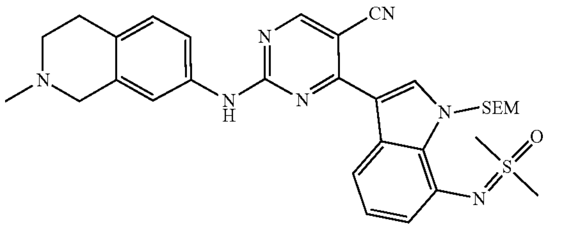

Int_78-5 (252 mg, 0.5 mmol) was dissolved in DMF (10 mL), and int_3-5 (81 mg, 0.5 mmol) and trifluoroacetic acid (57 mg, 0.5 mmol) were added. The reaction solution was heated to 80° C. and stirred for 16 h, until LC-MS indicated the completion of the reaction. The reaction solution was cooled to room temperature and concentrated at reduced pressure to give a crude product. The crude product was purified by column chromatography ($SiO_2$, DCM: MeOH=100:1 to 20:1) to give a pale yellow solid (100 mg, 33% yield).

ESI-MS m/z: 602 $[M+H]^+$

Step 6: Synthesis of Compound 78

78

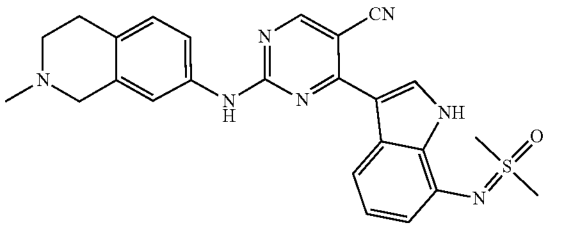

Int_78-6 (100 mg, 0.17 mmol) was dissolved in THE (5 mL), and TBAF (536 mg, 1.7 mmol) was added. The reaction solution was heated to 80° C. and stirred for 16 h, until LC-MS indicated the completion of the reaction. The reaction solution was cooled to room temperature and concentrated at reduced pressure to give a crude product. The crude product was purified by preparative HPLC to give a pale yellow solid (2 mg, 2.5% yield).

ESI-MS m/z: 472 $[M+H]^+$

Example 25: Synthesis of Compound 79

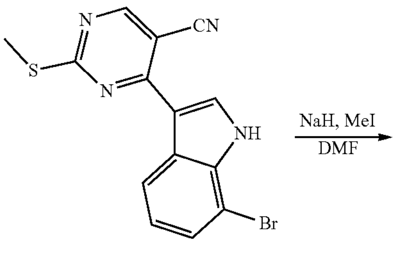

int_78-2

-continued

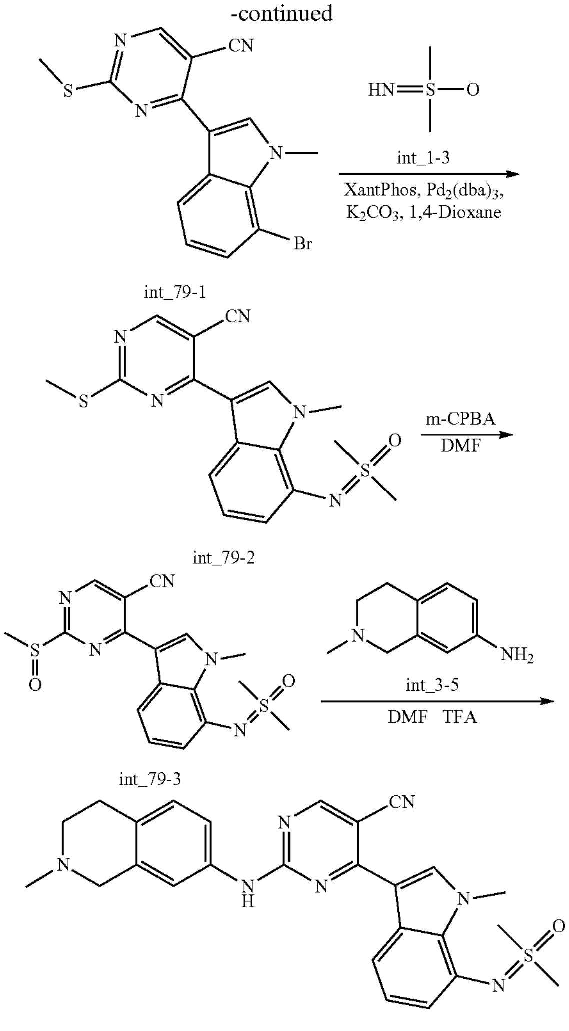

Step 1: Synthesis of Compound Int_79-1 int_79-1

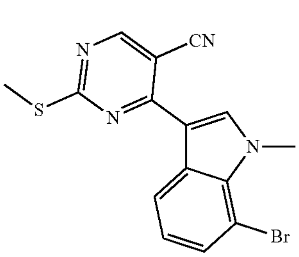

Int_78-2 (220 mg, 0.637 mmol) was dissolved in DMF (10 mL), and in nitrogen atmosphere, NaH (60% in oil, 40 mg, 1 mmol) was added at 0° C. The mixture was stirred for 10 min before iodomethane (117 mg, 0.828 mmol) was added, and then warmed to room temperature and stirred overnight, until LC-MS indicated the completion of the reaction. The reaction solution was poured into ice water, and a solid was precipitated and filtered to give a crude product (160 mg, 70% yield). The crude product was used directly in the next reaction.

ESI-MS m/z: 359 $[M+H]^+$

Step 2: Synthesis of Compound Int_79-2 int_79-2

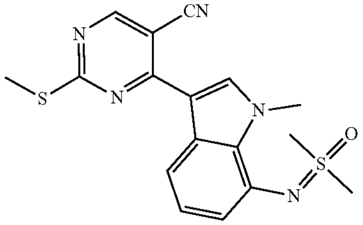

Int_79-1 (160 mg, 0.445 mmol), int_1-3 (84 mg, 0.9 mmol), cesium carbonate (362 mg, 1.11 mmol), $Pd_2(dba)_3$ (4 mg, 0.0445 mmol) and Xantphos (3 mg, 0.0534 mmol) were dissolved in DMF (10 mL), and the mixture was incubated at 85° C. in nitrogen atmosphere overnight, until LC-MS indicated the completion of the reaction. The reaction solution was poured into ice water, and a solid was precipitated and filtered to give a crude product (100 mg, 60% yield). The crude product was used directly in the next reaction.

ESI-MS m/z: 372 $[M+H]^+$

Step 3: Synthesis of Compound Int_79-3 int_79-3

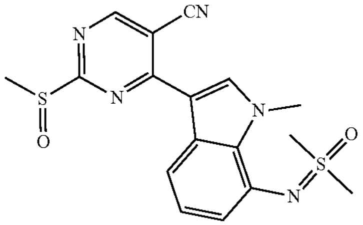

Int_79-2 (100 mg, 0.27 mmol) was dissolved in dichloromethane (10 mL) and DMF (10 mL), and m-CPBA (70 mg, 0.4 mmol) was added at room temperature. The mixture was stirred at room temperature for half an hour, until LC-MS indicated the completion of the reaction. The reaction solution was cooled to room temperature and concentrated at reduced pressure to give a crude product. The crude product was used directly in the next reaction.

ESI-MS m/z: 388 $[M+H]^+$

Step 5: Synthesis of Compound 79

79

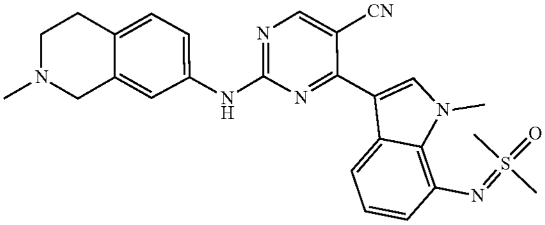

Int_79-3 (100 mg, 0.26 mmol) was dissolved in DMF (10 mL), and int_3-5 (65 mg, 0.4 mmol) and trifluoroacetic acid (62 mg, 0.54 mmol) were added. The reaction solution was heated to 80° C. and stirred for 16 h, until LC-MS indicated the completion of the reaction. The reaction solution was cooled to room temperature and concentrated at reduced pressure to give a crude product. The crude product was purified by preparative HPLC to give a pale yellow solid (2 mg, 15.8% yield).

ESI-MS m/z: 486 [M+H]$^+$

Example 26: Synthesis of Compound 80

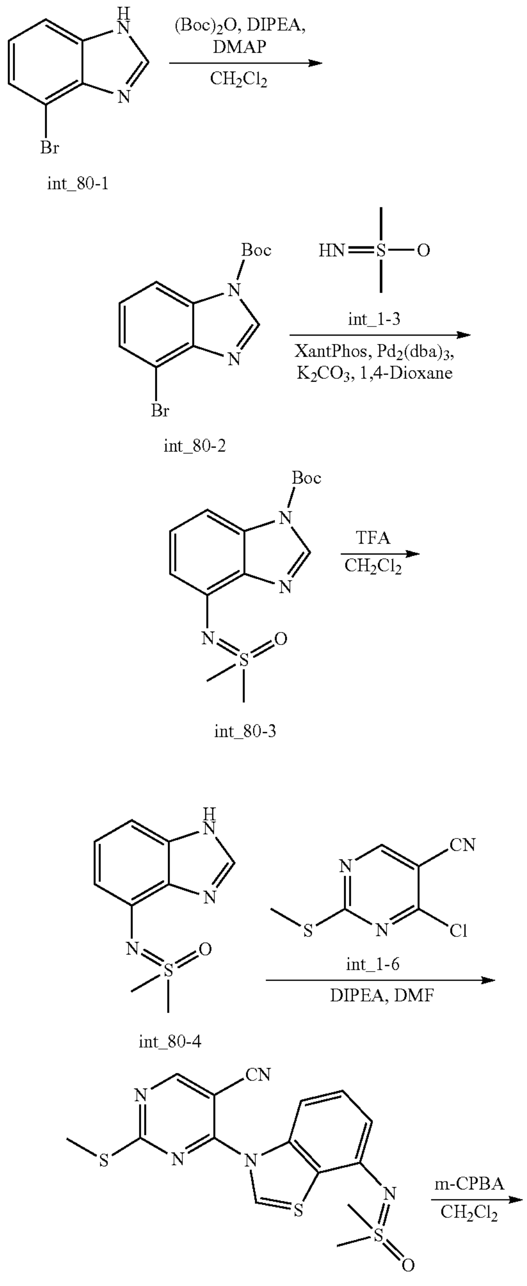

int_80-1, int_80-2, int_80-3, int_80-4, int_80-5

-continued

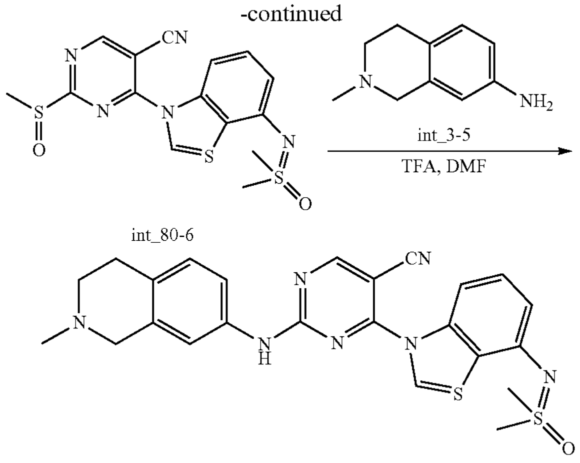

int_80-6

80

Step 1: Synthesis of Compound Int_80-2 int_80-2

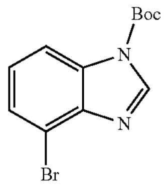

Int_80-1 (250 mg, 1.269 mmol) was dissolved in dichloromethane (20 mL), and DIPEA (655 mg, 5.075 mmol), DMAP (50 mg, 0.41 mmol), and $(Boc)_2O$ (325 mg, 2.538 mmol) were added. The mixture was incubated overnight at room temperature for reaction, until LC-MS indicated the completion of the reaction. The reaction mixture was diluted with dichloromethane (100 mL), washed with water (200 mL), washed with 2 N diluted HCl (100 mL), washed with an aqueous sodium bicarbonate solution (100 mL), washed with water (100 mL) and finally washed with a saturated brine (100 mL×1). The organic phase was dried over anhydrous sodium sulfate, filtered, and distilled at reduced pressure to give a crude product, and the crude product was subjected to column chromatography ($SiO_2$, PE:EA=10:1) to give a product (320 mg, 85% yield).

ESI-MS m/z: 197 [M+H]$^+$.

Step 2: Synthesis of Compound Int_80-3 int_80-3

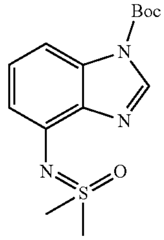

Int_80-2 (1.03 g, 3.468 mmol), int_1-3 (323 mg, 3.468 mmol), cesium carbonate (1.677 g, 5.202 mmol), $Pd_2(dba)_3$ (160 mg, 0.173 mmol), and Xantphos (201.6 mg, 0.346 mmol) were dissolved in 1,4-dioxane (50 mL), and in nitrogen atmosphere, the mixture was incubated at 85° C. overnight, until LC-MS indicated the completion of the reaction. The reaction solution was filtered and distilled at reduced pressure to give a crude product, and the crude product was subjected to preparative HPLC to give a solid product (640 mg, 60% yield).

ESI-MS m/z: 310 $[M+H]^+$

Step 3: Synthesis of Compound Int_80-4 int_80-4

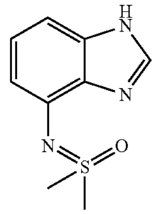

Int_80-3 (640 mg, 2.069 mmol) was dissolved in dichloromethane (10 mL), and trifluoroacetic acid (5 mL) was added. The mixture was incubated for 1 h at room temperature for reaction, until LC-MS indicated the completion of the reaction. The reaction solution was directly concentrated at reduced pressure to give a crude product (600 mg). The crude product was used directly in the next reaction.

ESI-MS m/z: 210 $[M+H]^+$

Step 4: Synthesis of Compound Int_80-5 int_80-5

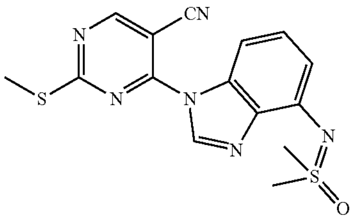

Int_80-4 (600 mg, 2.87 mmol) and int_1-6 (630 mg, 3.4 mmol) were dissolved in DMF (10 mL), and DIPEA (661 mg, 5.8 mmol) was added. The reaction solution was heated to 50° C. and incubated overnight, until LC-MS indicated the completion of the reaction. The reaction solution was filtered and distilled at reduced pressure to give a crude product, and the crude product was subjected to preparative HPLC to give a solid product (320 mg, 53% yield).

ESI-MS m/z: 359 $[M+H]^+$

Step 5: Synthesis of Compound Int_80-6 int_80-6

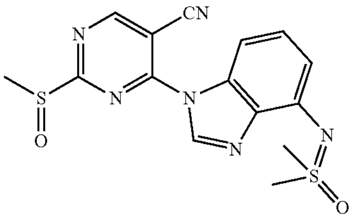

Int_80-5 (95 mg, 0.265 mmol) was dissolved in dichloromethane (20 mL), and m-CPBA (85%, 70 mg, 0.345 mmol) was added at room temperature. The mixture was stirred at room temperature for half an hour, until LC-MS indicated the completion of the reaction. The reaction solution was concentrated at reduced pressure to give a crude product (90 mg). The crude product was used directly in the next reaction.

ESI-MS m/z: 375 $[M+H]^+$

Step 6: Synthesis of Compound 80

80

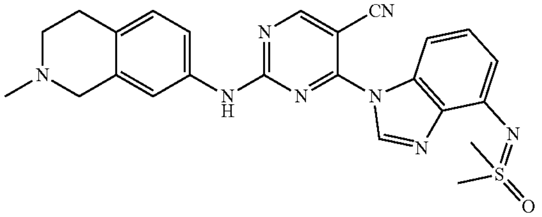

Int_80-6 (90 mg, 0.161 mmol) was dissolved in dichloromethane (5 mL), and int_3-5 (298 mg, 1.2 mmol) and trifluoroacetic acid (91 mg, 0.8 mmol) were added. The reaction solution was heated to 80° C. and stirred for 10 h, until LC-MS indicated the completion of the reaction. The reaction solution was cooled to room temperature and concentrated at reduced pressure to give a crude product. The crude product was purified by preparative HPLC to give a white solid (37 mg, 48.7% yield).

$^1H$ NMR (400 MHz, Chloroform-d) δ 8.73 (d, J=26.1 Hz, 2H), 7.81 (s, 1H), 7.61 (s, 1H), 7.37 (s, 1H), 7.14 (dd, J=22.2, 7.0 Hz, 4H), 3.50 (d, J=17.6 Hz, 2H), 3.31 (s, 6H), 2.92 (t, J=6.0 Hz, 2H), 2.70 (t, J=6.0 Hz, 2H), 2.45 (d, J=5.1 Hz, 3H).

ESI-MS m/z: 473 $[M+H]^+$

Examples 27-160: Synthesis of Compounds 2, 4-5, 10, 14-15, 17-18, 20-21, 23-28, 30-41, 44-51, 53-54, 56-59, 65-76, and 80-160

Target compounds 2, 4-5, 10, 14-15, 17-18, 20-21, 23-28, 30-41, 44-51, 53-54, 56-59, 65-76, and 80-160 in Table 1 were obtained by using the above synthesis methods with different starting materials.

The LC-MS analysis process is as follows:

Instrument: Agilent, LC: 1260 InfinityII+MS:G6125B

Column: Welch: Core-shell 2.7 am, 4.3×50 mm

Temperature: 30° C.

Wavelength: 254 nm/214 nm

Mobile phase A: $H_2O$ (0.1% o formic acid)
Mobile phase B: acetonitrile (0.1% o formic acid)
Gradient:
| Time (min) | Flow rate (mL/min) | Mobile phase B % | Mobile phase A % |
|---|---|---|---|
| 0 | 2 | 5 | 95 |
| 0.1 | 2 | 5 | 95 |
| 2.2 | 2 | 95 | 5 |
| 2.7 | 2 | 95 | 5 |
| 2.71 | 2 | 5 | 95 |
| 3 | 2 | 5 | 95 |
TABLE 1
| Compound | Compound structure | MS (M + H)+ | LC-MS RT(min) |
|---|---|---|---|
| 2 | 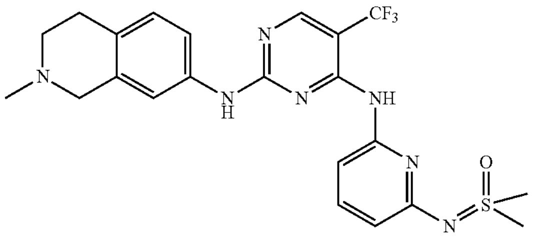 | 492 | — |
| 4 | 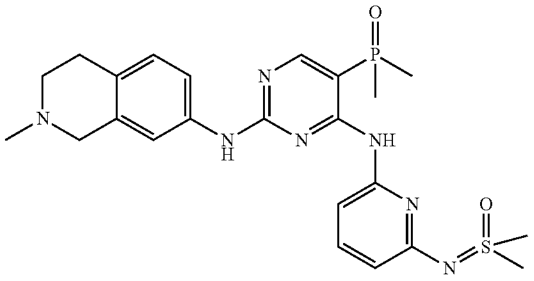 | 500 | 1.236 |
| 5 | 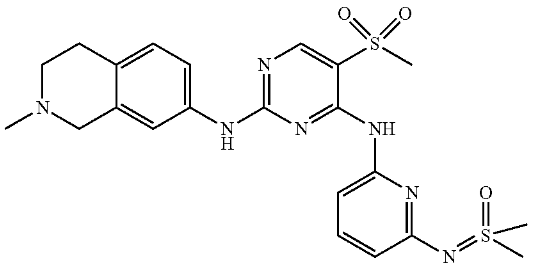 | 502 | — |
| 10 | 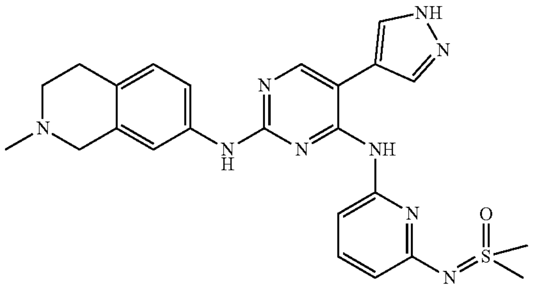 | 490 | 1.303 |

TABLE 1-continued
| Compound | Compound structure | MS (M + H)+ | LC-MS RT(min) |
| --- | --- | --- | --- |
| 14 | 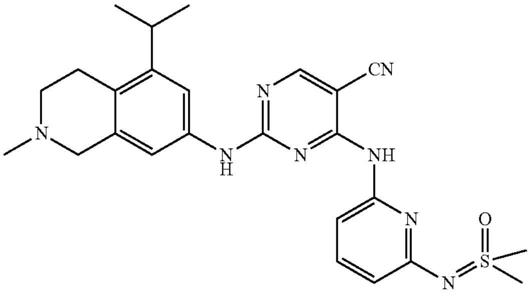 | 491 | 1.777 |
| 15 | 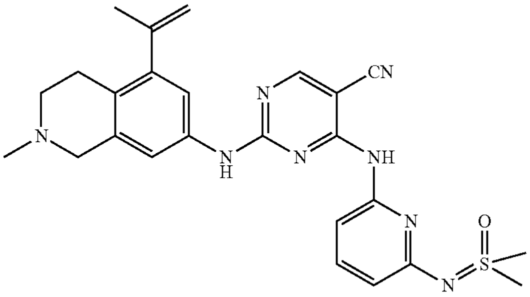 | 489 | 1.405 |
| 17 | 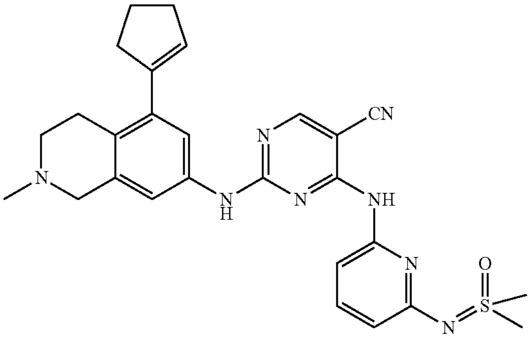 | 515 | 1.874 |
| 18 | 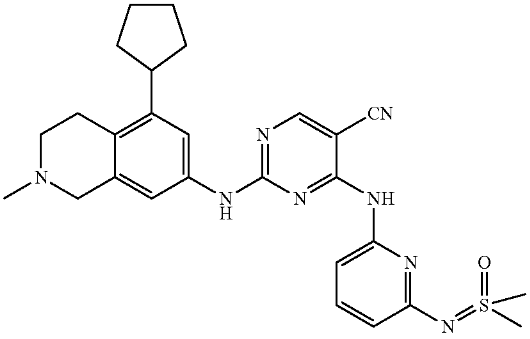 | 517 | 1.934 |
| 20 | 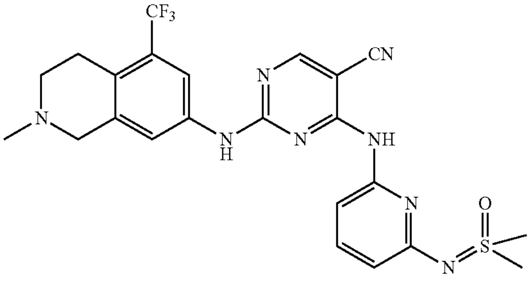 | 517 | 1.611 |

TABLE 1-continued
| Compound | Compound structure | MS (M + H)+ | LC-MS RT(min) |
|---|---|---|---|
| 21 | 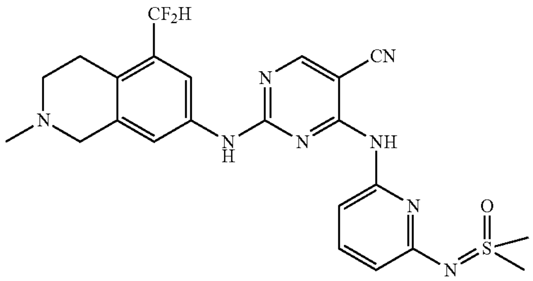 | 499 | — |
| 23 | 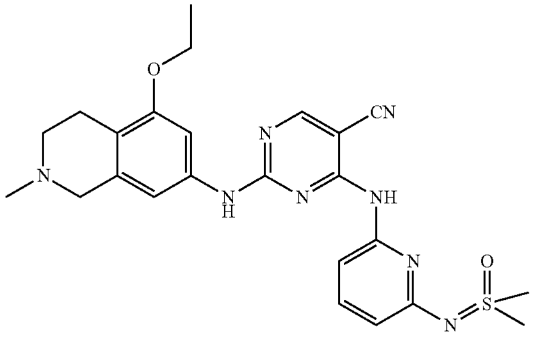 | 493 | — |
| 24 | 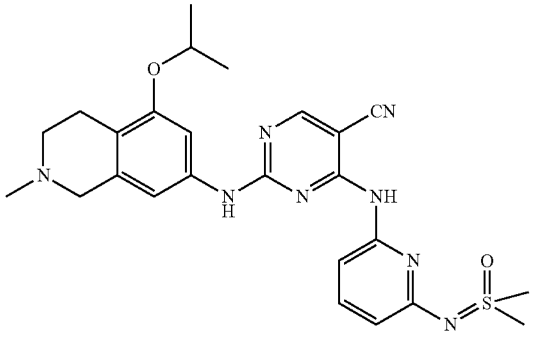 | 507 | — |
| 25 | 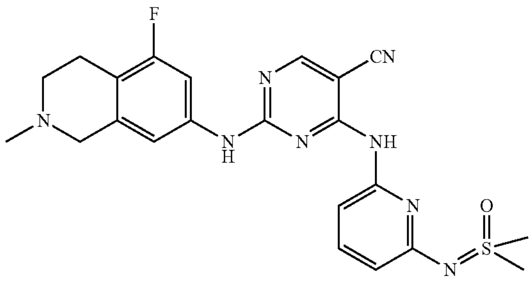 | 467 | 1.723 |
| 26 | 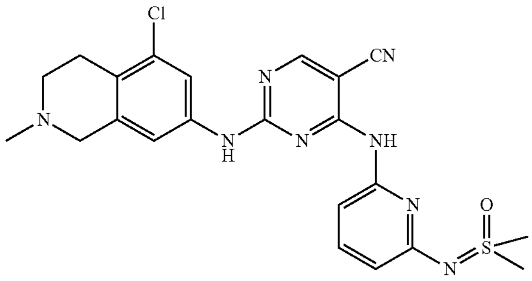 | 483 | — |

TABLE 1-continued
| Compound | Compound structure | MS (M + H)+ | LC-MS RT(min) |
| --- | --- | --- | --- |
| 27 | 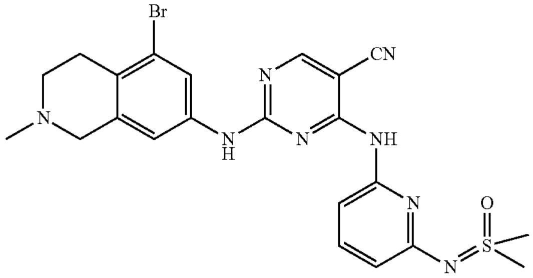 | 527 | — |
| 28 | 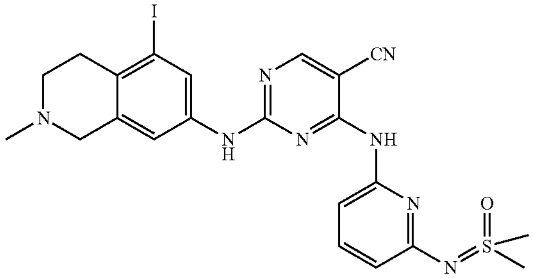 | 575 | — |
| 30 | 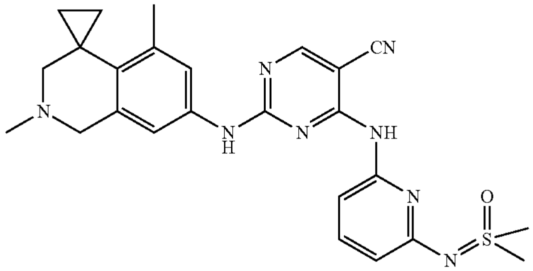 | 489 | — |
| 31 | 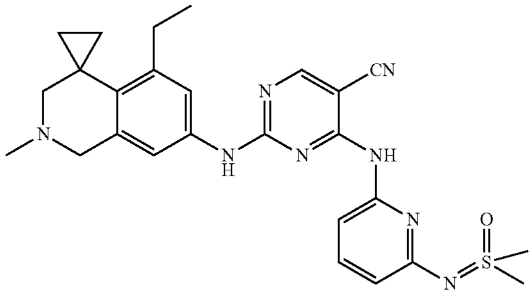 | 503 | — |
| 32 | 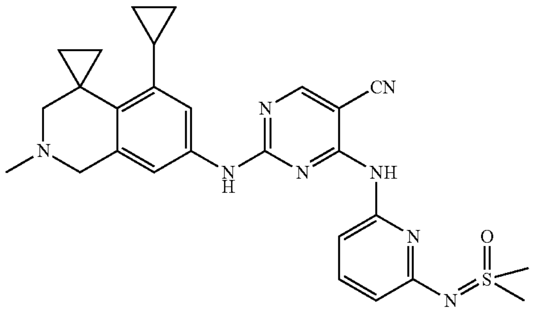 | 515 | — |

TABLE 1-continued
| Compound | Compound structure | MS (M + H)$^+$ | LC-MS RT(min) |
|---|---|---|---|
| 33 | 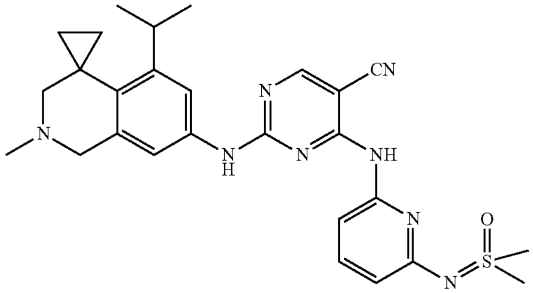 | 517 | — |
| 34 | 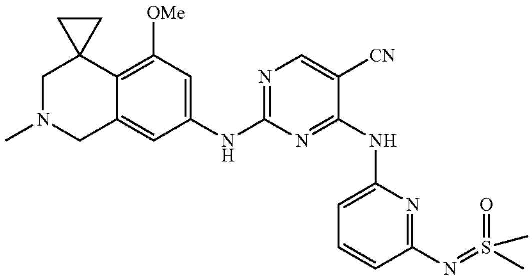 | 505 | — |
| 35 | 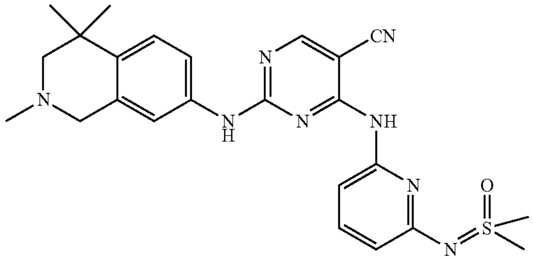 | 477 | — |
| 36 | 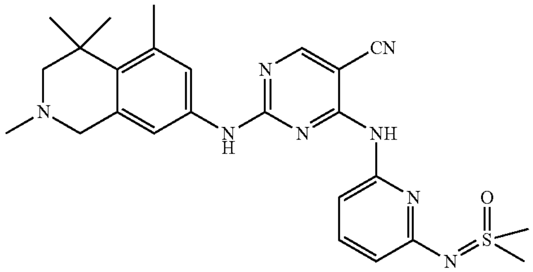 | 491 | — |
| 37 | 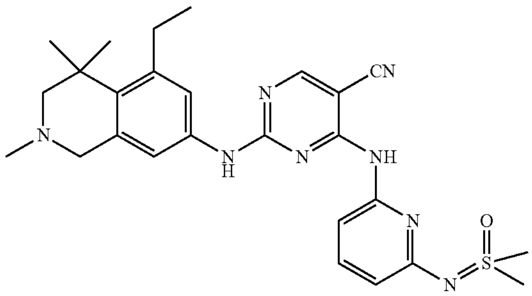 | 505 | — |

TABLE 1-continued
| Compound | Compound structure | MS (M + H)+ | LC-MS RT(min) |
|---|---|---|---|
| 38 | 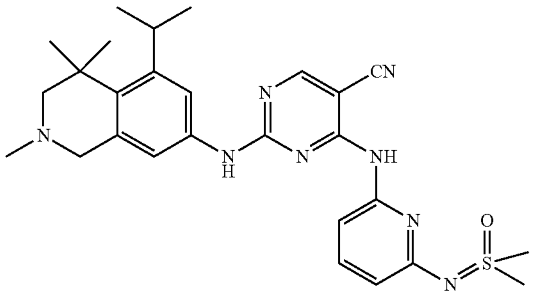 | 519 | — |
| 39 | 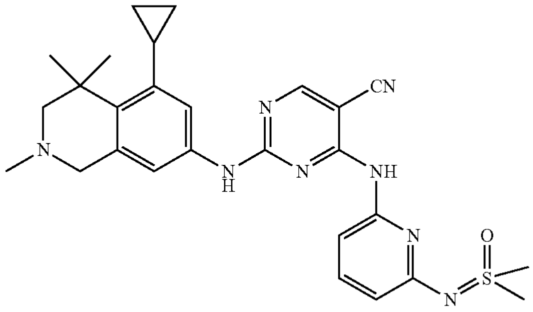 | 517 | — |
| 40 | 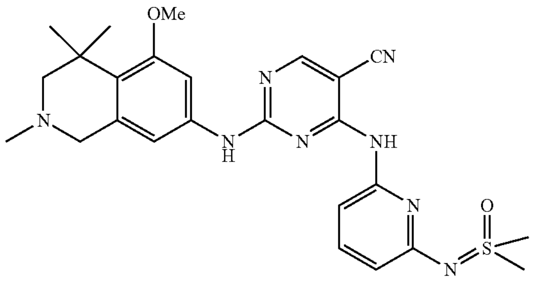 | 507 | — |
| 41 | 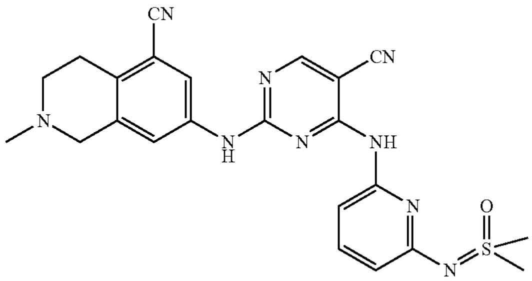 | 474 | — |
| 44 | 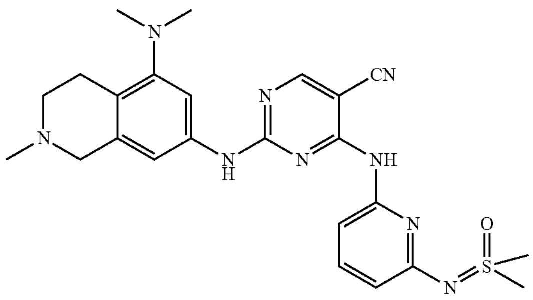 | 492 | — |

TABLE 1-continued
| Compound | Compound structure | MS (M + H)+ | LC-MS RT(min) |
|---|---|---|---|
| 45 | 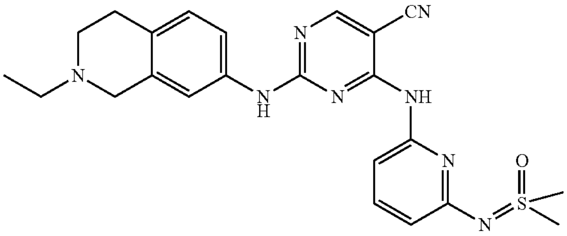 [SMILES: CCN1CCc2ccc(Nc3ncc(C#N)c(Nc4cccc(N=S(C)(C)=O)n4)n3)cc2C1] | 463 | — |
| 46 | 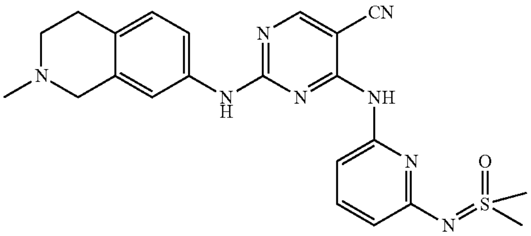 | 477 | — |
| 47 | 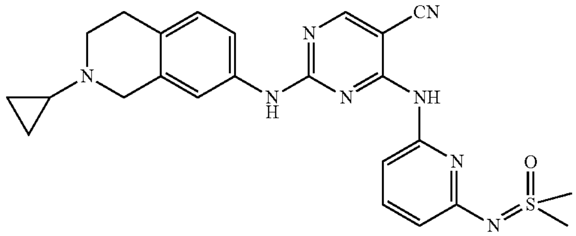 [SMILES: CS(C)(=O)=Nc1cccc(Nc2nc(Nc3ccc4c(c3)CN(C3CC3)CC4)ncc2C#N)n1] | 475 | — |
| 48 | 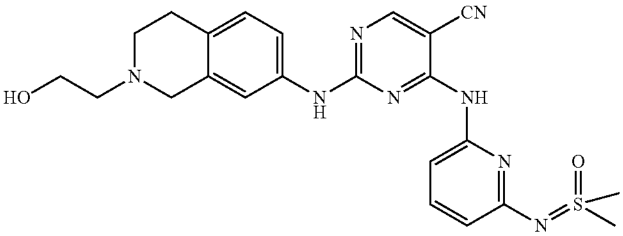 [SMILES: CS(C)(=O)=Nc1cccc(Nc2nc(Nc3ccc4c(c3)CN(CCO)CC4)ncc2C#N)n1] | 479 | — |
| 49 | 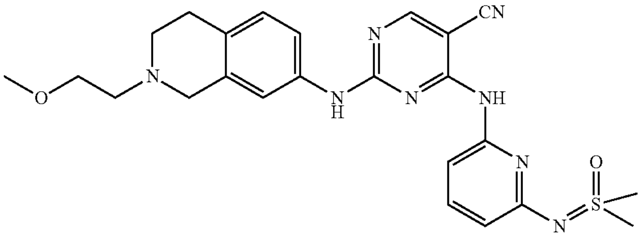 | 493 | — |
| 50 | 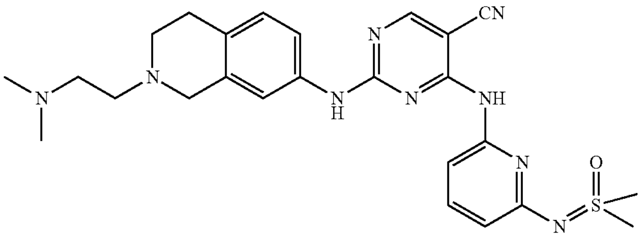 | 506 | — |

TABLE 1-continued
| Compound | Compound structure | MS (M + H)+ | LC-MS RT(min) |
| --- | --- | --- | --- |
| 51 | 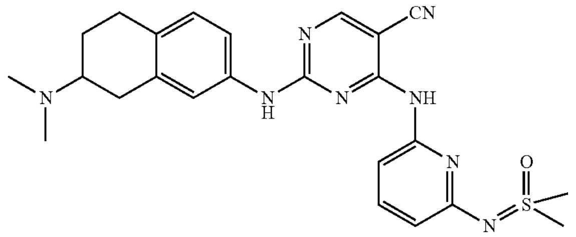 | 477 | — |
| 53 | 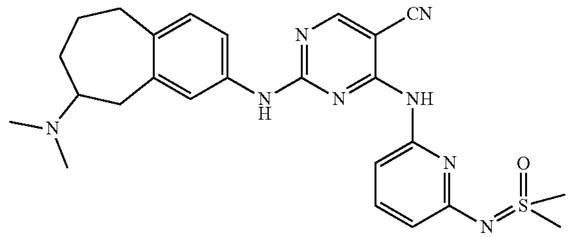 | 491 | — |
| 54 | 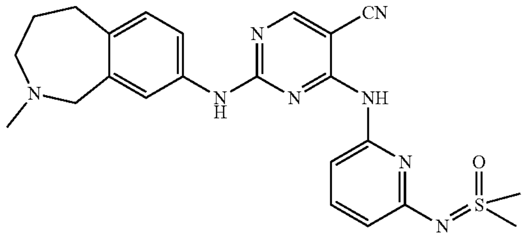 | 463 | — |
| 56 | 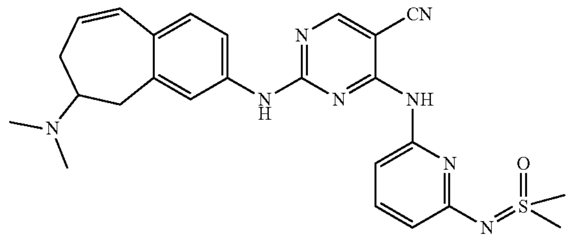 | 489 | — |
| 57 | 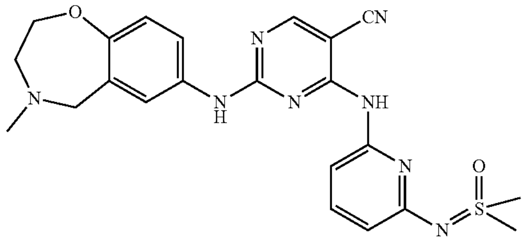 | 465 | — |
| 58 | 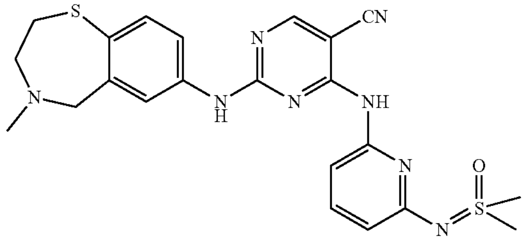 | 481 | — |

TABLE 1-continued
| Compound | Compound structure | MS (M + H)+ | LC-MS RT(min) |
|---|---|---|---|
| 59 | 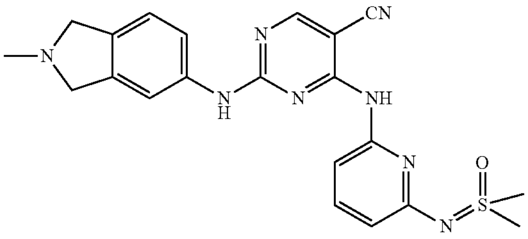 | 435 | — |
| 65 | 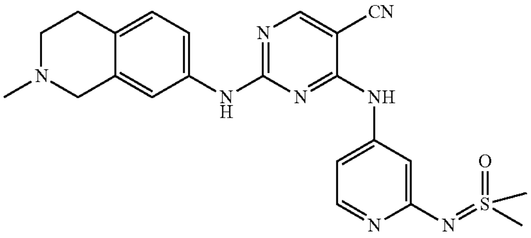 | 449 | — |
| 66 | 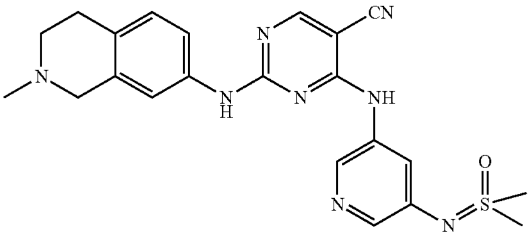 | 449 | — |
| 67 | 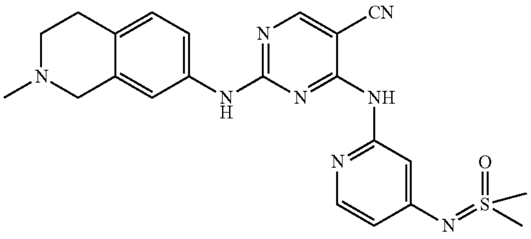 | 449 | — |
| 68 | 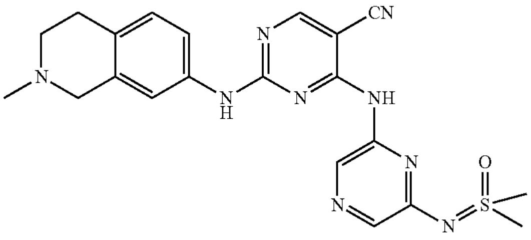 | 450 | — |
| 69 | 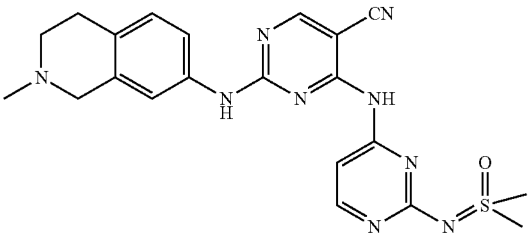 | 450 | — |

TABLE 1-continued
| Compound | Compound structure | MS (M + H)+ | LC-MS RT(min) |
|---|---|---|---|
| 70 | 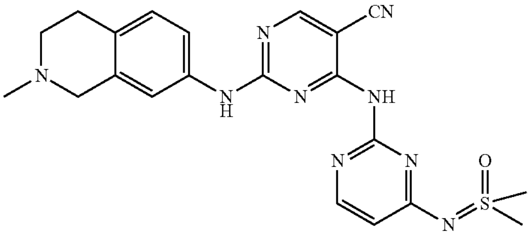 | 450 | — |
| 71 | 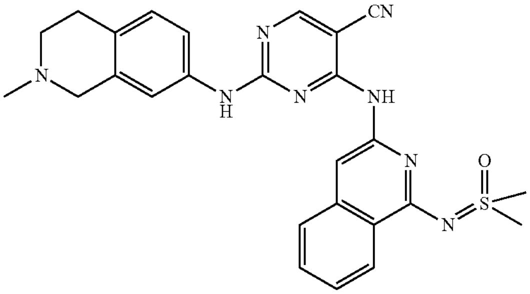 | 499 | — |
| 72 | 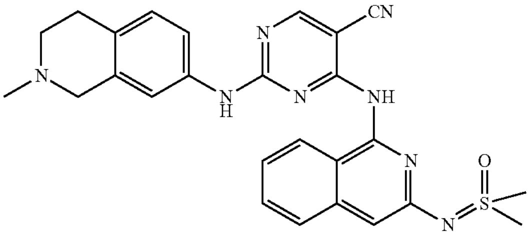 | 499 | — |
| 73 | 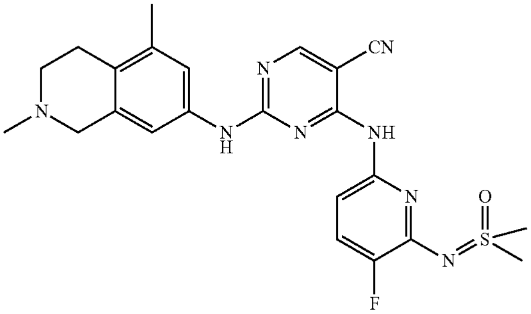 | 481 | — |
| 74 | 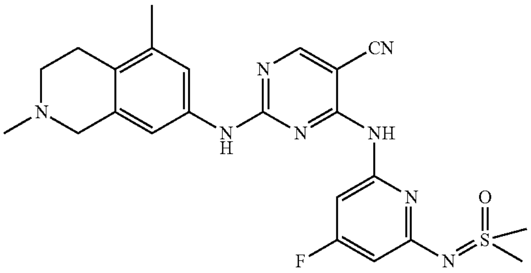 | 481 | — |

TABLE 1-continued
| Compound | Compound structure | MS (M + H)+ | LC-MS RT(min) |
|---|---|---|---|
| 75 | 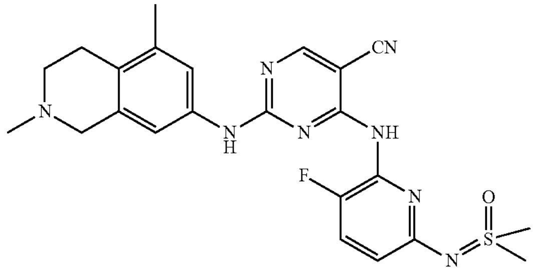 | 481 | — |
| 76 | 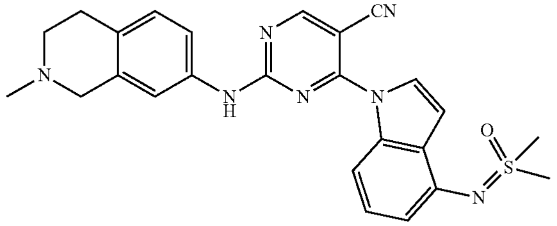 | 472 | 1.759 |
| 81 | 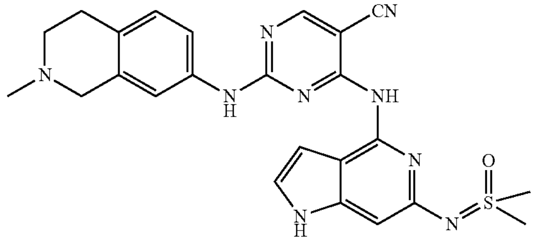 | 488 | — |
| 82 | 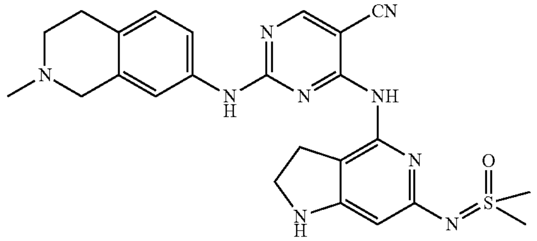 | 490 | — |
| 83 | 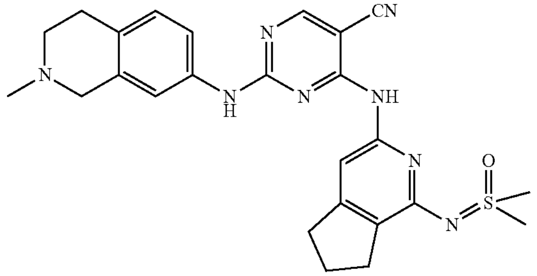 | 489 | — |
| 84 | 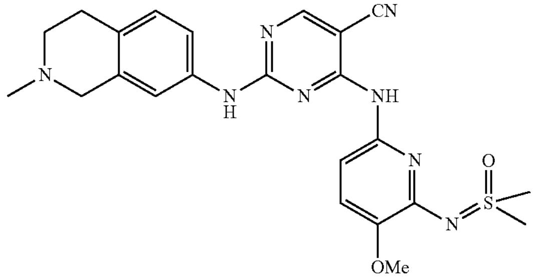 | 479 | — |

TABLE 1-continued
| Compound | Compound structure | MS (M + H)+ | LC-MS RT(min) |
| --- | --- | --- | --- |
| 85 | 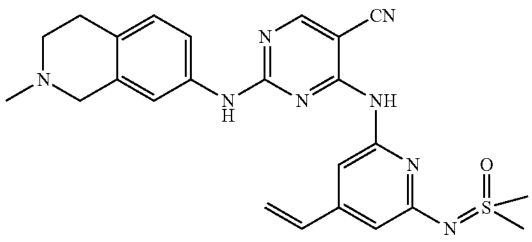 | 475 | — |
| 86 | 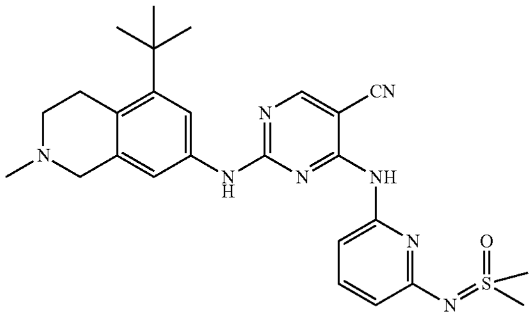 | 505 | — |
| 87 | 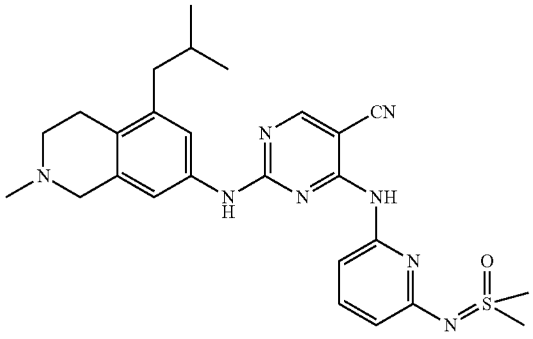 | 474 | 1.511 |
| 88 | 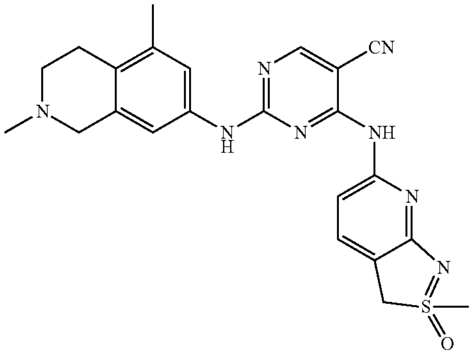 | 461 | — |

TABLE 1-continued
| Compound | Compound structure | MS (M + H)+ | LC-MS RT(min) |
|---|---|---|---|
| 89 | 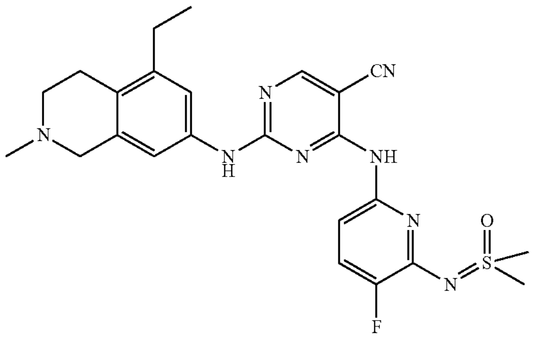 | 495 | — |
| 90 | 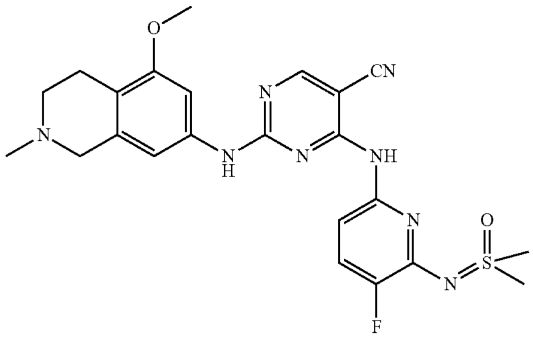 | 497 | — |
| 91 | 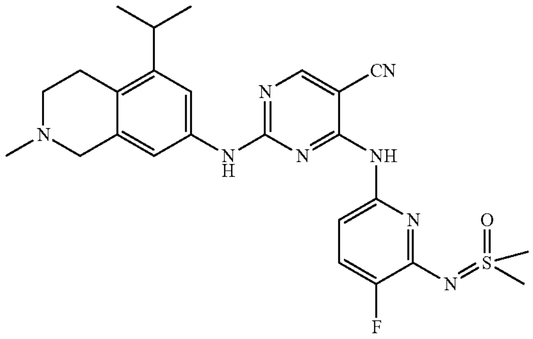 | 509 | — |
| 92 | 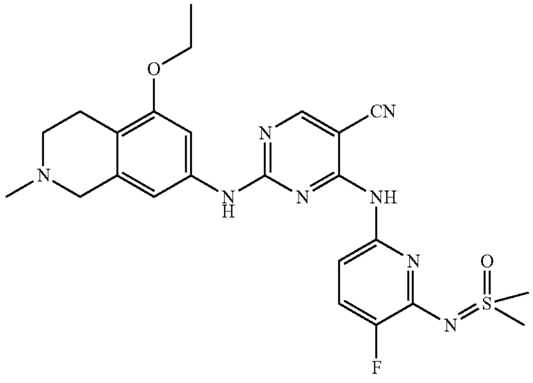 | 511 | — |

TABLE 1-continued
| Compound | Compound structure | MS (M + H)+ | LC-MS RT(min) |
|---|---|---|---|
| 93 | 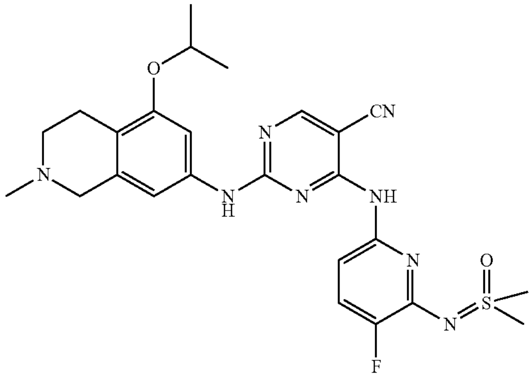 | 525 | — |
| 94 | 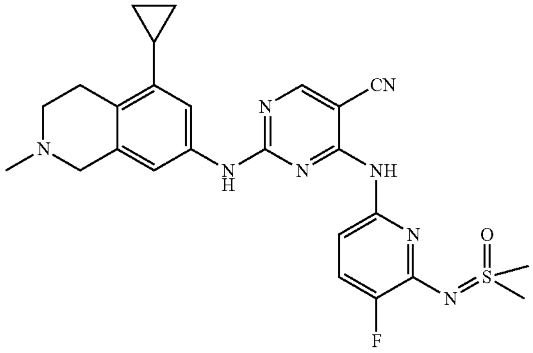 | 507 | — |
| 95 | 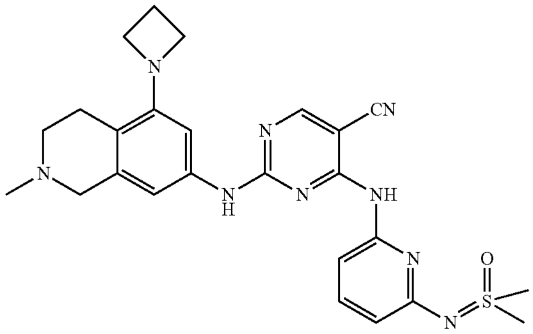 | 504 | — |
| 96 | 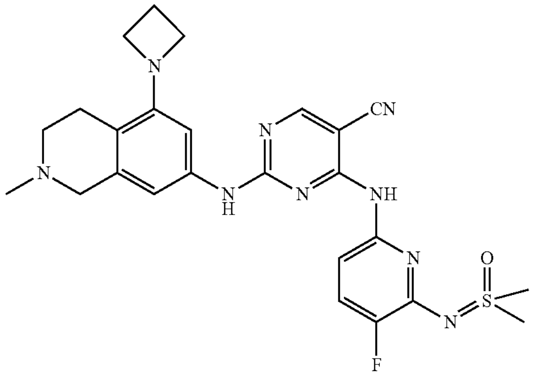 | 522 | — |

TABLE 1-continued
| Compound | Compound structure | MS (M + H)+ | LC-MS RT(min) |
| --- | --- | --- | --- |
| 97 | 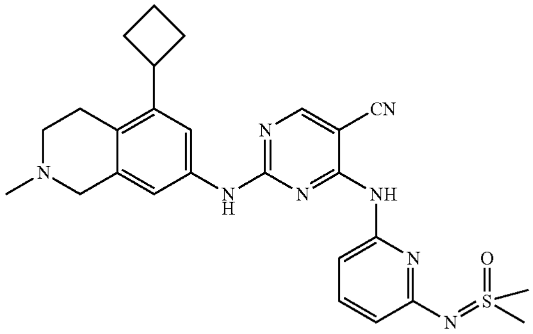 | 503 | 1.464 |
| 98 | 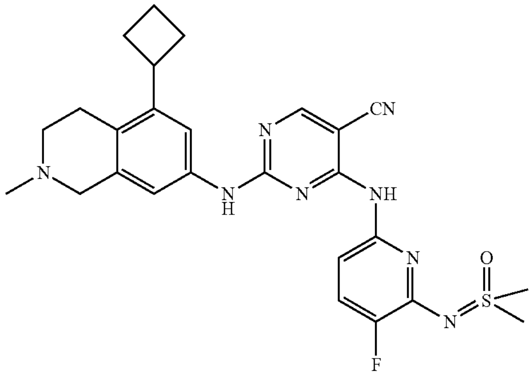 | 521 | — |
| 99 | 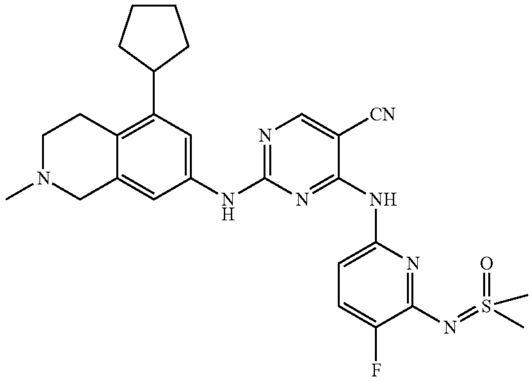 | 535 | — |
| 100 | 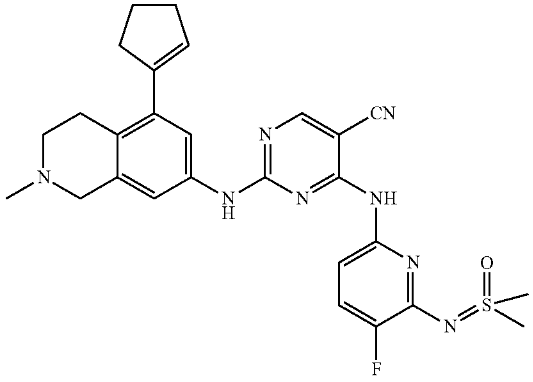 | 533 | — |

TABLE 1-continued
| Compound | Compound structure | MS (M + H)+ | LC-MS RT(min) |
|---|---|---|---|
| 101 | 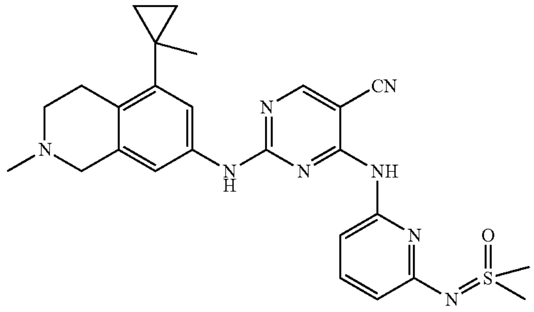 | 503 | 1.467 |
| 102 | 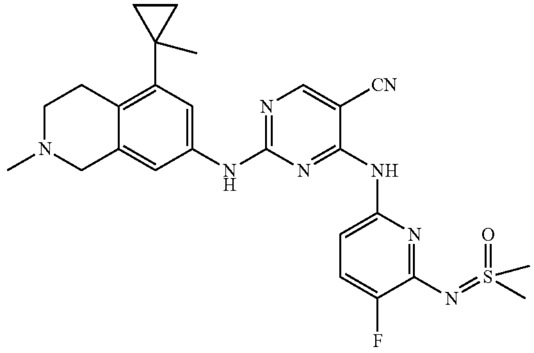 | 521 | — |
| 103 | 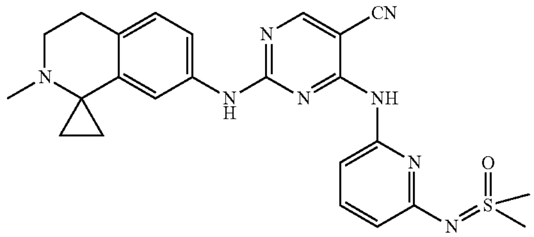 | 475 | — |
| 104 | 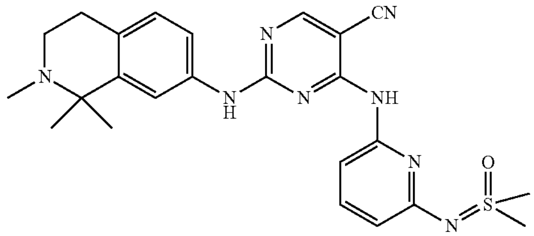 | 477 | — |
| 105 | 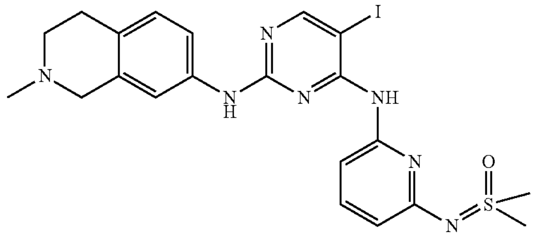 | 550 | 1.445 |

TABLE 1-continued
| Compound | Compound structure | MS $(M + H)^+$ | LC-MS RT(min) |
|---|---|---|---|
| 106 | 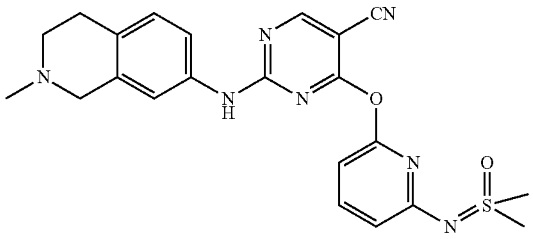 | 450 | 1.598 |
| 107 | 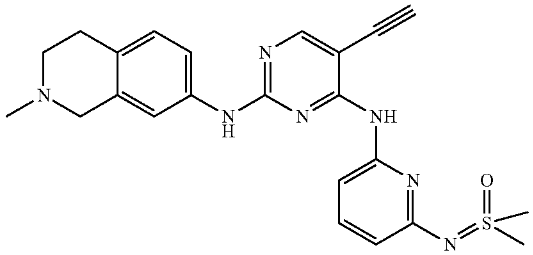 | 448 | 1.541 |
| 108 | 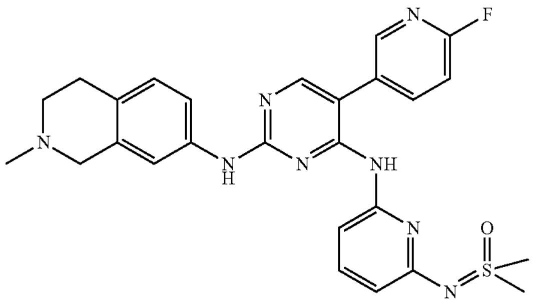 | 519 | — |
| 109 | 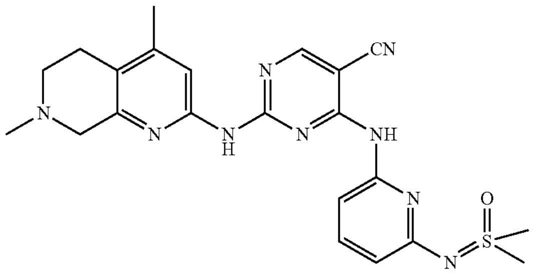 | 464 | — |
| 110 | 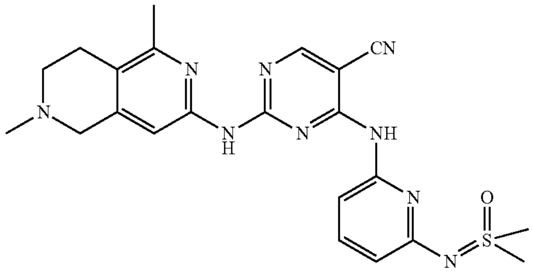 | 464 | — |

TABLE 1-continued
| Compound | Compound structure | MS (M + H)+ | LC-MS RT(min) |
|---|---|---|---|
| 111 | 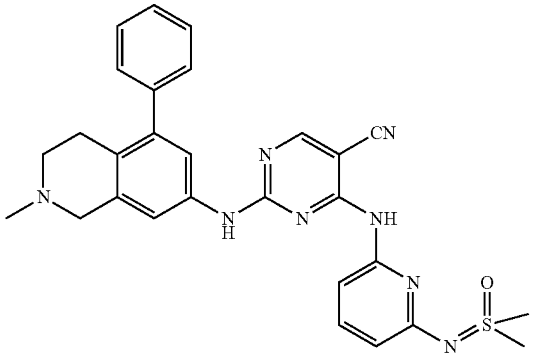 | 525 | 1.849 |
| 112 | 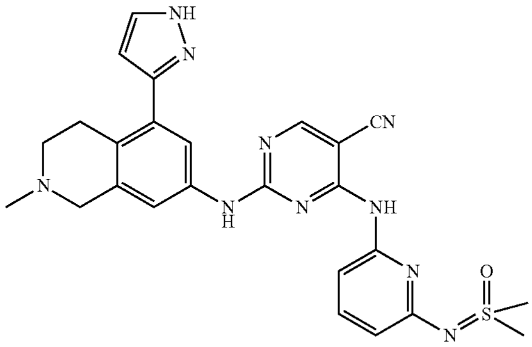 | 515 | 1.392 |
| 113 | 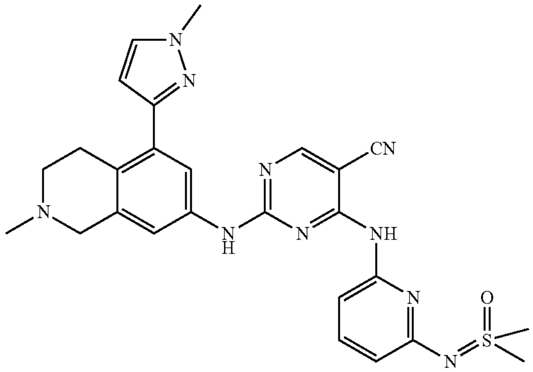 | 529 | 1.692 |
| 114 | 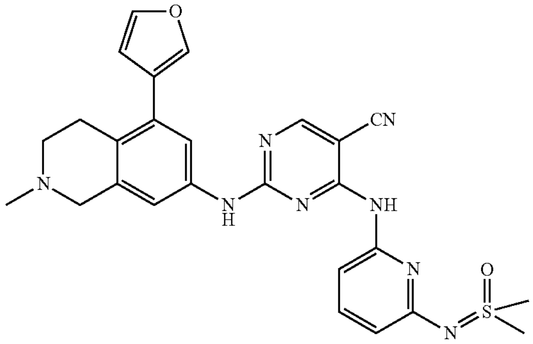 | 515 | — |

TABLE 1-continued
| Compound | Compound structure | MS $(M + H)^+$ | LC-MS RT(min) |
|---|---|---|---|
| 115 | 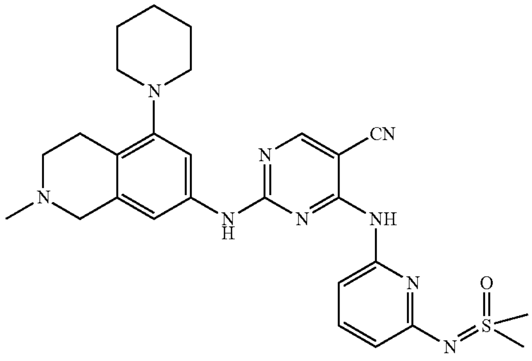 | 532 | 1.711 |
| 116 | 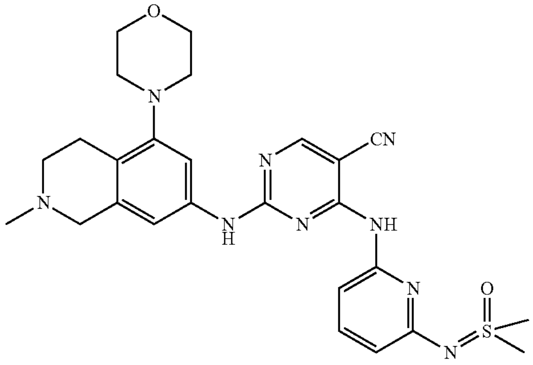 | 534 | 1.706 |
| 117 | 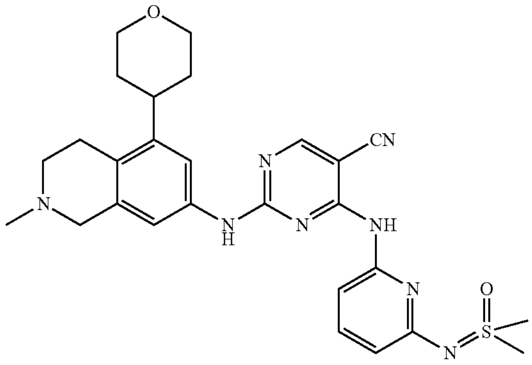 | 533 | 1.354 |
| 118 | 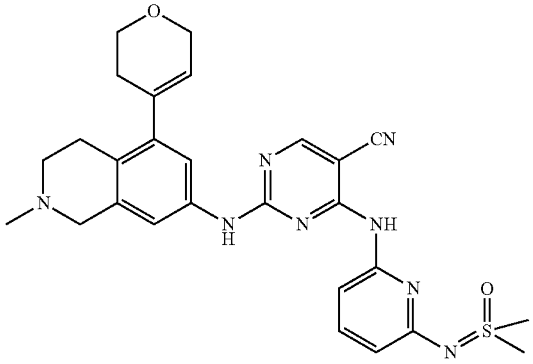 | 531 | 1.735 |

TABLE 1-continued
| Compound | Compound structure | MS (M + H)+ | LC-MS RT(min) |
|---|---|---|---|
| 119 | 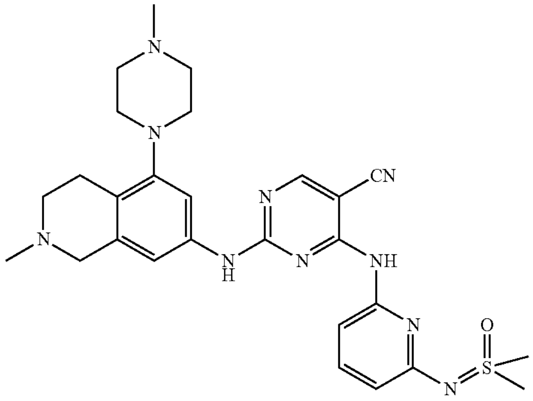 | 547 | 1.575 |
| 120 | 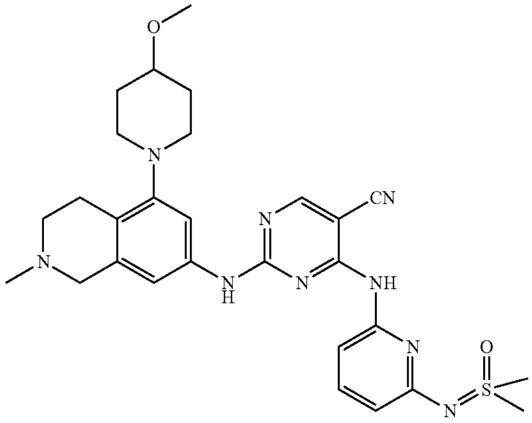 | 562 | 1.857 |
| 121 | 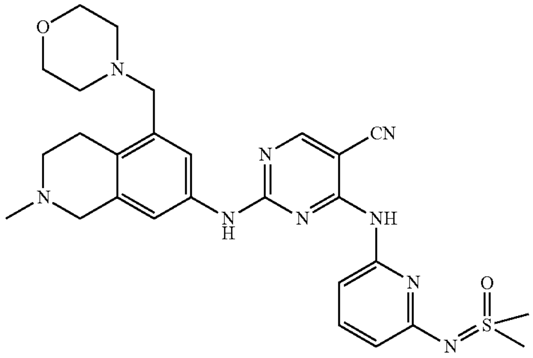 | 548 | — |
| 122 | 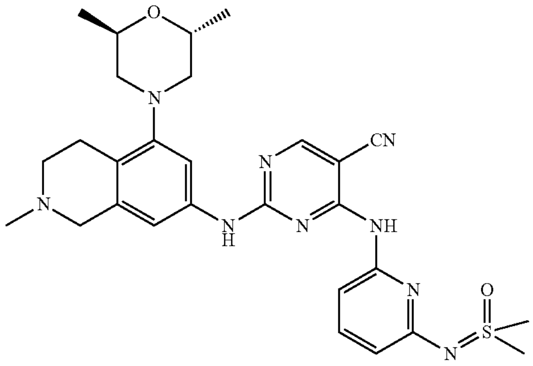 | 562 | 1.374 |

TABLE 1-continued
| Compound | Compound structure | MS $(M + H)^+$ | LC-MS RT(min) |
|---|---|---|---|
| 123 | 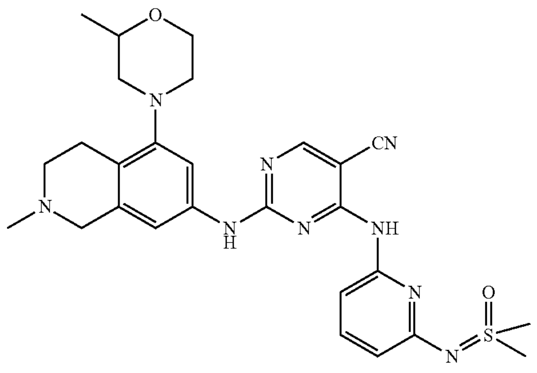 | 548 | 1.338 |
| 124 | 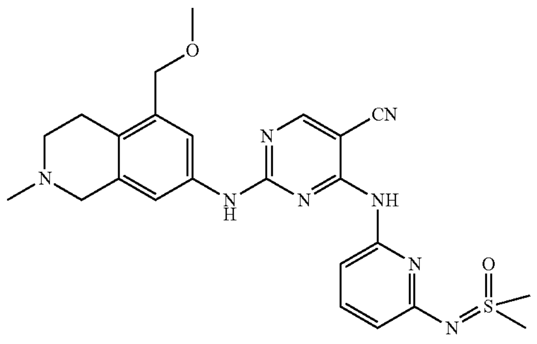 | 493 | 1.282 |
| 125 | 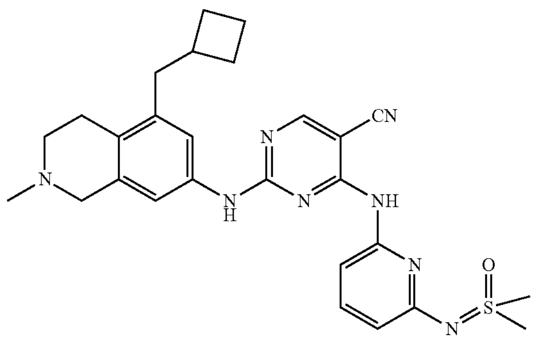 | 517 | — |
| 126 | 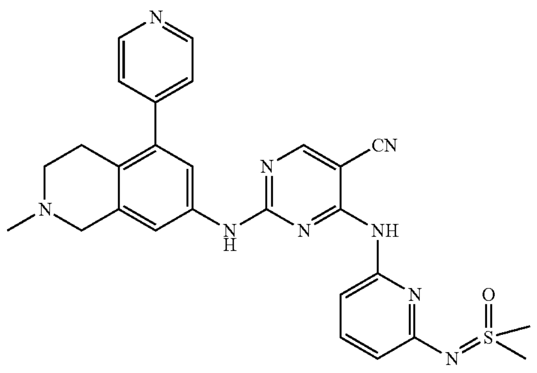 | 526 | — |

TABLE 1-continued
| Compound | Compound structure | MS $(M + H)^+$ | LC-MS RT(min) |
|---|---|---|---|
| 127 | 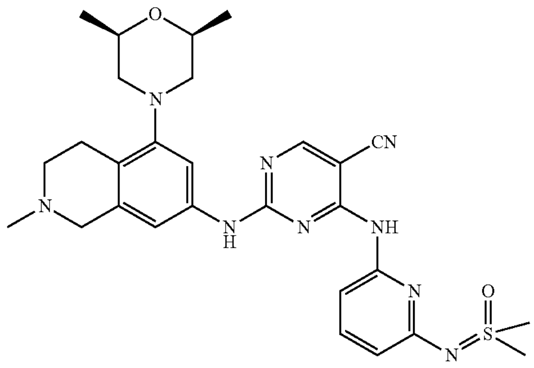 | 562 | 1.374 |
| 128 | 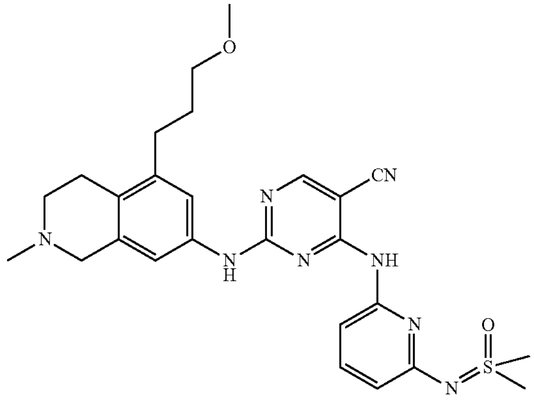 | 521 | 1.349 |
| 129 | 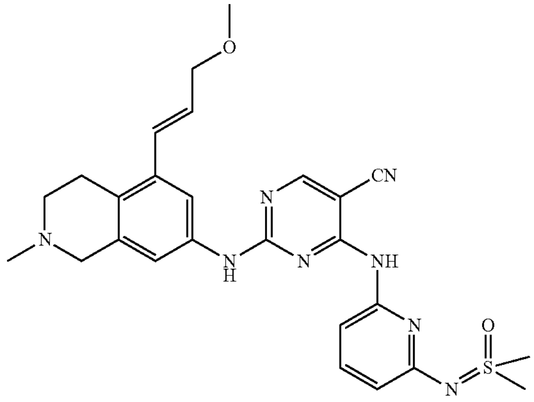 | 519 | — |
| 130 | 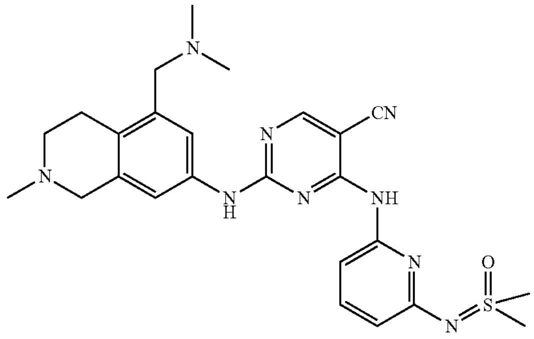 | 506 | 1.034 |

TABLE 1-continued
| Compound | Compound structure | MS (M + H)+ | LC-MS RT(min) |
| --- | --- | --- | --- |
| 131 | 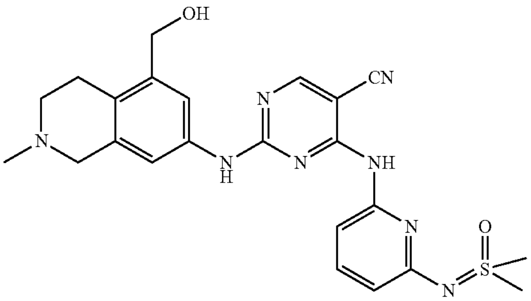 | 479 | 1.186 |
| 132 | 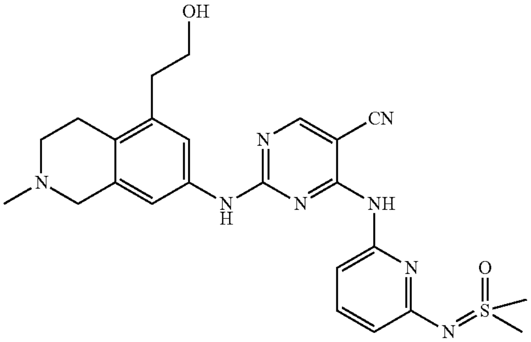 | 493 | — |
| 133 | 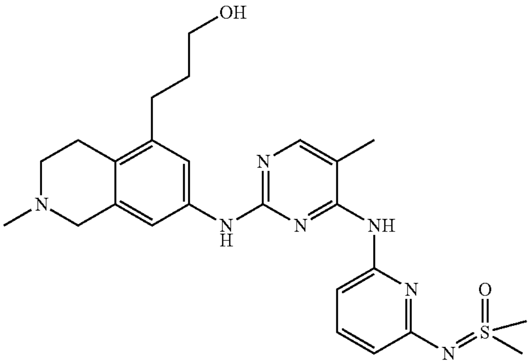 | 507 | 1.282 |
| 134 | 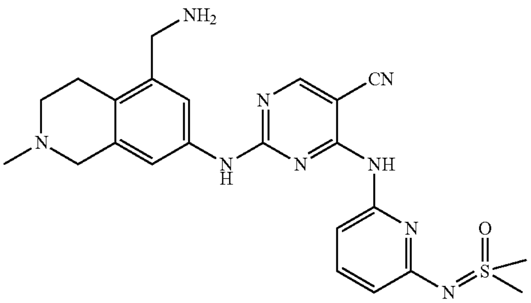 | 478 | — |

TABLE 1-continued
| Compound | Compound structure | MS (M + H)+ | LC-MS RT(min) |
| --- | --- | --- | --- |
| 135 | 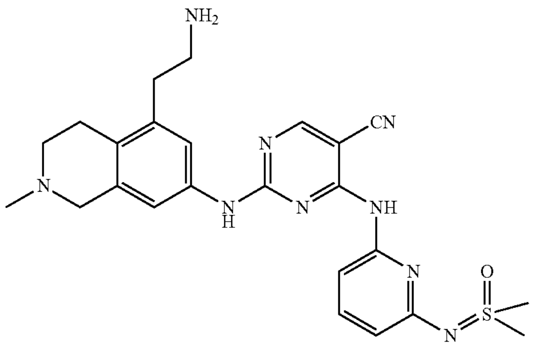 | 492 | — |
| 136 | 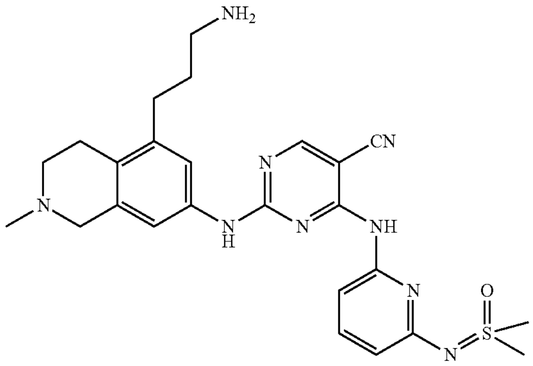 | 506 | — |
| 137 | 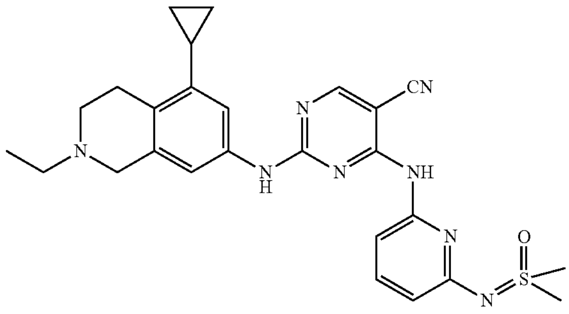 [SMILES: CCN1CCc2c(cc(Nc3ncc(C#N)c(Nc4cccc(N=S(C)(C)=O)n4)n3)cc2C2CC2)C1] | 503 | 1.326 |
| 138 | 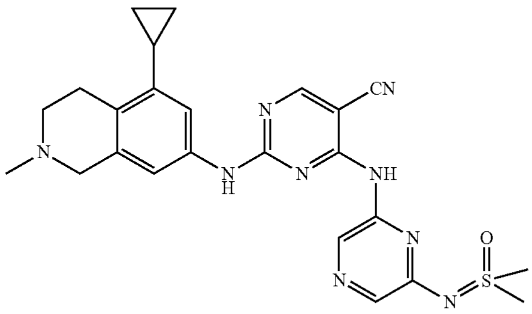 | 490 | — |

TABLE 1-continued
| Compound | Compound structure | MS (M + H)+ | LC-MS RT(min) |
|---|---|---|---|
| 139 | 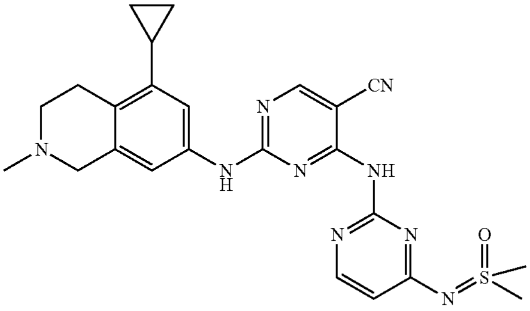 | 490 | — |
| 140 | 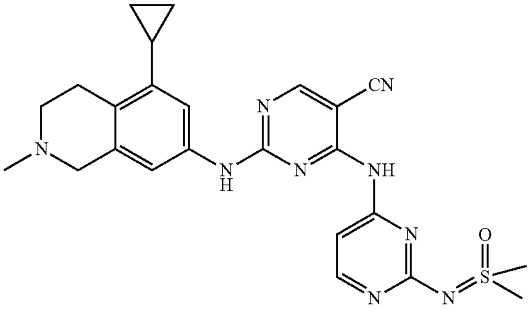 | 490 | — |
| 141 | 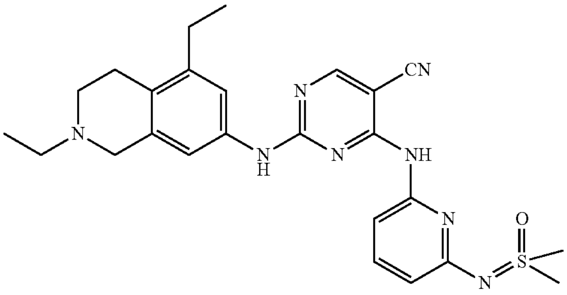 [SMILES: CCc1cc(Nc2ncc(C#N)c(Nc3cccc(N=S(C)(C)=O)n3)n2)cc2c1CCN(CC)C2] | 491 | — |
| 142 | 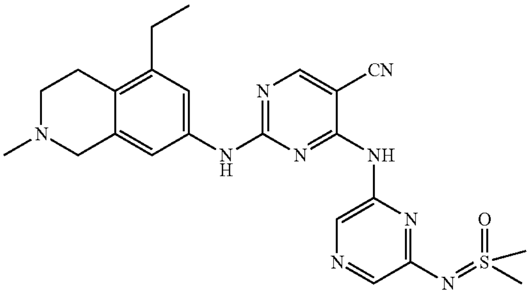 | 478 | — |
| 143 | 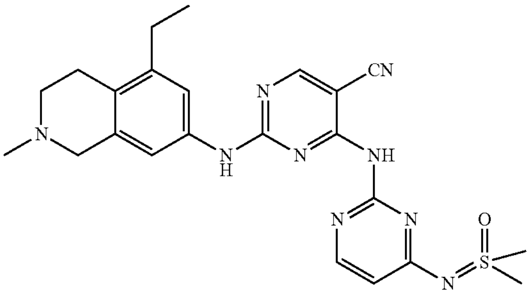 | 478 | — |

TABLE 1-continued
| Compound | Compound structure | MS (M + H)+ | LC-MS RT(min) |
|---|---|---|---|
| 144 | 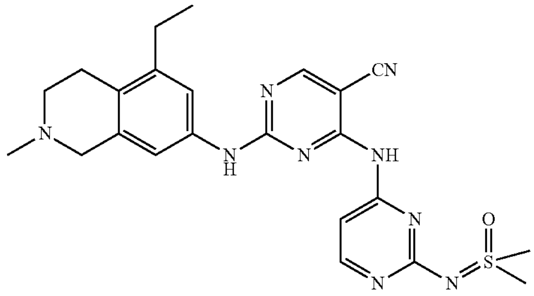 | 478 | — |
| 145 | 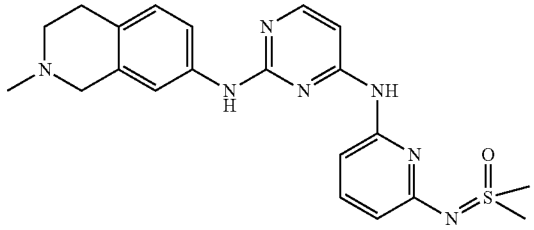 | 424 | 1.352 |
| 146 | 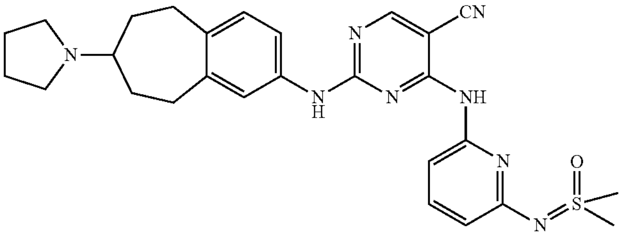 [SMILES: CS(C)(=O)=Nc1cccc(Nc2nc(Nc3ccc4c(c3)CCC(N3CCCC3)CC4)ncc2C#N)n1] | 517 | 1.564 |
| 147 | 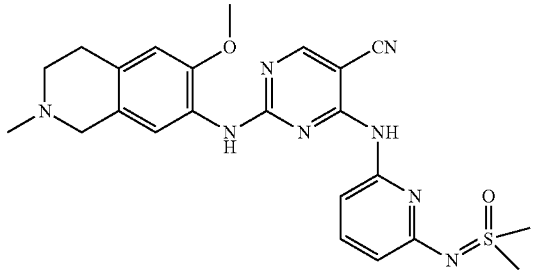 | 479 | 1.579 |
| 148 | 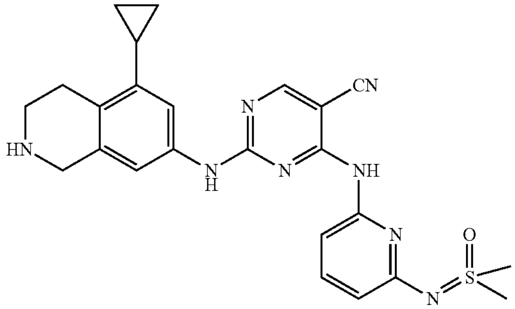 [SMILES: CS(C)(=O)=Nc1cccc(Nc2nc(Nc3cc4c(c(C5CC5)c3)CCNC4)ncc2C#N)n1] | 475 | 1.320 |

TABLE 1-continued
| Compound | Compound structure | MS (M + H)+ | LC-MS RT(min) |
|---|---|---|---|
| 149 | 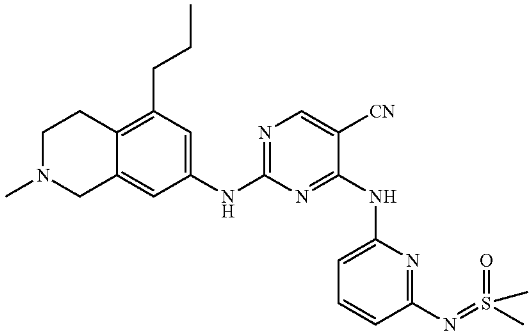 | 491 | — |
| 150 | 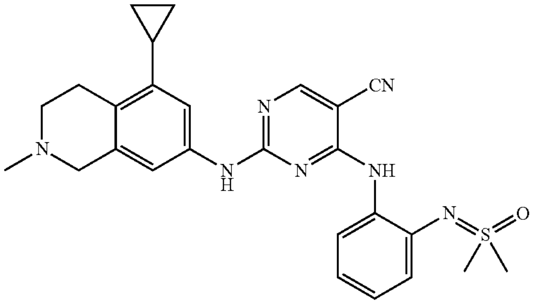 [SMILES: CN1CCc2c(cc(Nc3ncc(C#N)c(Nc4ccccc4N=S(C)(C)=O)n3)cc2C2CC2)C1] | 488 | — |
| 151 | 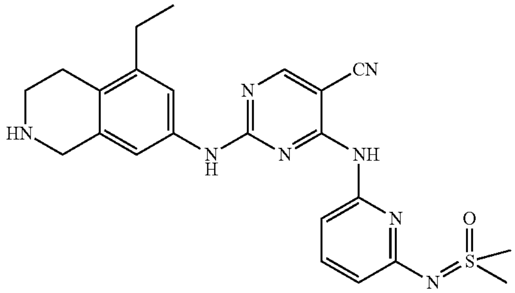 [SMILES: CCc1cc(Nc2ncc(C#N)c(Nc3cccc(N=S(C)(C)=O)n3)n2)cc2c1CCNC2] | 463 | — |
| 152 | 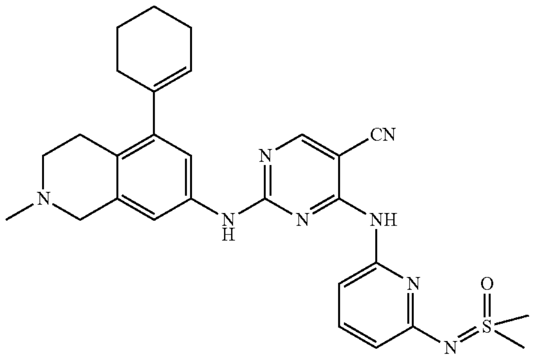 | 529 | — |

TABLE 1-continued
| Compound | Compound structure | MS (M + H)+ | LC-MS RT(min) |
|---|---|---|---|
| 153 | 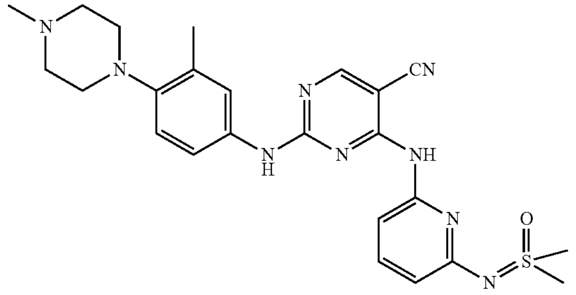 | 492 | — |
| 154 | 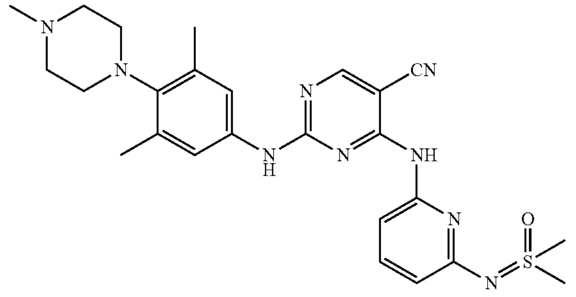 | 506 | — |
| 155 | 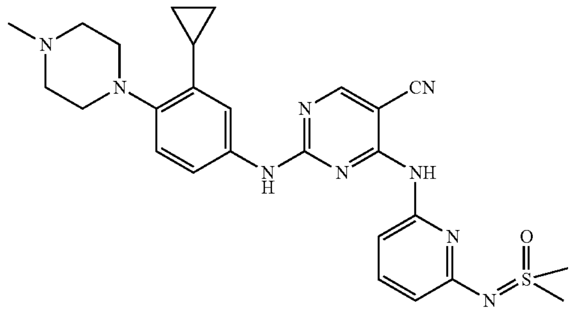 | 518 | — |
| 156 | 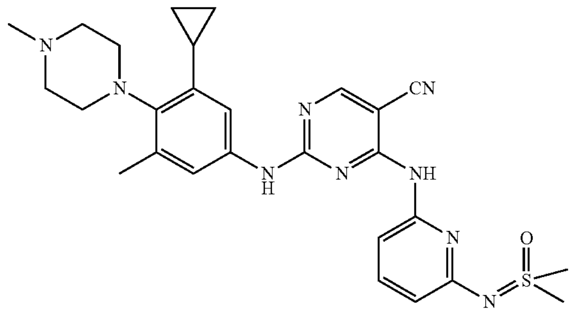 | 532 | — |
| 157 | 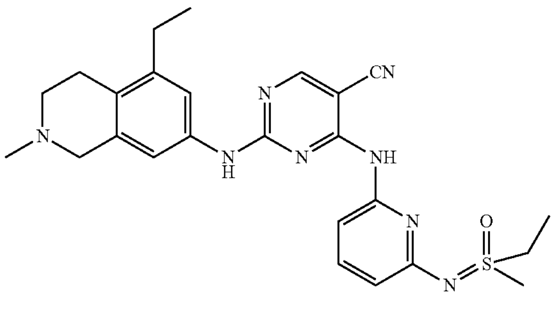 [SMILES: CCc1cc(Nc2ncc(C#N)c(Nc3cccc(N=S(C)(=O)CC)n3)n2)cc2c1CCN(C)C2] | 491 | — |

TABLE 1-continued

| Compound | Compound structure | MS (M + H)+ | LC-MS RT(min) |
|---|---|---|---|
| 158 | 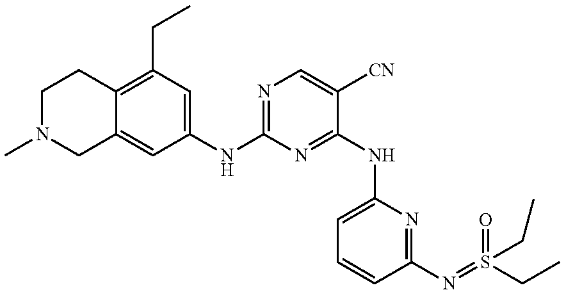 [SMILES: CCc1cc(Nc2ncc(C#N)c(Nc3cccc(N=S(=O)(CC)CC)n3)n2)cc2c1CCN(C)C2] | 505 | — |
| 159 | 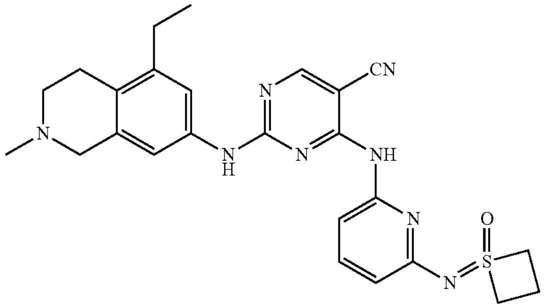 [SMILES: CCc1cc(Nc2ncc(C#N)c(Nc3cccc(N=S4(=O)CCC4)n3)n2)cc2c1CCN(C)C2] | 489 | — |
| 160 | 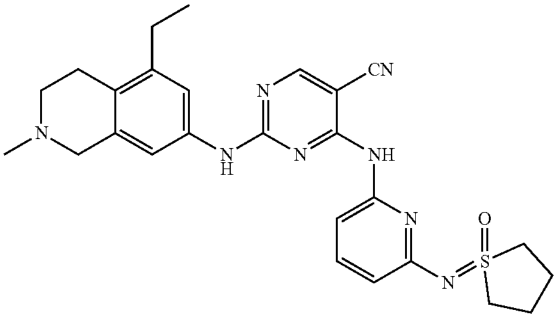 [SMILES: CCc1cc(Nc2ncc(C#N)c(Nc3cccc(N=S4(=O)CCCC4)n3)n2)cc2c1CCN(C)C2] | 503 | — |

TABLE 2

NMR data of some of the compounds in Table 1

| Compound | NMR |
|---|---|
| 5 | $^1$H NMR(400 MHz, DMSO-d6) δ = 10.07 (br s, 1 H), 9.32 (br s, 1 H), 8.52 (br s, 1 H), 7.71-7.16 (m, 4 H), 7.09 (br s, 1 H), 6.42 (br s, 1 H), 3.38-3.37 (m, 2 H), 3.33 (br s, 6 H), 3.24-2.97 (m, 2 H), 2.80 (br s, 2 H), 2.62 (br s, 3 H), 2.35 (br s, 3 H) |
| 10 | $^1$H NMR (400 MHZ, DMSO-d6) δ 13.16 (s, 1 H), 9.18 (m, 2 H), 8.04 (s, 1 H), 7.73 (s, 1 H), 7.45 (m, 3 H), 7.03-6.78 (s, 1 H), 6.40-6.14 (m, 1 H), 3.37 (m, 8 H), 2.71 (s, 2 H), 2.54 (s, 2 H), 2.45 (s, 3 H). |
| 14 | $^1$H NMR (400 MHZ, Chloroform-d) δ 8.37 (s, 1 H), 7.68 (s, 1 H), 7.52 (d, J = 24.8 Hz, 2 H), 7.38 (s, 1 H), 7.26 (s, 1 H), 7.00 (s, 1 H), 6.57 (d, J = 7.9 Hz, 1 H), 3.60 (s, 2 H), 3.37 (s, 6 H), 3.09 (p, J = 7.0 Hz, 1 H), 2.91 (d, J = 6.0 Hz, 2 H), 2.79 (d, J = 5.7 Hz, 2 H), 2.49 (s, 3 H), 1.19 (d, J = 6.8 Hz, 6 H). |
| 15 | $^1$H NMR (400 MHZ, Chloroform-d) δ 8.36 (s, 1 H), 7.75-7.57 (m, 2 H), 7.48 (s, 1 H), 7.26-7.19 (m, 1 H), 7.04 (s, 1 H), 6.56 (d, J = 7.9 Hz, 1 H), 5.23-5.12 (m, 1 H), 4.85 (dd, J = 2.2, 1.1 Hz, 1 H), 3.55 (s, 2 H), 3.36 (s, 5 H), 2.85 (t, J = 5.9 Hz, 2 H), 2.66 (t, J = 5.9 Hz, 2 H), 2.44 (s, 3 H), 1.99 (s, 3 H). |
| 17 | $^1$H NMR (400 MHZ, Chloroform-d) δ 8.36 (s, 1 H), 7.81 (s, 1 H), 7.66 (s, 1 H), 7.46 (s, 2 H), 7.23 (s, 1 H), 7.16 (s, 1 H), 6.55 (d, J = 7.9 Hz, 1 H), 5.85-5.67 (m, 1H), 3.70 (s, 2 H), 3.37 (s, 6 H), 2.97 (t, J = 5.8 Hz, 2 H), 2.82 (s, 2 H), 2.53 (m, 7.5 Hz, 7H), 1.96-1.90 (m, 2 H). |

TABLE 2-continued

NMR data of some of the compounds in Table 1

| Compound | NMR |
|---|---|
| 18 | $^1$H NMR (400 MHZ, Chloroform-d) δ 8.35 (s, 1 H), 7.60 (s, 2 H), 7.49 (d, J = 11.3 Hz, 1 H), 7.04 (s, 1 H), 6.56 (s, 1 H), 3.64 (s, 2 H), 3.41 (d, J = 42.2 Hz, 6 H), 3.10 (s, 1 H), 2.90 (d, J = 40.4 Hz, 4 H), 2.53 (s, 3 H), 1.98 (s, 2 H), 1.71 (d, J = 45.3 Hz, 4 H), 1.50 (s, 2 H). |
| 20 | $^1$H NMR (400 MHZ, Methanol-d4) δ 8.45 (s, 1 H), 7.76 (d, J = 25.0 Hz, 2 H), 7.53 (t, J = 7.7 Hz, 2 H), 6.52 (d, J = 8.4 Hz, 1 H), 3.80 (s, 2 H), 3.39 (s, 6 H), 3.10 (t, J = 6.1 Hz, 2 H), 2.99 (d, J = 6.2 Hz, 2 H), 2.61 (s, 3 H). |
| 25 | $^1$H NMR (400 MHZ, Chloroform-d) δ 8.37 (s, 1 H), 7.66 (t, J = 7.1 Hz, 2 H), 7.57-7.37 (m, 2 H), 6.93 (s, 1 H), 6.59 (dd, J = 7.9, 0.8 Hz, 1 H), 3.51 (s, 2 H), 3.37 (s, 6 H), 2.85 (t, J = 5.9 Hz, 2 H), 2.69 (t, J = 6.0 Hz, 2 H), 2.45 (s, 3 H). |
| 28 | $^1$H NMR (400 MHZ, Chloroform-d) δ 8.37 (s, 1 H), 7.93 (s, 1 H), 7.66 (d, J = 8.0 Hz, 1 H), 7.63-7.52 (m, 2 H), 7.39 (s, 1 H), 7.17 (s, 1 H), 6.58 (dd, J = 7.6, 1.9 Hz, 1 H), 3.49 (s, 2 H), 3.37 (d, J = 1.8 Hz, 6 H), 2.78 (d, J = 6.0 Hz, 2 H), 2.71 (d, J = 6.1 Hz, 2 H), 2.45 (d, J = 2.0 Hz, 3 H). |
| 45 | $^1$H NMR (400 MHZ, Chloroform-d) δ 8.34 (s, 1 H), 7.81-7.61 (m, 2 H), 7.47 (s, 2 H), 7.20 (s, 1 H), 6.86 (s, 1 H), 6.54 (d, J = 7.9 Hz, 1 H), 3.60 (s, 2 H), 3.36 (s, 6 H), 2.98 (d, J = 6.1 Hz, 2 H), 2.82 (t, J = 6.1 Hz, 2 H), 2.61 (q, J = 7.2 Hz, 2 H), 1.86-1.71 (m, 1 H), 1.21 (q, J = 9.0, 7.2 Hz, 3 H), 0.88 (d, J = 8.1 Hz, 2 H), 0.56 (d, J = 5.6 Hz, 2 H). |
| 76 | $^1$H NMR (400 MHz, Chloroform-d) δ 8.63 (s, 1 H), 7.94 (s, 2 H), 7.60 (s, 1 H), 7.39 (s, 1 H), 7.12 (s, 2 H), 7.05 (s, 1 H), 6.93 (s, 1 H), 3.56 (s, 2 H), 3.22 (s, 6 H), 2.93 (s, 2 H), 2.72 (s, 2 H), 2.46 (s, 3 H). |
| 87 | $^1$H NMR (400 MHZ, Chloroform-d) δ 8.36 (s, 1 H), 7.70 (d, J = 7.9 Hz, 1 H), 7.50 (d, J = 20.0 Hz, 2 H), 7.21 (d, J = 2.2 Hz, 1 H), 6.98 (s, 1 H), 6.61-6.51 (m, 1 H), 3.54 (s, 2 H), 3.36 (d, J = 0.6 Hz, 6 H), 2.84 (t, J = 6.0 Hz, 2 H), 2.70 (t, J = 5.9 Hz, 2 H), 2.43 (d, J = 11.0 Hz, 5 H), 1.89-1.81 (m, 1 H), 0.90 (d, J = 6.6 Hz, 6 H). |
| 97 | $^1$H NMR (400 MHz, Chloroform-d) δ 8.36 (s, 1 H), 7.67 (s, 1 H), 7.57 (d, J = 14.2 Hz, 2 H), 7.48 (s, 1 H), 7.24 (s, 1 H), 7.09 (s, 1 H), 6.57 (d, J = 7.9 Hz, 1 H), 3.68 (s, 2 H), 3.61-3.49 (m, 1 H), 3.36 (s, 6 H), 2.84 (s, 4 H), 2.55 (s, 3 H), 2.30 (d, J = 9.3 Hz, 2 H), 2.15-1.90 (m, 3 H), 1.78 (d, J = 9.4 Hz, 1 H). |
| 101 | $^1$H NMR (400 MHZ, Chloroform-d) δ 8.36 (s, 1 H), 7.67 (s, 1 H), 7.60 (s, 1 H), 7.47 (s, 1 H), 7.34 (s, 1 H), 7.29 (d, J = 2.3 Hz, 1 H), 7.09 (s, 1 H), 6.56 (d, J = 7.9 Hz, 1 H), 3.56 (s, 2 H), 3.37 (s, 6 H), 3.06 (t, J = 6.0 Hz, 2 H), 2.73 (t, J = 5.9 Hz, 2 H), 2.46 (s, 3 H), 1.28 (s, 3 H), 0.79-0.59 (m, 4 H). |
| 106 | $^1$H NMR (400 MHZ, Chloroform-d) δ 8.50 (s, 1 H), 7.66 (t, J = 7.8 Hz, 1 H), 7.45 (s, 1 H), 6.98 (s, 1 H), 6.91 (s, 1 H), 6.81-6.72 (m, 1 H), 6.60 (d, J = 7.7 Hz, 1 H), 3.34 (d, J = 7.9 Hz, 2 H), 3.15 (s, 6 H), 2.83 (d, J = 6.7 Hz, 2 H), 2.68 (t, J = 5.8 Hz, 2 H), 2.46 (s, 3 H). |
| 107 | $^1$H NMR (400 MHZ, Chloroform-d) δ 8.23 (s, 1 H), 7.85-7.70 (m, 2 H), 7.47 (t, J = 8.0 Hz, 1 H), 7.31 (s, 1 H), 7.20 (d, J = 8.0 Hz, 1 H), 7.16-6.99 (m, 2 H), 6.52 (d, J = 7.9 Hz, 1H), 3.54 (s, 2 H), 3.34 (s, 6 H), 2.89 (t, J = 6.1 Hz, 2 H), 2.69 (t, J = 6.0 Hz, 2 H), 2.44 (s, 3 H). |
| 111 | $^1$H NMR (400 MHZ, Chloroform-d) δ 8.37 (s, 1 H), 7.60 (s, 1 H), 7.51 (s, 1 H), 7.44-7.32 (m, 4 H), 7.26 (s, 3 H), 6.51 (d, J = 7.7 Hz, 1 H), 3.72 (s, 2 H), 3.36 (s, 6 H), 2.80 (s, 2 H), 2.72 (s, 2 H), 2.53 (s, 3 H). |
| 112 | $^1$H NMR (400 MHZ, Chloroform-d) δ 8.35 (s, 1 H), 7.60 (s, 4 H), 7.19 (s, 2 H), 6.44 (s, 2 H), 3.58 (s, 2 H), 3.34 (s, 6 H), 2.96 (s, 2 H), 2.70 (s, 2 H), 2.48 (s, 3 H). |
| 113 | $^1$H NMR (400 MHZ, DMSO-d6) δ 9.97 (s, 1 H), 9.15 (s, 1 H), 8.56 (s, 1 H), 7.71 (s, 1 H), 7.54 (s, 1 H), 7.42 (s, 1 H), 7.25 (s, 1 H), 6.36 (d, J = 10.0 Hz, 2 H), 3.85 (s, 3 H), 3.52 (s, 2 H), 3.37 (s, 6 H), 2.92 (d, J = 6.3 Hz, 2 H), 2.66 (s, 2 H), 2.39 (s, 3H). |
| 115 | $^1$H NMR (400 MHZ, Chloroform-d) δ 8.39 (d, J = 17.0 Hz, 1 H), 7.62 (d, J = 21.8 Hz, 2 H), 7.50 (s, 1 H), 7.36 (s, 1 H), 7.11 (d, J = 1.8 Hz, 1 H), 6.92 (d, J = 22.1 Hz, 1 H), 6.58 (d, J = 7.9 Hz, 1 H), 3.78 (s, 2 H), 3.37 (s, 6 H), 2.92 (d, J = 11.4 Hz, 4 H), 2.79 (s, 4 H), 2.60 (s, 3 H), 1.67 (s, 4 H), 1.55 (s, 2 H). |
| 116 | $^1$H NMR (400 MHZ, Chloroform-d) δ 8.38 (s, 1 H), 7.67 (s, 1 H), 7.57 (s, 1 H), 7.47 (s, 1 H), 7.29 (s, 1 H), 7.13 (s, 1 H), 6.57 (d, J = 7.9 Hz, 1 H), 3.82 (d, J = 5.5 Hz, 4 H), 3.57 (s, 2 H), 3.37 (d, J = 2.2 Hz, 6 H), 2.87 (d, J = 5.0 Hz, 6 H), 2.68 (d, J = 6.2 Hz, 2 H), 2.46 (s, 3 H). |
| 117 | $^1$H NMR (400 MHZ, Chloroform-d) δ 8.38 (s, 1 H), 7.67 (s, 1 H), 7.50 (d, J = 22.4 Hz, 3 H), 7.32 (s, 1 H), 6.57 (d, J = 7.9 Hz, 1 H), 4.07 (dd, J = 11.4, 4.1 Hz, 2 H), 3.62-3.46 (m, 4 H), 3.37 (s, 6 H), 3.00-2.84 (m, 3 H), 2.73 (t, J = 5.9 Hz, 2 H), 2.45 (s, 3 H), 1.78-1.62 (m, 4 H). |
| 118 | $^1$H NMR (400 MHZ, Chloroform-d) δ 8.37 (s, 1 H), 7.78-7.62 (m, 2 H), 7.44 (d, J = 34.6 Hz, 2 H), 7.27 (d, J = 2.4 Hz, 1 H), 7.02 (s, 1 H), 6.56 (d, J = 7.9 Hz, 1 H), 5.62 (s, 1 H), 4.26 (q, J = 2.8 Hz, 2 H), 3.87 (t, J = 5.3 Hz, 2 H), 3.57 (s, 2 H), 3.37 (s, 6 H), 2.85 (t, J = 5.9 Hz, 2 H), 2.67 (t, J = 5.9 Hz, 2 H), 2.45 (s, 3 H), 2.30 (s, 2 H). |
| 119 | $^1$H NMR (400 MHz, Chloroform-d) δ 8.38 (s, 1 H), 7.64 (s, 1 H), 7.52 (s, 2 H), 7.36 (s, 1 H), 6.58 (d, J = 8.0 Hz, 1 H), 3.74 (s, 2 H), 3.37 (s, 6 H), 3.06-2.83 (m, 8 H), 2.74 (m, 4 H), 2.57 (s, 3 H), 2.46 (s, 3 H) |

TABLE 2-continued

NMR data of some of the compounds in Table 1

| Compound | NMR |
|---|---|
| 120 | $^1$H NMR (400 MHZ, Chloroform-d) δ 8.36 (s, 1 H), 7.56 (d, J = 52.4 Hz, 3 H), 7.09 (s, 1 H), 6.91 (s, 1 H), 6.56 (s, 1 H), 3.68 (s, 2 H), 3.36 (s, 10 H), 3.04 (s, 2 H),2.93 (s, 2 H), 2.81 (s, 2 H), 2.63 (s, 2 H), 2.55 (s, 3 H), 1.98 (s, 2 H), 1.68 (s, 2 H). |
| 122 | $^1$H NMR (400 MHZ, Chloroform-d) δ 8.35 (d, J = 14.1 Hz, 2 H), 7.67-7.46 (m, 3 H), 7.21 (s, 1 H), 6.95 (s, 1 H), 6.58 (d, J = 7.8 Hz, 1 H), 4.12 (s, 2 H), 3.89 (s, 2 H), 3.37 (s, 6 H), 3.03 (s, 4 H), 2.89 (d, J = 12.0 Hz, 2 H), 2.68 (s, 3 H), 2.59 (dd, J = 11.4, 5.6 Hz, 2 H), 1.31 (d, J = 6.4 Hz, 6 H). |
| 124 | $^1$H NMR (400 MHZ, Chloroform-d) δ 8.37 (s, 1 H), 7.81-7.39 (m, 4 H), 6.57 (d, J = 7.9 Hz, 1 H), 4.40 (s, 2 H), 3.54 (s, 2 H), 3.38 (d, J = 10.9 Hz, 9 H), 2.86 (s, 2 H), 2.73 (s, 2 H), 2.45 (s, 3 H). |
| 127 | $^1$H NMR (400 MHZ, Chloroform-d) δ 8.37 (s, 1 H), 7.63 (s, 2 H), 7.54 (d, J = 10.3 Hz, 2 H), 7.20 (s, 1 H), 6.93 (s, 1 H), 6.57 (d, J = 7.8 Hz, 1 H), 3.86-3.76 (m, 3 H), 3.65 (p, J = 6.7 Hz, 1 H), 3.36 (s, 6 H), 3.13-2.95 (m, 4 H), 2.89 (d, J = 11.4 Hz, 2 H), 2.68 (s, 3 H), 2.38 (t, J = 10.5 Hz, 2 H), 1.18 (d, J = 6.3 Hz, 6 H). |
| 128 | $^1$H NMR (400 MHZ, Chloroform-d) δ 8.36 (s, 1 H), 7.68 (d, J = 8.0 Hz, 1 H), 7.50 (d, J = 14.2 Hz, 2 H), 7.37 (s, 1 H), 7.21 (d, J = 2.3 Hz, 1 H), 7.06 (s, 1 H), 6.62-6.52 (m, 1 H), 3.58 (s, 2 H), 3.46-3.23 (m, 11 H), 2.87 (t, J = 5.9 Hz, 2 H), 2.76 (t, J = 5.9 Hz, 2 H), 2.68-2.59 (m, 2 H), 2.48 (s, 3 H), 1.82 (q, J = 7.5, 7.0 Hz, 2 H). |
| 130 | $^1$H NMR (400 MHZ, DMSO-d6) δ 10.01 (s, 1 H), 8.56 (s, 1 H), 7.57 (t, J = 7.9 Hz, 1 H), 7.48 (s, 1 H), 7.38 (s, 1 H), 7.18 (s, 1 H), 6.44 (d, J = 7.9 Hz, 1 H), 3.91 (s, 3 H), 3.36 (s, 5 H), 3.23-3.06 (m, 2 H), 3.01 (s, 2 H), 2.67 (s, 3 H), 2.49 (s, 3 H), 2.28 (s, 6 H). |
| 131 | $^1$H NMR (400 MHZ, DMSO-d6) δ 9.91 (s, 1 H), 9.11 (s, 1 H), 8.54 (s, 1 H), 7.50 (t, J = 7.9 Hz, 1 H), 7.33 (s, 3 H), 6.40 (d, J = 8.0 Hz, 1 H), 4.38 (d, J = 5.1 Hz, 2 H), 3.36 (s, 6 H), 2.65 (d, J = 5.8 Hz, 2 H), 2.56 (t, J = 5.9 Hz, 2 H), 2.29 (s, 2 H). |
| 137 | $^1$H NMR (400 MHZ, Chloroform-d) δ 8.34 (s, 1 H), 7.81-7.61 (m, 2H), 7.47 (s, 2 H), 7.20 (s, 1 H), 6.86 (s, 1 H), 6.54 (d, J = 7.9 Hz, 1 H), 3.60 (s, 2 H), 3.36 (s, 6 H), 2.98 (d, J = 6.1 Hz, 2 H), 2.82 (t, J = 6.1 Hz, 2 H), 2.61 (q, J = 7.2 Hz, 2 H), 1.86-1.71 (m, 1 H), 1.21 (q, J = 9.0, 7.2 Hz, 3 H), 0.88 (d, J = 8.1 Hz, 2 H), 0.56 (d, J = 5.6 Hz, 2 H). |
| 145 | $^1$H NMR (400 MHZ, Methanol-d4) δ 7.98 (d, J = 5.7 Hz, 1 H), 7.53 (s, 1 H), 7.47 (t, J = 8.0 Hz, 1 H), 7.39 (d, J = 8.3 Hz, 1 H), 7.26 (d, J = 8.0 Hz, 1 H), 7.09 (d, J = 8.4 Hz, 1 H), 6.95 (d, J = 5.8 Hz, 1 H), 6.36 (d, J = 7.6 Hz, 1 H), 4.02 (s, 2 H), 3.39 (s, 6 H), 3.19 (t, J = 6.1 Hz, 2 H), 3.02 (d, J = 6.3 Hz, 2 H), 2.76 (s, 3 H). |
| 147 | $^1$H NMR (400 MHZ, Chloroform-d) δ 8.31 (s, 1 H), 7.85 (s, 1 H), 7.76-7.56 (m, 3 H), 7.48 (t, J = 8.0 Hz, 1 H), 6.58 (s, 1 H), 6.52 (d, J = 7.9 Hz, 1 H), 3.80 (s, 3 H), 3.41 (d, J = 13.4 Hz, 2 H), 3.31 (s, 6 H), 2.83 (t, J = 6.0 Hz, 2 H), 2.62 (t, J = 5.9 Hz, 2 H), 2.38 (s, 3 H). |
| 148 | $^1$H NMR (400 MHZ, DMSO-d6) δ 9.82 (s, 1 H), 8.55 (s, 1 H), 8.30 (s, 1 H), 7.52 (t, J = 7.9 Hz, 1 H), 7.35 (s, 1 H), 6.97 (s, 1 H), 6.40 (d, J = 7.9 Hz, 1 H), 3.86 (s, 2 H), 3.36 (s, 6 H), 3.14 (d, J = 5.5 Hz, 2 H), 2.81 (t, J = 6.1 Hz, 2 H), 1.81 (s, 1 H), 0.86 (s, 2 H), 0.46 (s, 2 H). |
| 149 | $^1$H NMR (400 MHZ, DMSO-d6) δ 9.79 (s, 1 H), 9.22 (s, 1 H), 8.54 (s, 1 H), 7.50 (t, J = 8.0 Hz, 1 H), 7.21 (d, J = 34.9 Hz, 3 H), 6.41 (d, J = 7.9 Hz, 1 H), 3.35 (s, 3 H), ) 3.29 (m, 2 H), 2.75-2.62 (m, 2 H), 2.58 (d, J = 5.7 Hz, 2 H), 2.40 (d, J = 8.0 Hz, 2 H), 2.31 (s, 3 H), 2.18 (t, J = 8.1 Hz, 1 H), 1.90 (p, J = 7.6 Hz, 1 H), 0.91 (t, J = 7.4 Hz, 3 H). |
| 150 | $^1$H NMR (400 MHZ, DMSO-d6) δ 9.78 (s, 1 H), 8.79 (s, 1 H), 8.50 (s, 1 H), 7.29 (s, 1 H), 7.12 (dd, J = 7.7, 1.5 Hz, 1 H), 7.01-6.76 (m, 3 H), 3.41 (s, 2 H), 3.32 (s, 6 H), 2.84 (t, J = 6.1 Hz, 2 H), 2.62 (t, J = 6.0 Hz, 2 H), 2.32 (s, 3 H), 1.83 (tt, J = 8.4, 5.4 Hz, 1 H), 0.93-0.74 (m, 2 H), 0.51 (dt, J = 5.6, 2.8 Hz, 2 H). |
| 153 | $^1$H NMR (400 MHZ, Chloroform-d) δ 8.34 (s, 1 H), 7.81-7.51 (m, 3 H), 7.36 (s, 2 H), 7.03 (d, J = 8.5 Hz, 1 H), 6.55 (d, J = 7.9 Hz, 1 H), 3.35 (s, 6 H), 2.95 (t, J = 4.4 Hz, 4 H), 2.65 (d, J = 36.5 Hz, 4 H), 2.38 (s, 3 H), 2.30 (s, 3 H). |
| 154 | $^1$H NMR (400 MHZ, Chloroform-d) δ 8.33 (s, 1 H), 7.67 (d, J = 40.8 Hz, 2 H), 7.43 (s, 1 H), 7.25 (s, 1 H), 6.55 (s, 1 H), 3.35 (s, 6 H), 3.12 (m, 4 H), 2.53 (m, 4 H), 2.33 (d, J = 24.5 Hz, 9 H). |
| 155 | $^1$H NMR (400 MHZ, Chloroform-d) δ 8.33 (s, 1 H), 7.63 (s, 3 H), 7.37 (s, 1 H), 7.02 (d, J = 8.5 Hz, 1 H), 6.78 (s, 1 H), 6.53 (d, J = 7.9 Hz, 1 H), 3.35 (s, 6 H), 3.07 (m, 4 H), 2.61 (m, 4 H), 2.37 (s, 3 H), 2.34-2.26 (m, 1 H), 0.96 (d, J = 8.2 Hz, 2 H), 0.64 (s, 2 H). |

Example 161. In-Vitro Assay of the Compounds of the Present Invention for Inhibiting Enzymatic Activity of Recombinant Protein Wee-1

The inhibitory effect of the compounds on the enzyme activity of recombinant protein Wee-1 was determined by HTRF. The procedures are as follows:

After DMSO or serially diluted compounds (up to 200 nM, 1:5 diluted) and recombinant proteins were co-incubated in a kinase buffer at 37° C. for 30 min before Fluorescein-PolyGAT and ATP were added, and the reaction was initiated by addition of a substrate. After incubation at room temperature for 90 min, an antibody and a detection solution were added, and after further incubation at room temperature for 60 min, fluorescence values were detected (excitation wavelength: 340 nm, emission wavelengths: 495 and 520 nm). The 520 nm/495 nm fluorescence intensity ratio value was calculated, and compared with that of the DMSO group, and then the inhibition percentages and $IC_{50}$ values of the compounds were calculated. The results are shown in Table 3 below.

TABLE 3

Inhibitory activity of the compounds of the present invention against recombinant protein Wee-1

| Compound | ($IC_{50}$) | Compound | ($IC_{50}$) | Compound | ($IC_{50}$) | Compound | ($IC_{50}$) |
|---|---|---|---|---|---|---|---|
| 1 | +++ | 2 | + | 3 | + | 4 | + |
| 5 | + | 6 | + | 7 | + | 8 | + |
| 9 | + | 10 | + | 11 | +++ | 12 | +++ |
| 13 | +++ | 14 | +++ | 15 | +++ | 16 | +++ |
| 17 | +++ | 18 | +++ | 19 | +++ | 20 | +++ |
| 21 | +++ | 22 | +++ | 23 | +++ | 24 | +++ |
| 25 | +++ | 26 | +++ | 27 | +++ | 28 | +++ |
| 29 | +++ | 30 | +++ | 31 | +++ | 32 | +++ |
| 33 | +++ | 34 | +++ | 35 | +++ | 36 | +++ |
| 37 | +++ | 38 | +++ | 39 | +++ | 40 | +++ |
| 41 | ++ | 42 | +++ | 43 | +++ | 44 | +++ |
| 45 | +++ | 46 | +++ | 47 | +++ | 48 | +++ |
| 49 | +++ | 50 | +++ | 51 | +++ | 52 | +++ |
| 53 | +++ | 54 | +++ | 55 | +++ | 56 | +++ |
| 57 | +++ | 58 | +++ | 59 | +++ | 60 | +++ |
| 61 | +++ | 62 | +++ | 63 | +++ | 64 | +++ |
| 65 | +++ | 66 | +++ | 67 | +++ | 68 | +++ |
| 69 | +++ | 70 | +++ | 71 | +++ | 72 | +++ |
| 73 | +++ | 74 | +++ | 75 | +++ | 76 | +++ |
| 77 | +++ | 78 | +++ | 79 | +++ | 80 | ++ |
| 81 | +++ | 82 | +++ | 83 | +++ | 84 | +++ |
| 85 | +++ | 86 | +++ | 87 | +++ | 88 | + |
| 89 | +++ | 90 | +++ | 91 | +++ | 92 | +++ |
| 93 | +++ | 94 | +++ | 95 | +++ | 96 | +++ |
| 97 | +++ | 98 | +++ | 99 | +++ | 100 | +++ |
| 101 | +++ | 102 | +++ | 103 | +++ | 104 | +++ |
| 105 | +++ | 106 | +++ | 107 | +++ | 108 | ++ |
| 111 | +++ | 112 | +++ | 113 | +++ | 114 | +++ |
| 115 | +++ | 116 | +++ | 117 | +++ | 118 | +++ |
| 119 | +++ | 120 | +++ | 121 | +++ | 122 | +++ |
| 123 | +++ | 124 | +++ | 125 | +++ | 126 | +++ |
| 127 | +++ | 128 | +++ | 129 | +++ | 130 | +++ |
| 131 | +++ | 132 | +++ | 133 | +++ | 134 | +++ |
| 135 | +++ | 136 | +++ | 137 | +++ | 138 | +++ |
| 139 | +++ | 140 | +++ | 141 | +++ | 142 | +++ |
| 143 | +++ | 144 | +++ | 145 | + | 146 | +++ |
| 147 | +++ | 148 | +++ | 149 | +++ | 150 | ++ |
| 151 | +++ | 152 | +++ | 153 | +++ | 154 | +++ |
| 155 | +++ | 156 | +++ | 157 | +++ | 158 | +++ |
| 159 | +++ | 160 | +++ | | | | |

+++ means that $IC_{50}$ is less than or equal to 10 nM
++ means that $IC_{50}$ is 10 nM to 50 nM
+ means that $IC_{50}$ is greater than 50 nM.

As can be seen from the data in Table 3, the compounds of the present invention have good inhibitory activities against the enzymatic activity of recombinant protein Wee-1.

Example 162. In-Vitro Anti-Proliferative Activity of the Compounds of the Present Invention on MIA PaCa-2 Cells MIA PaCa-2 cells were seeded on a 384-well plate at 3000 cells/well. After overnight adherence culture, DMSO or the compounds serially 1:5-diluted from 5 μM were added. The viability was assessed 72 h after dosing by measuring the intracellular ATP content. The inhibition percentage of viable cells by the compounds was calculated by comparing with the DMSO group, and the $IC_{50}$ value was calculated. The results are shown in table 4 below.

TABLE 4

| Antiproliferative activity of the compounds of the present invention against MIA PaCa-2 cells | | | | | | | |
|---|---|---|---|---|---|---|---|
| Compound | $IC_{50}$ (nM) | Compound | $IC_{50}$ (nM) | Compound | $IC_{50}$ (nM) | Compound | $IC_{50}$ (nM) |
| 1 | 735 | 2 | 398 | 3 | 879 | 4 | >5000 |

As can be seen from the data in Table 4, the compounds of the present invention have strong anti-proliferative activities against MIA PaCa-2 cells.

Example 163. In-Vitro Anti-Proliferative Activity of the Compounds of the Present Invention in Combination with Gemcitabine on MIA PaCa-2 Cells MIA PaCa-2 cells were seeded on a 384-well plate at 3000 cells/well, and 20 nM or 200 nM gemcitabine (GMC) was added. After overnight adherence culture, DMSO or the compounds serially 1:5-diluted from 100 nM were added. The viability was assessed 72 h after dosing by measuring the intracellular ATP content. The inhibition percentage of viable cells by the compounds was calculated by comparing with the DMSO group, and the $IC_{50}$ value was calculated. The results are shown in table 5 below.

TABLE 5

In-*vitro* anti-proliferative activity of the compounds of the present invention in combination with gemcitabine on MIA PaCa-2 cells

| Compound | in combination with 20 nM GMC $IC_{50}$ (nM) | in combination with 200 nM GMC $IC_{50}$ (nM) | Compound | in combination with 20 nM GMC $IC_{50}$ (nM) | in combination with 200 nM GMC $IC_{50}$ (nM) |
|---|---|---|---|---|---|
| 1 | 4.6 | | 2 | 30 | |
| 3 | | >100 | 4 | >100 | |
| 5 | >100 | | 6 | >100 | |
| 7 | >100 | | 8 | >100 | |
| 9 | >100 | | 10 | >100 | |
| 11 | 16 | | 12 | 1.4 | |
| 13 | | 1 | 14 | 1 | |
| 15 | 1.8 | | 16 | | 1 |
| 17 | 11 | | 18 | 2.1 | |
| 19 | | 640 | 20 | 25 | |
| 22 | | 1.2 | 25 | 18.6 | |
| 28 | 14.5 | | 29 | 3.7 | |
| 41 | | >100 | 42 | | 10 |
| 43 | 21.2 | | 52 | 4.5 | |
| 55 | 11.3 | | 60 | 10.3 | |
| 61 | 7.5 | | 62 | 12.5 | |
| 63 | 18.4 | | 64 | 34 | |
| 77 | | >100 | 78 | >100 | |
| 79 | | >100 | 80 | | >100 |
| 85 | | >100 | 87 | 1.8 | |
| 97 | 1.6 | | 101 | 4.4 | |
| 105 | 26.5 | | 106 | >100 | |
| 107 | 26.6 | | 108 | >100 | |
| 111 | 6.5 | | 112 | >100 | |
| 113 | 11.7 | | 115 | 9.3 | |
| 116 | 1.3 | | 117 | 1.5 | |
| 118 | 1.1 | | 119 | 2.6 | |
| 120 | 4.5 | | 121 | 113 | |
| 122 | 49 | | 123 | 28 | |
| 124 | 2.7 | | 127 | 8.2 | |
| 128 | 2.5 | | 129 | 4.2 | |
| 130 | 10 | | 131 | 6.7 | |
| 133 | 1.1 | | 137 | 3.3 | |
| 145 | >100 | | 146 | 4.8 | |
| 147 | 50 | | 148 | 2.1 | |

TABLE 5-continued

In-*vitro* anti-proliferative activity of the compounds of the present invention in combination with gemcitabine on MIA PaCa-2 cells

| Compound | in combination with 20 nM GMC $IC_{50}$ (nM) | in combination with 200 nM GMC $IC_{50}$ (nM) | Compound | in combination with 20 nM GMC $IC_{50}$ (nM) | in combination with 200 nM GMC $IC_{50}$ (nM) |
|---|---|---|---|---|---|
| 150 | 3.5 | | 152 | 3.8 | |
| 153 | 3.5 | | 154 | 2.4 | |
| 155 | 5.4 | | 156 | 6 | |

As can be seen from the data in Table 5, the compounds of the present invention, in combination with gemcitabine, have strong anti-proliferative activities against MIA PaCa-2 cells.

Example 164: In Vivo Efficacy Study—Mouse 11T29 Subcutaneous Xenograft Tumor Model HT29 is a colon cancer cell. Each nude mouse was grafted subcutaneously with $5\times10^6$HT29 cells. When the tumor grew to 100-200 $mm^3$, the compound was administered orally once a day alone or in combination with 15 mg/kg of gemcitabine injected intraperitoneally once a week, and the tumor volume was measured twice a week and at the end of treatment. Tumor growth inhibition of the compound was calculated according to the following equation: tumor growth inhibition (TGI)=1−(tumor volume on day 20 in treatment group−tumor volume on day 1 in treatment group)/(tumor volume on day 20 in vehicle control group−tumor volume on day 1 in treatment group). The results are shown in Tables 6 and 7.

TABLE 6

Growth inhibition in mouse HT29 subcutaneous xenograft tumor-monotherapy

| Compound | Dose | Tumor volume on day 1 of treatment ($mm^3$) | Tumor volume on day 20 of treatment ($mm^3$) | TGI |
|---|---|---|---|---|
| Control | Not applicable | 102 | 1079 | Not applicable |
| Gemcitabine | 15 mg/kg | 102 | 550 | 54% |
| Compound 13 | 30 mg/kg | 102 | 129 | 97% |
| Compound 16 | 30 mg/kg | 102 | 307 | 79% |
| Compound 137 | 30 mg/kg | 102 | 573 | 51% |

TABLE 7

Growth inhibition in mouse HT29 subcutaneous xenograft tumor-in combination with 15 mg/kg of gemcitabine

| Compound | Dose | Tumor volume on day 1 of treatment ($mm^3$) | Tumor volume on day 20 of treatment ($mm^3$) | TGI |
|---|---|---|---|---|
| Control | Not applicable | 102 | 1079 | Not applicable |
| Gemcitabine | 15 mg/kg | 102 | 550 | 54% |
| Compound 13 | 30 mg/kg | 102 | 14 | 109% |
| Compound 16 | 30 mg/kg | 102 | 58 | 104% |
| Compound 137 | 30 mg/kg | 102 | 97 | 100% |

Example 165: In Vivo Efficacy Study—Mouse HT29 Subcutaneous Xenograft Tumor Model HT29 is a colon cancer cell. Each nude mouse was grafted subcutaneously with $5\times10^6$HT29 cells. When the tumor grew to 100-200 $mm^3$, the compound was administered orally once a day in combination with 30 mg/kg of gemcitabine injected intraperitoneally once a week, and the tumor volume was measured twice a week and at the end of treatment. Tumor growth inhibition of the compound was calculated according to the following equation: tumor growth inhibition (TGI)=1−(tumor volume on day 20 in treatment group−tumor volume on day 1 in treatment group)/(tumor volume on day 20 in vehicle control group−tumor volume on day 1 in treatment group). The results are shown in Table 8.

TABLE 8

Growth inhibition in mouse HT29 subcutaneous xenograft tumor-in combination with 30 mg/kg of gemcitabine

| Compound | Dose | Tumor volume on day 1 of treatment ($mm^3$) | Tumor volume on day 20 of treatment ($mm^3$) | TGI |
|---|---|---|---|---|
| Control | Not applicable | 121 | 1457 | Not applicable |
| Gemcitabine | 30 mg/kg | 121 | 653 | 60% |
| Compound 14 | 30 mg/kg | 121 | 38 | 106% |
| Compound 18 | 30 mg/kg | 121 | 218 | 92% |
| Compound 87 | 30 mg/kg | 121 | 395 | 79% |
| Compound 97 | 30 mg/kg | 121 | 278 | 88% |
| Compound 101 | 30 mg/kg | 121 | 95 | 102% |
| Compound 117 | 30 mg/kg | 121 | 283 | 87% |
| Compound 128 | 30 mg/kg | 121 | 284 | 87% |

As can be seen from Tables 6, 7, and 8, when the compounds of the present invention were used alone, the compounds can inhibit tumor growth in the mouse HT29 subcutaneous xenograft tumor, and when the compounds of the present invention were used in combination with gemcitabine, the compounds exhibited more significant inhibitory effect on tumor growth.

Although specific embodiments of the present invention have been described above, it will be appreciated by those skilled in the art that these embodiments are merely illustrative and that many changes or modifications can be made to these embodiments without departing from the principles and spirit of the present invention. The scope of protection of the present invention is therefore defined by the appended claims.

The invention claimed is:

1. A compound of general formula (1), or an isomer, a crystalline form, a pharmaceutically acceptable salt, a hydrate or a solvate thereof:

(1)

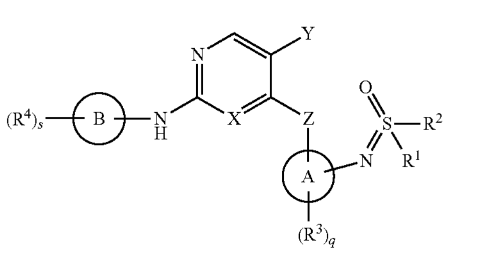

wherein, in general formula (1):

X is CH or N;

Y is —H, halogen, —CN, —$S(O)_2R^5$, —$P(O)(R^6)_2$, —$C(O)NR^8R^9$, (C1-C6) alkyl, (C1-C6) haloalkyl, (C2-C6) alkynyl, (C3-C14) cycloalkyl, (C6-C14) aryl, 3- to 11-membered heterocycloalkyl, or 5- to 11-membered heteroaryl, wherein the (C1-C6) alkyl, (C1-C6) haloalkyl, (C2-C6) alkynyl, (C3-C14) cycloalkyl, (C6-C14) aryl, 3- to 11-membered heterocycloalkyl, or 5- to 11-membered heteroaryl may be each independently and optionally substituted with 1, 2, 3, or 4 of the following groups: —H, halogen, $R^8$, —OH, —$(CH_2)_n$ $OR^8$—, —$(CH_2)_nNR^8R^9$, —$OR^8$, —$NR^8R^9$, —CN, —$C(O)NR^8R^9$, —$NR^8C(O)R^8$, —$NR^9S(O)_2R^8$, —$S(O)_pR^8$, and —$S(O)_2NR^8R^9$;

Z is a chemical bond, —$CH_2$—, —O—, or —NH—;

ring A is 5- to 14-membered heteroaryl or 3- to 14-membered heterocycloalkyl;

$R^1$ and $R^2$ are each independently (C1-C6) alkyl, (C1-C6) haloalkyl, (C2-C6) alkenyl, or (C3-C6) cycloalkyl, wherein the (C1-C6) alkyl, (C1-C6) haloalkyl, (C2-C6) alkenyl, or (C3-C6) cycloalkyl may be each independently and optionally substituted with 1, 2, 3, or 4 of the following groups: —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^8C(O)R^8$, —$NR^9S(O)_2R^8$, —$S(O)_pR^8$, and —$S(O)_2NR^8R^9$; or $R^1$ and $R^2$, along with the S atom connected thereto, are capable of forming 4- to 7-membered heterocycloalkyl, wherein the 4- to 7-membered heterocycloalkyl may be optionally substituted with 1, 2, 3, or 4 of the following groups: —H, halogen, $R^8$, —$OR^8$, —$NR^8R^9$, and —CN;

each $R^3$ is independently —H, -D, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^8C(O)R^8$, —$NR^9S(O)_2R^8$, —$S(O)_pR^8$, —$S(O)_2NR^8R^9$, (C1-C6) alkyl, (C1-C6) haloalkyl, (C2-C6) alkenyl, (C2-C6) alkynyl, (C3-C9) cycloalkyl, (C6-C14) aryl, 3- to 11-membered heterocycloalkyl, or 5- to 11-membered heteroaryl, wherein the (C1-C6) alkyl, (C1-C6) haloalkyl, (C2-C6) alkenyl, (C2-C6) alkynyl, (C3-C9) cycloalkyl, (C6-C14) aryl, 3- to 11-membered heterocycloalkyl, or 5- to 11-membered heteroaryl may be each independently and optionally substituted with 1, 2, 3, or 4 of the following groups: —H, halogen, $R^8$, —OH, —$(CH_2)_nOR^8$, —$(CH_2)_nNR^8R^9$, —$OR^8$, —$NR^8R^9$, —CN, —C(O) $NR^8R^9$, —$NR^8C(O)R^8$, —$NR^9S(O)_2R^8$, —$S(O)_pR^8$, and —$S(O)_2NR^8R^9$; or two adjacent $R^3$, along with the atoms connected thereto, are capable of forming 5- to 9-membered heterocycloalkyl or (C5-C9) cycloalkyl, wherein the 5- to 9-membered heterocycloalkyl or the (C5-C9) cycloalkyl may be optionally substituted with 1, 2, 3, or 4 of the following groups: —H, halogen, $R^8$, —OH, —$(CH_2)_nOR^8$, —$(CH_2)_nNR^8R^9$, —$OR^8$, —$NR^8R^9$, —CN, —$C(O)NR^8R^9$, —$NR^8C(O)R^8$, —$NR^9S(O)_2R^8$, —$S(O)_pR^8$, and —$S(O)_2NR^8R^9$;

ring B is (C6-C14) aryl or 5- to 11-membered heteroaryl;

each $R^4$ is independently —H, halogen, $R^8$, —OH, —$(CH_2)_nOR^8$, —$OR^8$, —$(CH_2)$ $NR^8R^9$, —$NR^8R^9$, —CN, —$O(CH_2)_mNR^8R^9$, —$N(R^9)(CH_2)_mNR^8R^9$, —$C(O)NR^8R^9$, —$NR^8C(O)R^8$, —$NR^9S(O)_2R^8$, —$S(O)_pR^8$, —$S(O)_2NR^8R^9$, (C1-C6) alkyl, (C1-C6) haloalkyl, (C2-C6) alkenyl, (C2-C6) alkynyl, (C3-C9) cycloalkyl, (C1-C6) alkoxy, —$CH_2$-3- to 15-membered heterocycloalkyl, 3- to 15-membered heterocycloalkyl, 5- to 9-membered heteroaryl, or (C6-C10) aryl, wherein the (C1-C6) alkyl, (C1-C6) haloalkyl, (C2-C6) alkenyl, (C2-C6) alkynyl, (C3-C9) cycloalkyl, (C1-C6) alkoxy, —$CH_2$-3- to 15-membered heterocycloalkyl, 3- to 15-membered heterocycloalkyl, 5- to 9-membered heteroaryl, or (C6-C10) aryl may be optionally substituted with 1, 2, 3, or 4 of the following groups: —H, halogen, $R^8$, —OH, —$(CH_2)_nOR^8$, —$OR^8$, —$(CH_2)_n$ $NR^8R^9$, —$NR^8R^9$, —CN, —$O(CH_2)_mNR^8R^9$, —$N(R^9)$ $(CH_2)_mNR^8R^9$, (C1-C6) alkyl, (C1-C6) haloalkyl, (C2-C6) alkenyl, (C2-C6) alkynyl, (C3-C9) cycloalkyl, (C1-C6) alkoxy, —$CH_2$-3- to 15-membered heterocycloalkyl, 3- to 15-membered heterocycloalkyl, 5- to 9-membered heteroaryl, (C6-C10) aryl, and —$R^7$; or two adjacent $R^4$, along with the atoms connected thereto, are capable of forming 5- to 9-membered heterocycloalkyl or (C5-C9) cycloalkyl, wherein the 5- to 9-membered heterocycloalkyl or (C5-C9) cloalkyl may be optionally substituted with 1, 2, 3, or 4 of the following groups: —H, halogen, $R^8$, —OH, —$(CH_2)_n$ $OR^8$, —$OR^8$, —$(CH_2)$ $NR^8R^9$, —$NR^8R^9$, —CN, —$O(CH_2)_mNR^8R^9$, —$N(R^9)(CH_2)_mNR^8R^9$, —C(O) $R^8$, —$C(O)NR^8R^9$, —$NR^8C(O)R^8$, —$NR^9S(O)_2R^8$, —$S(O)_pR^8$, —$S(O)_2NR^8R^9$,

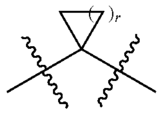, (C1-C6) alkyl, (C1-C6) haloalkyl, (C2-C6) alkenyl, (C2-C6) alkynyl, (C3-C9) cycloalkyl, (C1-C6) alkoxy, —$CH_2$-4- to 9-membered heterocycloalkyl, 4- to 9-membered heterocycloalkyl, 5- to 9-membered heteroaryl, and (C6-C10) aryl;

$R^5$ is (C1-C3) alkyl or (C3-C6) cycloalkyl;

$R^6$ is (C1-C3) alkyl or (C3-C6) cycloalkyl;

$R^7$ is 3- to 11-membered heterocycloalkyl, wherein the heterocycloalkyl may be optionally substituted with 1, 2, 3, or 4 of the following groups: —H, $R^8$, —$OR^8$, and —$NR^8R^9$;

$R^8$ and $R^9$ are each independently —H, (C1-C6) alkyl or (C3-C14) cycloalkyl, or $R^8$ and $R^9$ on the same N atom, along with the N atom connected thereto, are capable of forming 3- to 11-membered heterocycloalkyl, wherein the 3- to 11-membered heterocycloalkyl may be optionally substituted with 1, 2, 3, or 4 of the following groups: —H, halogen, $R^{10}$, and —$OR^{10}$;

$R^{10}$ is —H, (C1-C3) alkyl, or (C3-C6) cycloalkyl;

and p is an integer of 0, 1, or 2, q is an integer of 1, 2, 3, or 4, r is an integer of 1, 2, or 3, s is an integer of 1, 2, 3, or 4, n is an integer of 0, 1, 2, or 3, and m is an integer of 1, 2, or 3.

2. The compound, or the isomer, the crystalline form, the pharmaceutically acceptable salt, the hydrate or the solvate thereof according to claim 1, wherein, in general formula (1), Y is —H, —F, —Cl, —Br, —I, —CN, —$S(O)_2CH_3$, —$P(O)(CH_3)_2$, —$C(O)NH_2$, —$C(O)NH(CH_3)$, —$C(O)N(CH_3)_2$, (C1-C3) alkyl, (C1-C3) haloalkyl, (C3-C5) cycloalkyl, (C2-C3) alkynyl, or 5- to 6-membered heteroaryl, wherein the (C1-C3) alkyl, (C1-C3) haloalkyl, (C3-C5) cycloalkyl, (C2-C3) alkynyl, or 5- to 6-membered heteroaryl may be each independently and optionally substituted with 1, 2, 3, or 4 of the following groups: —H, —F, —CN, —$CH_3$, and —$OCH_3$.

3. The compound, or the isomer, the crystalline form, the pharmaceutically acceptable salt, the hydrate or the solvate thereof according to claim 2, wherein, in general formula (1), Y is —H, —F, —Cl, —Br, —I, —CN, —$S(O)_2CH_3$, —$P(O)(CH_3)_2$, —$C(O)NH_2$, —$C(O)NH(CH_3)$, —$C(O)N(CH_3)_2$, —$CH_3$, —$CF_3$,

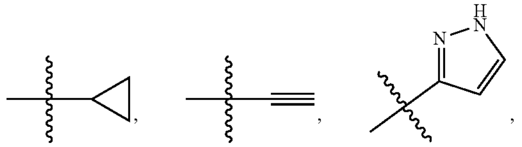

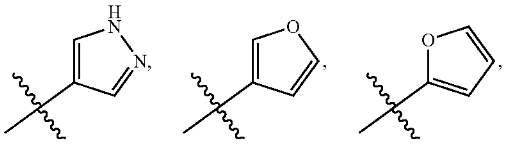

or

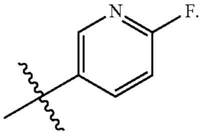

4. The compound, or the isomer, the crystalline form, the pharmaceutically acceptable salt, the hydrate or the solvate thereof according to claim 1, wherein, in general formula (1), ring A is 5- to 10-membered heteroaryl, or 5- to 10-membered heterocycloalkyl.

5. The compound, or the isomer, the crystalline form, the pharmaceutically acceptable salt, the hydrate or the solvate thereof according to claim 4, wherein, in general formula (1), ring A is:

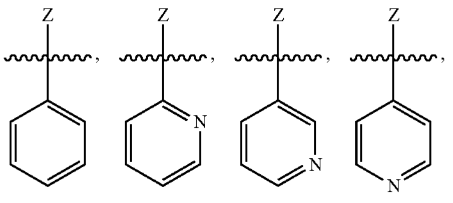

-continued

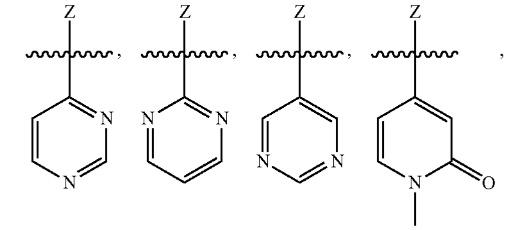

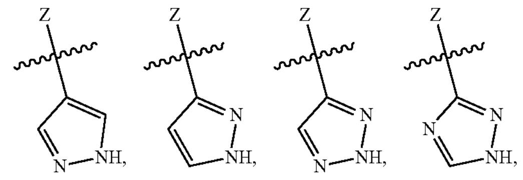

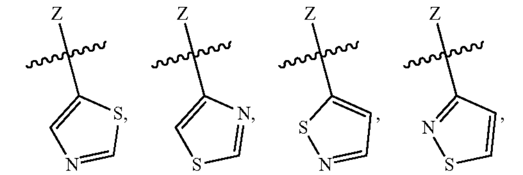

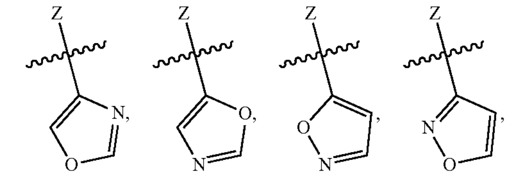

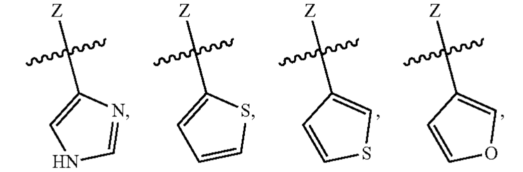

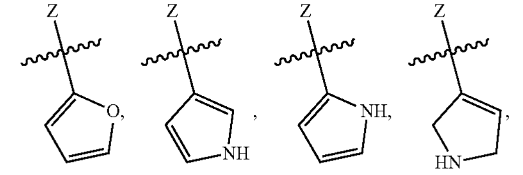

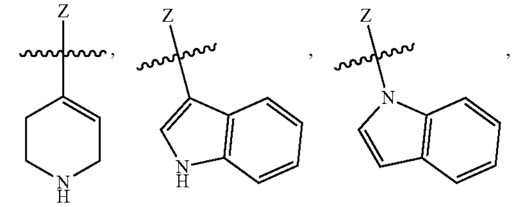

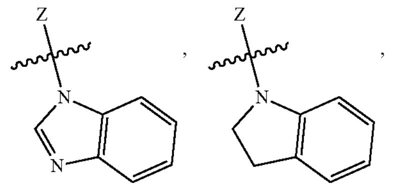

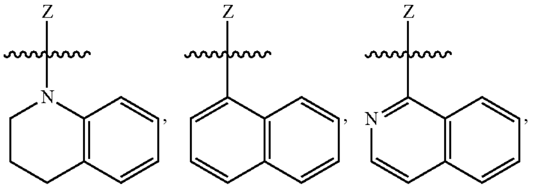

-continued

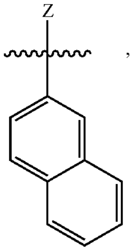, 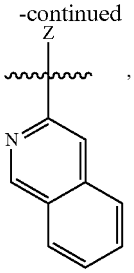, 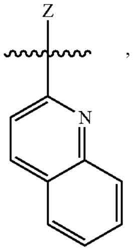, 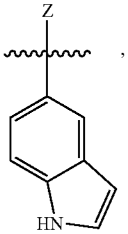, 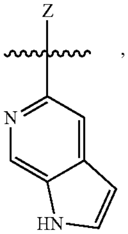, 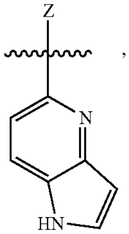, 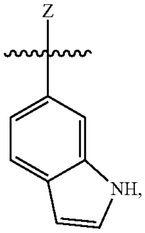 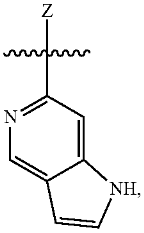 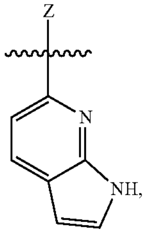 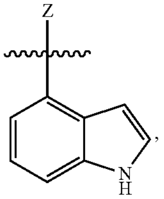, 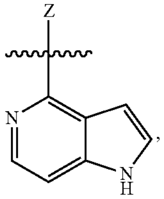, 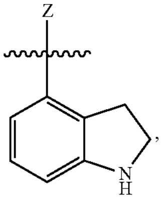, or 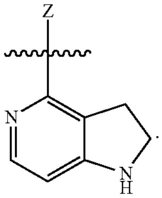.

6. The compound, or the isomer, the crystalline form, the pharmaceutically acceptable salt, the hydrate or the solvate thereof according to claim 4, wherein, in general formula (1), ring A is:

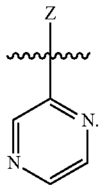

7. The compound, or the isomer, the crystalline form, the pharmaceutically acceptable salt, the hydrate or the solvate thereof according to claim 1, wherein, in general formula (1), $R^1$ and $R^2$ are each independently (C1-C3) alkyl, (C1-C3) haloalkyl, (C2-C4) alkenyl, or (C3-C5) cycloalkyl, wherein the (C1-C3) alkyl, (C1-C3) haloalkyl, (C2-C4) alkenyl, or (C3-C5) cycloalkyl may be each independently and optionally substituted with 1, 2, 3, or 4 of the following groups: —H, -D, —F, —Cl, —Br, —I, —$CH_3$, —OH, —$CH_2OCH_3$, —$CH_2N(CH_3)_2$, —$OCH_3$, —$N(CH_3)_2$, and —CN; or $R^1$ and $R^2$, along with the S atom connected thereto, are capable of forming 4- to 6-membered heterocycloalkyl, wherein the 4- to 6-membered heterocycloalkyl may be optionally substituted with 1, 2, 3, or 4 of the following groups: —H, —F, —Cl, —Br, —I, —$CH_3$, —OH, —$OCH_3$, —$N(CH_3)_2$, and —CN.

8. The compound, or the isomer, the crystalline form, the pharmaceutically acceptable salt, the hydrate or the solvate thereof according to claim 7, wherein, in general formula (1), structure unit

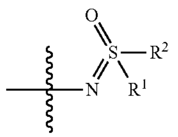

is:

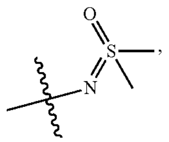, 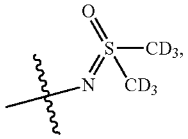, 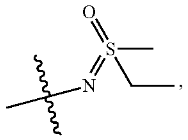, 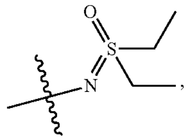, 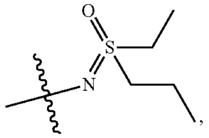, 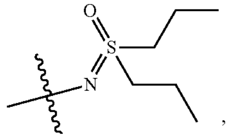, 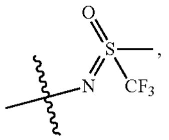, 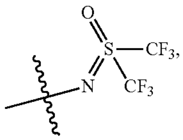, 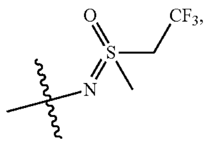, 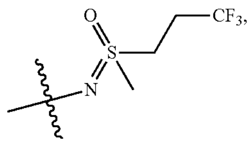, 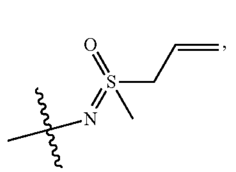, 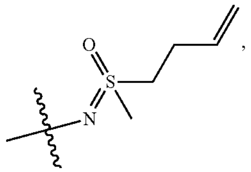, 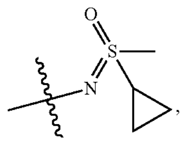, 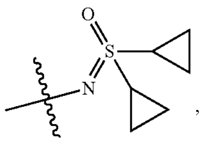, -continued

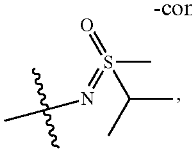, 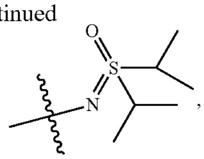,

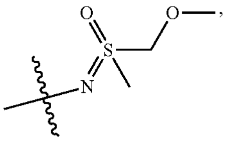, 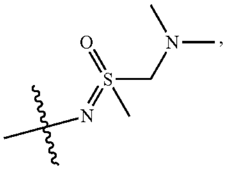,

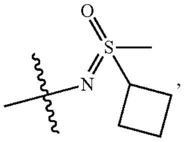, 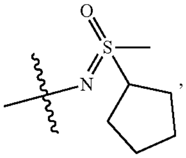,

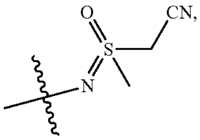, 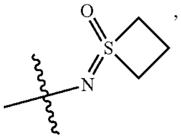,

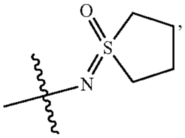, or 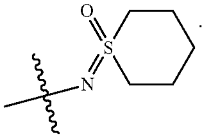.

9. The compound, or the isomer, the crystalline form, the pharmaceutically acceptable salt, the hydrate or the solvate thereof according to claim 1, wherein, in general formula (1), each $R^3$ is independently —H, -D, —F, —Cl, —Br, —I, —OH, $—CH_2OR^{11}$, $—CH_2NR^{11}R^{12}$, $—OR^{11}$, $—NR^{11}R^{12}$, —CN, $—C(O)NR^{11}R^{12}$, $—NR^{12}C(O)R^{11}$, $—NR^{12}S(O)_2R^{11}$, $—SR^{11}$, $—S(O)_2R^{11}$, $—S(O)_2NR^{11}R^{12}$, (C1-C3) alkyl, (C1-C3) haloalkyl, (C2-C4) alkenyl, (C2-C4) alkynyl, (C3-C6) cycloalkyl, phenyl, 4- to 8-membered heterocycloalkyl, or 5- to 6-membered heteroaryl, wherein the (C1-C3) alkyl, (C1-C3) haloalkyl, (C2-C4) alkenyl, (C2-C4) alkynyl, (C3-C6) cycloalkyl, phenyl, 4- to 8-membered heterocycloalkyl, or 5- to 6-membered heteroaryl may be each independently and optionally substituted with 1, 2, 3, or 4 of the following groups: —H, —F, —Cl, —Br, —I, —OH, $—OCH_3$, $—N(CH_3)_2$, and —CN; or two adjacent $R^3$, along with the atoms connected thereto, are capable of forming 5- to 7-membered heterocycloalkyl or (C5-C7) cycloalkyl, wherein the 5- to 7-membered heterocycloalkyl or (C5-C7) cycloalkyl may be independently and optionally substituted with 1, 2, 3, or 4 of the following groups: —H, —F, —Cl, —Br, —I, $—CH_3$, —OH, $—CH_2OCH_3$, $—CH_2N(CH_3)_2$, $—OCH_3$, $—N(CH_3)_2$, and —CN; and $R^{11}$ and $R^{12}$ are each independently —H, (C1-C3) alkyl or (C3-C6) cycloalkyl, or $R^{11}$ and $R^{12}$ on the same N atom, along with the N atom connected thereto, are capable of forming 4- to 6-membered heterocycloalkyl.

10. The compound, or the isomer, the crystalline form, the pharmaceutically acceptable salt, the hydrate or the solvate thereof according to claim 9, wherein, in general formula (1), each $R^3$ is independently: —H, -D, —F, —Cl, —Br, —I, —OH, $—CH_2OCH_3$, $—CH_2N(CH_3)_2$, $—OCH_3$, $—N(CH_3)_2$, —CN, $—C(O)NH_2$, $—C(O)NH(CH_3)$, $—C(O)N(CH_3)_2$, $—NHC(O)CH_3$, $—N(CH_3)—C(O)CH_3$, $—NHS(O)_2CH_3$, $—NCH_3S(O)_2CH_3$, $—SCH_3$, $—S(O)_2CH_3$, $—S(O)_2NH_2$, $—S(O)_2NH(CH_3)$, $—S(O)_2N(CH_3)_2$,

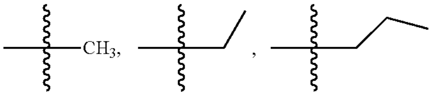,

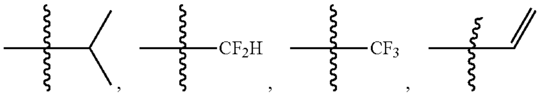,

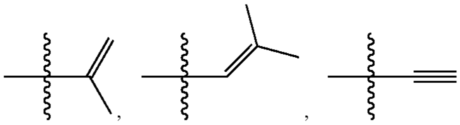,

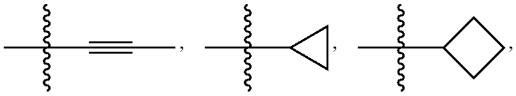,

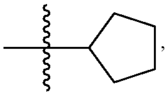, 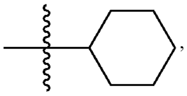, 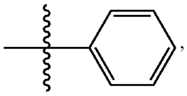,

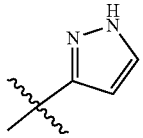, 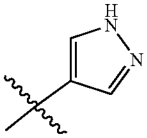, 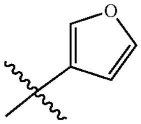,

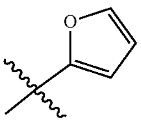, 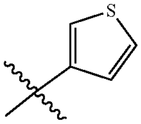, 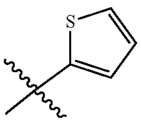,

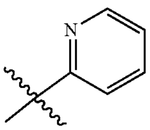, 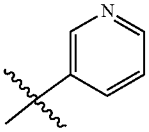, 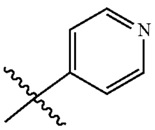,

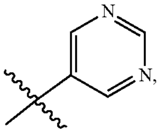, 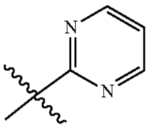, 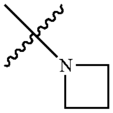,

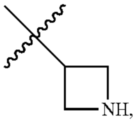, 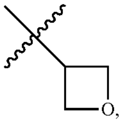, 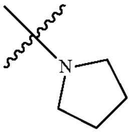,

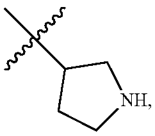, 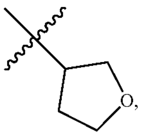, 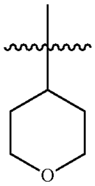, 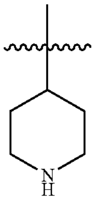,

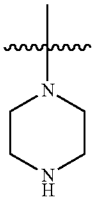, 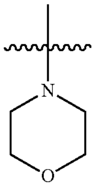, or 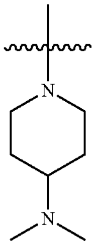.

11. The compound, or the isomer, the crystalline form, the pharmaceutically acceptable salt, the hydrate or the solvate thereof according to claim 1, wherein, in general formula (1), structural unit is
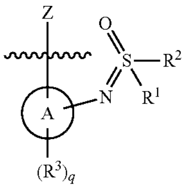
is
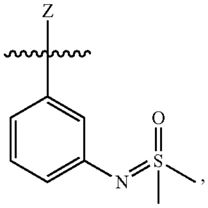
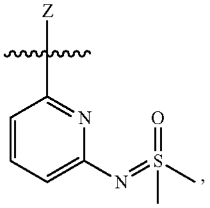
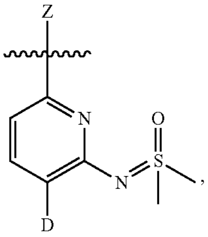
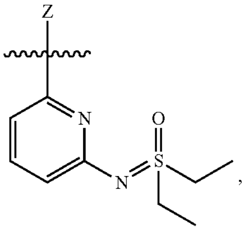
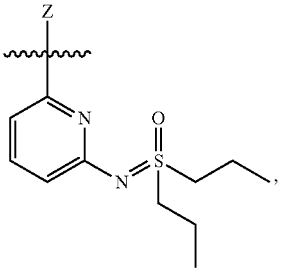
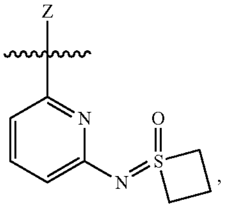
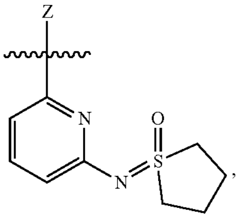
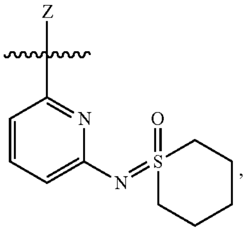
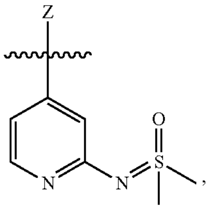
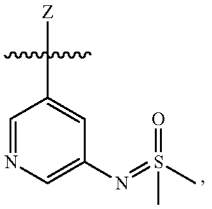
-continued
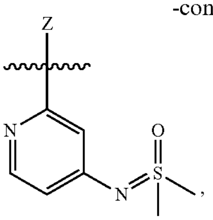
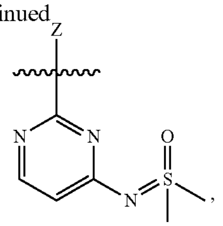
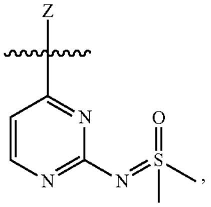
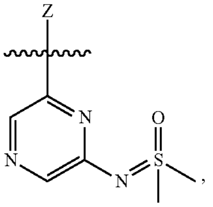
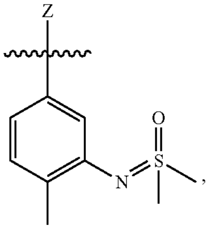
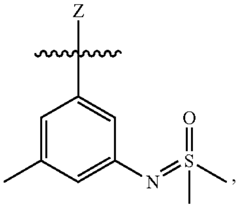
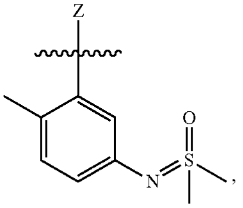
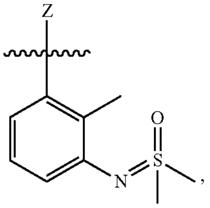
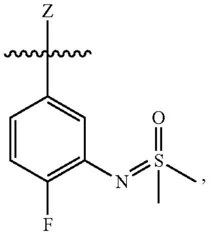
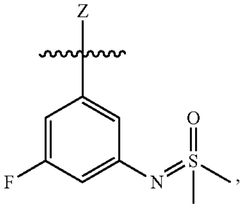
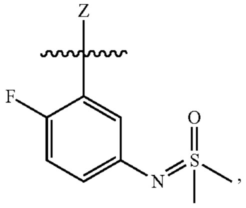
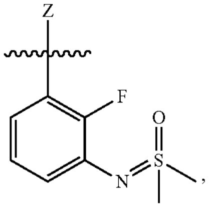
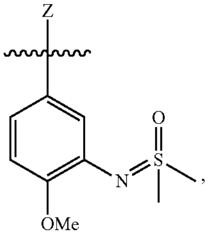
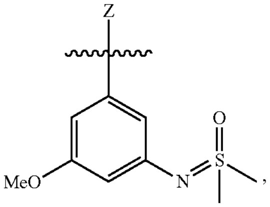
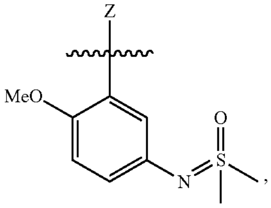
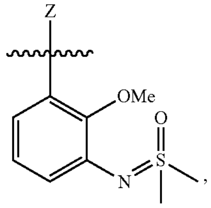

-continued
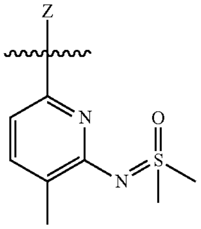
,
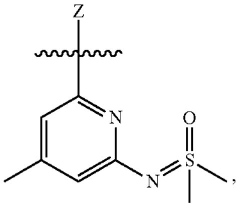
,
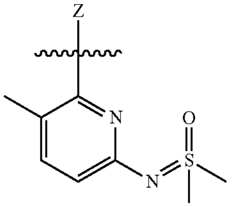
,
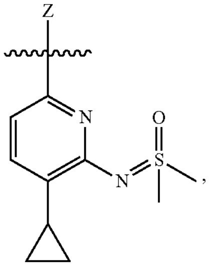
,
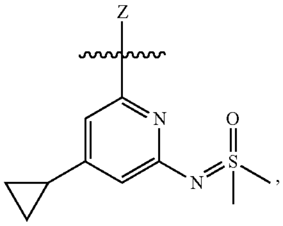
,
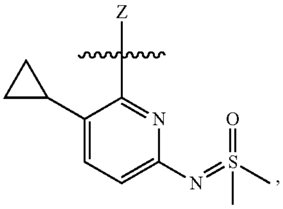
,
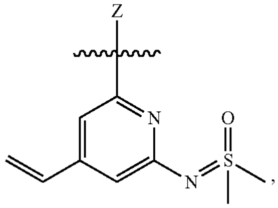
,
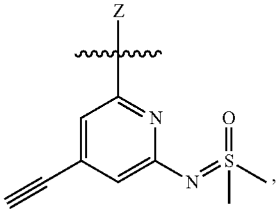
,
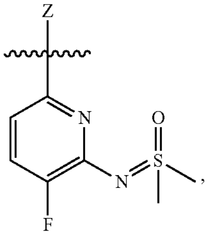
,
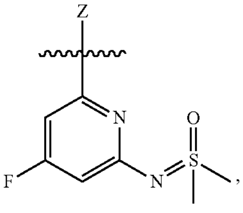
,
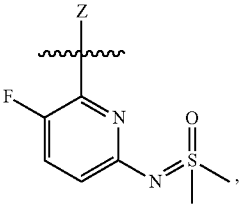
,
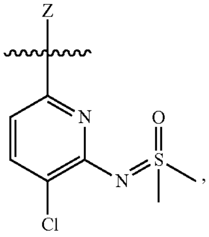
,
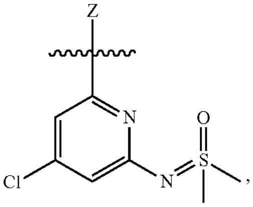
,
-continued
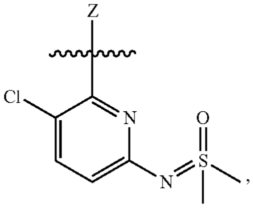
,
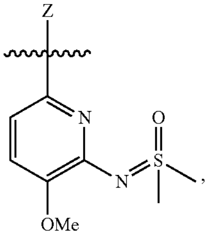
,
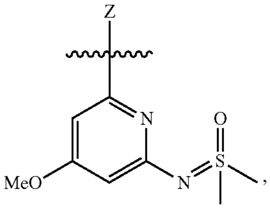
,
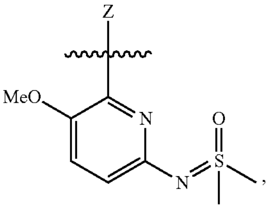
,
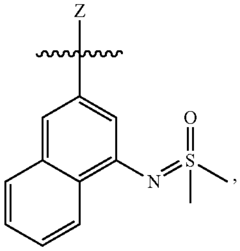
,
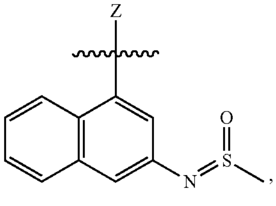
,
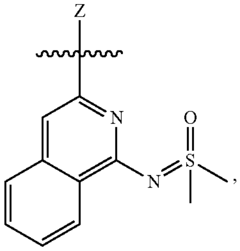
,
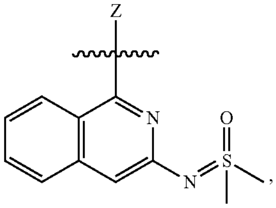
,
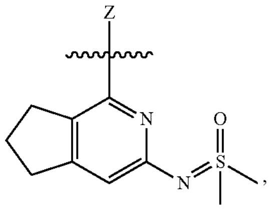
,
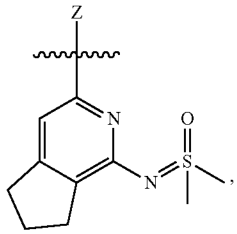
,
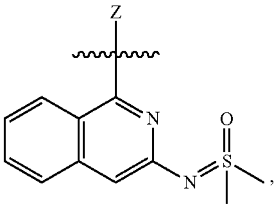
,
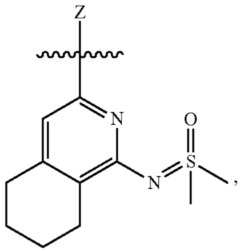
,
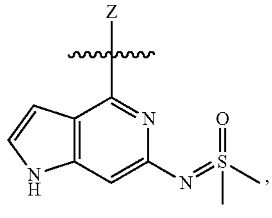
,
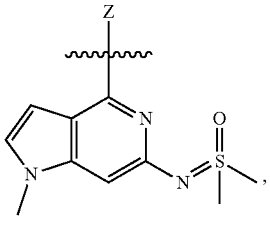
, -continued

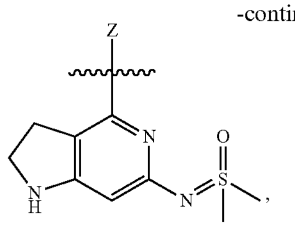

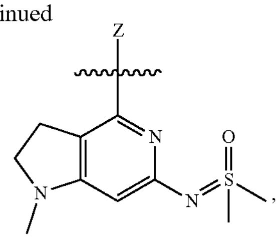

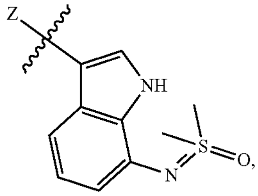

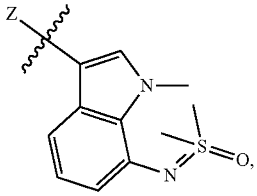

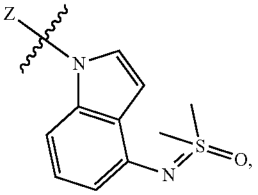

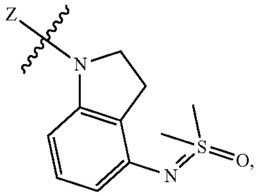

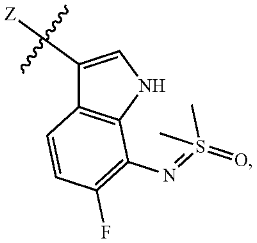

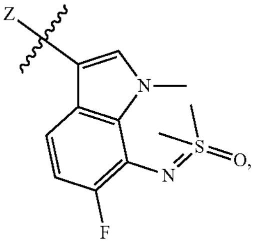

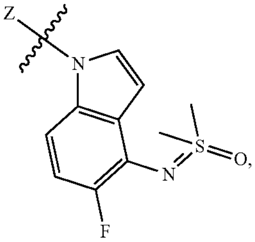

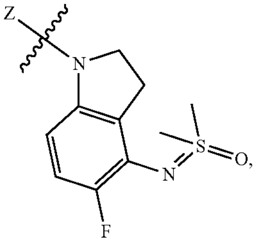

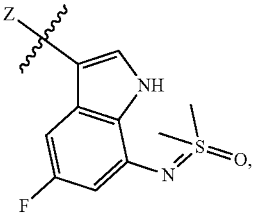

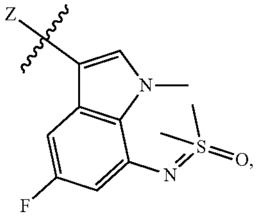

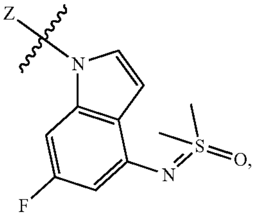

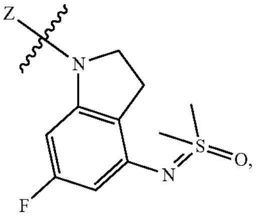

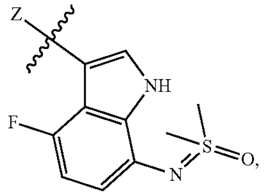

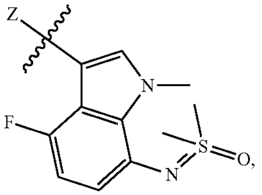

-continued

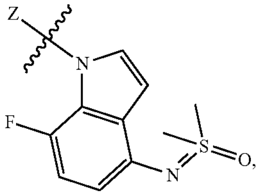

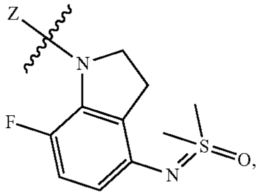

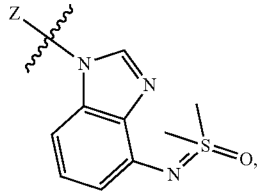

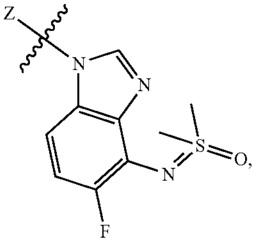

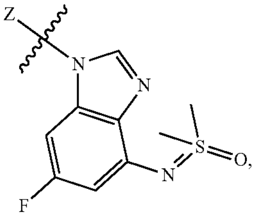

or

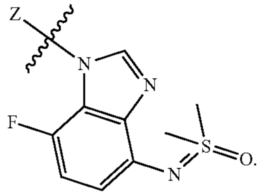

12. The compound, or the isomer, the crystalline form, the pharmaceutically acceptable salt, the hydrate or the solvate thereof according to claim 1, wherein, in general formula (1), ring B is (C6-C10) aryl or 5- to 10-membered heteroaryl.

13. The compound, or the isomer, the crystalline form, the pharmaceutically acceptable salt, the hydrate or the solvate thereof according to claim 12, wherein, in general formula (1), ring B is:

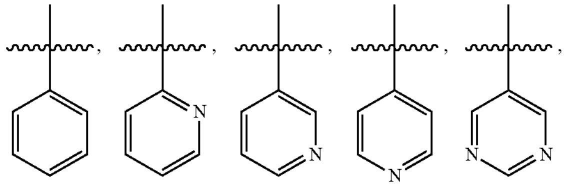

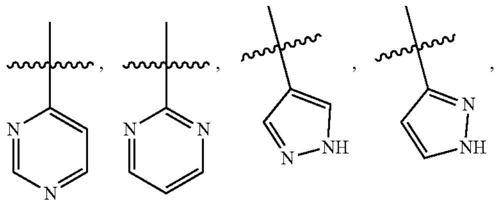

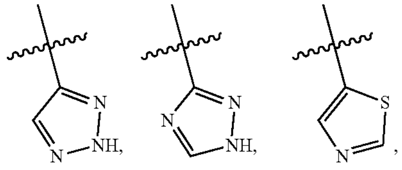

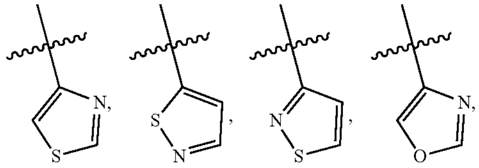

-continued

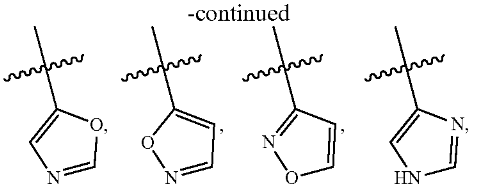

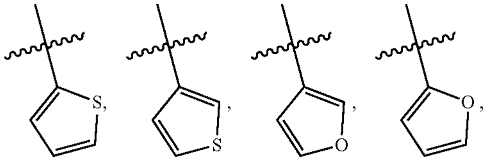

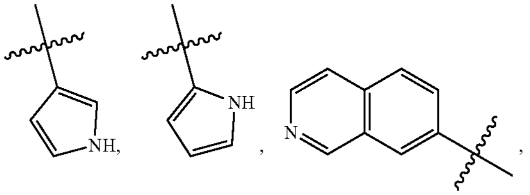

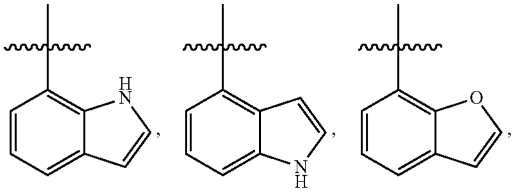

or

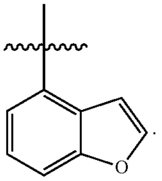

14. The compound, or the isomer, the crystalline form, the pharmaceutically acceptable salt, the hydrate or the solvate thereof according to claim 1, wherein, in general formula (1), each $R^4$ is independently —H, —F, —Cl, —Br, —I, —OH, $—CH_2OR^{11}$, $—(CH_2)_2OR^{11}$, $—(CH_2)_3OR^{11}$, $—OR^{11}$, $—CH_2NR^{11}R^{12}$, $—(CH_2)_2NR^{11}R^{12}$, $—(CH_2)_3NR^{11}R^{12}$, $—NR^{11}R^{12}$, —CN, $—O(CH_2)_2NR^{11}R^{12}$, $—N(R^{12})(CH_2)_2NR^{11}R^{12}$, $—C(O)NR^{11}R^{12}$, $—NR^{12}C(O)R^{11}$, $—NR^{12}S(O)_2R^{11}$, $—S(O)_2R^{11}$, $—SR^{11}$, $—S(O)_2NR^{11}R^{12}$, (C1-C4) alkyl, (C1-C4) haloalkyl, (C2-C4) alkenyl, (C2-C4) alkynyl, (C3-C6) cycloalkyl, (C1-C4) alkoxy, $—CH_2$-4- to 11-membered heterocycloalkyl, 4- to 11-membered heterocycloalkyl, 5- to 9-membered heteroaryl, or 5- to 9-membered aryl, wherein the (C1-C4) alkyl, (C1-C4) haloalkyl, (C2-C4) alkenyl, (C2-C4) alkynyl, (C3-C6) cycloalkyl, (C1-C4) alkoxy, $—CH_2$-4- to 11-membered heterocycloalkyl, 4- to 11-membered heterocycloalkyl, 5- to 9-membered heteroaryl, or 5- to 9-membered aryl may be independently and optionally substituted with 1, 2, 3, or 4 of the following groups: —H, —F, —Cl, —Br, —I, —OH, $—CH_2OCH_3$, $—(CH_2)_2OCH_3$, $—OCH_3$, $—OCH_2CH_3$, $—OCH(CH_3)_2$, $—CH_2N(CH_3)_2$, $—(CH_2)_2N(CH_3)_2$, $—N(CH_3)_2$, —CN, $—O(CH_2)_2N(CH_3)_2$, $—NH—(CH_2)_2N(CH_3)_2$, $—N(CH_3)—(CH_2)_2N(CH_3)_2$,

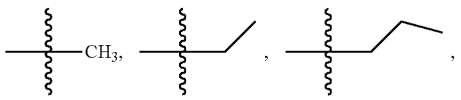

-continued

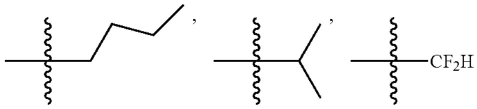

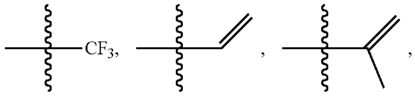

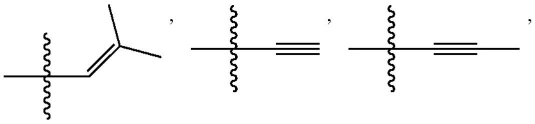

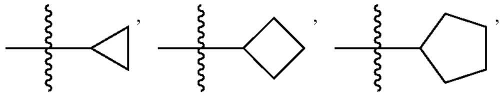

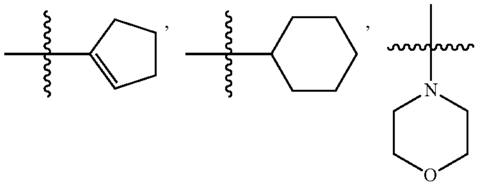

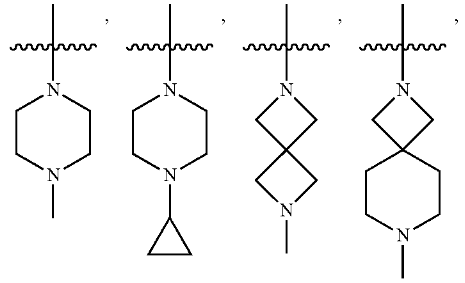

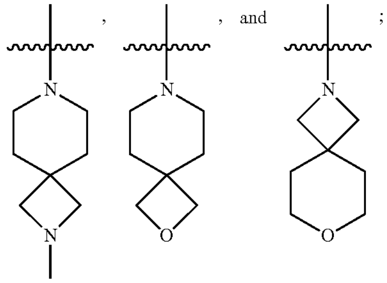

;

or two adjacent $R^4$ on ring B, along with the atoms connected thereto, are capable of forming 5- to 7-membered heterocycloalkyl or (C5-C7) cycloalkyl, wherein the 5- to 7-membered heterocycloalkyl or (C5-C7) cycloalkyl may be independently and optionally substituted with 1, 2, 3, or 4 of the following groups: —H, —F, —Cl, —Br, —I, —OH, $—CH_2OCH_3$, $—(CH_2)_2OCH_3$, $—(CH_2)_2OH$, $—OCH_3$, $—OCH_2CH_3$, $—OCH(CH_3)_2$, $—CH_2N(CH_3)_2$, $—(CH_2)_2N(CH_3)_2$, $—N(CH_3)_2$, —CN, $—O(CH_2)_2N(CH_3)_2$, $—NH—(CH_2)_2N(CH_3)_2$, $—N(CH_3)—(CH_2)_2N(CH_3)_2$, $—C(O)CH_3$, $—C(O)NH_2$, $—C(O)N(CH_3)_2$, $—S(O)_2CH_3$, $—SCH_3$, $—S(O)_2NH_2$, $—S(O)_2N(CH_3)_2$,

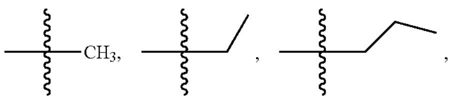

-continued

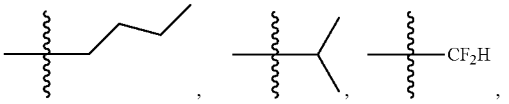,

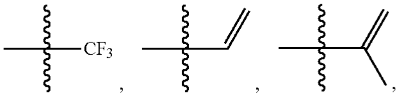,

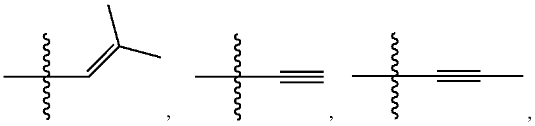,

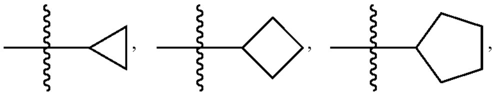,

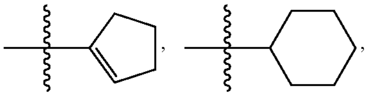,

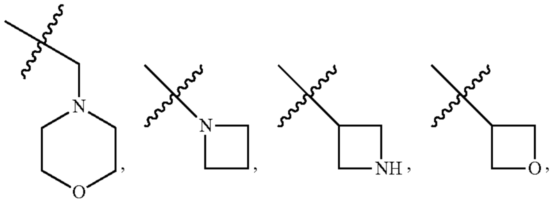,

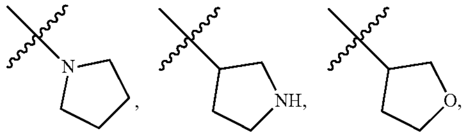,

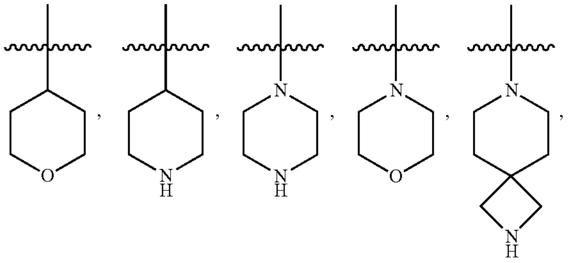,

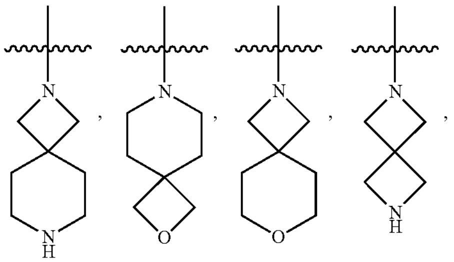,

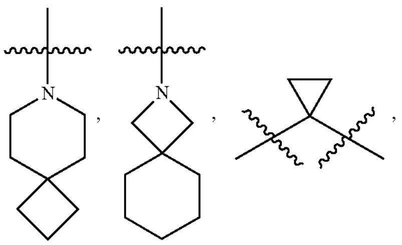,

-continued

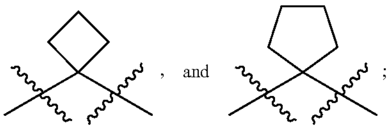;

and $R^{11}$ and $R^{12}$ are each independently —H, (C1-C3) alkyl or (C3-C6) cycloalkyl, or $R^{11}$ and $R^{12}$ on the same N atom, along with the N atom connected thereto, are capable of forming 4- to 6-membered heterocycloalkyl.

15. The compound, or the isomer, the crystalline form, the pharmaceutically acceptable salt, the hydrate or the solvate thereof according to claim 14, wherein, in general formula (1), each $R^4$ is independently —H, —F, —Cl, —Br, —I, —OH, $—CH_2OCH_3$, $—(CH_2)_2OCH_3$, $—(CH_2)_3OCH_3$, $—CH_2OH$, $—(CH_2)_2OH$, $—(CH_2)_3OH$, $—CH_2NH_2$, $—(CH_2)_2NH_2$, $—(CH_2)_3NH_2$, $—OCH_3$, $—OCH_2CH_3$, $—OCH(CH_3)_2$, $—OCF_3$, $—OCF_2H$, $—CH_2N(CH_3)_2$, $—(CH_2)_2N(CH_3)_2$, $—N(CH_3)_2$, —CN, $—O(CH_2)_2N(CH_3)_2$, $—NH—(CH_2)_2N(CH_3)_2$, $—N(CH_3)—(CH_2)_2N(CH_3)_2$, $—C(O)NH_2$, $—C(O)N(CH_3)_2$, $—S(O)_2CH_3$, $—SCH_3$, $—S(O)_2NH_2$, $—S(O)_2N(CH_3)_2$,

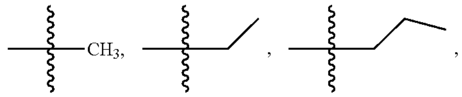,

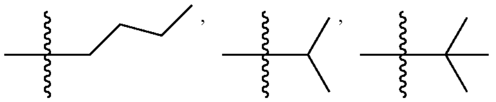,

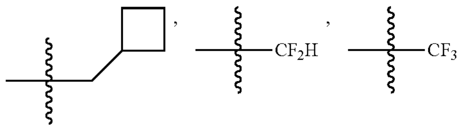,

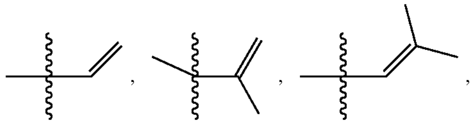,

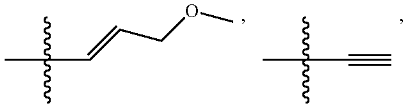,

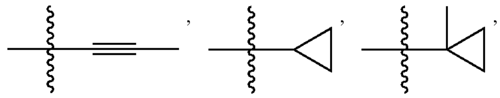,

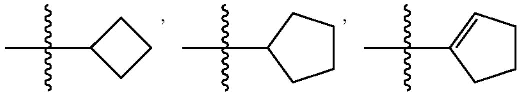,

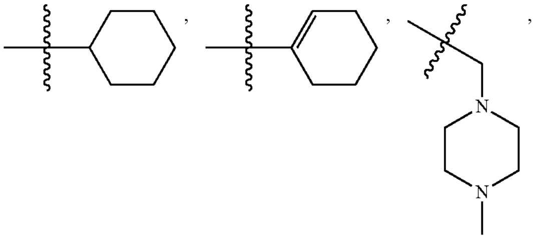

-continued
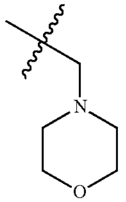, 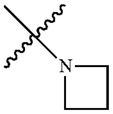, 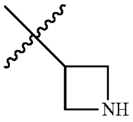,
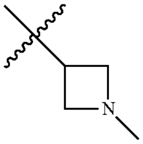, 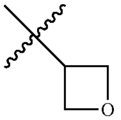, 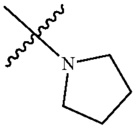,
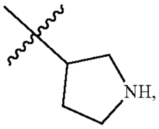, 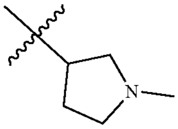, 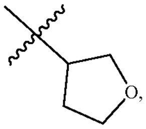,
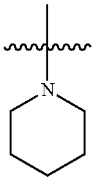, 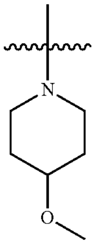, 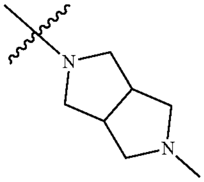,
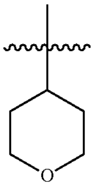, 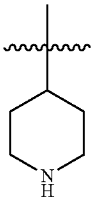, 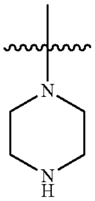, 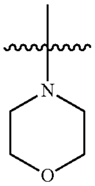,
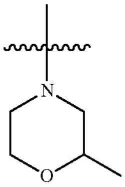, 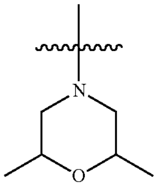, 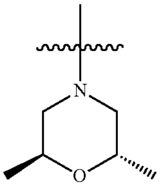,
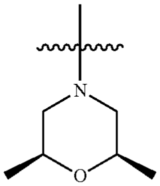, 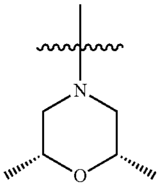, 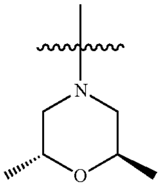,
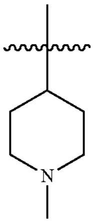, 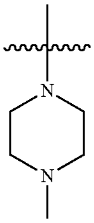, 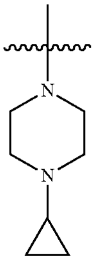, 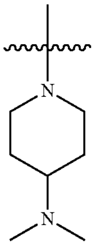,
-continued
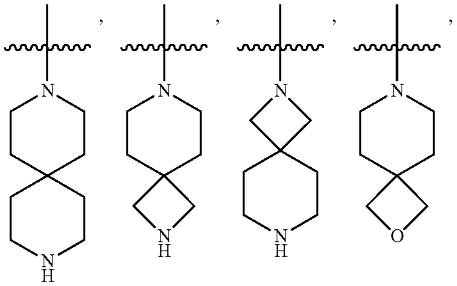
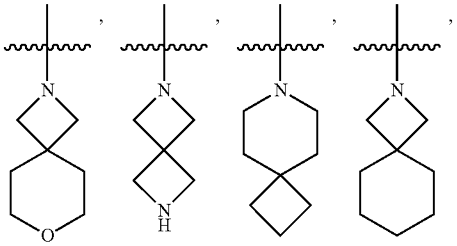
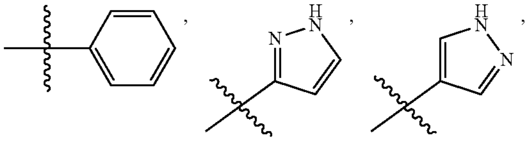
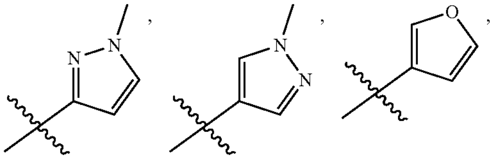
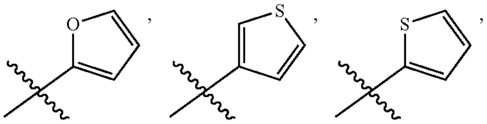
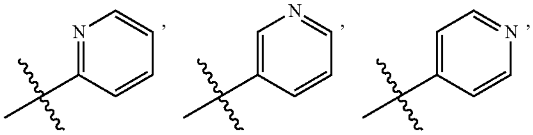
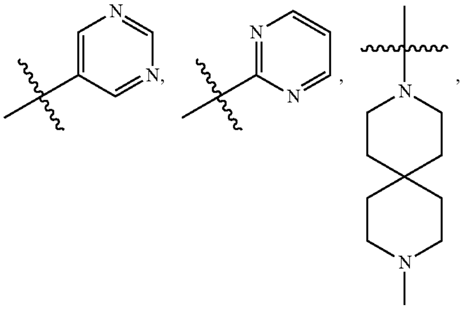

-continued

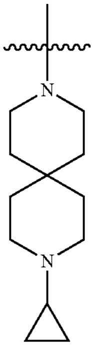, 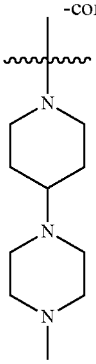, 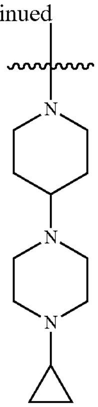, 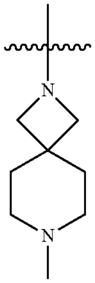,

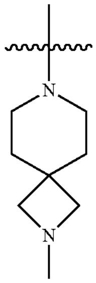, 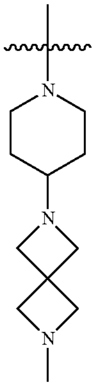, 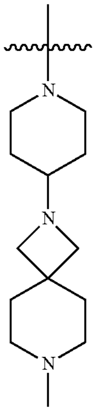, or 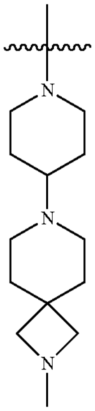.

16. The compound, or the isomer, the crystalline form, the pharmaceutically acceptable salt, the hydrate or the solvate thereof according to claim 14, wherein, in general formula (1), each $R^4$ is independently

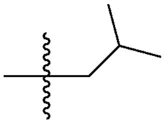 or 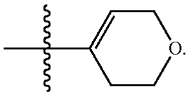

17. The compound, or the isomer, the crystalline form, the pharmaceutically acceptable salt, the hydrate or the solvate thereof according to claim 14, wherein, in general formula (1), two adjacent $R^4$ on ring B, along with the atoms connected thereto, are capable of forming 5- to 7-membered heterocycloalkyl, wherein the 5- to 7-membered heterocycloalkyl is:

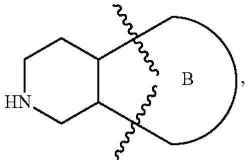, 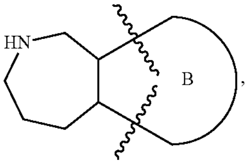,

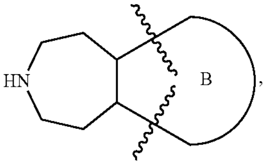, 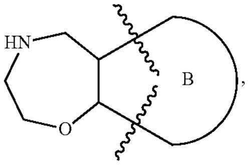,

-continued

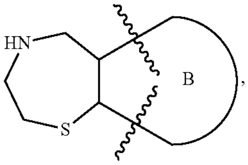, 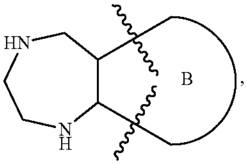, or

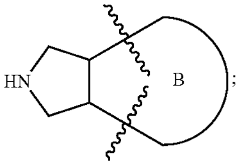;

or two adjacent $R^4$ on ring B, along with the atoms connected thereto, are capable of forming C5-7 cycloalkyl, wherein the 5- to 7-membered cycloalkyl is:

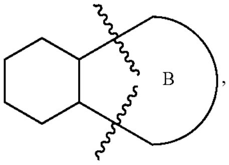, 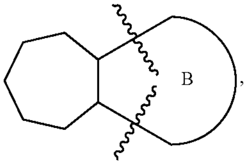, or

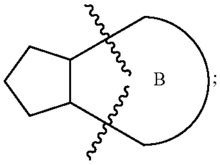;

wherein the heterocycloalkyl and the cycloalkyl may be optionally substituted with 1, 2, 3, or 4 of the following groups: —H, —F, —Cl, —Br, —I, —OH, $—CH_2OCH_3$, $—(CH_2)_2OCH_3$, $—(CH_2)_2OH$, $—OCH_3$, $—OCH_2CH_3$, $—OCH(CH_3)_2$, $—CH_2N(CH_3)_2$, $—(CH_2)_2N(CH_3)_2$, $—N(CH_3)_2$, —CN, $—O(CH_2)_2N(CH_3)_2$, $—NH—(CH_2)_2N(CH_3)_2$, $—N(CH_3)—(CH_2)_2N(CH_3)_2$, $—C(O)CH_3$, $—C(O)NH_2$, $—C(O)N(CH_3)_2$, $—S(O)_2CH_3$, $—SCH_3$, $—S(O)_2NH_2$, $—S(O)_2N(CH_3)_2$,

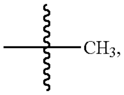, 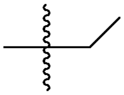, 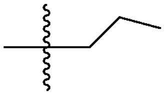,

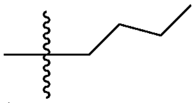, 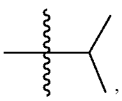,

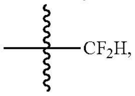, 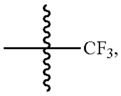, 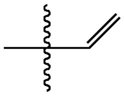,

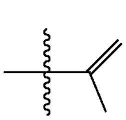, 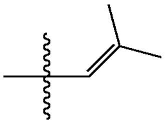, 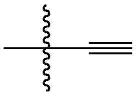,

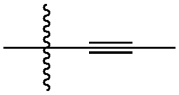, 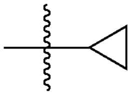, 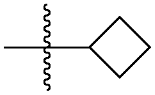,

-continued
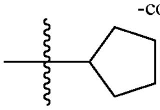, 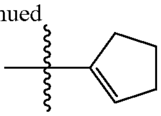,
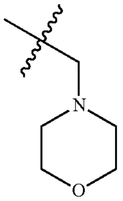
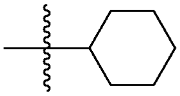, 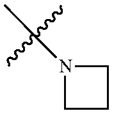,
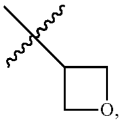
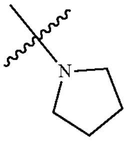, 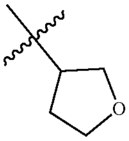,
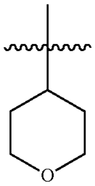, 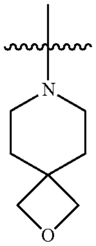, 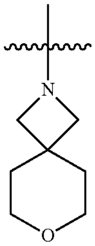,
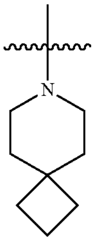, 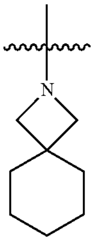, 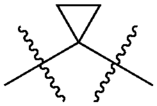,
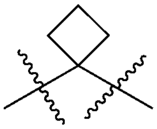, and 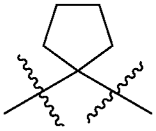.
18. The compound, or the isomer, the crystalline form, the pharmaceutically acceptable salt, the hydrate or the solvate thereof according to claim 1, wherein, in general formula (1), structural unit
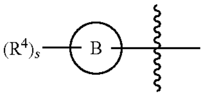
is:
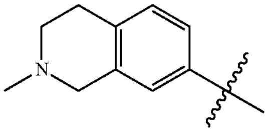,
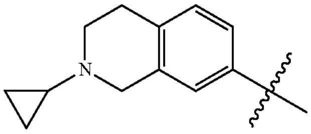,
-continued
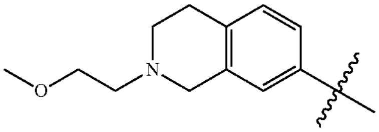,
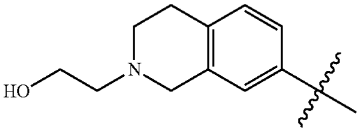,
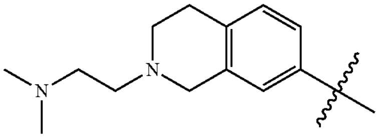,
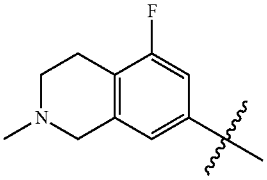, 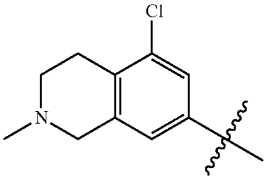,
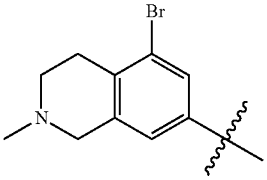, 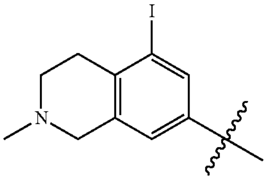,
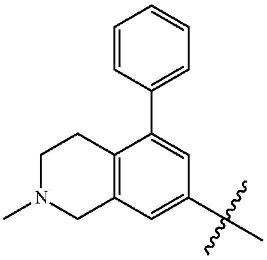, 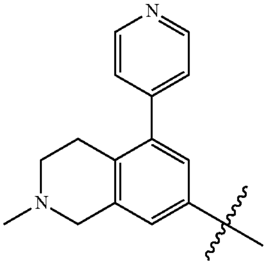,
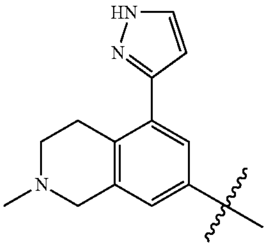, 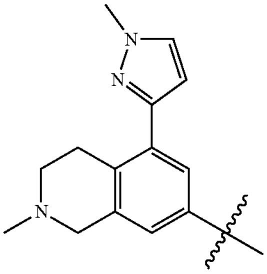,
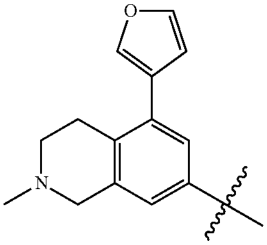, 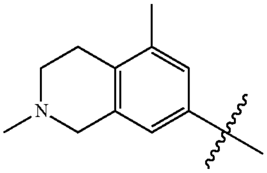, -continued
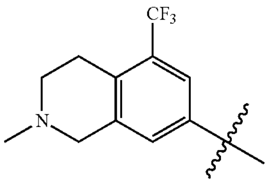
,
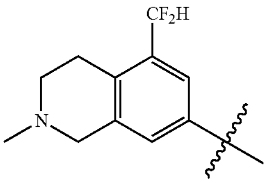
,
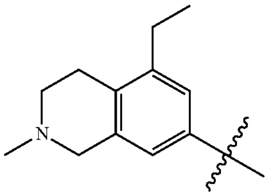
,
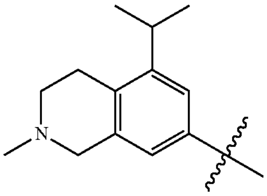
,
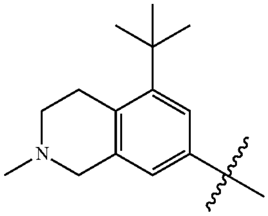
,
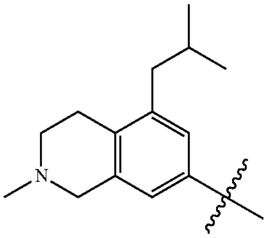
,
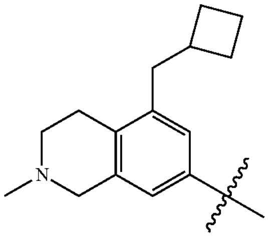
,
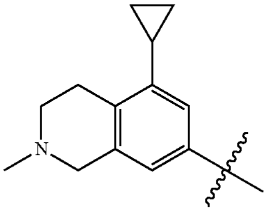
,
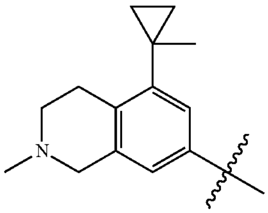
,
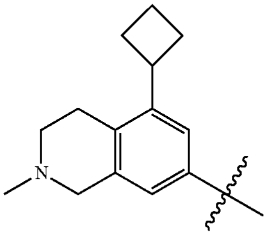
,
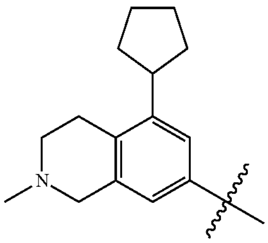
,
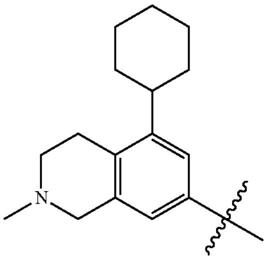
,
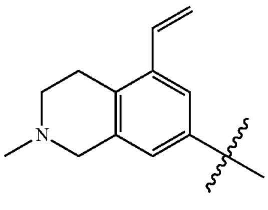
,
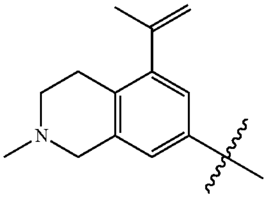
,
-continued
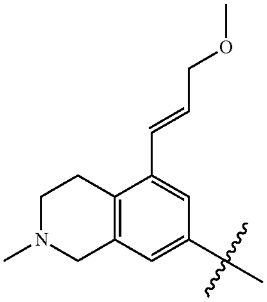
,
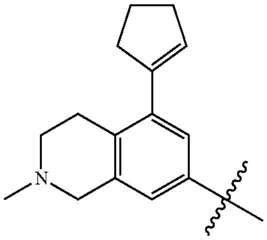
,
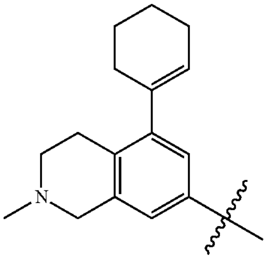
,
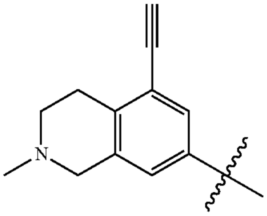
,
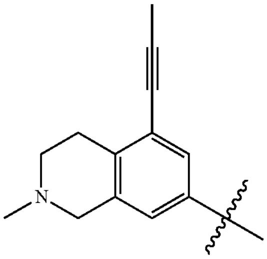
,
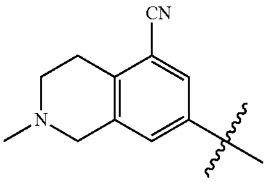
,
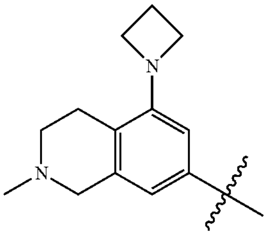
,
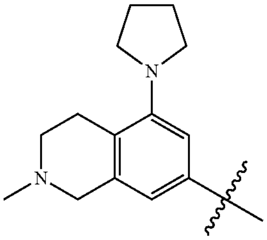
,
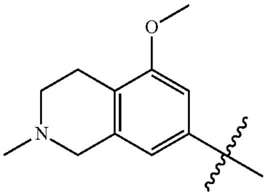
,
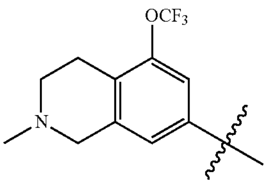
,
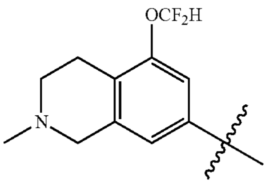
,
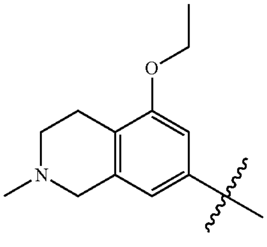
, -continued
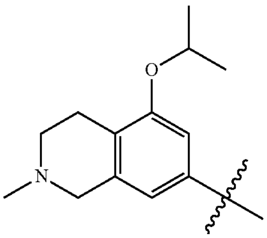,
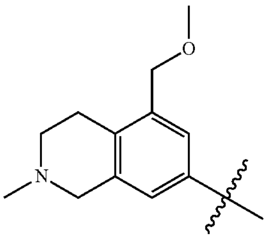,
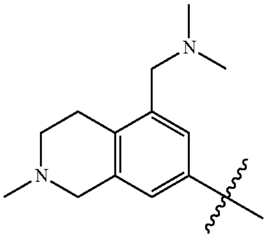,
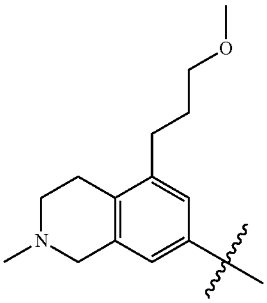,
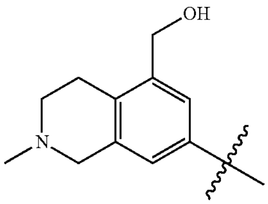,
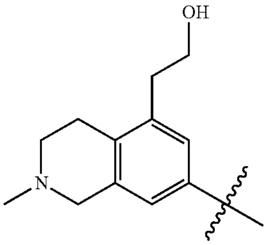,
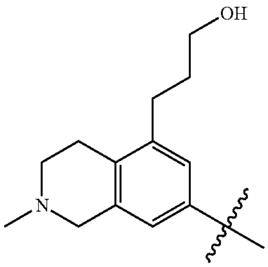,
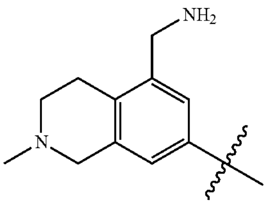,
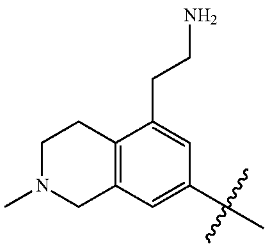,
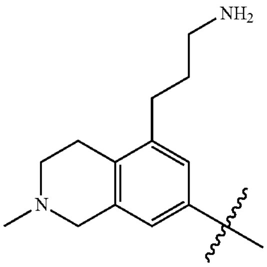,
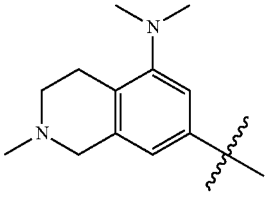,
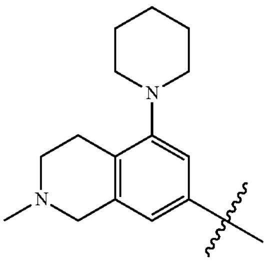,
-continued
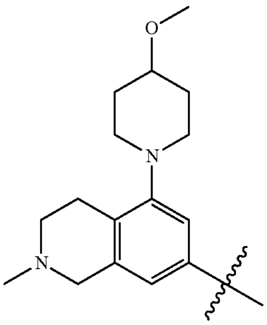,
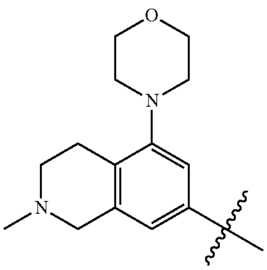,
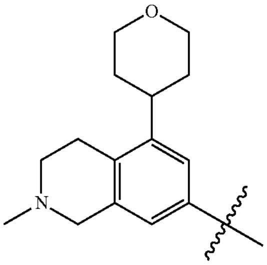,
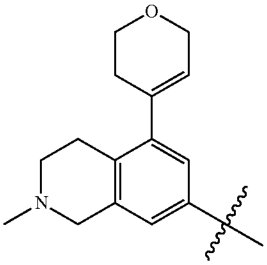,
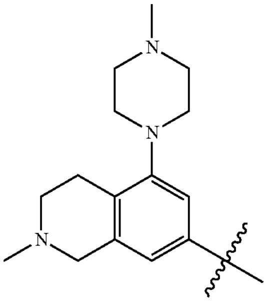,
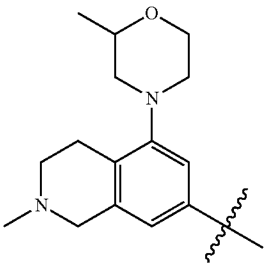,
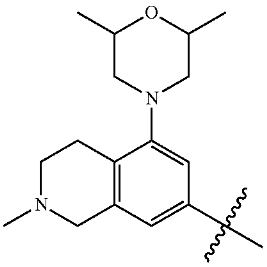,
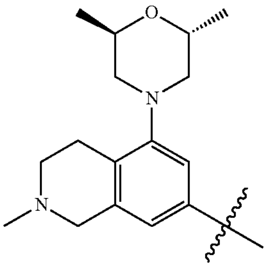,
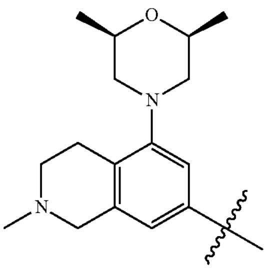,
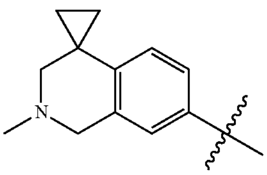,
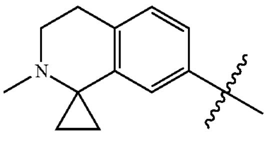,
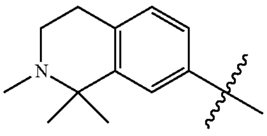, -continued
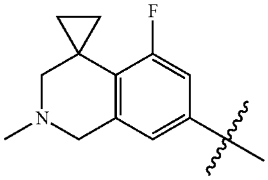,
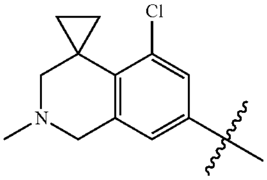,
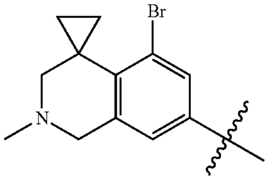,
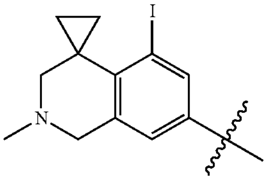,
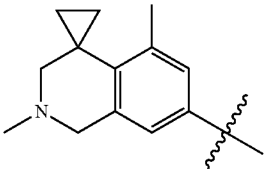,
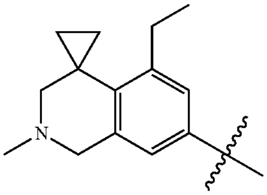,
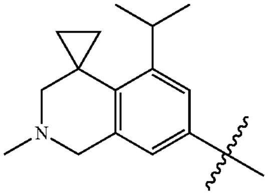,
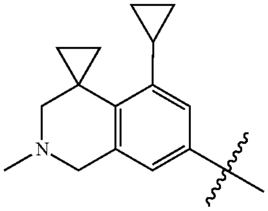,
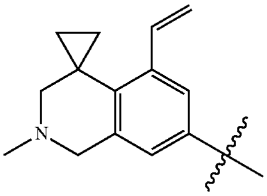,
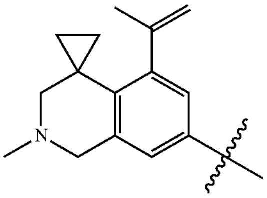,
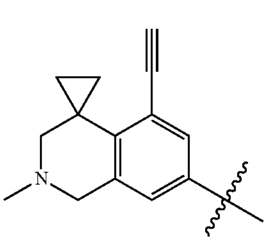,
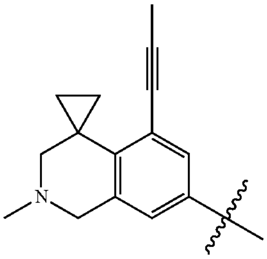,
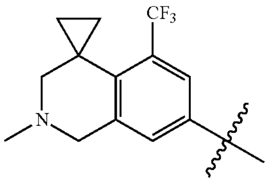,
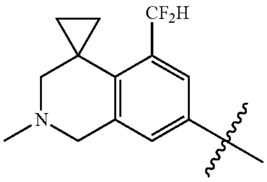,
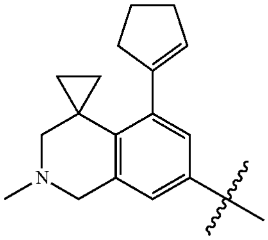,
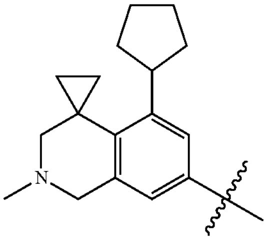,
-continued
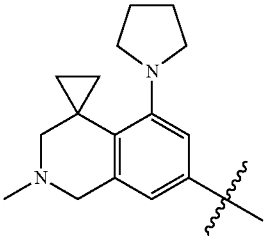,
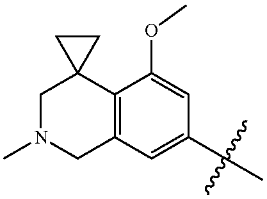,
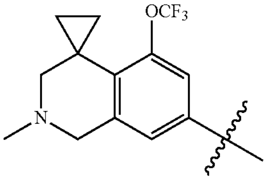,
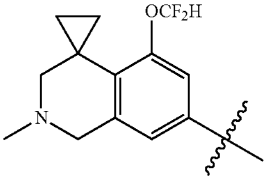,
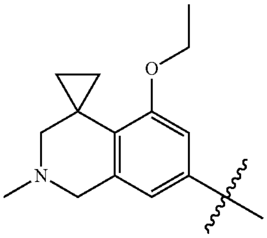,
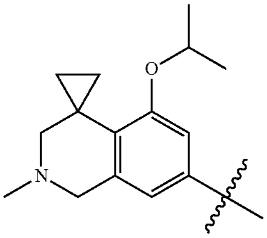,
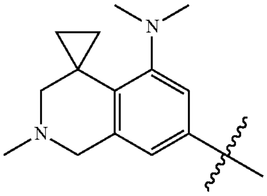,
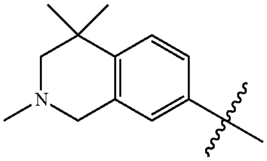,
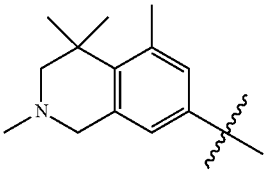,
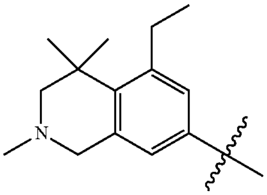,
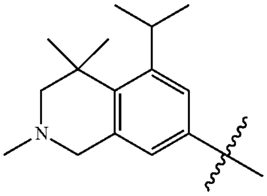,
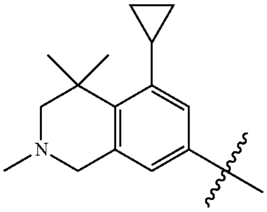,
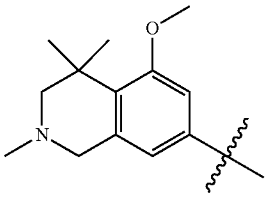,
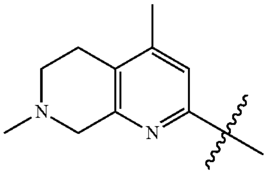,
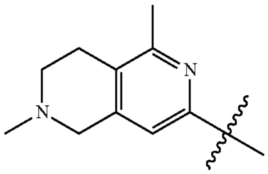,
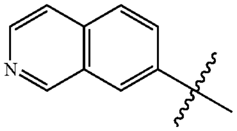, -continued
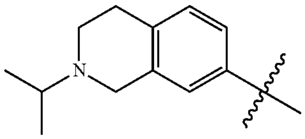
,
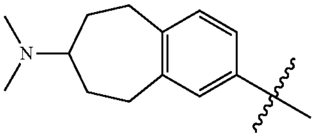
,
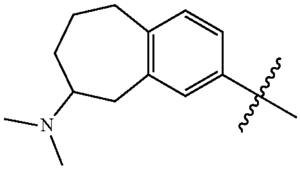
,
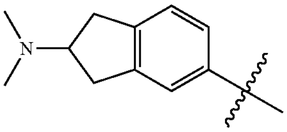
,
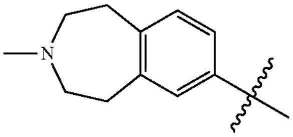
,
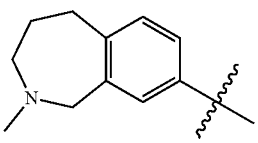
,
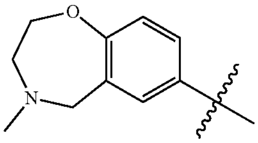
,
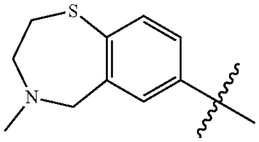
,
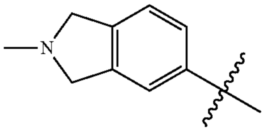
,
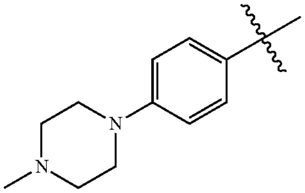
,
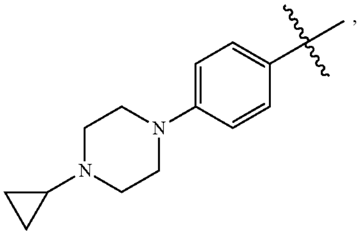
,
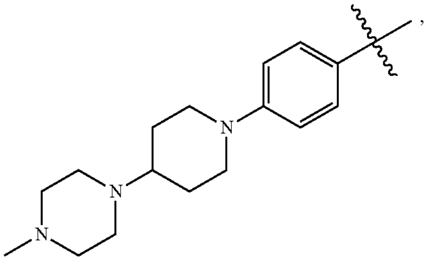
,
-continued
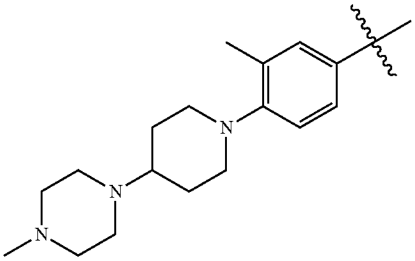
,
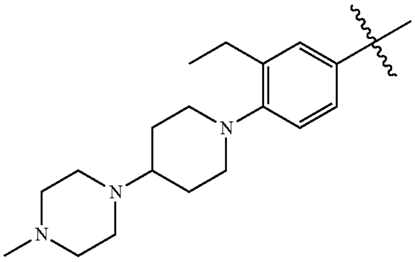
,
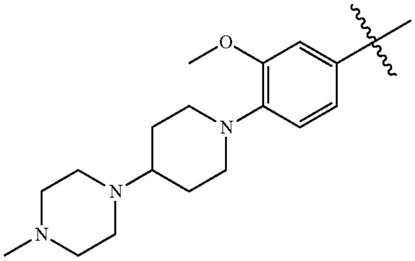
,
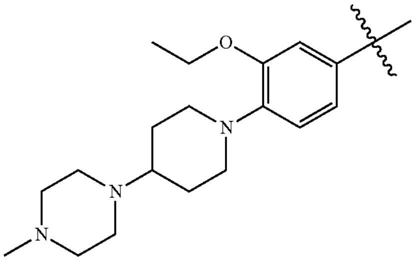
,
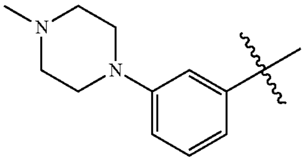
,
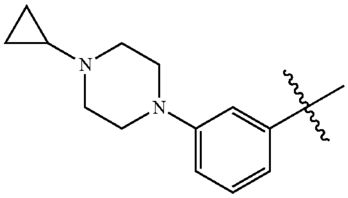
,
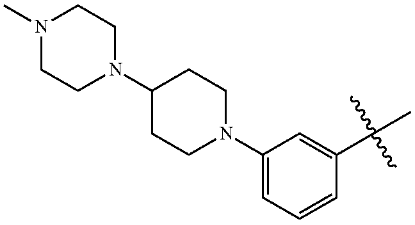
, -continued

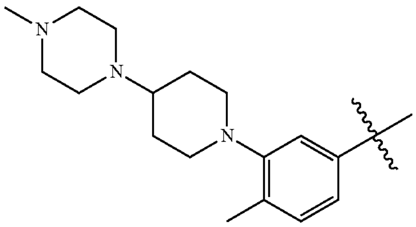

,

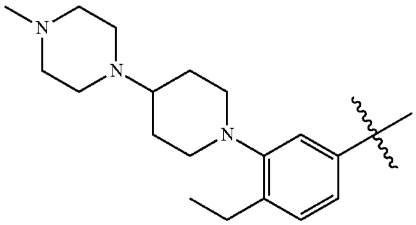

,

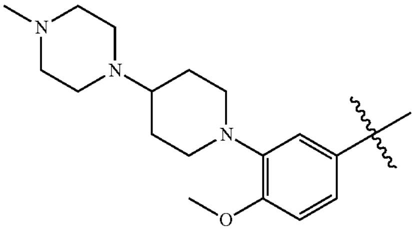

, or

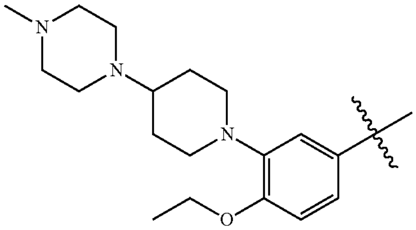

.

19. The compound, or the isomer, the crystalline form, the pharmaceutically acceptable salt, the hydrate or the solvate thereof according to claim 1, wherein, in general formula (1), structural unit

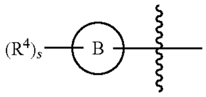

is:

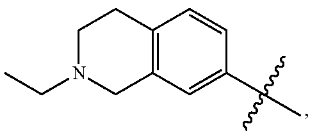

,

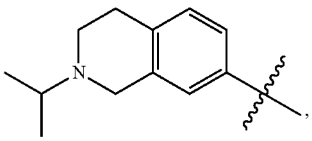

,

-continued

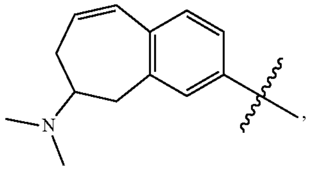

, or

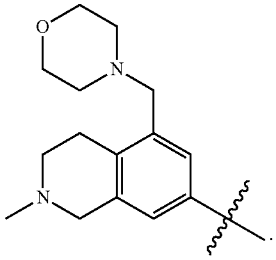

.

20. The compound, or the isomer, the crystalline form, the pharmaceutically acceptable salt, the hydrate or the solvate thereof according to claim 1, wherein, in general formula (1), structural unit

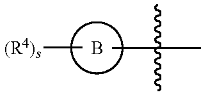

is:

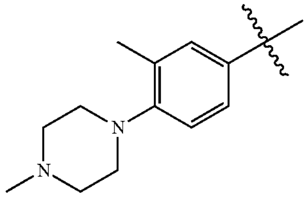

,

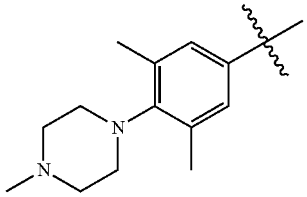

,

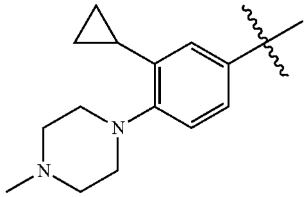

,

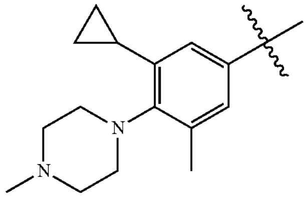

,

-continued
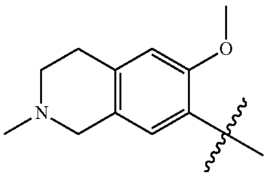
,
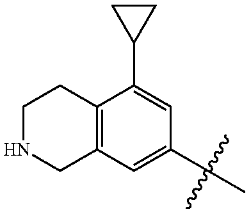
,
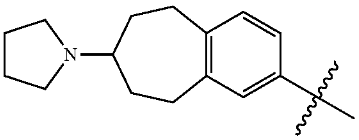
,
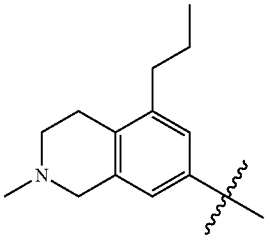
, or
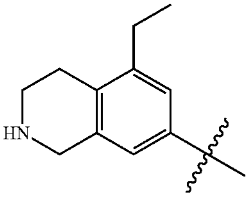
.
21. The compound, or the isomer, the crystalline form, the pharmaceutically acceptable salt, the hydrate or the solvate thereof according to claim 1, wherein the compound has one of the following structures:
1
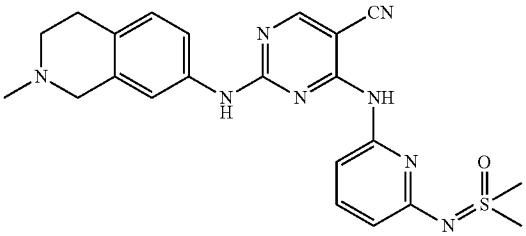
2
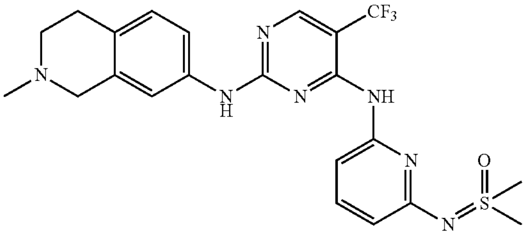
-continued
3
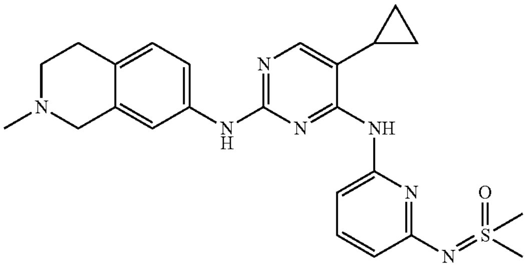
4
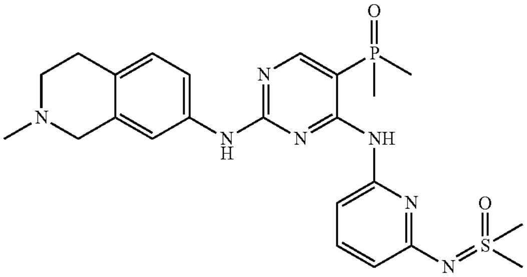
5
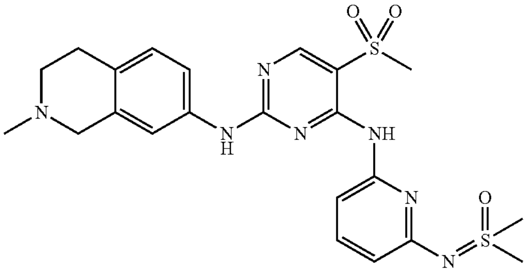
6
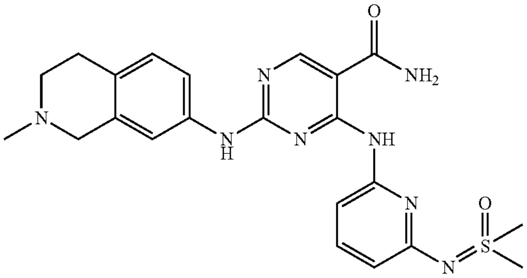
7
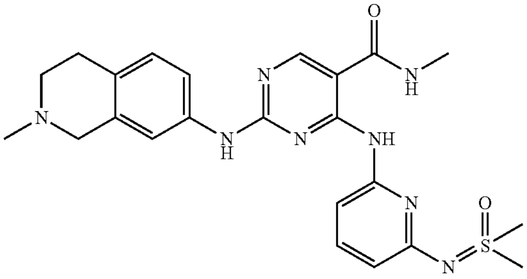

-continued
8
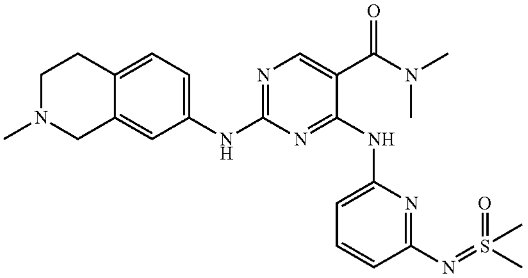
9
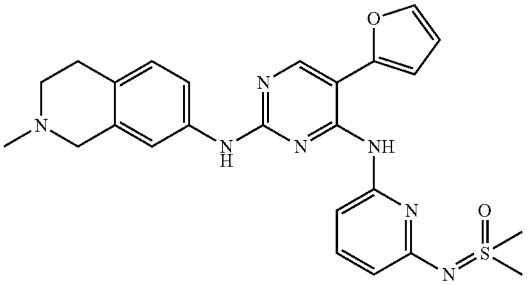
10
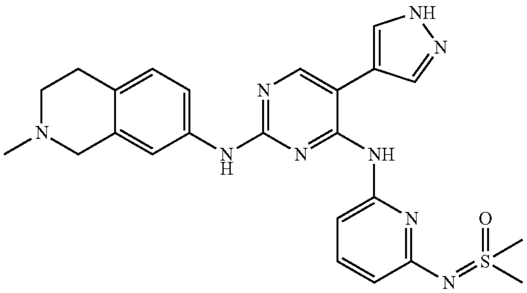
11
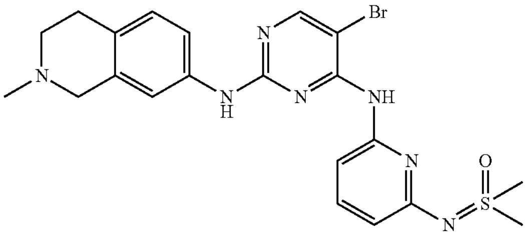
12
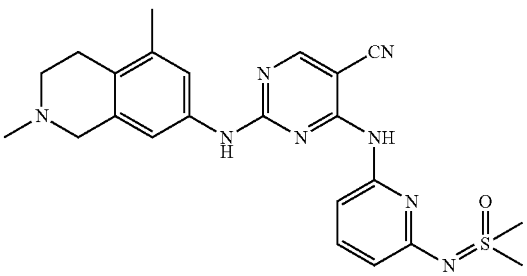
-continued
13
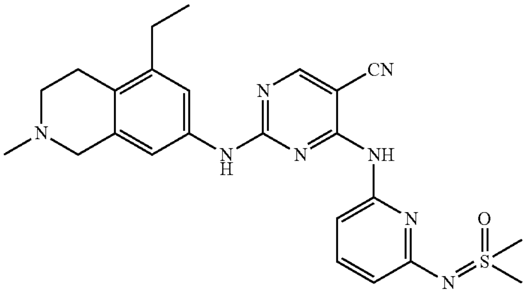
14
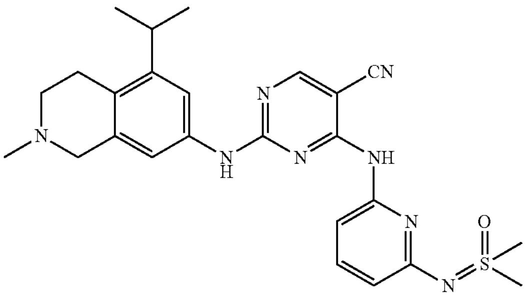
15
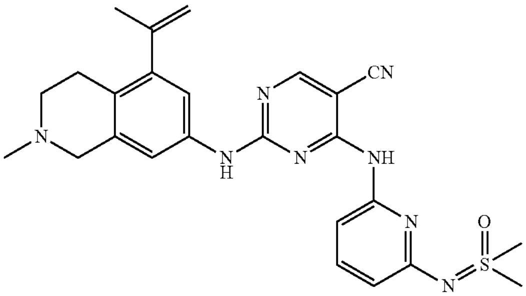
16
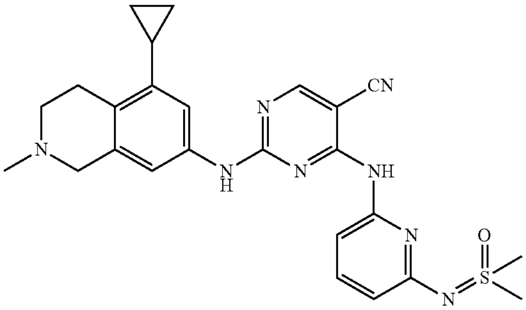

-continued
17
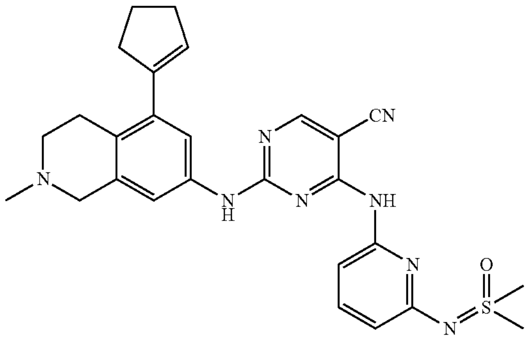
18
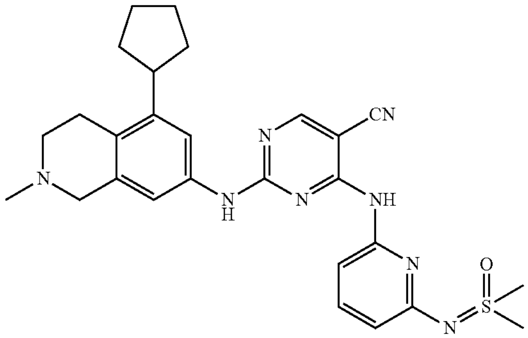
19
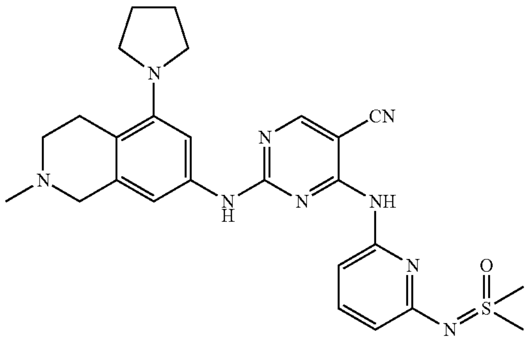
20
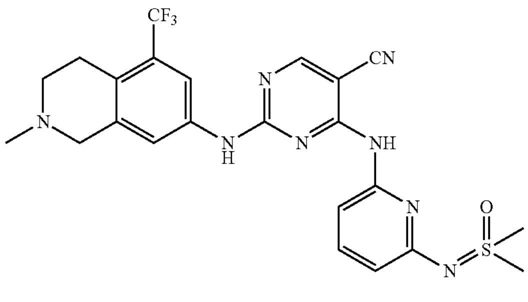
-continued
21
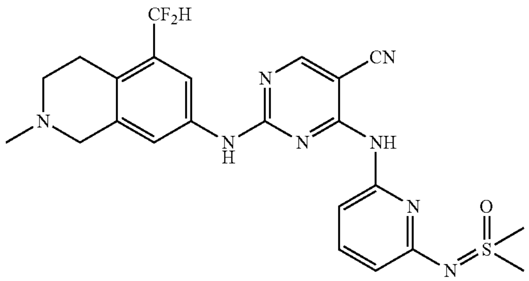
22
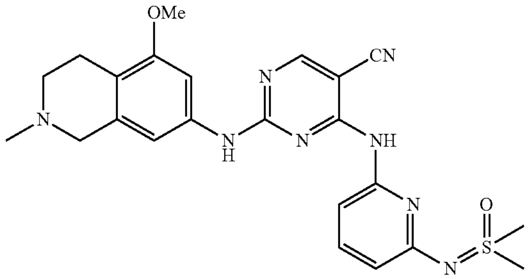
23
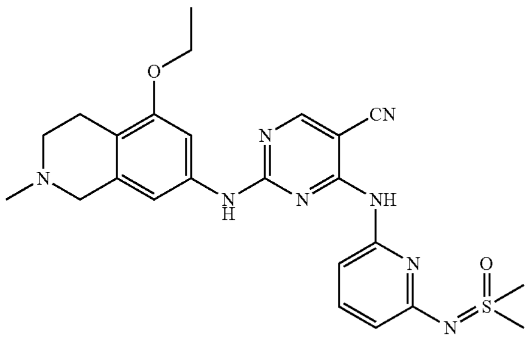
24
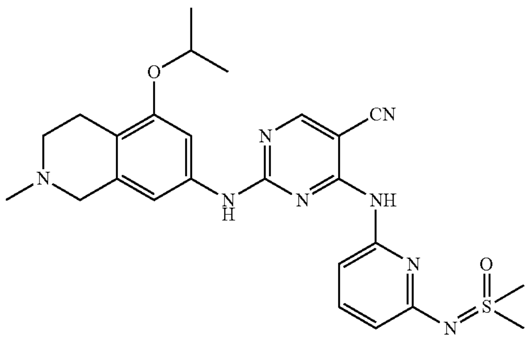
25
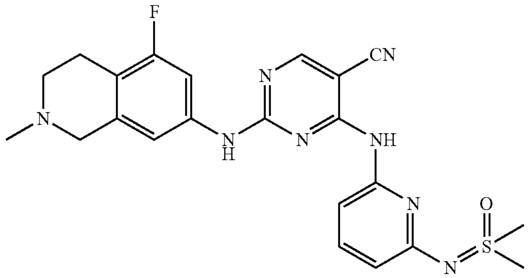

-continued
26
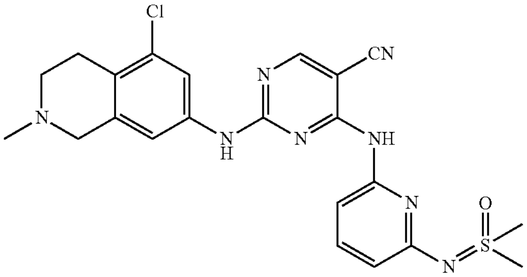
27
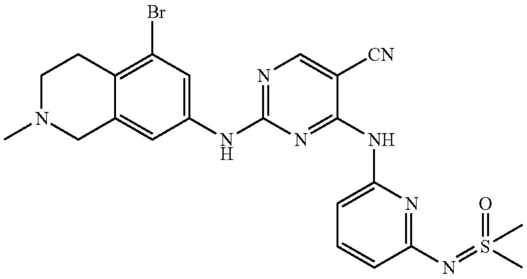
28
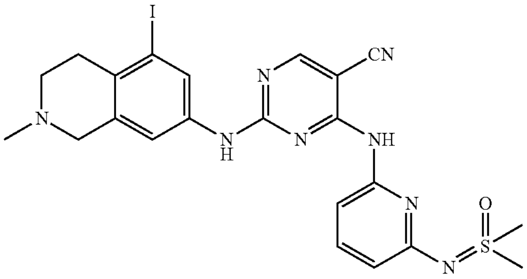
29
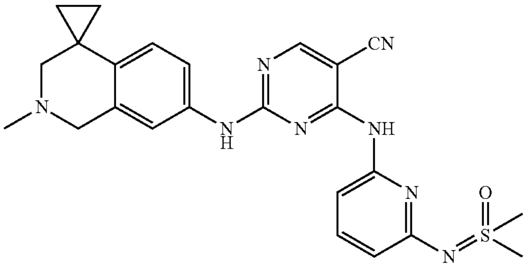
30
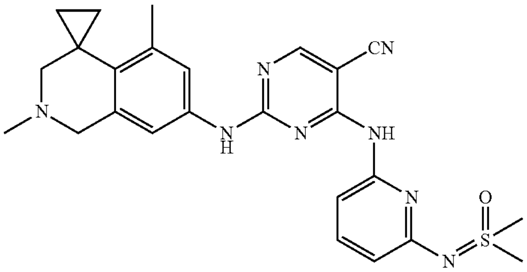
-continued
31
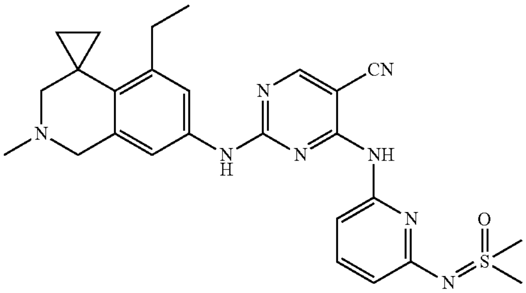
32
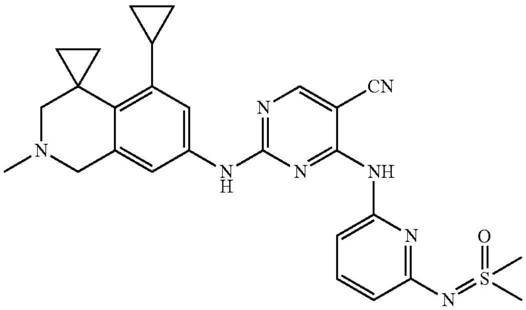
33
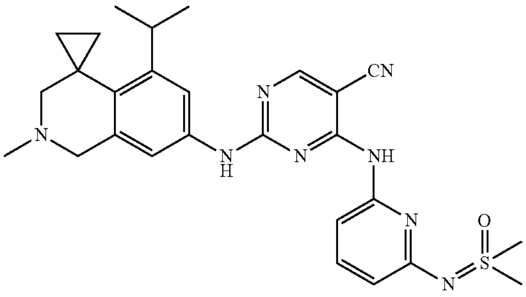
34
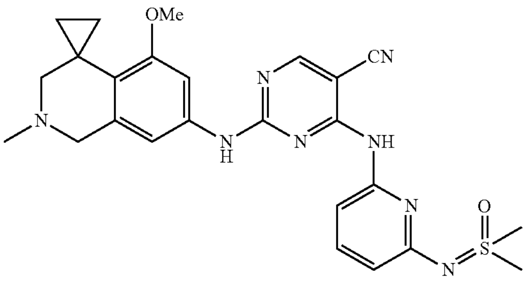
35
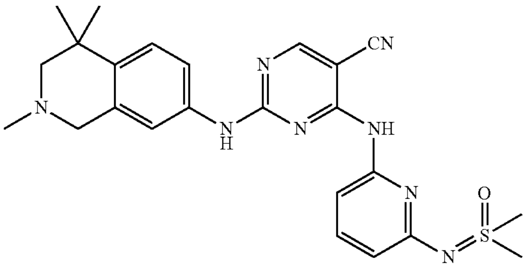

-continued
36
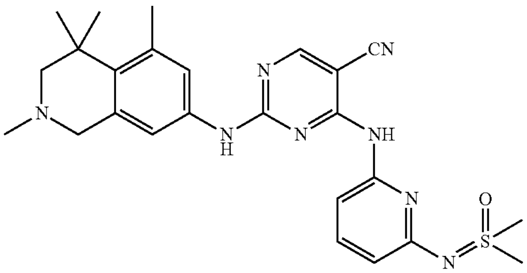
37
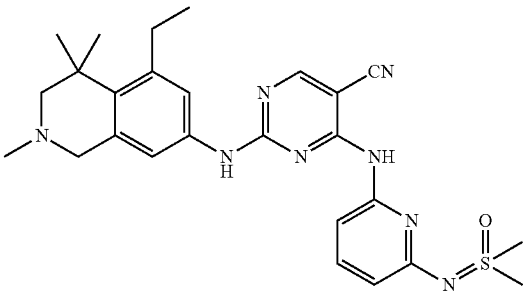
38
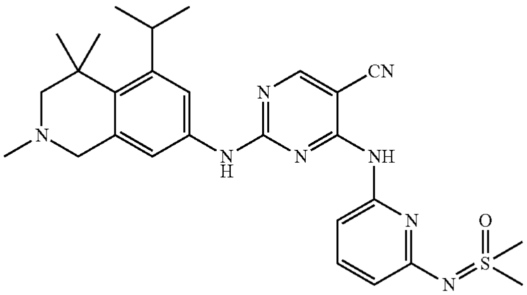
39
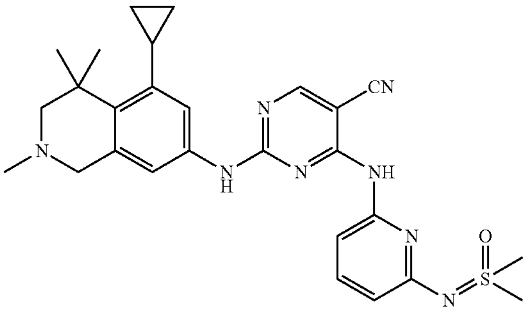
40
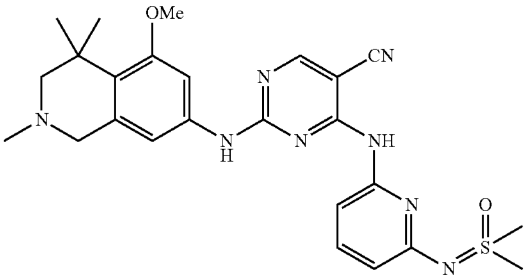
-continued
41
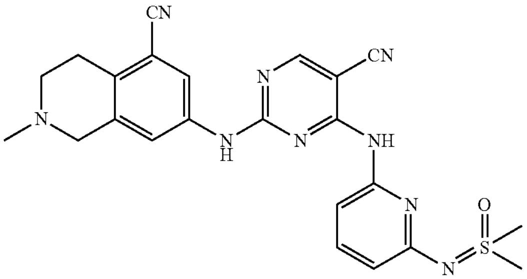
42
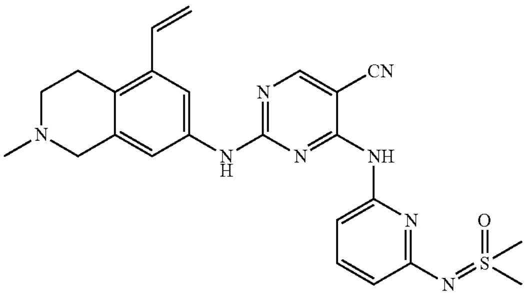
43
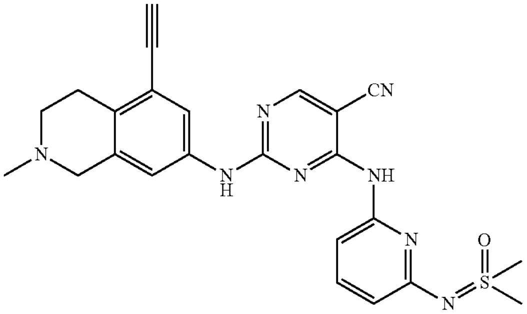
44
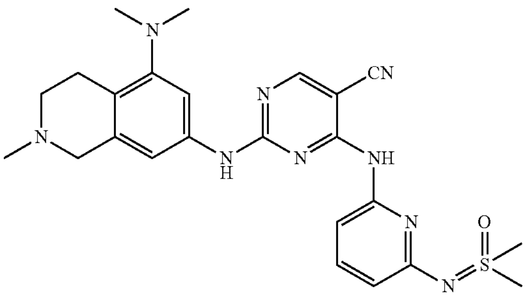
45
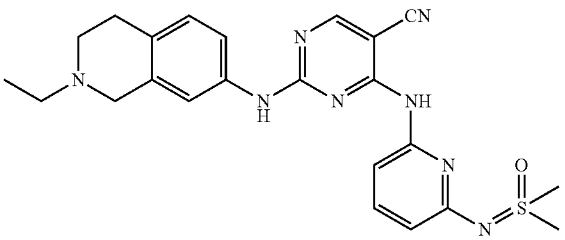

-continued
46
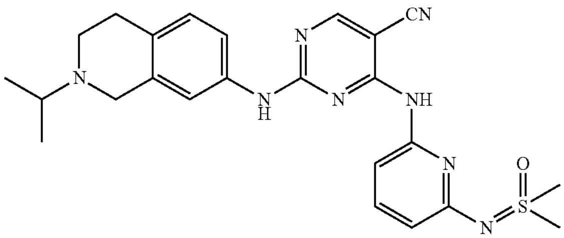
47
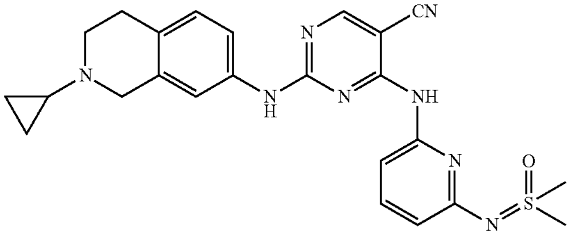
48
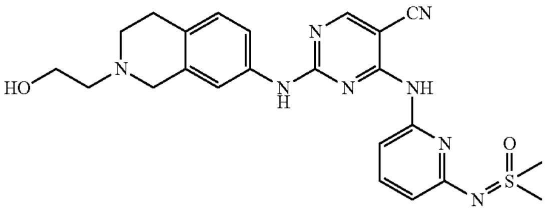
49
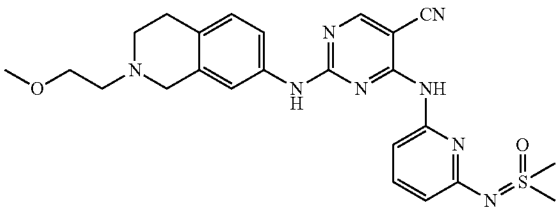
50
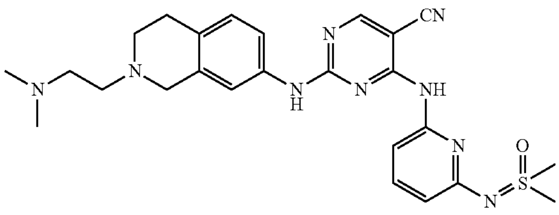
51
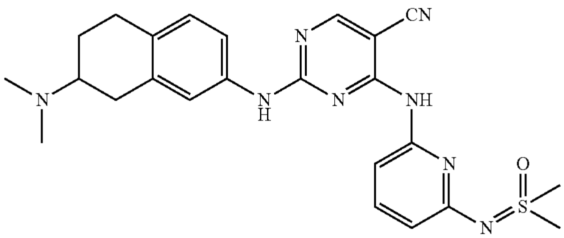
-continued
52
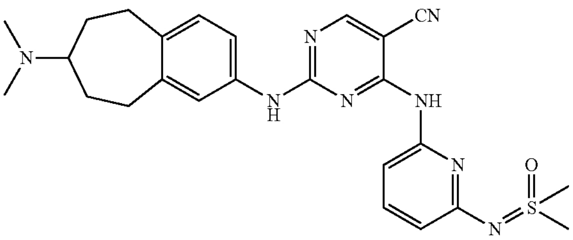
53
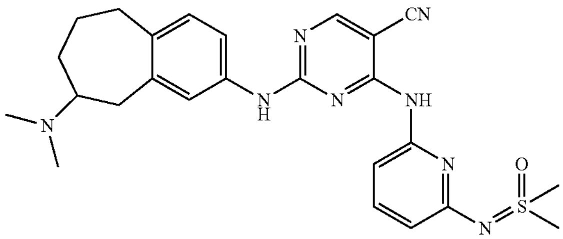
54
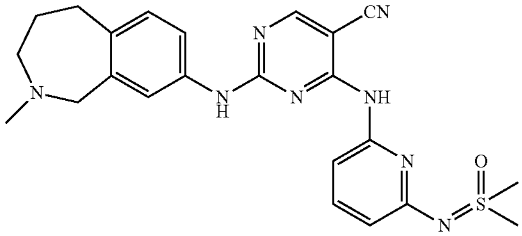
55
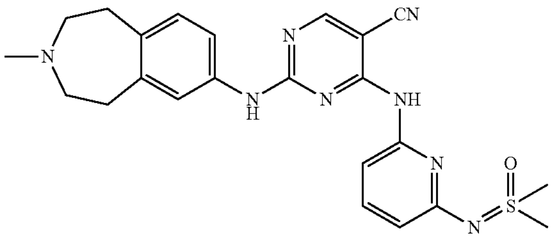
56
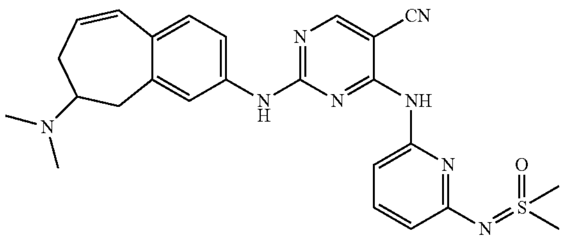
57
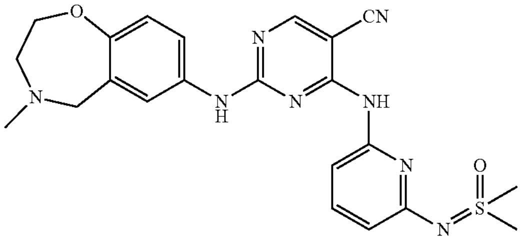

-continued
58
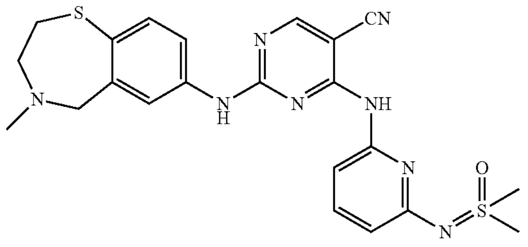
59
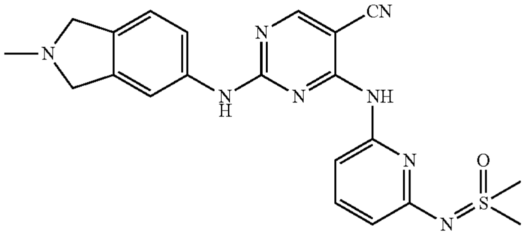
60
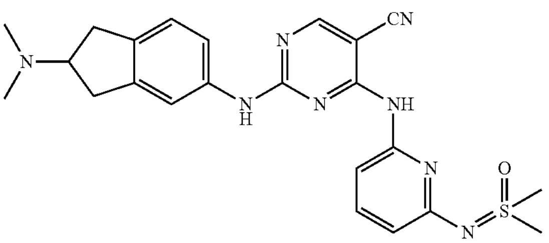
61
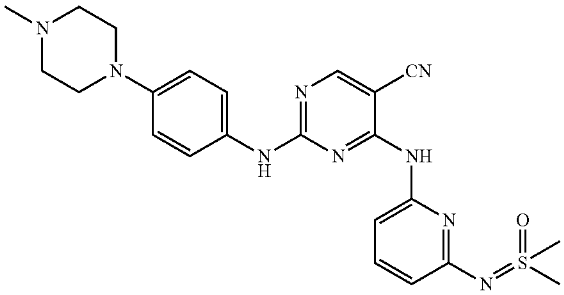
62
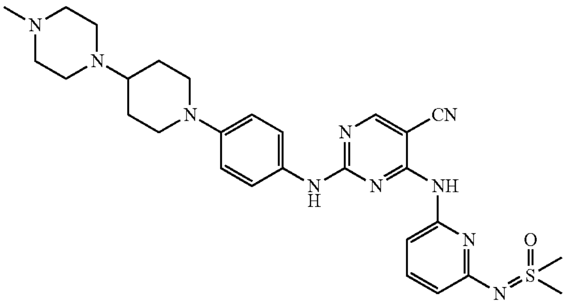
-continued
63
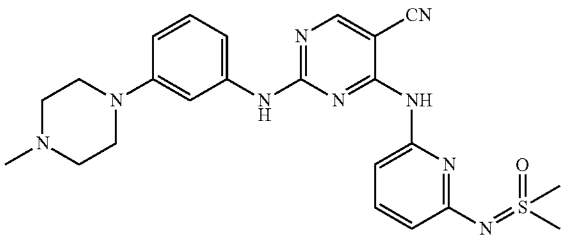
65
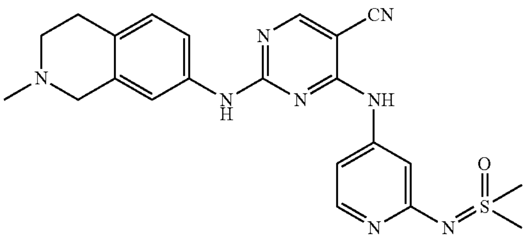
66
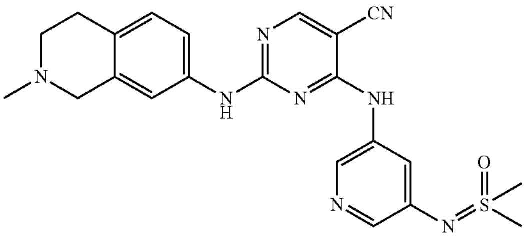
67
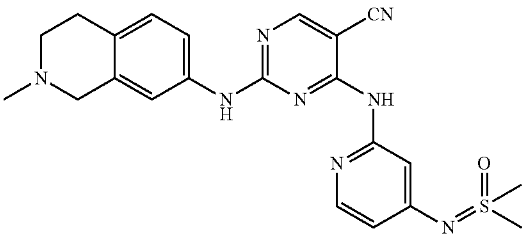
68
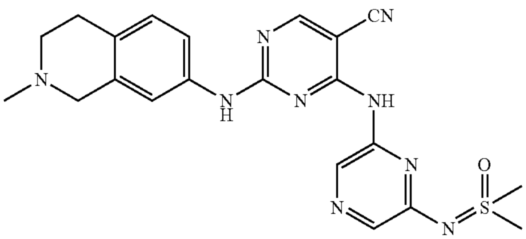
69
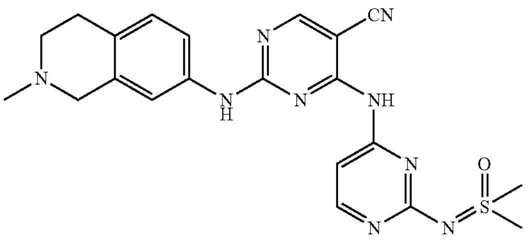

70
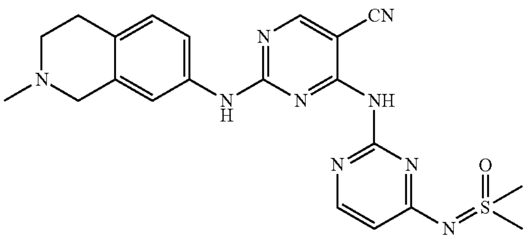
71
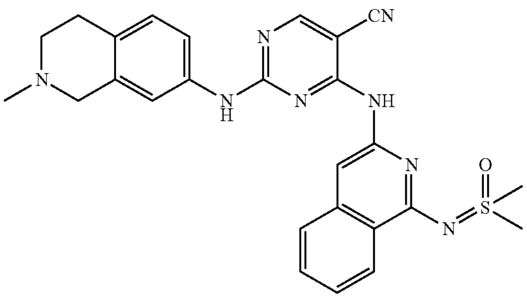
72
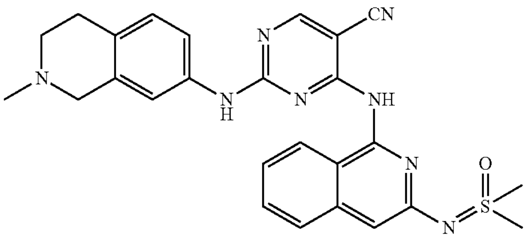
73
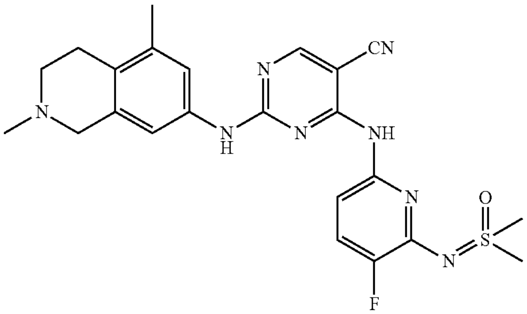
74
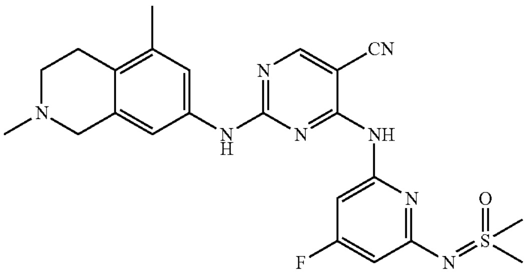
75
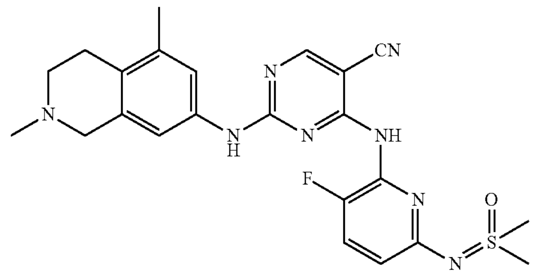
76
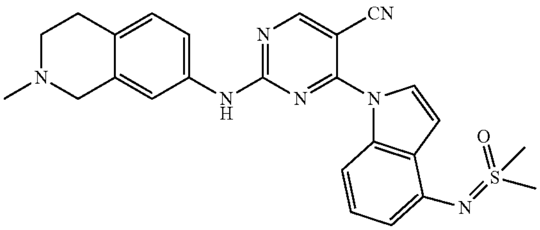
77
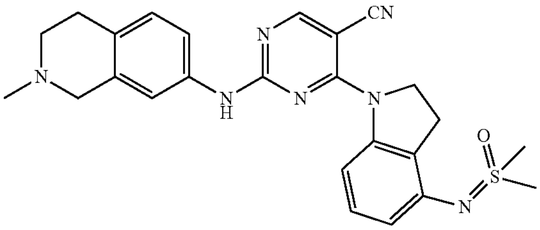
78
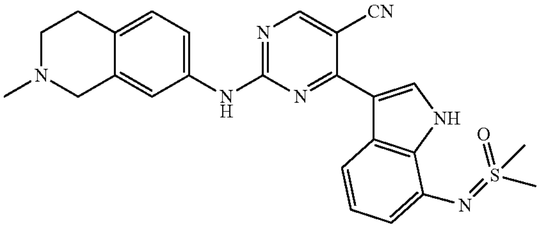
79
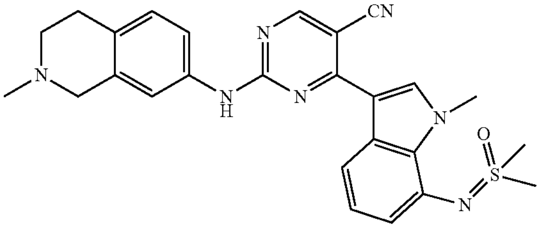
80
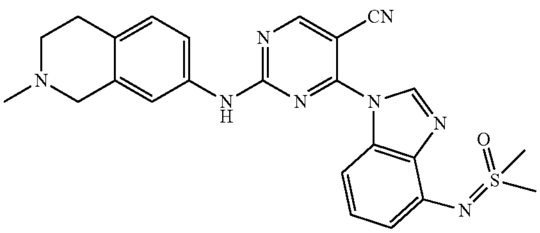

-continued
81
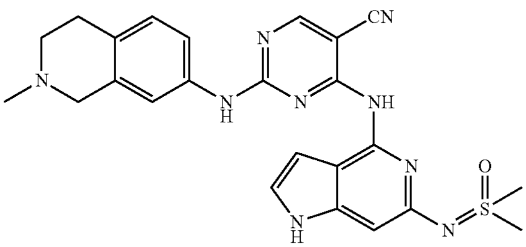
82
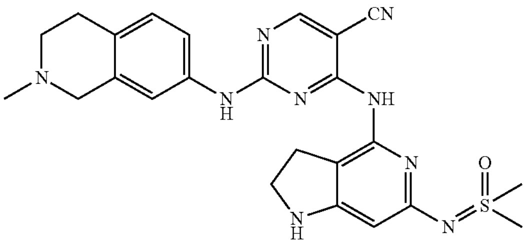
83
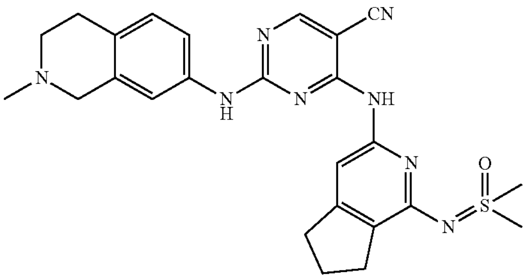
84
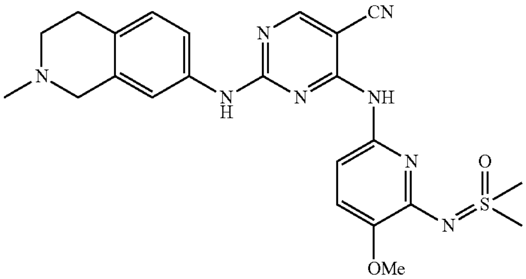
85
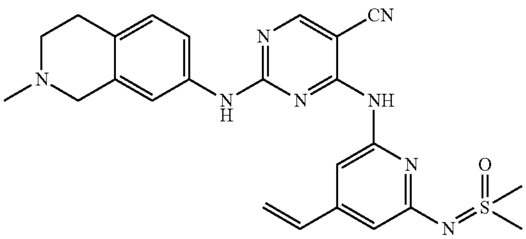
-continued
86
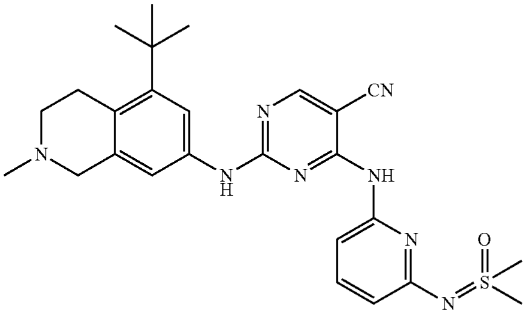
87
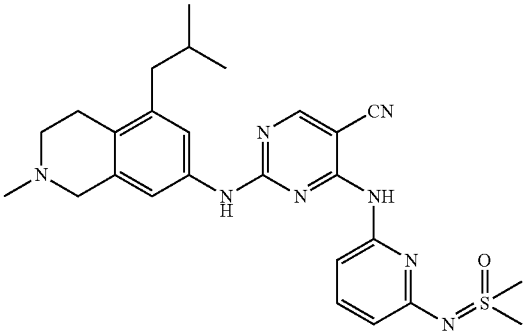
89
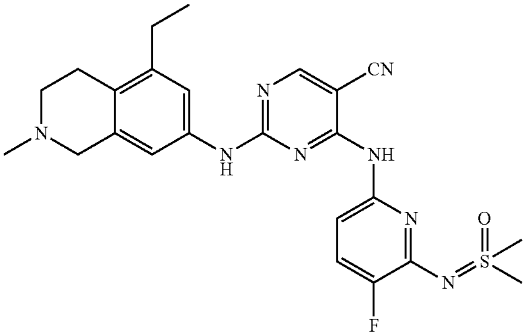
90
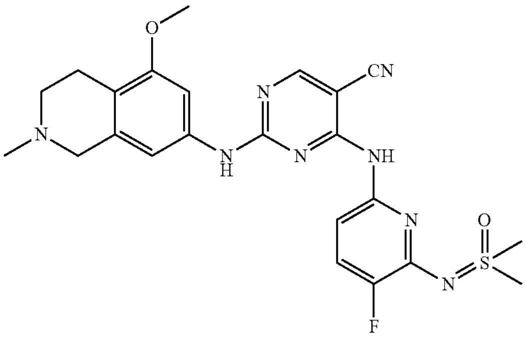

-continued
91
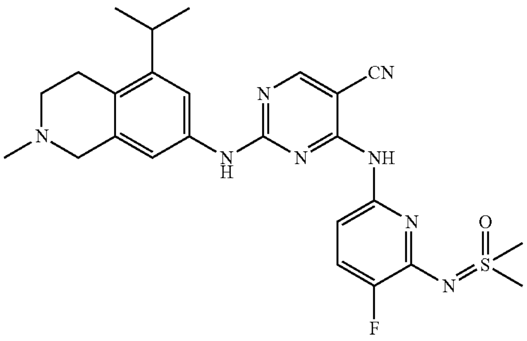
92
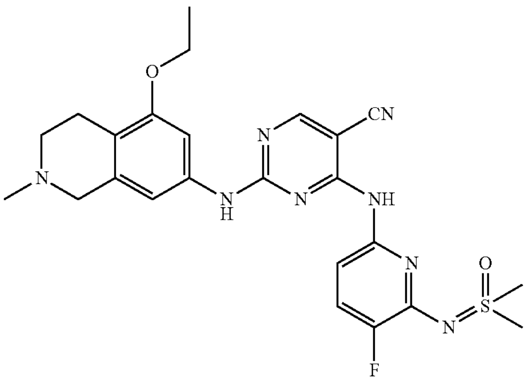
93
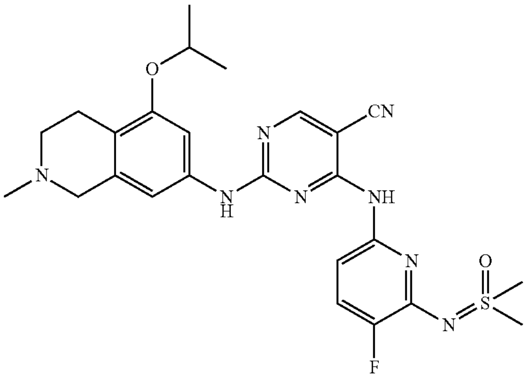
94
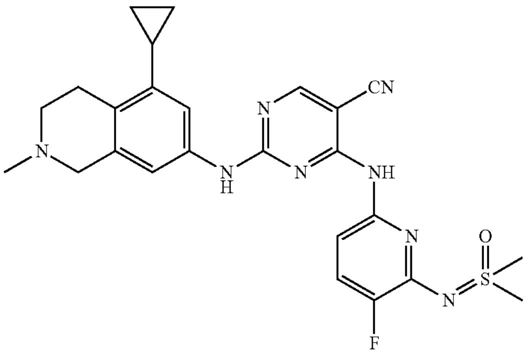
-continued
95
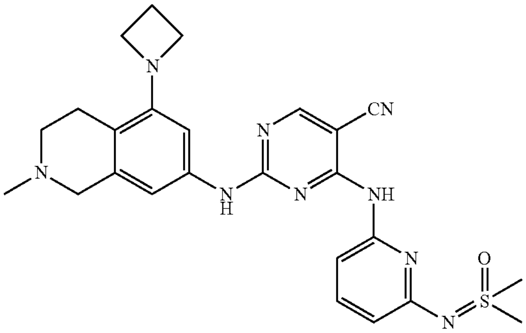
96
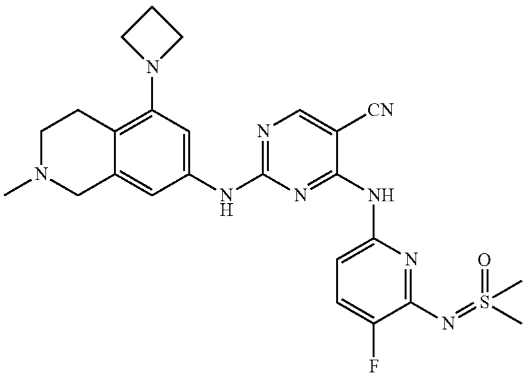
97
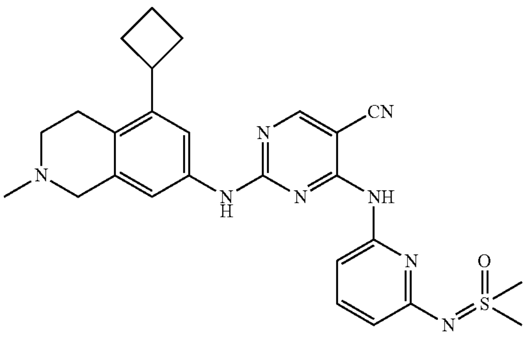
98
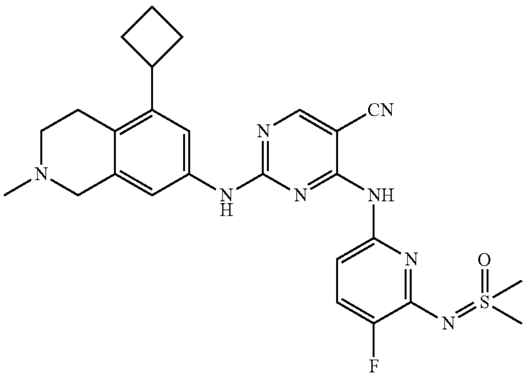

-continued
99
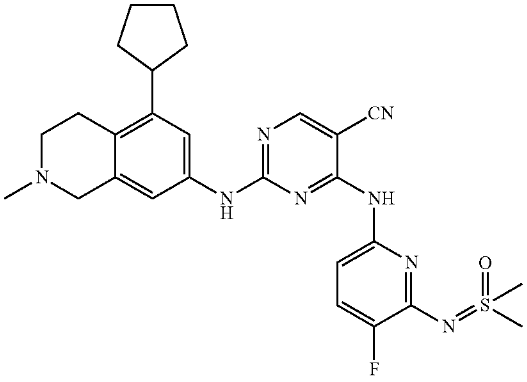
100
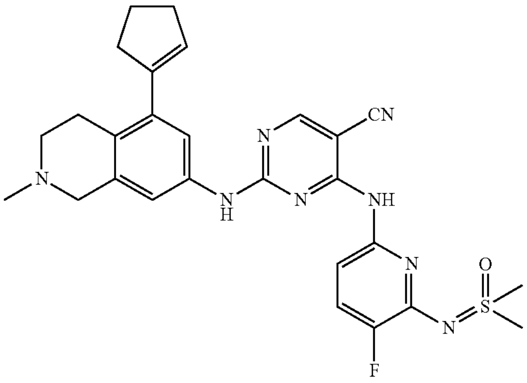
101
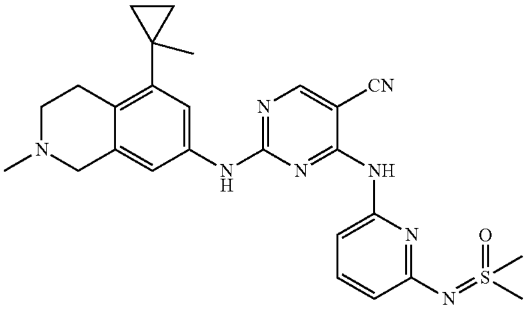
102
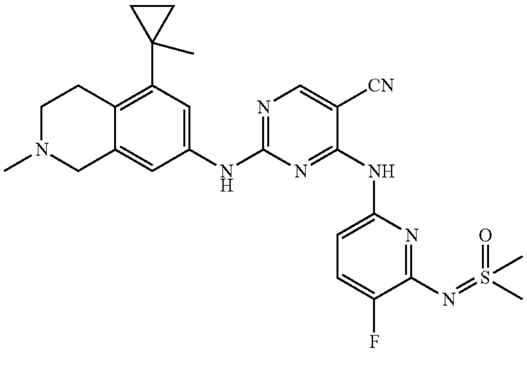
-continued
103
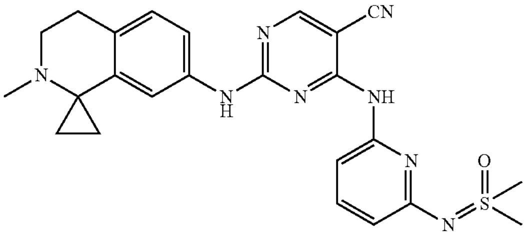
104
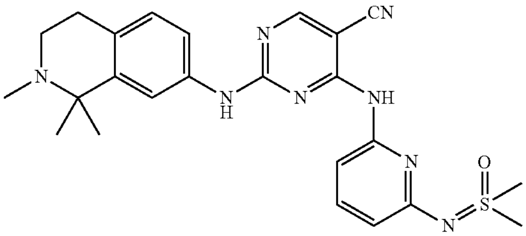
105
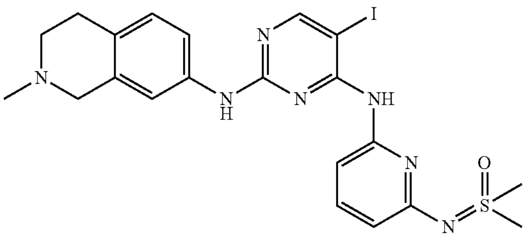
106
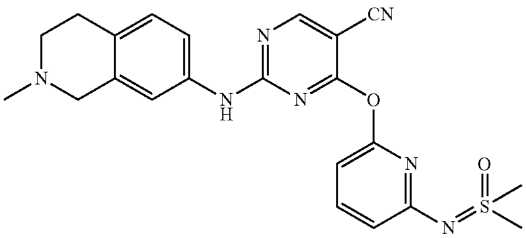
107
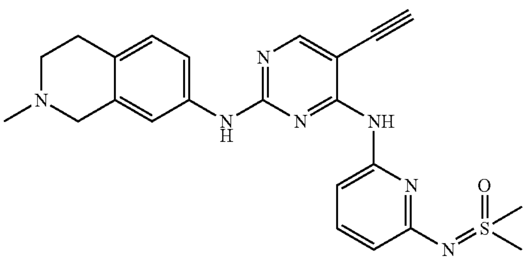

108
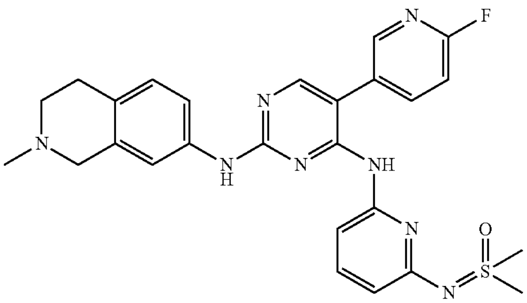
109
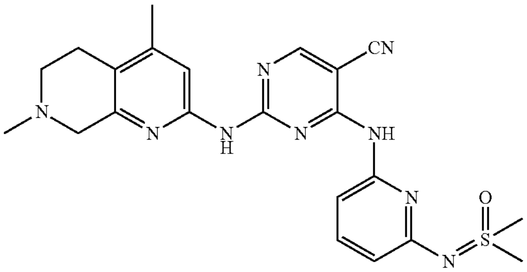
110
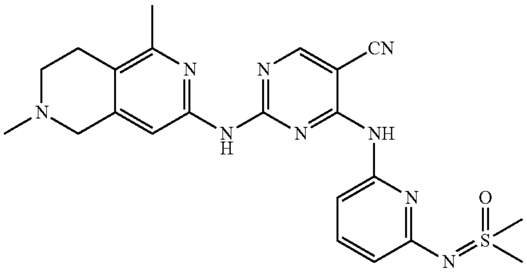
111
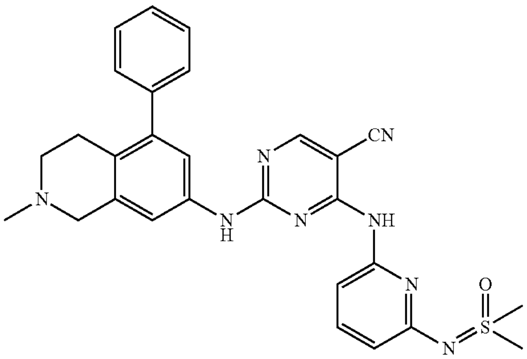
112
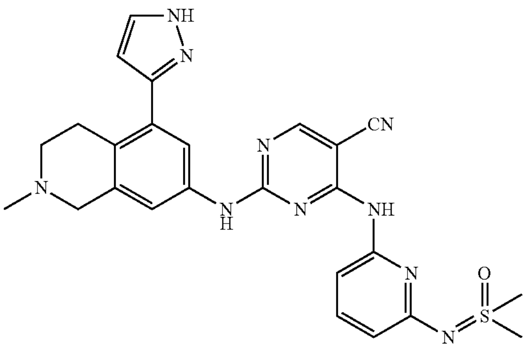
113
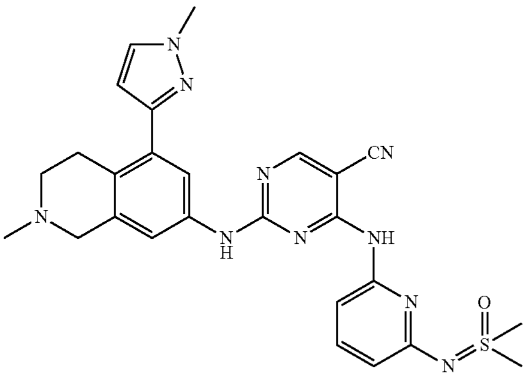
114
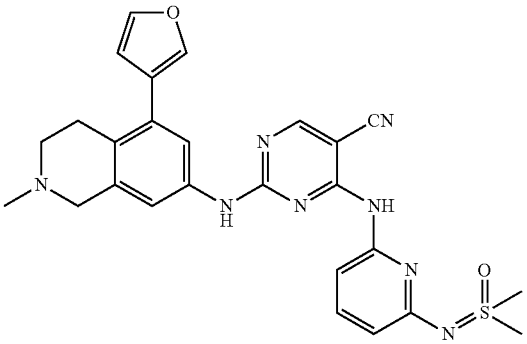
115
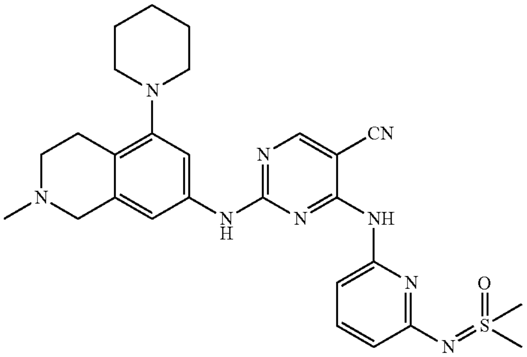

-continued
116
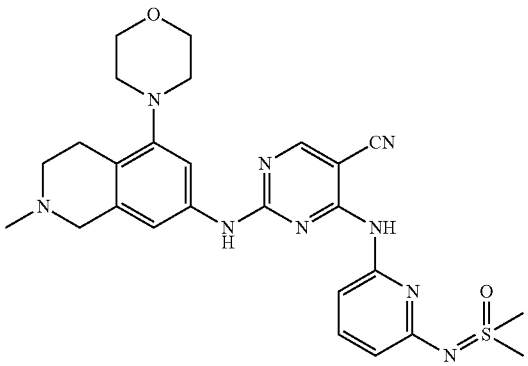
117
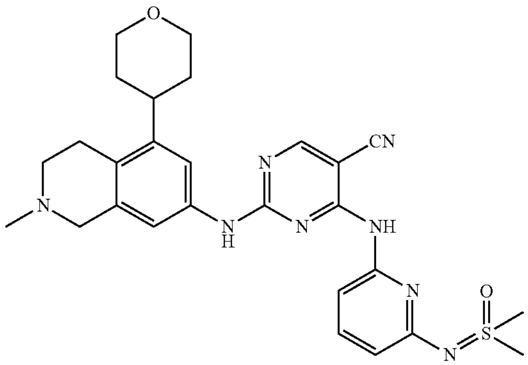
118
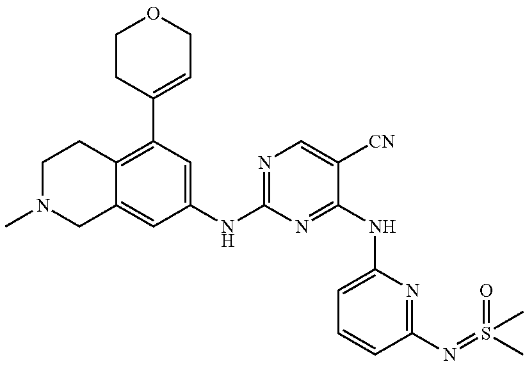
119
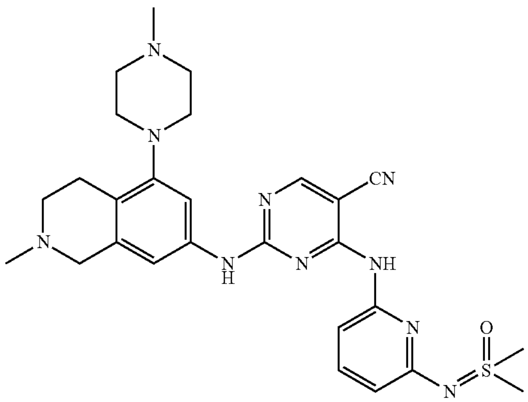
-continued
120
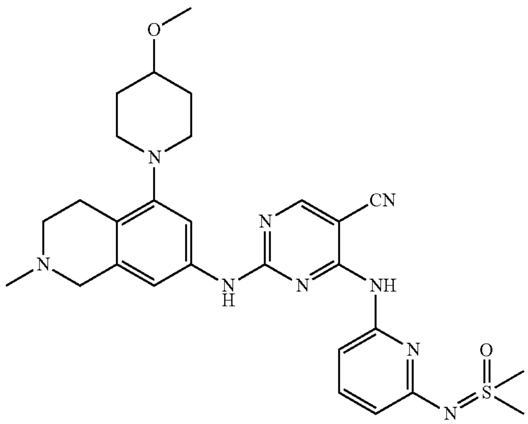
121
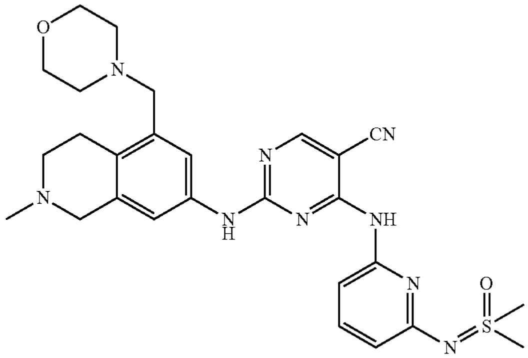
122
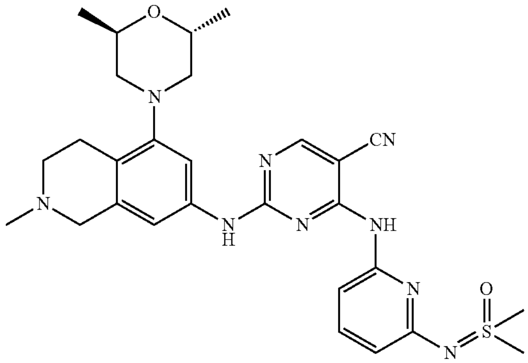
123
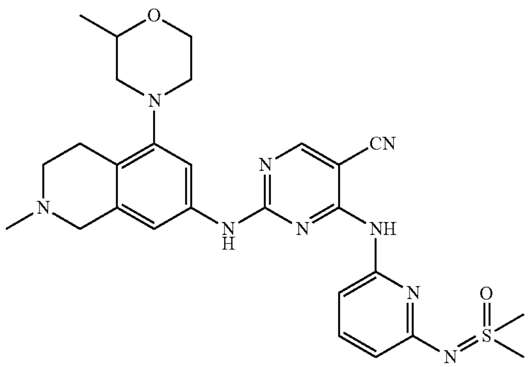

-continued
124
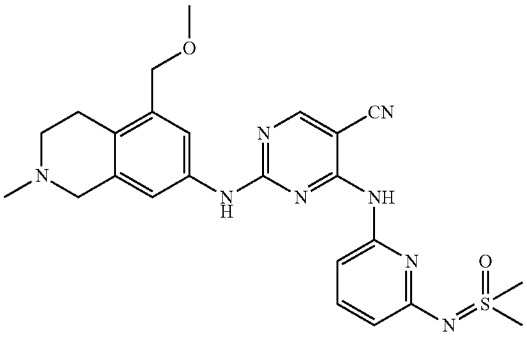
125
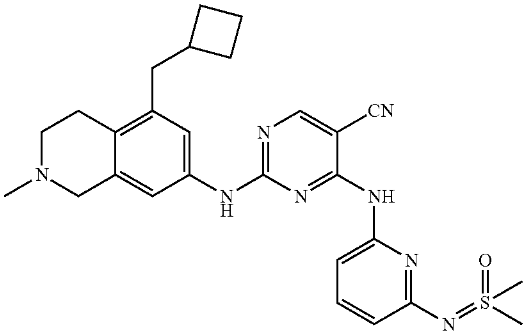
126
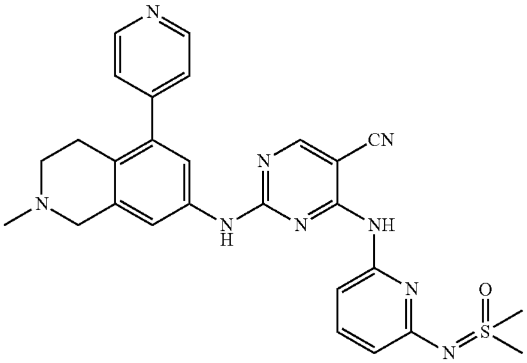
127
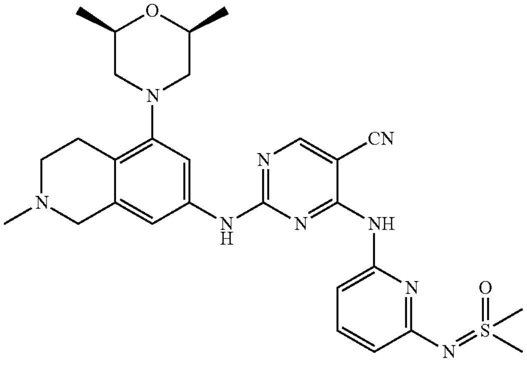
-continued
128
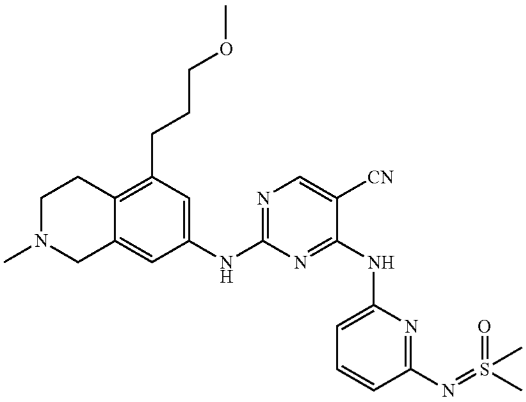
129
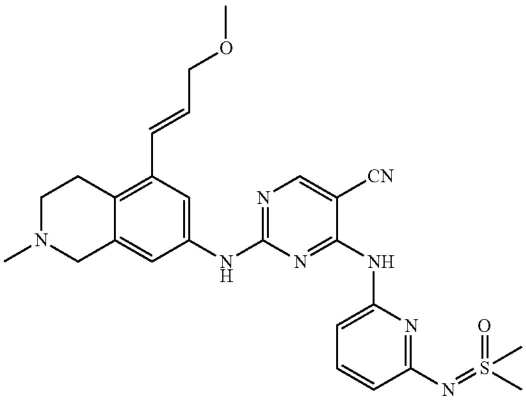
130
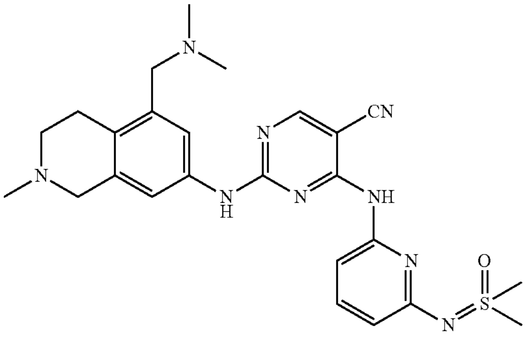
131
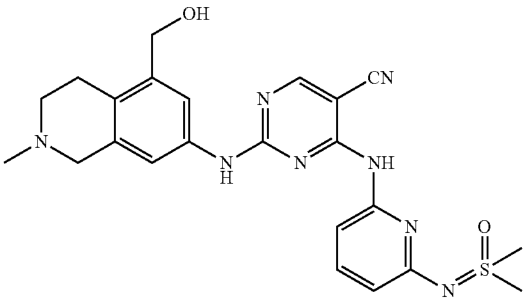

-continued
132
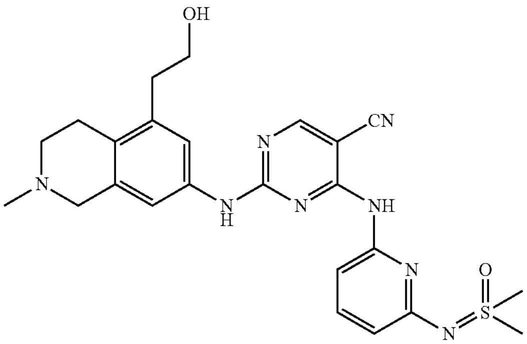
133
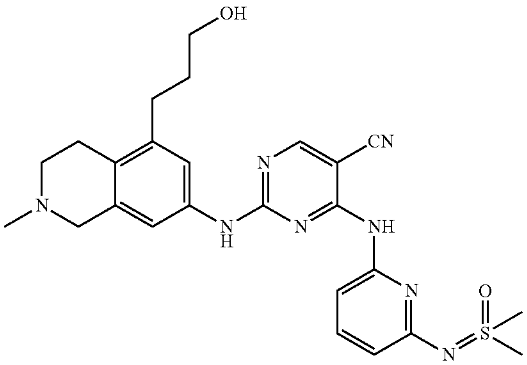
134
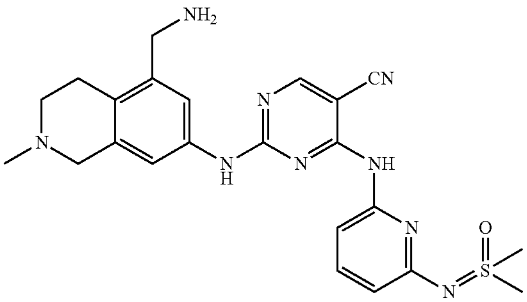
135
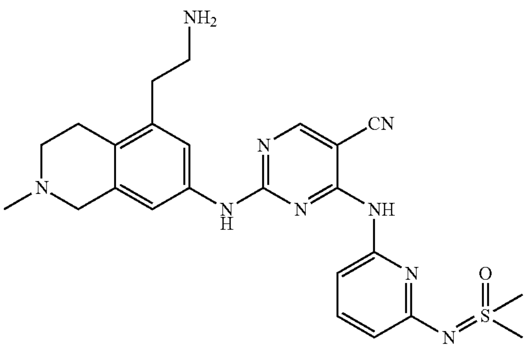
-continued
136
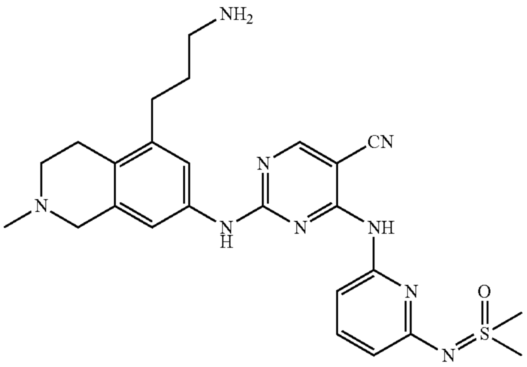
137
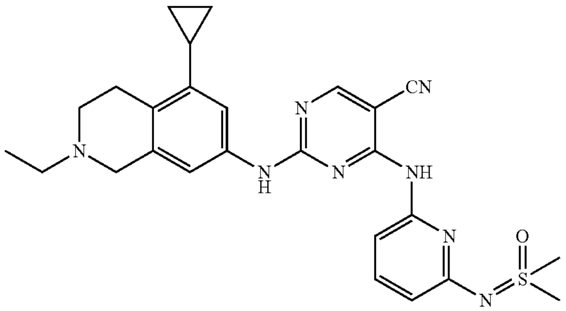
138
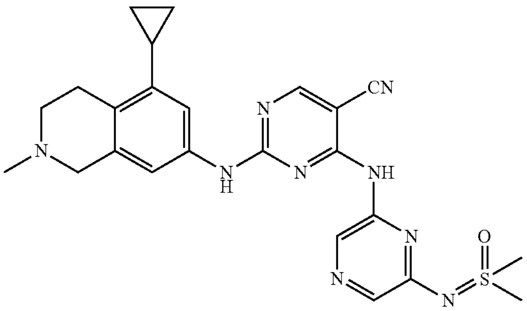
139
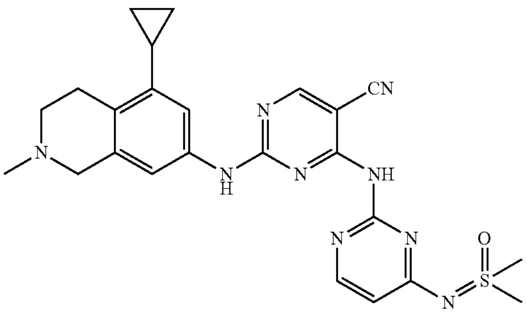

-continued
140
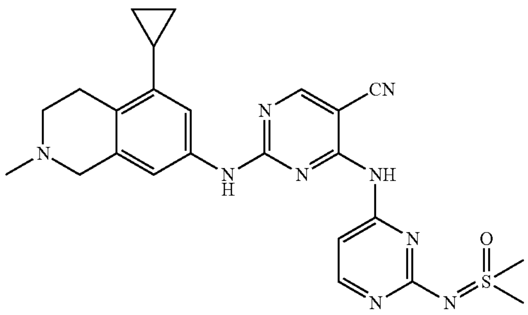
141
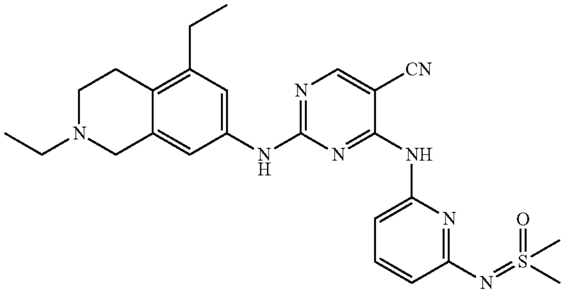
142
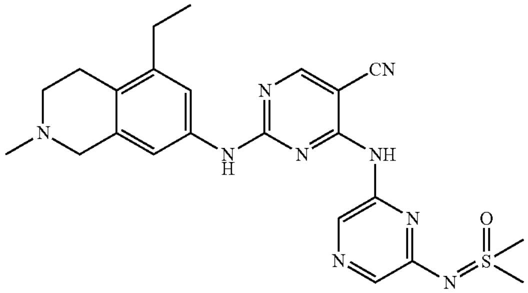
143
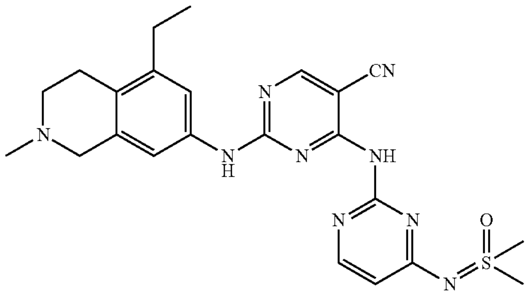
144
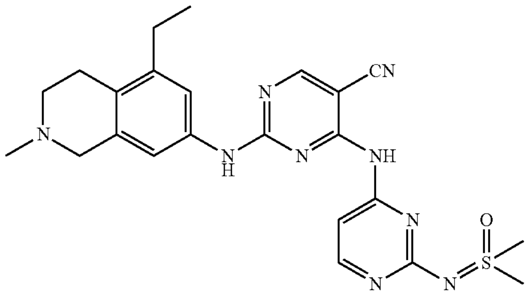
-continued
145
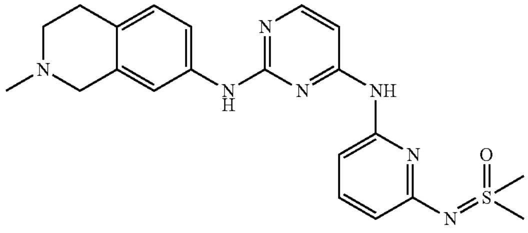
146
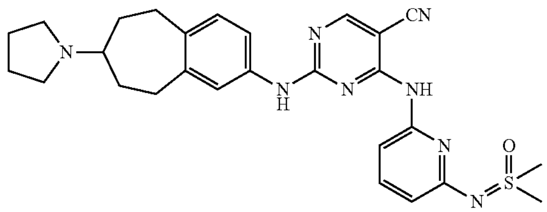
147
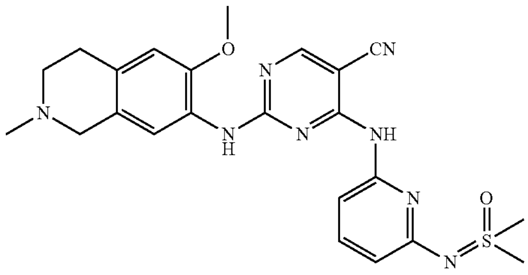
148
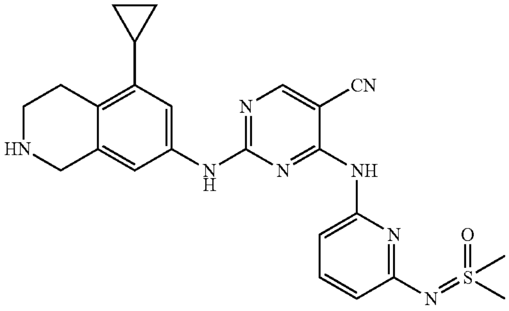
149
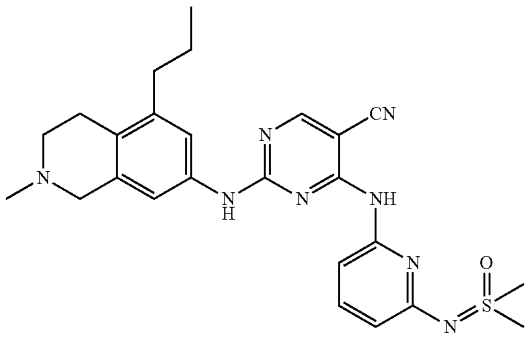

-continued
151
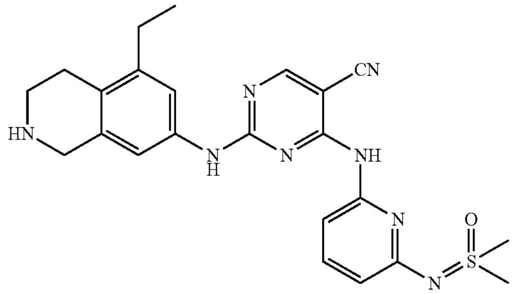
152
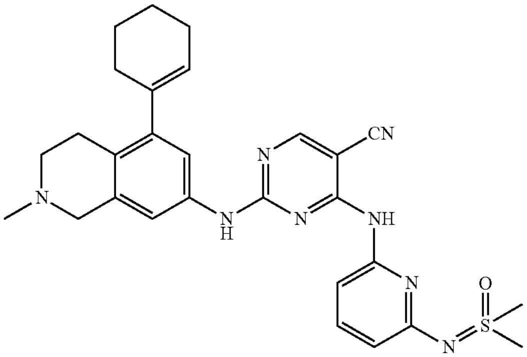
153
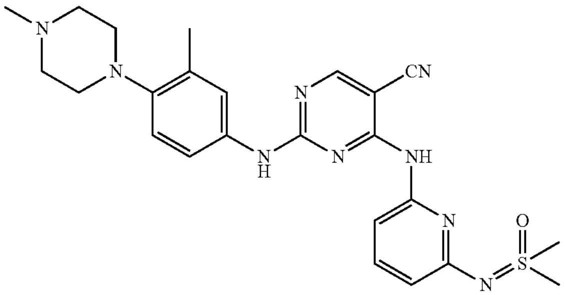
154
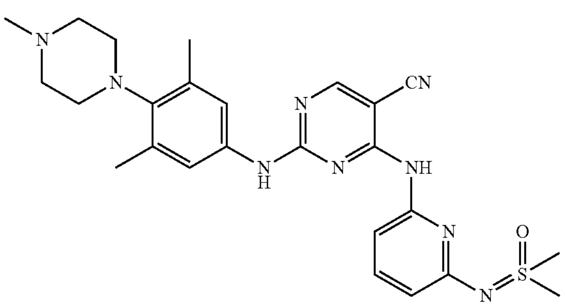
-continued
155
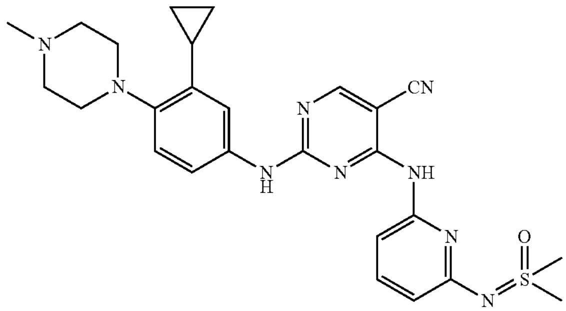
156
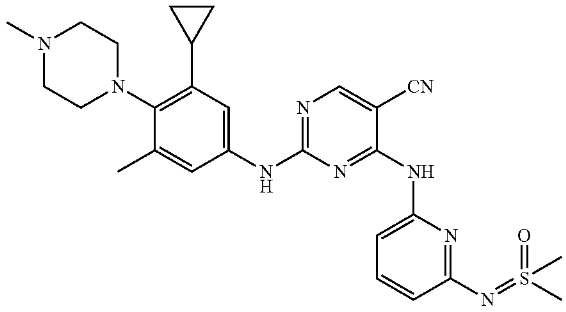
157
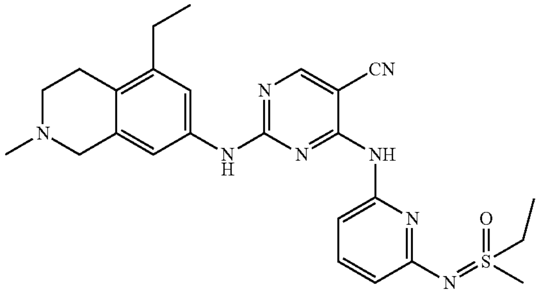
158
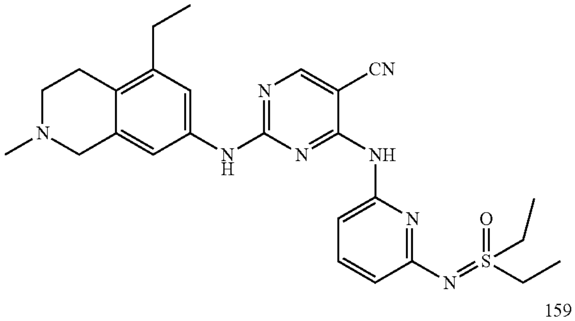
159
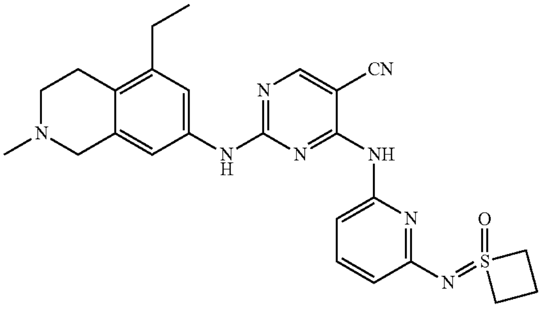

-continued
160
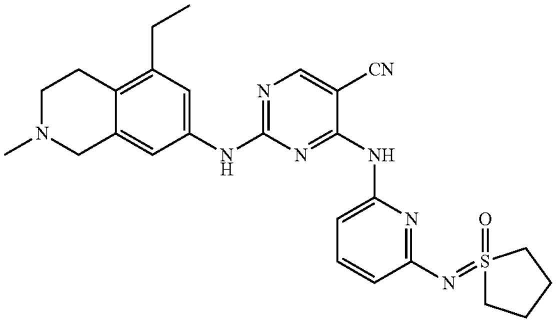
* * * * *